(12) United States Patent
Huang et al.

(10) Patent No.: US 7,998,978 B2
(45) Date of Patent: Aug. 16, 2011

(54) SUBSTITUTED 2-AMINO-FUSED HETEROCYCLIC COMPOUNDS

(75) Inventors: Liming Huang, San Diego, CA (US); Song Liu, San Diego, CA (US); Elizabeth A. Lunney, San Diego, CA (US); Simon P. Planken, San Diego, CA (US)

(73) Assignee: Pfizer Inc., Madison, NJ (US)

( * ) Notice: Subject to any disclaimer, the term of this patent is extended or adjusted under 35 U.S.C. 154(b) by 0 days.

(21) Appl. No.: 12/299,381

(22) PCT Filed: Apr. 19, 2007

(86) PCT No.: PCT/IB2007/001123
§ 371 (c)(1),
(2), (4) Date: Nov. 6, 2009

(87) PCT Pub. No.: WO2007/125405
PCT Pub. Date: Nov. 8, 2007

(65) Prior Publication Data
US 2010/0056506 A1 Mar. 4, 2010

Related U.S. Application Data

(60) Provisional application No. 60/746,087, filed on May 1, 2006.

(51) Int. Cl.
*A61K 31/472* (2006.01)
(52) U.S. Cl. ........................... 514/310; 546/143
(58) Field of Classification Search .................... 546/143
See application file for complete search history.

(56) References Cited

U.S. PATENT DOCUMENTS 3,535,321 A 10/1970 Dunn

FOREIGN PATENT DOCUMENTS

| WO | WO01/17995 | 3/2001 |
|---|---|---|
| WO | WO01/81311 | 11/2001 |
| WO | WO02/079197 | 10/2002 |
| WO | WO2004/065378 | 8/2004 |
| WO | WO2007/000240 | 1/2007 |

OTHER PUBLICATIONS

Zdrojewski et al. A General Approach to 3-Aminoisoquinoline, Its N-Mono-and N,N-Disubstituted Derivatives.1995, Tetrahedron, 51,12439-12444.*
West, Anthony R., Solid State Chemistry and its Applications, Wiley, New York, 1988, pp. 358 and 365.*
Morissette et al. "High-throughput crystallization: polymorphs, salts, co-crystals and solvates of pharmaceutical solids." 2004, Advanced Drug Delivery Reviews, 56, 275-300.*
Neumeyer et al., 3-(Dialkylaminoalkylamino)isoquinolines as Potential Antimalarial Drugs, J. of Medicinal Chemistry, 1970, V 13, No. 5, p. 999-1002.
Still, et al., Rapid Chromatographic Technique for Preparative Separations with Moderate Resolution, J. Org. Chem.,1978, vol. 43, No. 14, p. 2923-25.
Avraamides et al., Elimination Reactions of Stilbene Dibromides. Dehydrobromination by Acetate, Cyaninde or Chloride Ions in Dimethylfo . . . , Aust. J. Chem., 1983, V36, p. 1705-17.
van Benthem, A Practical synthesis of Geometrically Pure N-Boc-Protected Primary Allylic Amines, Synlett,1994 p. 368-370.
Patani, et al., Bioisosterism: A Rational Approach in Drug Design, Chemical Review, 1996, vol. 96, p. 3147-3176.
Zdrojewski et al., A general Approach to 3-Aminoisoquinoline, its N-Mono-N,N-Disubstituted Derivatives, Tetrahedron, 1995,V51, No. 45, p. 12439-444.
Gibson, et al., epidermal Growth Factor receptor Tyrosine Kinase:Structure-Activity Relationships and Antitumour Activity of . . . , Bioorg. & Med. Chem. Letters, V7, p. 2723-28.
Minden et al., Regulation and Function of the JNK subgroup of MAP Kinases, Biochimica et Beiophysica Acta 1333, 1997, F85-F104.
Thavonekham, A Practical synthesis of Ureas from Phenyl Carbamates, Synthesis, 1997, p. 1189-94.
Tomassy, et al., Stereoselective Routes to E and Z Straight-Shcin Primary Allylic amines', Synthetic Commun., V28:7, p. 1201-14.
Greene, et al., The Role of Protective Groups in Organic Synthesis, Protective Groups in Organic Synthesis, 1999, p. 1-16.
Frutos, et al., Synthesis of Bezo[b]phenanthridines and Related Naturally occurring 2-Aryl . . . , Eur. J. Org. Chem, 2001 p. 163-71.
Hirosumi et al., A Central Role for JNK in obesity and insulin resistance, Nature, 2002, V420, p. 333-36.
Swanson, et al., Identification and Biological Evaluation of 4-3-Trifluoromethylpyridin-2-yl) . . . , J. Med. chem 2005, V48, p. 1857-72.
Kanuma, et al., Discovery of 4-(dimethylamino)quinazolines as potent . . . , Bioorg. Med. Chem. Lett, 2005, V.15, 2565-69.
Bathini, et al., 2-Aminoquinazoline inhibitors of cyclin-dependent kinases, Bioorg. Med. Chem. Lett, 2005, V15 p. 3881-85.

(Continued)

*Primary Examiner* — James O Wilson
*Assistant Examiner* — Brian McDowell
(74) *Attorney, Agent, or Firm* — Ram W. Sabnis

(57) ABSTRACT

The present invention relates to compounds of formula (I), or a pharmaceutically acceptable salt or solvate thereof, wherein: $R^1$, $R^2$, $Z^1$, t, and ring A are as defined in the specification. The invention also relates to pharmaceutical compositions comprising the compounds of formula (I) and methods of treating a condition that is mediated by the modulation of JNK, such as diabetes, the method comprising administering to a mammal an effective amount of a compound of formula (I).

(I)

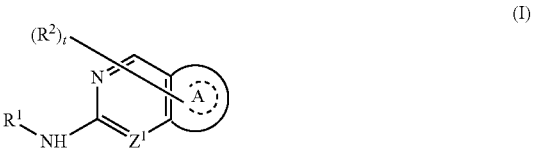

6 Claims, No Drawings

OTHER PUBLICATIONS

Graczyk, et al., The neuroprotective action of JNK3 inhibitors based on the 6,7-dihydro- . . . Bioorg. Med. Chem. Lett., 2005, V15, 4666-4670.

Sasse, 1978 Communications, p. 379-382.

Gibson, KH., et al.; Bioorganic & Medicinal Chemistry Letters, vol. 7, No. 21, pp. 2723-2728, 1997.

Beata Tomassy and Andrzej Zwierzak; Synthetic Communications, vol. 28 (7), pp. 1201-1214, 1998.

Denmark, et al., (E)-3-(Trimethylsilyl)-2-propen-1-ol. An improved preparation, J. Org. Chem., 1982, vol. 47, p. 4595-97.

* cited by examiner

SUBSTITUTED 2-AMINO-FUSED HETEROCYCLIC COMPOUNDS

CROSS-REFERENCES TO RELATED APPLICATIONS

This application is a U.S. National phase under 35 U.S.C. 371 of PCT Application No. PCT/IB2007/001123, filed on Apr. 19, 2007, which claims the benefit of U.S. Provisional Application No. 60/746,087, filed May 1, 2006, each of which is hereby incorporated by reference in its entirety.

FIELD OF THE INVENTION

The present invention relates to novel substituted 2-amino-fused heterocyclic compounds, such as 2-amino-quinolines, 2-amino-isoquinolines, and 2-amino-quinazolines, compounds of formula (I), to pharmaceutical compositions comprising the compounds, as well as to the use of the compounds in the preparation of a medicament for use in the treatment or prevention of a disease or medical condition mediated through c-Jun N-terminal kinases (JNKs), leading to a decreased glucose threshold for insulin secretion. In addition the compounds are predicted to lower blood glucose by increasing hepatic glucose uptake. Such compounds may have utility in the treatment of Type 2 diabetes and obesity.

BACKGROUND OF THE INVENTION

Mammalian cells respond to extracellular stimuli by activating signaling cascades that are mediated by members of the mitogen-activated protein (MAP) kinase family, which include the c-Jun N-terminal kinases (JNKs), also known as stress activated protein kinase (SAPK). Three distinct genes, JNK1, JNK2, JNK3 have been identified and at least ten different splicing isoforms of JNKs exist in mammalian cells [Gupta et al., EMBO J., 15:2760-70 (1996)]. While JNK1 and JNK2 express in many tissues, JNK3 specifically expresses in the brain. Thus, JNK3 has a potential to be particularly involved in nervous function. The JNK signal transduction system of stress response MAP kinase family system is activated by changes in osmotic pressure, DNA damage, anisomycine, heat shock, ultraviolet radiation, ischemia, inflammatory cytokines and the like and various stress stimulations relating to apoptosis induction, it is considered to constitute a major intracellular information transduction path responsible for stress response (Biochemica et Biophysica Acta, vol. 1333, pp. F85-F104 (1997)). From an experiment using a JNK1 deletion mouse, JNK is reported to be an important mediator involved in obesity and insulin resistance (Nature, vol. 420, pp. 333-336 (2002)).

SUMMARY OF THE INVENTION

The present invention relates to a compound of formula (I):

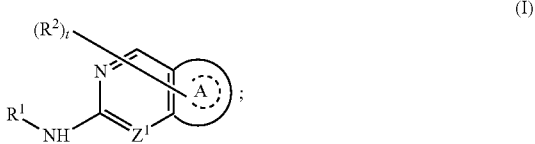

or a pharmaceutically acceptable salt or solvate thereof, wherein:

$Z^1$ is CH or N;
Ring A is a 5- or 6-membered ring which may optionally contain at least one heteroatom;
$R^1$ is hydroxy, $(C_1-C_6)$alkoxy, $(C_1-C_6)$alkyl, —(C=O)—$R^3$, —(C=O)—$(CR^3R^4)_q$—O—$(CR^3R^4)_p$—$R^3$, —(C=O)—$(CR^3R^4)_q$—O—$(CR^3R^4)_p$—(C=O)—$R^3$, —(C=O)—$NR^3R^4$, —$(CR^3R^4)_q$—$NR^3$—(C=O)$R^4$, —(C=O)—$(CR^3R^4)_q$—$NR^3$—(C=O)—$R^4$, —(C=O)—$(CR^3R^4)_q$—(C=O)—$NR^3R^4$, —S(O)$_k$$NR^3R^4$, —S(O)$_j$$R^3$, —$(CR^3R^4)_v$(3-10)-membered cycloalkyl, —$(CR^3R^4)_v$($C_6$-$C_{10}$aryl), —$(CR^3R^4)_v$(4-10)-membered heterocyclyl, —$(CR^3R^4)_q$(C=O)$(C_1$-$C_6$)alkyl, —$(CR^3R^4)_q$(C=O)$(CR^3R^4)_v$(3-10)-membered cycloalkyl, —$(CR^3R^4)_q$(C=O)$(CR^3R^4)_v$($C_6$-$C_{10}$)aryl, —$(CR^3R^4)_q$(C=O)$(CR^3R^4)_v$(4-10)-membered heterocyclyl, —$(CR^5R^6)_q$O$(CR^5R^6)_v$(3-10)-membered cycloalkyl, —$(CR^5R^6)_q$O$(CR^5R^6)_v$($C_6$-$C_{10}$)aryl, —$(CR^5R^6)_q$O$(CR^5R^6)_v$(4-10)-membered heterocyclyl, —$(CR^3R^4)_q$S(O)$_j$$(CR^3R^4)_v$($C_6$-$C_{10}$)aryl, or —$(CR^3R^4)_q$S(O)$_j$$(CR^3R^4)_v$(4-10)-membered heterocyclyl;

$R^2$ is H, halo, cyano, nitro, —$CF_3$, —$CHF_2$, —$CH_2F$, trifluoromethoxy, azido, hydroxy, $(C_1-C_6)$alkoxy, $(C_1-C_6)$alkyl, $(C_2-C_6)$alkenyl, $(C_2-C_6)$alkynyl, —(C=O)—$R^5$, —(C=O)—O—$R^5$, —O—(C=O)—$R^5$, —$NR^5$(C=O)—$R^7$—(C=O)—$NR^5R^6$, —$NR^5R^6$, —$NR^5OR^6$, —S(O)$_k$$NR^5R^6$, —S(O)$_j$$(C_1-C_6)$alkyl, —O—SO$_2$—$R^5$, —$NR^5$—S(O)$_k$—$R^6$—$(CR^5R^6)_v$(3-10)-membered cycloalkyl, —$(CR^5R^6)_v$($C_6$-$C_{10}$)aryl), —$(CR^5R^6)_v$(4-10)-membered heterocyclyl, —$(CR^5R^6)_q$(C=O)$(CR^5R^6)_v$(3-10)-membered cycloalkyl, —$(CR^5R^6)_q$(C=O)$(CR^5R^6)_v$($C_6$-$C_{10}$)aryl, —$(CR^5R^6)_q$(C=O)$(CR^5R^6)_v$(4-10)-membered heterocyclyl, —$(CR^5R^6)_q$O$(CR^5R^6)_v$(3-10)-membered cycloalkyl, —$(CR^5R^6)_q$O$(CR^5R^6)_v$($C_6$-$C_{10}$)aryl, —$(CR^5R^6)_q$O$(CR^5R^6)_v$(4-10)-membered heterocyclyl, —$(CR^5R^6)_q$S(O)$_j$$(CR^5R^6)_v$($C_6$-$C_{10}$)aryl, or —$(CR^5R^6)_q$S(O)$_j$$(CR^5R^6)_v$(4-10)-membered heterocyclyl;

each of $R^3$, $R^4$, $R^5$, $R^6$ and $R^7$ are independently selected from H, $(C_1-C_6)$alkyl, —$(CR^8R^9)_p$(3-10)-membered cycloalkyl, —$(CR^8R^9)_p$($C_6$-$C_{10}$)aryl, and —$(CR^8R^9)_p$(4-10)-membered heterocyclyl;

any carbon atoms of the $(C_1-C_6)$alkyl, the (3-10)-membered cycloalkyl, the $(C_6$-$C_{10})$aryl and the (4-10)-membered heterocyclyl moieties of the foregoing $R^1$, $R^2$, $R^3$, $R^4$, $R^5$, $R^6$ and $R^7$ are optionally substituted with 1 to 3 $R^{11}$ substituents each independently selected from oxo, halo, cyano, nitro, —$CF_3$, —$CHF_2$, —$CH_2F$, trifluoromethoxy, azido, hydroxy, $(C_1-C_6)$alkoxy, $(C_1-C_6)$alkyl, $(C_2-C_6)$alkenyl, $(C_2-C_6)$alkynyl, —(C=O)—$R^8$, —(C=O)—O—$R^8$, —O—(C=O)—$R^8$, —$NR^8$(C=O)—$R^{10}$, —$NR^8$(C=O)—O—$R^{10}$, —(C=O)—$NR^8R^9$, —(C=O)—$NR^8R^{9a}$, —$NR^8R^9$, —$NR^8OR^9$, —S(O)$_k$$NR^8R^9$, —S(O)$_j$$R^8$, —O—SO$_2$—$R^8$, —$NR^8$—S(O)$_k$—$R^9$, —$NR^8$—S(O)$_k$—$R^{9a}$, —$(CR^8R^9)_p$(3-10)-membered cycloalkyl, —(C $R^8R^9)_p$($C_6$-$C_{10}$aryl), —$(CR^8R^9)_p$(4-10)-membered heterocyclyl, —$(CR^8R^9)_q$(C=O)$(CR^8R^9)_p$(3-10)-membered cycloalkyl, —$(CR^8R^9)_q$(C=O)$(CR^8R^9)_p$($C_6$-$C_{10}$)aryl, —$(CR^8R^9)_q$(C=O)$(CR^8R^9)_p$(4-10)-membered heterocyclyl, —$(CR^8R^9)_v$O$(CR^8R^9)_p$(3-10)-membered cycloalkyl, —$(CR^8R^9)_v$O$(CR^8R^9)_p$($C_6$-$C_{10}$)aryl, —$(CR^8R^9)_v$O$(CR^8R^9)_p$(4-10)-membered heterocyclyl, —$(CR^8R^9)_q$S(O)$_j$$(CR^8R^9)_p$($C_6$-$C_{10}$)aryl, or —$(CR^8R^9)_q$S(O)$_j$$(CR^8R^9)_p$(4-10)-membered heterocyclyl;

wherein any carbon atoms of each of the $(C_1-C_6)$alkyl, the (3-10)-membered cycloalkyl, the $(C_6$-$C_{10})$aryl and the (4-10)-membered heterocyclyl moieties of the foregoing $R^{11}$ are optionally substituted with 1 to 3 $R^{12}$ substituents each independently selected from halo, cyano, nitro, —$CF_3$, —$CHF_2$, —$CH_2F$, trifluoromethoxy, azido, hydroxy, $(C_1-C_6)$ alkoxy, $(C_1-C_6)$alkyl, $(C_2-C_6)$alkenyl, $(C_2-C_6)$alkynyl, —(C=O)—$R^8$, —(C=O)—O—$R^8$, —O—(C=O)—$R^8$, —$NR^8$(C=O)—$R^{10}$, —(C=O)—$NR^8R^9$, —$NR^8R^9$, —$NR^8OR^9$, —S(O)$_k NR^8R^9$, —S(O)$_j(C_1-C_6)$alkyl, —O—SO$_2$—$R^8$, and —$NR^8$—S(O)$_k$—$R^9$;

any nitrogen atoms of the (4-10)-membered heterocyclyl of the foregoing $R^1$, $R^2$, $R^3$, $R^4$, $R^5$, $R^6$, $R^7$, $R^{11}$, and $R^{12}$ are optionally substituted with 1 to 3 $R^{13}$ substituents each independently selected from $(C_1-C_6)$alkyl, $(C_2-C_6)$alkenyl, $(C_2-C_6)$alkynyl, —(C=O)—$R^8$, —(C=O)—$R^{9a}$, —(C=O)—O—$R^8$, —(C=O)—$NR^8R^9$, —$(CR^8R^9)_q$—$NR^8R^9$, —$(CR^8R^9)_p$(3-10)-membered cycloalkyl, —$(CR^8R^9)_p(C_6-C_{10}$aryl), —$(CR^8R^9)_p$(4-10)-membered heterocyclyl, —$(CR^8R^9)_q$(C=O)$(CR^8R^9)_p$(3-10)-membered cycloalkyl, —$(CR^8R^9)_q$(C=O)$(CR^8R^9)_p(C_6-C_{10}$)aryl, or —$(CR^8R^9)_q$(C=O)$(CR^8R^9)_p$(4-10)-membered heterocyclyl;

each $R^8$, $R^9$, and $R^{10}$ are independently H or $(C_1-C_6)$alkyl;

each $R^{9a}$ is independently —$(CR^8R^9)_p$(3-10)-membered cycloalkyl, —$(CR^8R^9)_p(C_6-C_{10}$aryl), or —$(CR^8R^9)_p$(4-10)-membered heterocyclyl;

p, q, and v are each independently 0, 1, 2, 3, 4, or 5;

n and j are each independently 0, 1, or 2;

t is 1, 2, 3, or 4;

w is 1, 2, or 3, and k is 1 or 2.

In another embodiment, the invention relates to compounds of the formula (I) selected from the group consisting of:

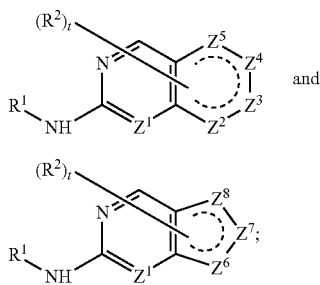

wherein in each of said compounds (Ia) and (Ib):
the dotted lined are optional double bonds;
$Z^1$ is CH or N;
$Z^2$, $Z^3$, $Z^4$, and $Z^5$ are each independently C or N;
$Z^6$, $Z^7$, and $Z^8$ are each independently C, S, O, or N;
Wherein $R^2$ attached to any of $Z^2$, $Z^3$, $Z^4$, $Z^5$, $Z^6$, $Z^7$, and $Z^8$ is independently selected from the group consisting of H, halo, cyano, nitro, —CF$_3$, —CHF$_2$, —CH$_2$F, trifluoromethoxy, azido, hydroxy, $(C_1-C_6)$alkoxy, $(C_1-C_6)$alkyl, $(C_2-C_6)$alkenyl, $(C_2-C_6)$alkynyl, —(C=O)—$R^{14}$, —(C=O)—O—$R^{14}$, —O—(C=O)—$R^{14}$, —$NR^{14}$(C=O)—$R^{15}$, —(C=O)—$NR^{14}R^{15}$, —$NR^{14}R^{15}$, —$NR^{14}OR^{15}$, —S(O)$_k NR^{14}R^{15}$, —S(O)$_j R^{14}$, —O—SO$_2$—$R^{14}$, —$NR^{14}$—S(O)$_k$—$R^{15}$, —$(CR^{14}R^{15})$(3-10)-membered cycloalkyl, —$(CR^{14}R^{15})_p(C_6-C_{10}$aryl), —$(CR^{14}R^{15})_p$(4-10)-membered heterocyclyl, —$(CR^{14}R^{15})_q$(C=O)$(CR^{14}R^{15})_p(C_6-C_{10}$)aryl, —$(CR^{14}R^{15})_q$(C=O)$(CR^{14}R^{15})_p$(4-10)-membered heterocyclyl, —$(CR^{14}R^{15})_v O(CR^{14}R^{15})_p(C_6-C_{10}$)aryl, —$(CR^{14}R^{15})_v O(CR^{14}R^{15})_p$(4-10)-membered heterocyclyl, —$(CR^{14}R^{15})_q S(O)_j(CR^{14}R^{15})_p(C_6-C_{10}$)aryl, and —$(CR^{14}R^{15})_q S(O)_j(CR^{14}R^{15})_p$(4-10)-membered heterocyclyl; and each of $R^{14}$ and $R^{15}$ are independently selected from the group consisting of H, $(C_1-C_6)$alkyl, —$(CR^8R^9)_p$(3-10)-membered cycloalkyl, —$(CR^8R^9)_p(C_6-C_{10}$)aryl, and —$(CR^8R^9)_p$(4-10)-membered heterocyclyl.

In another embodiment, the invention relates to compounds of the formula (Ia) selected from the group consisting of:

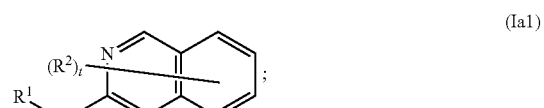

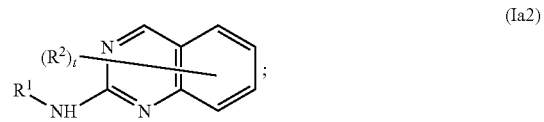

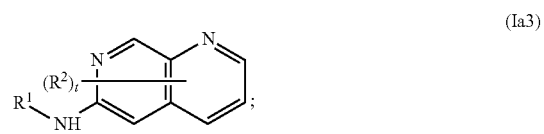

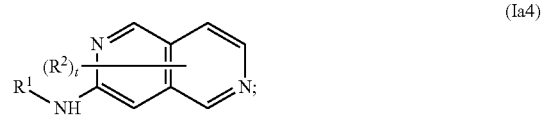

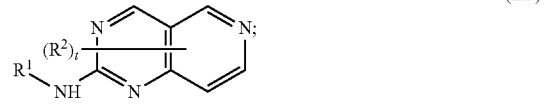

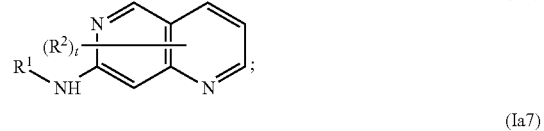

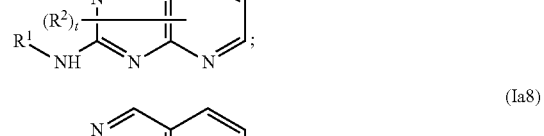

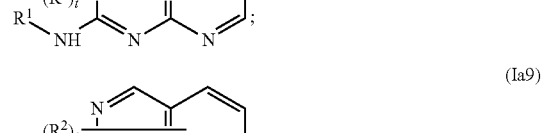

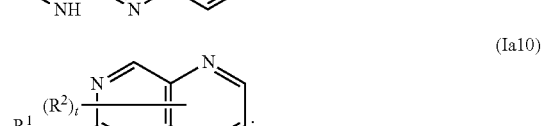

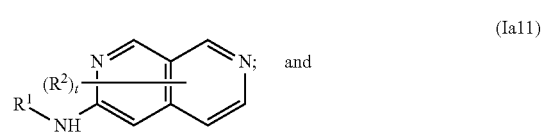

and

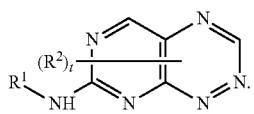
(Ia12)

In another embodiment, the invention relates to compounds of the formula (Ib) selected from the group consisting of:

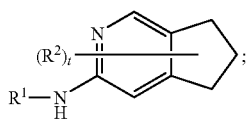
(Ib1)

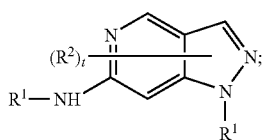
(Ib2)

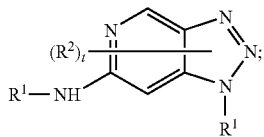
(Ib3)

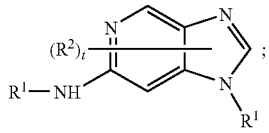
(Ib4)

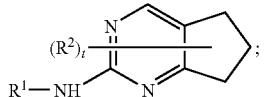
(Ib5)

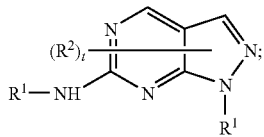
(Ib6)

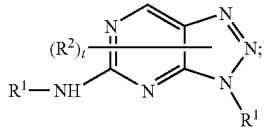
(Ib7)

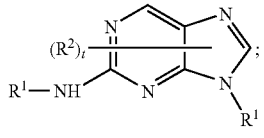
(Ib8)

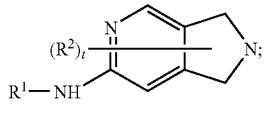
(Ib9)

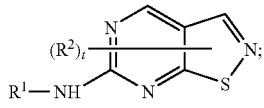
(Ib10)

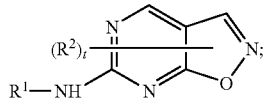
(Ib11)

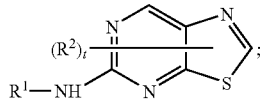
(Ib12)

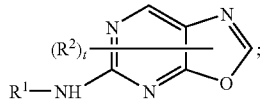
(Ib13)

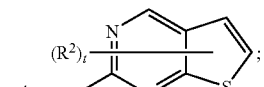
(Ib14)

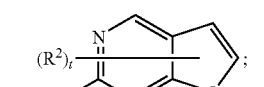
(Ib15)

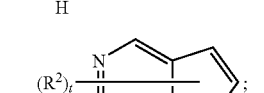
(Ib16)

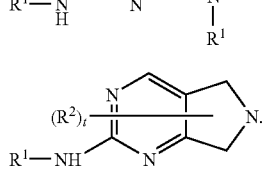
(Ib17)

In a preferred embodiment, the invention relates to compounds of the formula (Ia), specifically compound of formula (Ia1):

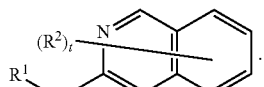
(Ia1)

In another sub-embodiment, the invention relates to compounds of the formula (II):

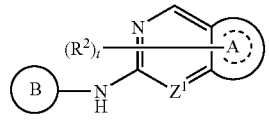
(II)

wherein ring B is selected from $-(CR^3R^4)_v$(3-10)-membered cycloalkyl, $-(CR^3R^4)_v(C_6-C_{10})$aryl, $-(CR^3R^4)_v$(4-10)-membered heterocyclyl, $-(CR^3R^4)_q(C=O)(CR^3R^4)_v$ (3-10)-membered cycloalkyl, $-(CR^3R^4)_q(C=O)(CR^3R^4)_v$ $(C_6-C_{10})$aryl, and $-(CR^3R^4)_q(C=O)(CR^3R^4)_v$(4-10)-membered heterocyclyl.

In another embodiment, the invention relates to compounds of the formula (I), wherein $R^2$ is H, halo, hydroxy, $(C_1-C_6)$alkoxy, $(C_1-C_6)$alkyl, $-(C=O)-R^5$, $-(C=O)-NR^5R^6$, $-(CR^5R^6)_v$(3-10)-membered cycloalkyl, —(CR⁵R⁶)ᵥ(C₆-C₁₀aryl), —(CR⁵R⁶)ᵥ(4-10)-membered heterocyclyl, —(CR⁵R⁶)_qO(CR⁵R⁶)ᵥ(3-10)-membered cycloalkyl, —(CR⁵R⁶)_qO(CR⁵R⁶)ᵥ(C₆-C₁₀)aryl, or —(CR⁵R⁶)_qO(CR⁵R⁶)ᵥ(4-10)-membered heterocyclyl.

In another embodiment, the invention relates to compounds of the formula (I), wherein R² is —(CR⁵R⁶)ᵥ(3-10)-membered cycloalkyl, —(CR⁵R⁶)ᵥ(C₆-C₁₀aryl), —(CR⁵R⁶)ᵥ(4-10)-membered heterocyclyl, —(CR⁵R⁶)_q(C=O)(CR⁵R⁶)ᵥ (3-10)-membered cycloalkyl, —(CR⁵R⁶)_q(C=O)(CR⁵R⁶)ᵥ(C₆-C₁₀)aryl, —(CR⁵R⁶)_q(C=O)(CR⁵R⁶)ᵥ(4-10)-membered heterocyclyl, —(CR⁵R⁶)_qO(CR⁵R⁶)ᵥ(3-10)-membered cycloalkyl, —(CR⁵R⁶)_qO(CR⁵R⁶)ᵥ(C₆-C₁₀)aryl, —(CR⁵R⁶)_qO(CR⁵R⁶)ᵥ(4-10)-membered heterocyclyl, —(CR⁵R⁶)_qS(O)_j(CR⁵R⁶)ᵥ(C₆-C₁₀)aryl, or —(CR⁵R⁶)_qS(O)_j(CR⁵R⁶)ᵥ(4-10)-membered heterocyclyl.

In another embodiment, the invention relates to compounds of the formula (I), wherein R² is pyrazolyl wherein any nitrogen atoms of the pyrazolyl are optionally substituted with (C₁-C₆)alkyl, —(CR⁸R⁹)_p(C₆-C₁₀aryl), —(CR⁸R⁹)_p(4-10)-membered heterocyclyl, —(CR⁸R⁹)_q(C=O)(CR⁸R⁹)_p(C₆-C₁₀)aryl, or —(CR⁸R⁹)_q(C=O)(CR⁸R⁹)_p(4-10)-membered heterocyclyl.

In another embodiment, the invention relates to compounds of the formula (I), wherein R² is —(C=O)—NR⁵R⁶, wherein each of R⁵ and R⁶ are independently selected from H, (C₁-C₆)alkyl, —(CR⁸R⁹)_p(3-10)-membered cycloalkyl, —(CR⁸R⁹)_p(C₆-C₁₀)aryl, and —(CR⁸R⁹)_p(4-10)-membered heterocyclyl.

In another embodiment, the invention relates to compounds of the formula (I), wherein R¹ is (C₁-C₆)alkyl, —(CR³R⁴)ᵥ(3-10)-membered cycloalkyl, —(CR³R⁴)ᵥ(C₆-C₁₀aryl), or —(CR³R⁴)ᵥ(4-10)-membered heterocyclyl.

In another embodiment, the invention relates to compounds of the formula (I), wherein R¹ is —(CR³R⁴)ᵥ(3-10)-membered cycloalkyl, —(CR³R⁴)ᵥ(C₆-C₁₀aryl), —(CR³R⁴)ᵥ(4-10)-membered heterocyclyl, —(CR³R⁴)_q(C=O)(CR³R⁴)ᵥ(3-10)-membered cycloalkyl, —(CR³R⁴)_q(C=O)(CR³R⁴)ᵥ(C₆-C₁₀)aryl, —(CR³R⁴)_q(C=O)(CR³R⁴)ᵥ(4-10)-membered heterocyclyl, —(CR³R⁴)_qS(O)_j(CR³R⁴)ᵥ(C₆-C₁₀)aryl, or —(CR³R⁴)_qS(O)_j(CR³R⁴)ᵥ(4-10)-membered heterocyclyl.

In another embodiment, the invention relates to compounds of the formula (I), wherein any carbon atoms of the (C₁-C₆)alkyl, the (3-10)-membered cycloalkyl, the (C₆-C₁₀) aryl and the (4-10)-membered heterocyclyl moieties of the foregoing R¹, R², R³, R⁴, R⁵, R⁶ and R⁷ are optionally substituted with 1 to 3 R¹¹ substituents each independently selected from halo, cyano, hydroxy, (C₁-C₆)alkoxy, (C₁-C₆)alkyl, —(C=O)—R⁸, —NR⁸(C=O)—R¹⁰, —(C=O)—NR⁸R⁹, —(C=O)—NR⁸R⁹ᵃ, —NR⁸R⁹, —S(O)_jR⁸, —NR⁸—S(O)_k—R⁹, —NR⁸—S(O)_k—R⁹ᵃ, —(CR⁸R⁹)ᵥ(3-10)-membered cycloalkyl, —(CR⁸R⁹)_p(C₆-C₁₀aryl), —(CR⁸R⁹)_p(4-10)-membered heterocyclyl, —(CR⁸R⁹)_q(C=O)(CR⁸R⁹)_p(3-10)-membered cycloalkyl, —(CR⁸R⁹)_q(C=O)(CR⁸R⁹)_p(C₆-C₁₀)aryl, and —(CR⁸R⁹)_q(C=O)(CR⁸R⁹)_p(4-10)-membered heterocyclyl.

In another embodiment, the invention relates to compounds of the formula (I), wherein any carbon atoms of the (C₁-C₆)alkyl, the (3-10)-membered cycloalkyl, the (C₆-C₁₀) aryl and the (4-10)-membered heterocyclyl moieties of the foregoing R¹¹ are optionally substituted with 1 to 3 R¹² substituents each independently selected from halo, hydroxy, (C₁-C₆)alkoxy, (C₁-C₆)alkyl, and —NR⁸R⁹.

In another embodiment, the invention relates to compounds of the formula (I), wherein any nitrogen atoms of the (4-10)-membered heterocyclyl of the foregoing R¹, R², and R¹¹ are optionally substituted with 1 to 3 R¹³ substituents each independently selected from (C₁-C₆)alkyl, —(C=O)—R⁸, —(C=O)—R⁹ᵃ, —(C=O)—O—R⁸, —(C=O)—NR⁸R⁹, —(CR⁸R⁹)_q—NR⁸R⁹, —(CR⁸R⁹)_p(3-10)-membered cycloalkyl, and —(CR⁸R⁹)_p(C₆-C₁₀aryl), —(CR⁸R⁹)_p (4-10)-membered heterocyclyl.

In another embodiment, the invention relates to compounds of the formula (I), wherein R¹ is optionally substituted —(CR³R⁴)_q(C=O)(CR³R⁴)ᵥ(4-10)-membered heterocyclyl selected from the group consisting of:

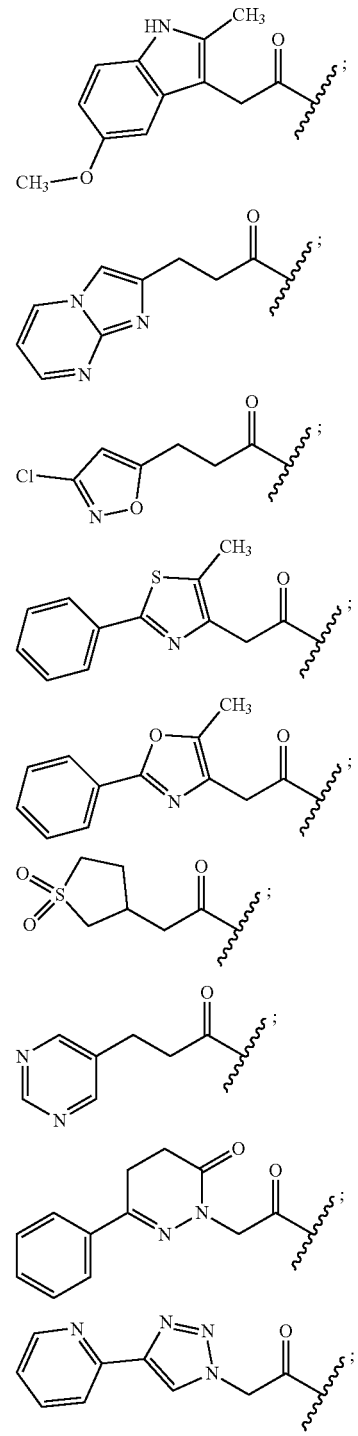

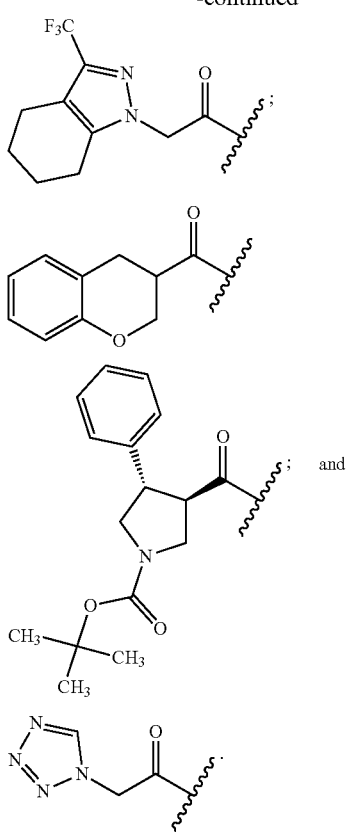

In another embodiment, the invention relates to compounds of the formula (I), wherein $R^1$ is optionally substituted —$(CR^3R^4)_q(C=O)(CR^3R^4)_v(C_6$-$C_{10})$aryl selected from the group consisting of:

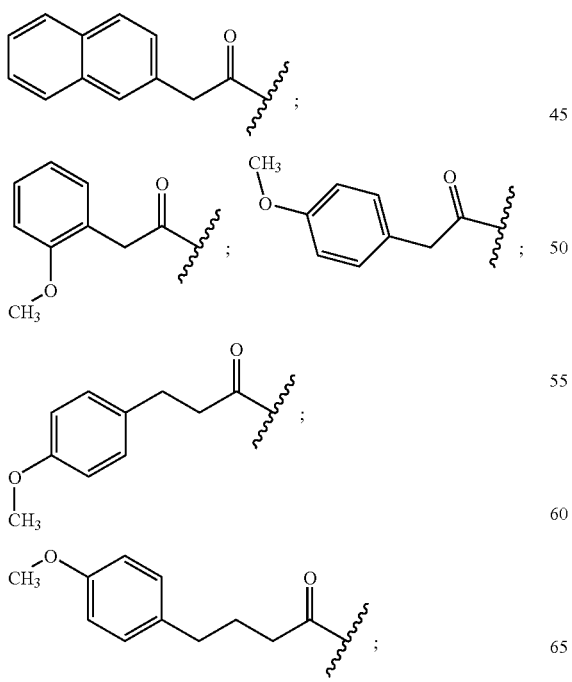

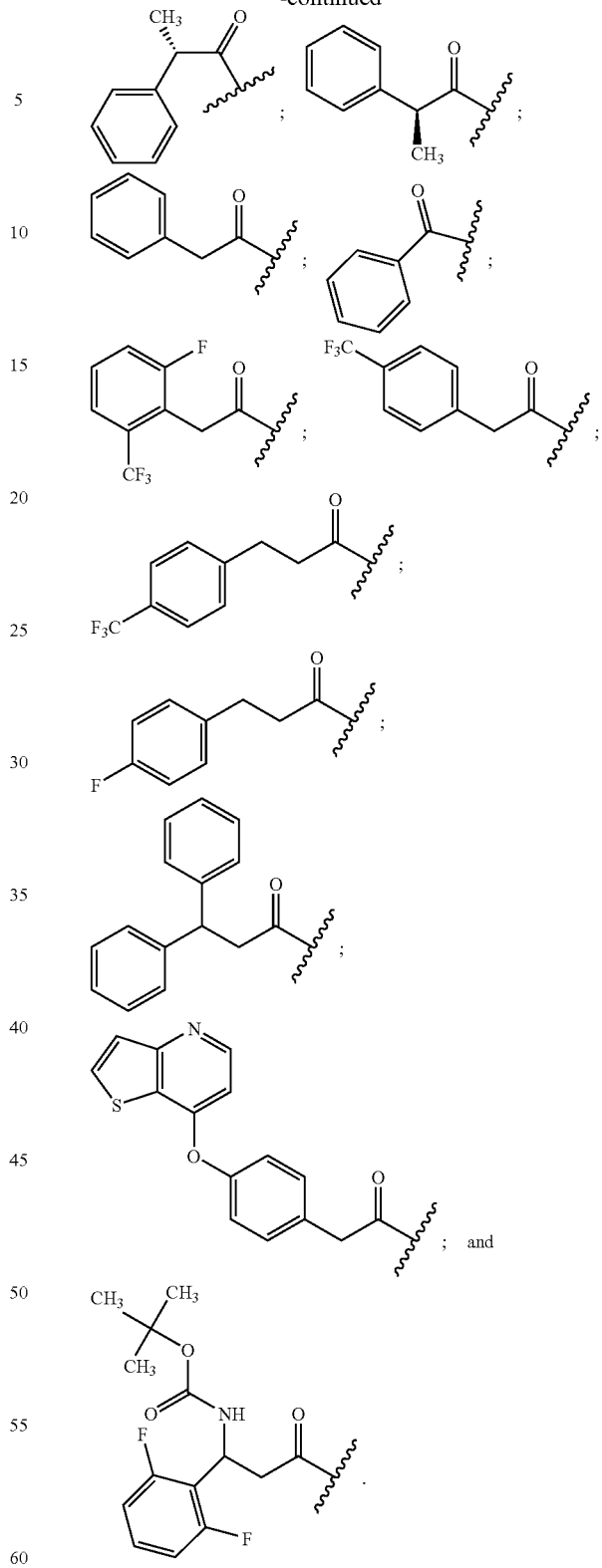

In another embodiment, the invention relates to compounds of the formula (I), wherein $R^1$ is optionally substituted —$(C=O)$—$R^3$, —$(C=O)$—$(CR^3R^4)_q$—$O$—$(CR^3R^4)_p$—$R^3$, —$(C=O)$—$(CR^3R^4)_q$—$O$—$(CR^3R^4)_p(C=O)$—$R^3$, —$(C=O)$—$NR^3R^4$, —$(C=O)$—$(CR^3R^4)_q$—$NR^3$—$(C=O)$—$R^4$, or —$(C=O)$—$(CR^3R^4)_q$—$(C=O)$—$NR^3R^4$.

In another embodiment, the invention relates to compounds of the formula (I), wherein R¹ is selected from the group consisting of:
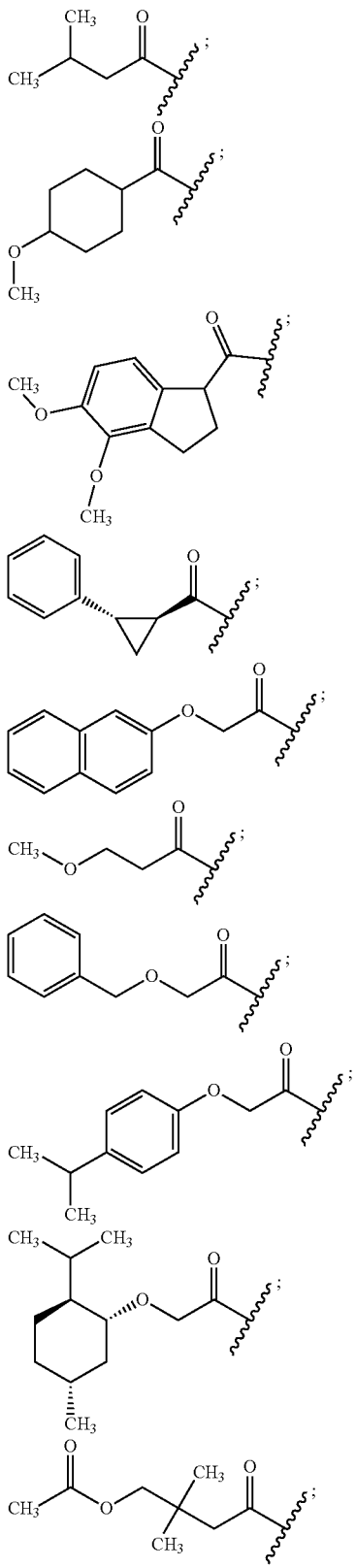
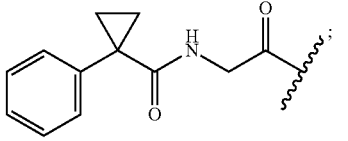
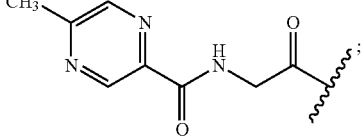
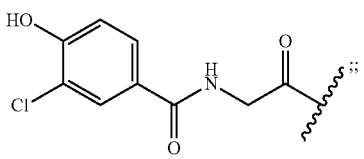
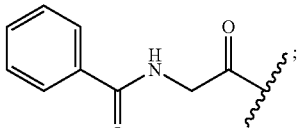
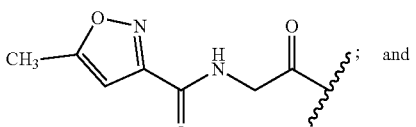
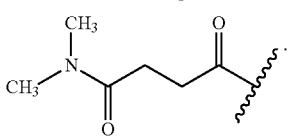 and
Specific embodiments of compounds of the formula (I) are selected from the group consisting of:
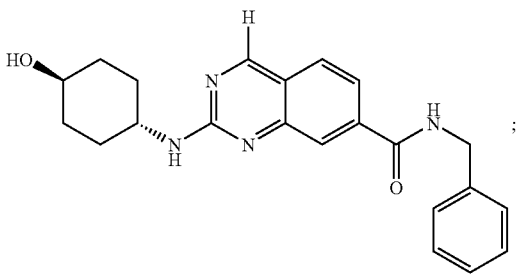
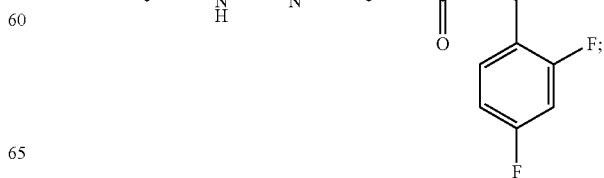

-continued
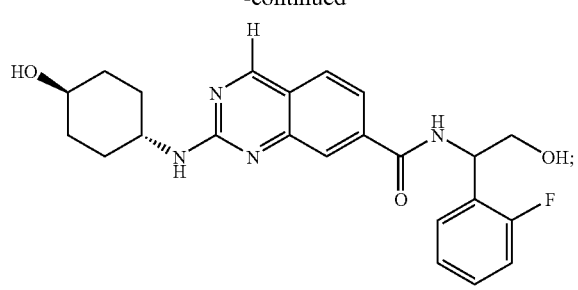
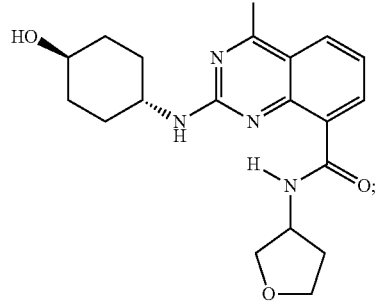
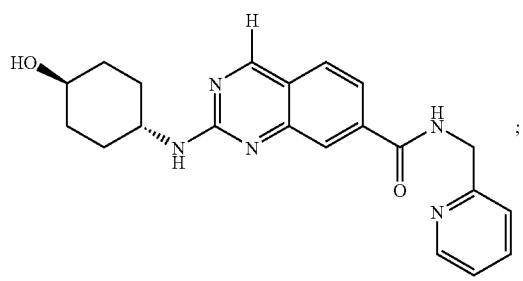
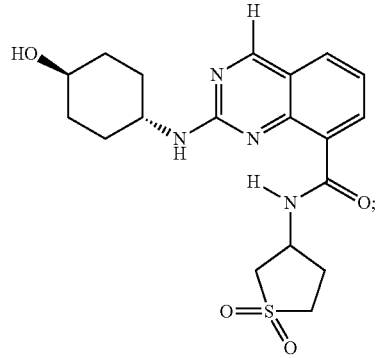
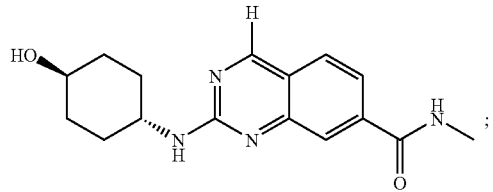
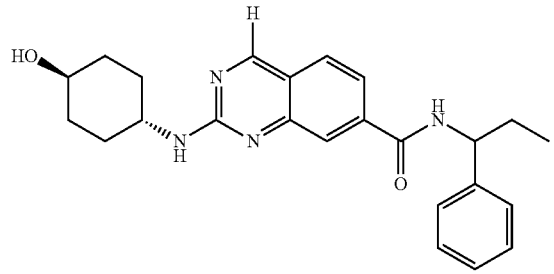
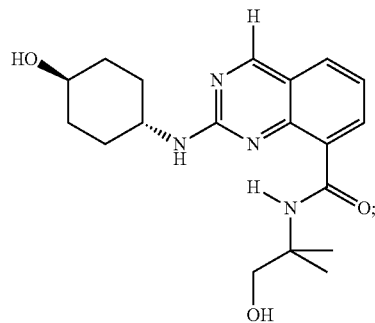
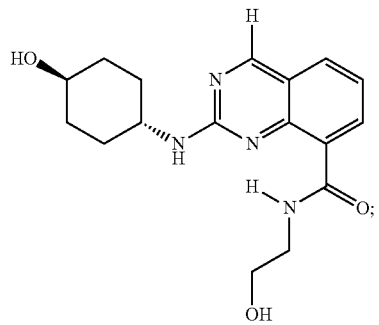
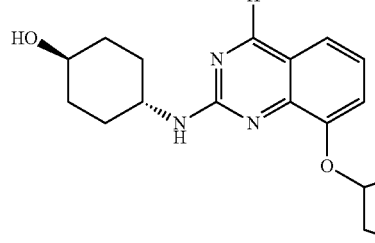
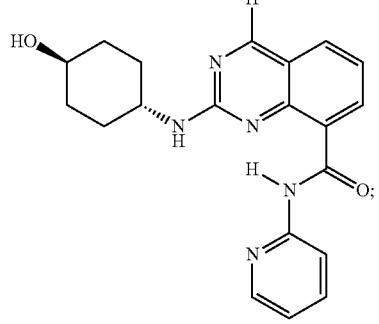
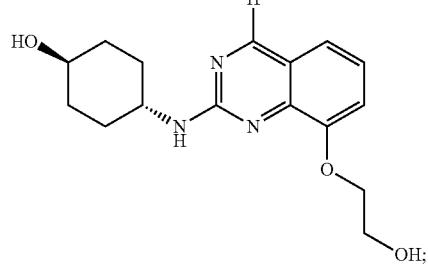

-continued
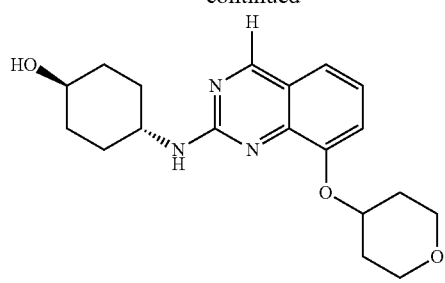
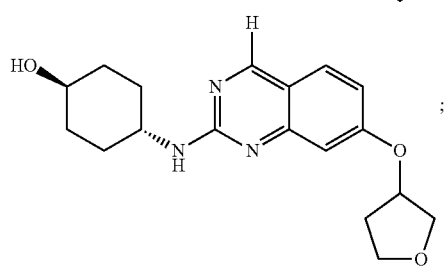
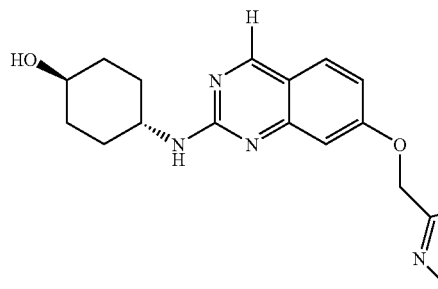
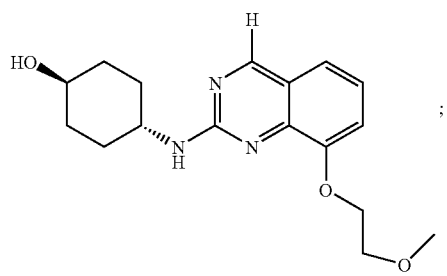
; and
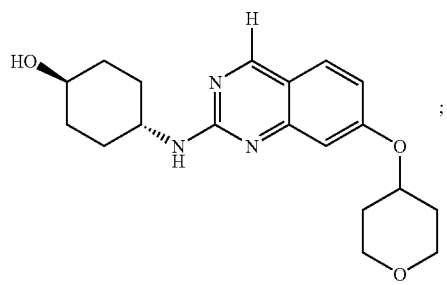
or a pharmaceutically acceptable salt or solvate thereof.
Other specific embodiments of compounds of the formula (I) are selected from the group consisting of:
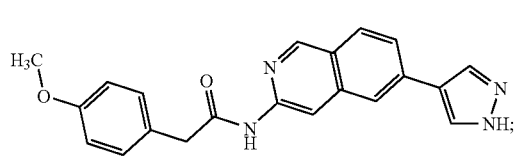
-continued
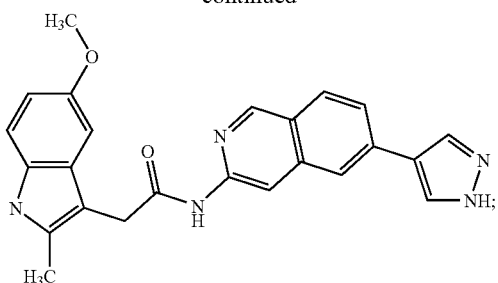
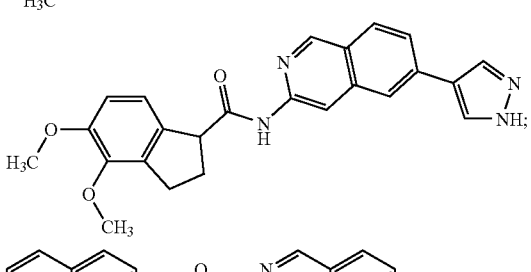
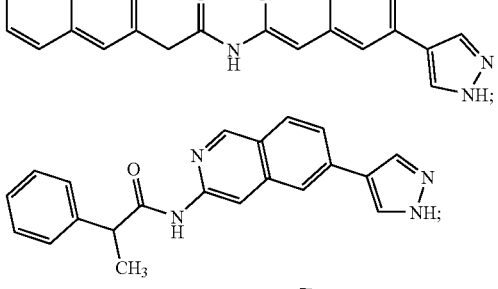
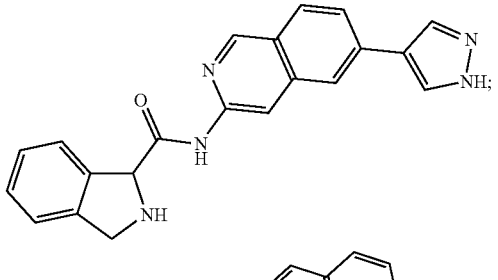
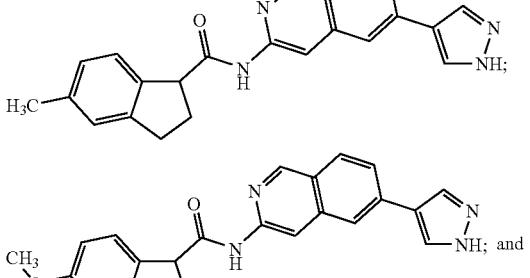
or a pharmaceutically acceptable salt or solvate thereof.

Other specific embodiments of compounds of the formula (I) are selected from the group consisting of:
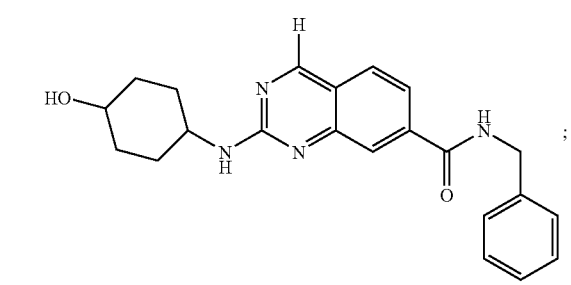
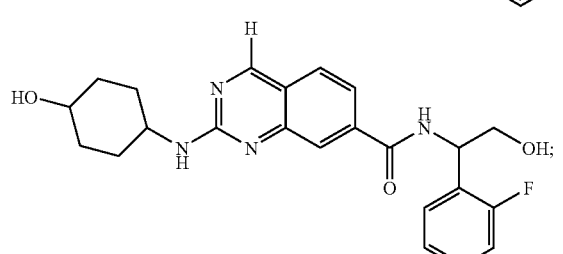
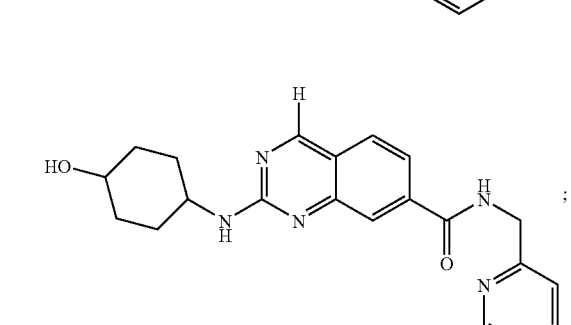
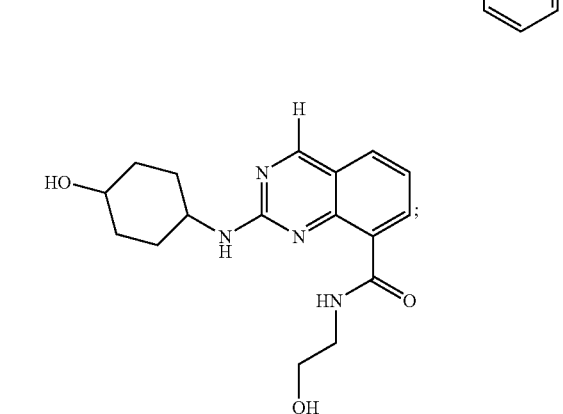
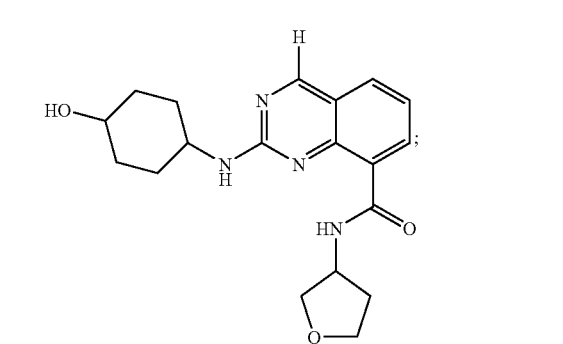
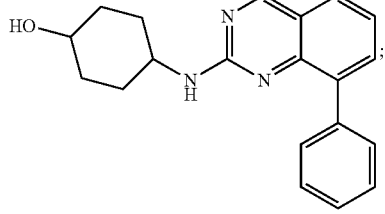
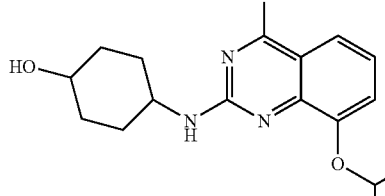
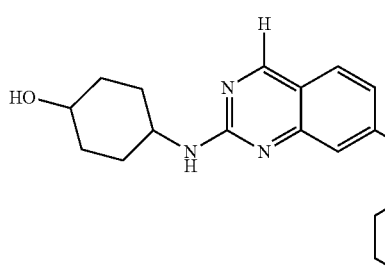
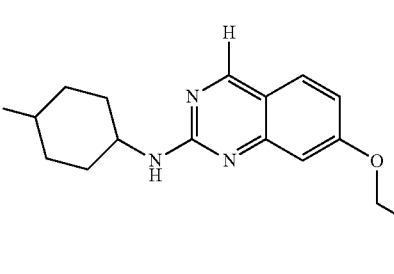
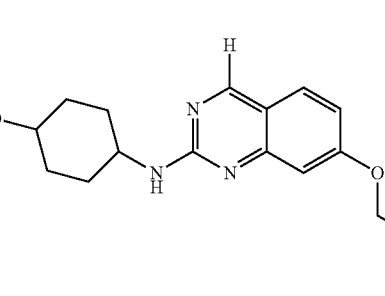
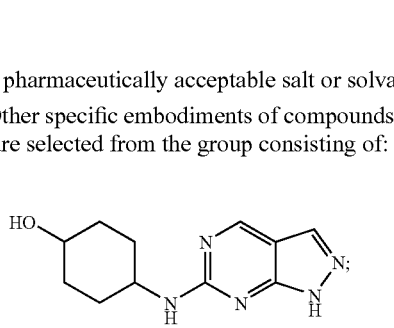
or a pharmaceutically acceptable salt or solvate thereof.
Other specific embodiments of compounds of the formula (I) are selected from the group consisting of:

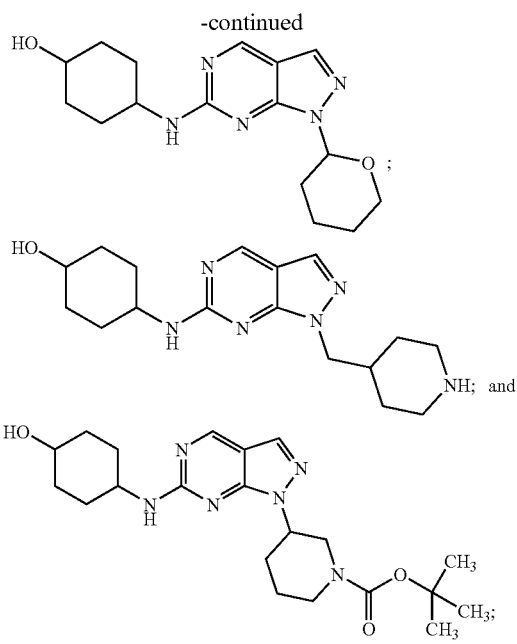

or a pharmaceutically acceptable salt or solvate thereof.

The present invention also relates to a pharmaceutical composition comprising an effective amount of compounds of the formula (I), or a pharmaceutically acceptable salt or solvate thereof, and a pharmaceutically acceptable carrier.

The present invention also relates to a method of treating a condition that is mediated by the modulation of JNK, the method comprising administering to a mammal an effective amount of compounds of the formula (I), or a pharmaceutically acceptable salt or solvate thereof.

The present invention also relates to a method of treating diabetes, metabolic syndrome, insulin resistance syndrome, obesity, glaucoma, hyperlipidemia, hyperglycemia, hyperinsulinemia, osteoporosis, tuberculosis, atherosclerosis, dementia, depression, virus diseases, inflammatory disorders, or diseases in which the liver is a target organ, the method comprising administering to a mammal an effective amount of compounds of the formula (I) or a pharmaceutically acceptable salt or solvate thereof.

The present invention also relates to a method of treating chronic or acute cardiac failure, cardiac hypertrophy, dilated, hypertrophic or restrictive cardiomyopathy, acute myocardial infarction, post-myocardial infarction, acute or chronic myocarditis, diastolic dysfunction of the left ventricle, systolic dysfunction of the left ventricle, hypertension and nephropathy and nephritis as complications thereof, endothelial dysfunction, arteriosclerosis or post-angioplasty restenosis, which comprises administering an effective amount of compounds of the formula (I) to a mammal in need thereof.

The present invention also relates to a method of treating chronic rheumatoid arthritis, osteoarthritis, gout, chronic obstructive pulmonary disease, asthma, bronchitis, cystic fibrosis, inflammatory bowel disease, irritable colon syndrome, mucous colitis, ulcerative colitis, Crohn's disease, gastritis, esophagitis, multiple sclerosis, eczema, dermatitis, hepatitis, glomerulonephritis, diabetes, ophthalmic diseases, diabetic retinopathy, diabetic macular edema, diabetic nephropathy, diabetic neuropathy, obesity, psoriasis or cancer, which comprises administering an effective amount of compounds of the formula (I) to a mammal in need thereof.

The present invention also relates to a method of treating Alzheimer's disease, Huntington's chorea, Parkinson's syndrome, epilepsy, amyotrophic lateral sclerosis, peripheral neuropathy, neurodegenerative disease or spinal injury, which comprises administering an effective amount of compounds of the formula (I) to a mammal in need thereof.

The present invention also relates to a method of treating cerebral apoplexy, cerebrovascular disorder, an ischemic disorder of an organ selected from the heart, kidney, liver and brain, ischemia-reperfusion injury, organ failure, endotoxin shock or rejection in transplantation, which comprises administering an effective amount of compounds of the formula (I) to a mammal in need thereof.

DEFINITIONS

For purposes of the present invention, as described and claimed herein, the following terms are defined as follows:

As used herein, the terms "comprising" and "including" are used in their open, non-limiting sense.

The term "halo", as used herein, unless otherwise indicated, means fluoro, chloro, bromo or iodo.

The term "alkyl", as used herein, unless otherwise indicated, includes saturated monovalent hydrocarbon radicals having straight or branched moieties.

The term "alkenyl", as used herein, unless otherwise indicated, includes alkyl moieties having at least one carbon-carbon double bond wherein alkyl is as defined above and including E and Z isomers of said alkenyl moiety.

The term "alkynyl", as used herein, unless otherwise indicated, includes alkyl moieties having at least one carbon-carbon triple bond wherein alkyl is as defined above.

The term "alkoxy", as used herein, unless otherwise indicated, includes O-alkyl groups wherein alkyl is as defined above.

The term "Me" means methyl, "Et" means ethyl, and "Ac" means acetyl.

The term "cycloalkyl", as used herein, unless otherwise indicated refers to a non-aromatic, saturated or partially saturated, monocyclic or fused, spiro or unfused bicyclic or tricyclic hydrocarbon referred to herein containing a total of from 3 to 10 carbon atoms, preferably 5-8 ring carbon atoms. Exemplary cycloalkyls include monocyclic rings having from 3-10 carbon atoms, such as cyclopropyl, cyclobutyl, cyclopentyl, cyclohexyl, cycloheptyl, and adamantyl. Illustrative examples of cycloalkyl are derived from, but not limited to, the following:

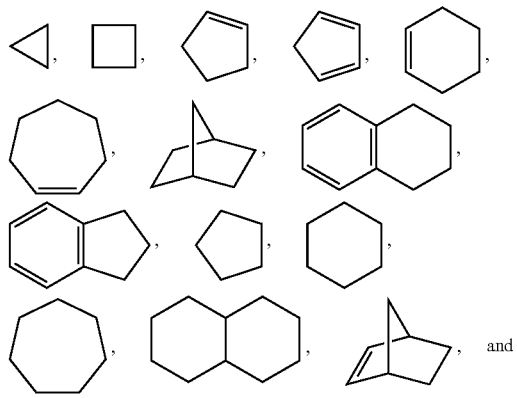

-continued

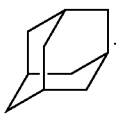

The term "aryl", as used herein, unless otherwise indicated, includes an organic radical derived from an aromatic hydrocarbon by removal of one hydrogen, such as phenyl or naphthyl.

The term "(4-12)-membered heterocyclyl" or "(4-10)-membered heterocyclyl", as used herein, unless otherwise indicated, includes aromatic and non-aromatic heterocyclic groups containing one to four heteroatoms each selected from O, S and N, wherein each heterocyclic group has from 3-7, 6-10, or 4-10 atoms, respectively, in its ring system, and with the proviso that the ring of said group does not contain two adjacent O or S atoms. Non-aromatic heterocyclic groups include groups having only 3 atoms in their ring system, but aromatic heterocyclic groups must have at least 5 atoms in their ring system. The heterocyclic groups include benzo-fused ring systems. An example of a 3 membered heterocyclic group is aziridine, an example of a 4 membered heterocyclic group is azetidinyl (derived from azetidine). An example of a 5 membered heterocyclic group is thiazolyl, an example of a 7 membered ring is azepinyl, and an example of a 10 membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). The 4-7 membered heterocyclic may be optionally substituted on any ring carbon, sulfur, or nitrogen atom(s) by one to two oxo, per ring. An example of a heterocyclic group wherein 2 ring carbon atoms are substituted with oxo moieties is 1,1-dioxo-thiomorpholinyl. Other Illustrative examples of 4-7 membered heterocyclic are derived from, but not limited to, the following:

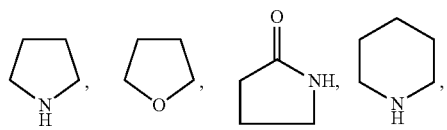

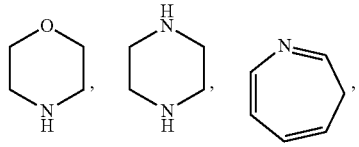

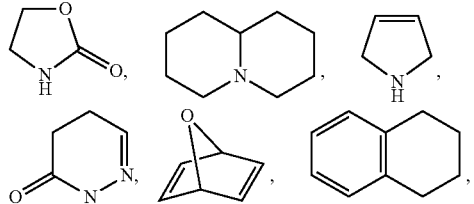

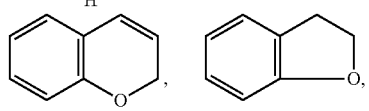

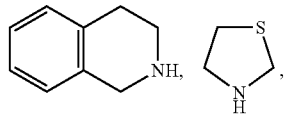

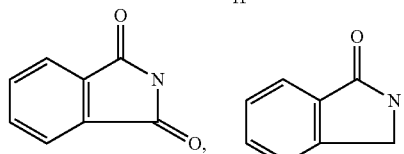

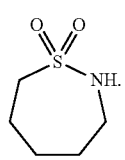

Unless otherwise indicated, the term "oxo" refers to =O.

A "solvate" is intended to mean a pharmaceutically acceptable solvate form of a specified compound that retains the biological effectiveness of such compound. Examples of solvates include compounds of the invention in combination with water, isopropanol, ethanol, methanol, DMSO (dimethylsulfoxide), ethyl acetate, acetic acid, or ethanolamine.

The phrase "pharmaceutically acceptable salt(s)", as used herein, unless otherwise indicated, includes salts of acidic or basic groups which may be present in the compounds of formula (I). The compounds of formula (I) that are basic in nature are capable of forming a wide variety of salts with various inorganic and organic acids. The acids that may be used to prepare pharmaceutically acceptable acid addition salts of such basic compounds of formula (I) are those that form non-toxic acid addition salts, i.e., salts containing pharmacologically acceptable anions, such as the acetate, benzenesulfonate, benzoate, bicarbonate, bisulfate, bitartrate, borate, bromide, calcium edetate, camsylate, carbonate, chloride, clavulanate, citrate, dihydrochloride, edetate, edislyate, estolate, esylate, ethylsuccinate, fumarate, gluceptate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsylate, nitrate, oleate, oxalate, pamoate (embonate), palmitate, pantothenate, phosphate/diphosphate, polygalacturonate, salicylate, stearate, subacetate, succinate, tannate, tartrate, teoclate, tosylate, triethiodode, and valerate salts.

The term "diseases in which the liver is a target organ", as used herein, unless otherwise indicated means diabetes, hepatitis, liver cancer, liver fibrosis, and malaria.

The term "Metabolic syndrome", as used herein, unless otherwise indicated means psoriasis, diabetes mellitus, wound healing, inflammation, neurodegenerative diseases, galactosemia, maple syrup urine disease, phenylketonuria, hypersarcosinemia, thymine uraciluria, sulfinuria, isovaleric acidemia, saccharopinuria, 4-hydroxybutyric aciduria, glucose-6-phosphate dehydrogenase deficiency, and pyruvate dehydrogenase deficiency.

In the compounds of formula (I), where terms such as $(CR^5R^6)_v$ or $(CR^8R^9)_p$ are used, $R^5$, $R^6$, $R^8$ and $R^9$ may vary with each iteration of v or p. For instance, where v or p is 2 the terms $(CR^5R^6)_v$ or $(CR^8R^9)_p$ may equal —$CH_2CH_2$—, or —$CH(CH_3)C(CH_2CH_3)(CH_2CH_2CH_3)$—, or any number of similar moieties falling within the scope of the definitions of $R^5$, $R^6$, $R^8$ and $R^9$.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

The term "modulate" or "modulating", as used herein, refers to the ability of a modulator for a member of the steroid/thyroid superfamily to either directly (by binding to the receptor as a ligand) or indirectly (as a precursor for a ligand or an inducer which promotes production of ligand from a precursor) induce expression of gene(s) maintained under hormone expression control, or to repress expression of gene(s) maintained under such control.

The term "obesity" or "obese", as used herein, refers generally to individuals who are at least about 20-30% over the average weight for his/her age, sex and height. Technically, "obese" is defined, for males, as individuals whose body mass index is greater than 27.8 kg/m$^2$, and for females, as individuals whose body mass index is greater than 27.3 kg/m$^2$. Those of skill in the art readily recognize that the invention method is not limited to those who fall within the above criteria. Indeed, the method of the invention can also be advantageously practiced by individuals who fall outside of these traditional criteria, for example, by those who may be prone to obesity.

The term "inflammatory disorders", as used herein, refers to disorders such as rheumatoid arthritis, ankylosing spondylitis, psoriatic arthritis, psoriasis, chondrocalcinosis, gout, inflammatory bowel disease, ulcerative colitis, Crohn's disease, fibromyalgia, and cachexia.

The phrase "therapeutically effective amount", as used herein, refers to that amount of drug or pharmaceutical agent that will elicit the biological or medical response of a tissue, system, animal, or human that is being sought by a researcher, veterinarian, medical doctor or other.

The phrase "amount . . . effective to lower blood glucose levels", as used herein, refers to levels of compound sufficient to provide circulating concentrations high enough to accomplish the desired effect. Such a concentration typically falls in the range of about 10 nM up to 2 μM; with concentrations in the range of about 100 nM up to 500 nM being preferred. As noted previously, since the activity of different compounds which fall within the definition of Formula (I) as set forth above may vary considerably, and since individual subjects may present a wide variation in severity of symptoms, it is up to the practitioner to determine a subject's response to treatment and vary the dosages accordingly.

The phrase "insulin resistance", as used herein, refers to the reduced sensitivity to the actions of insulin in the whole body or individual tissues, such as skeletal muscle tissue, myocardial tissue, fat tissue or liver tissue. Insulin resistance occurs in many individuals with or without diabetes mellitus.

The phrase "insulin resistance syndrome", as, used herein, refers to the cluster of manifestations that include insulin resistance, hyperinsulinemia, non insulin dependent diabetes mellitus (NIDDM), arterial hypertension, central (visceral) obesity, and dyslipidemia.

Certain compounds of formula (I) may have asymmetric centers and therefore exist in different enantiomeric forms. All optical isomers and stereoisomers of the compounds of formula (I), and mixtures thereof, are considered to be within the scope of the invention. With respect to the compounds of formula (I), the invention includes the use of a racemate, one or more enantiomeric forms, one or more diastereomeric forms, or mixtures thereof. The compounds of formula (I) may also exist as tautomers. This invention relates to the use of all such tautomers and mixtures thereof.

Certain functional groups contained within the compounds of the present invention can be substituted for bioisosteric groups, that is, groups which have similar spatial or electronic requirements to the parent group, but exhibit differing or improved physicochemical or other properties. Suitable examples are well known to those of skill in the art, and include, but are not limited to moieties described in Patini et al., Chem. Rev, 1996, 96, 3147-3176 and references cited therein.

The subject invention also includes isotopically-labelled compounds, which are identical to those recited in formula (I), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention and pharmaceutically acceptable salts or solvates of said compounds which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of formula (I) of this invention thereof can generally be prepared by carrying out the procedures disclosed in the Schemes and/or in the Examples below, by substituting a readily available isotopically labelled reagent for a non-isotopically labelled reagent.

Other aspects, advantages, and features of the invention will become apparent from the detailed description below.

DETAILED DESCRIPTION AND EMBODIMENTS OF THE INVENTION

The schemes below describe and depict general routes to prepare specific examples of the present invention of formula (I) wherein the definitions are given in the summary of the invention.

Scheme A: Preparation of compounds of an embodiment of compounds of formula (I):

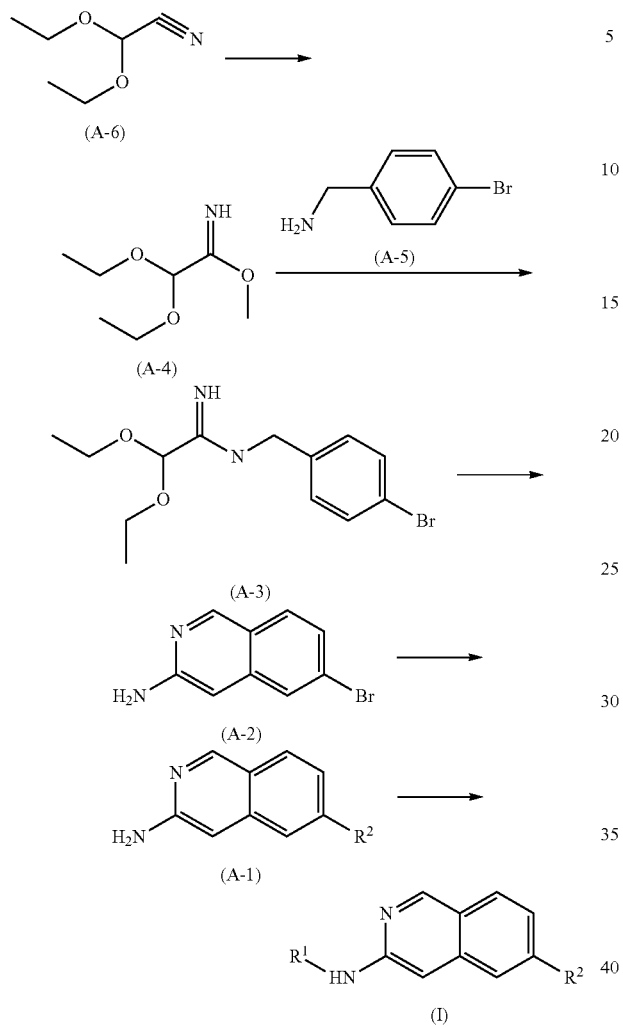

Referring to Scheme A above, the compound of formula (I) may be prepared by reacting compounds (A-1) with a suitable —R¹ delivering agents (e.g. phenylacetyl carboxylic acid) in a suitable solvent (e.g. N,N-dimethylformamide) at a temperature between −20 and 200 degrees Celcius. Compounds of formula (A-1) may be prepared by reacting compound (A-2) with a suitable —R² delivering agents (e.g. dietherBorane-R² reagent such as

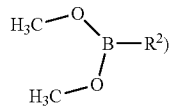

in a suitable solvent (e.g. dicholoromethane) at a temperature between 0 and 150 degrees Celcius. Compound (A-2) may be obtained by reacting compound (A-3) with a suitable deprotecting agent (e.g. sulfonic acid) in a suitable solvent (e.g. water) at a temperature between −78 and 100 degrees Celcius. Compound (A-3) may be obtained by reacting compound (A-4) with a compound of formula (A-5) in a suitable solvent (e.g. methanol) at a temperature between 0 and 200 degrees Celcius. Compound (A-4) may be obtained by reacting compound (A-6) with an ether salt (e.g. sodium methoxide) in a suitable solvent (e.g. methanol) at a temperature between −20 and 100 degrees Celcius. Compounds of formula (A-5) and (A-6) are commercially available or can be prepared by methods known to those skilled in the art.

Scheme B: Preparation of compounds of an alternative embodiment of compounds of formula (I):

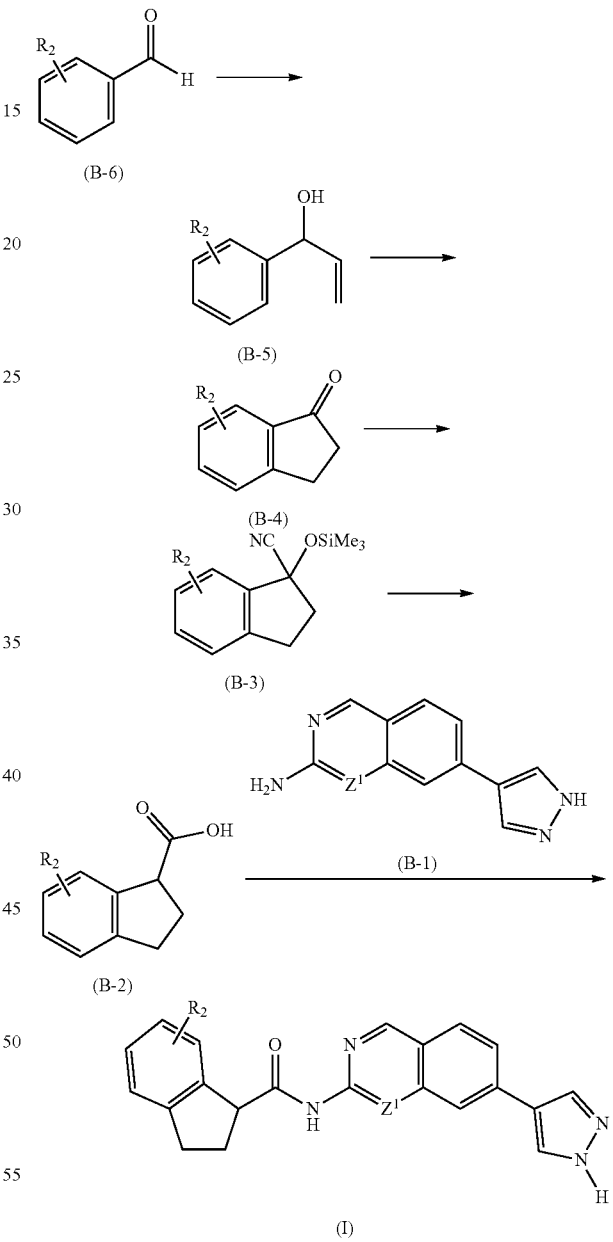

Alternatively, referring to Scheme B above, the compound of formula (I) may also be prepared by reacting compounds (B-2) with a compound of formula (B-1) (e.g. 6-(1H-pyrazol-4-yl)-isoquinolin-3-ylamine) in a suitable solvent (e.g. N,N-dimethylacetamide) at a temperature between 0 and 200 degrees Celcius. Compounds of formula (B-2) may be prepared by reacting compound (B-3) under a suitable hydrolysis condition (e.g. HCl/H₂O/SnCl₂) in a suitable solvent (e.g.

acetic acid) at a temperature between 0 and 150 degrees Celcius. Compound (B-3) may be obtained by reacting compound (B-4) with a suitable agent (e.g. Me₃SiCN/ZnI) in a suitable solvent (e.g. toluenene and acetonitrile) at a temperature between 0 and 100 degrees Celcius. Compound (B-4) may be obtained by reacting compound (B-5) with an oxidizing agent (e.g. CrO₃/Pyridine) in a suitable solvent (e.g. water) at a temperature between −20 and 50 degrees Celcius, followed by treatment of a acid (e.g. H₂SO4) in a suitable solvent (e.g. pentane) at a temperature between 0 to 150 degree Celcius. Compound (B-5) may be obtained by reacting compound (B-6) with an organometallic reagent (e.g. CH₂=CHMgBr) in a suitable solvent (e.g. tetrhydrofuran) at a temperature between −20 and 100 degrees Celcius. Compounds of formula (B-6) are commercially available or can be prepared by methods known to those skilled in the art. (Australian Journal of Chemistry, 36(9), 1705-17; 1983 and European Journal of Organic Chemistry, (1), 163-171; 2001)

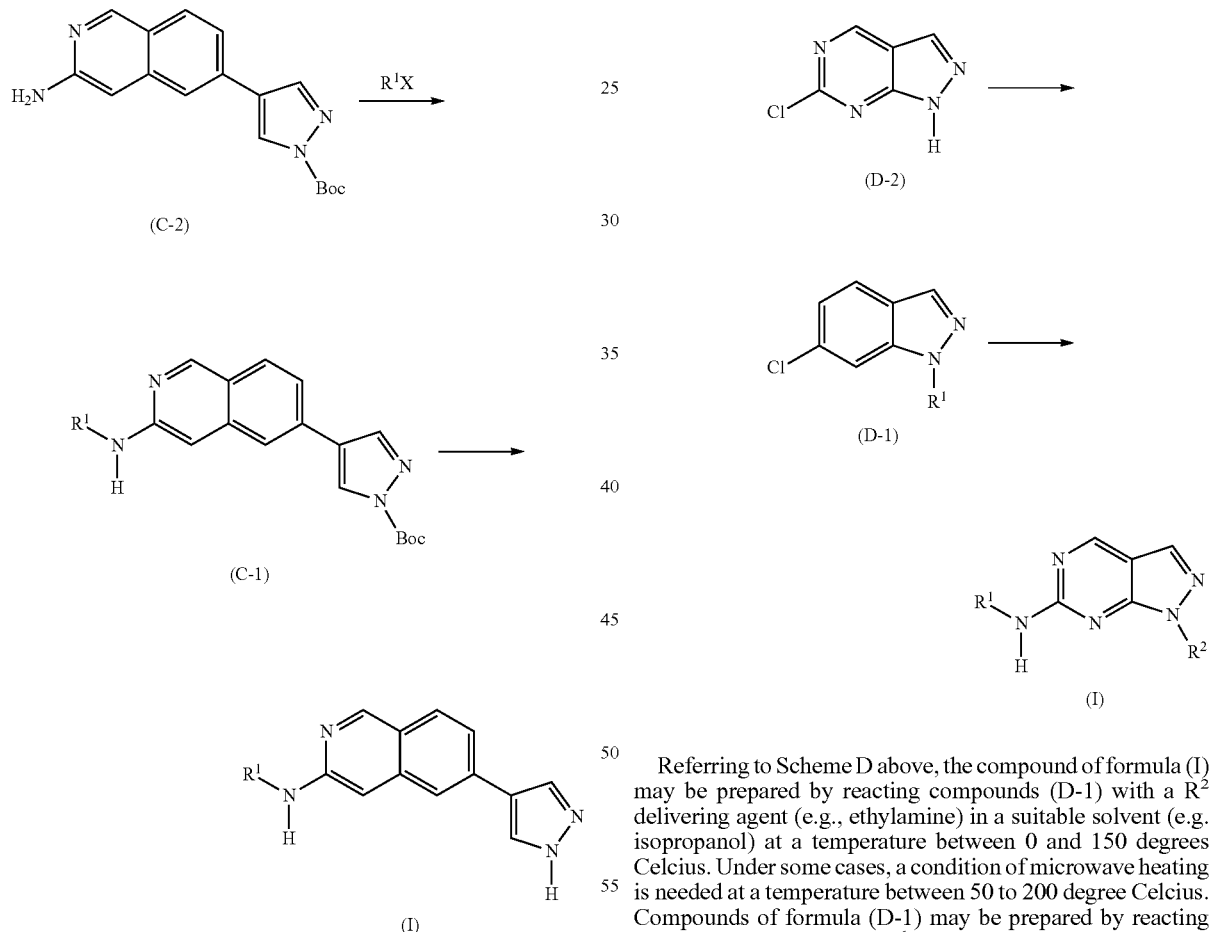

Referring to Scheme C above, the compound of formula (I), may be prepared by reacting compounds (C-1) with a reagent such as HCl in a suitable solvent mixture (e.g. aqueous tetrahydrofuran) at a temperature between 0 and 150 degrees Celcius. Compounds of formula (C-1) may be prepared by reacting compound (C-2) with a suitable —R¹ delivering agent (e.g. cyclohexyl bromide) and a bass such as sodium hydride in a suitable solvent (e.g. N,N-dimethylformamide) at a temperature between 0 and 200 degrees Celcius.

Referring to Scheme D above, the compound of formula (I) may be prepared by reacting compounds (D-1) with a R² delivering agent (e.g., ethylamine) in a suitable solvent (e.g. isopropanol) at a temperature between 0 and 150 degrees Celcius. Under some cases, a condition of microwave heating is needed at a temperature between 50 to 200 degree Celcius. Compounds of formula (D-1) may be prepared by reacting compound (D-2) with a R¹ delivering agent (e.g. methyl iodide) and a bass such as Cs₂CO₃ in a suitable solvent (e.g. acetonitrile) at a temperature between 0 and 100 degrees Celcius. Compounds of formula (D-2) may be prepared by reacting compound (D-3) with hydrazine in a suitable solvent mixture (e.g. water and tetrahydrofuran) at a temperature between 0 and 150 degrees Celcius. Compounds of formula (D-3) may be prepared by reacting compound (D-4) with POCl₃ in a suitable solvent (e.g. toluene) at a temperature between 0 and 150 degrees Celcius. Compounds of formula (D-4) is commercially available.

Scheme E: Preparation of compounds of an alternative embodiment of compounds of formula (I):

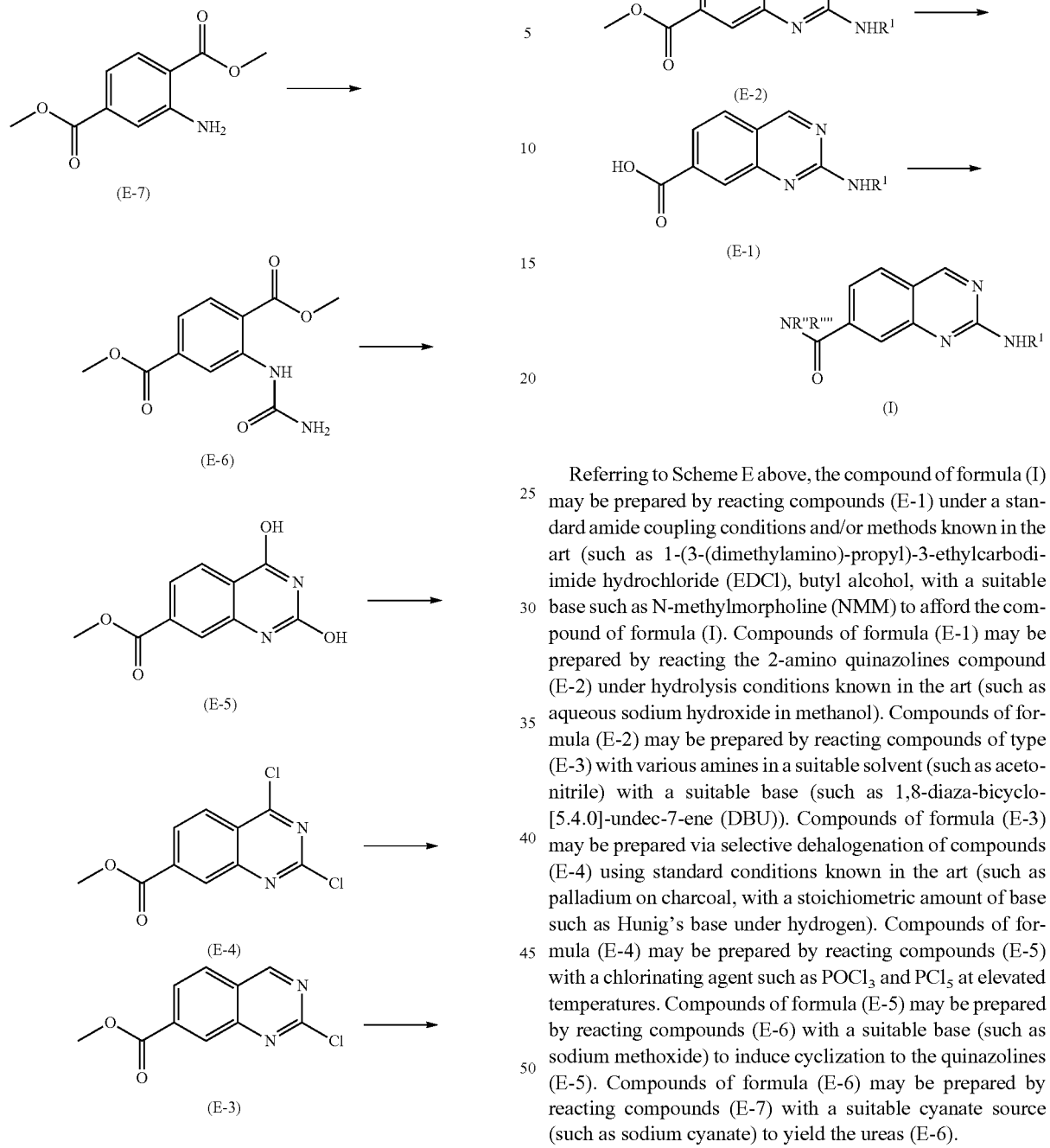

Referring to Scheme E above, the compound of formula (I) may be prepared by reacting compounds (E-1) under a standard amide coupling conditions and/or methods known in the art (such as 1-(3-(dimethylamino)-propyl)-3-ethylcarbodiimide hydrochloride (EDCl), butyl alcohol, with a suitable base such as N-methylmorpholine (NMM) to afford the compound of formula (I). Compounds of formula (E-1) may be prepared by reacting the 2-amino quinazolines compound (E-2) under hydrolysis conditions known in the art (such as aqueous sodium hydroxide in methanol). Compounds of formula (E-2) may be prepared by reacting compounds of type (E-3) with various amines in a suitable solvent (such as acetonitrile) with a suitable base (such as 1,8-diaza-bicyclo-[5.4.0]-undec-7-ene (DBU)). Compounds of formula (E-3) may be prepared via selective dehalogenation of compounds (E-4) using standard conditions known in the art (such as palladium on charcoal, with a stoichiometric amount of base such as Hunig's base under hydrogen). Compounds of formula (E-4) may be prepared by reacting compounds (E-5) with a chlorinating agent such as POCl$_3$ and PCl$_5$ at elevated temperatures. Compounds of formula (E-5) may be prepared by reacting compounds (E-6) with a suitable base (such as sodium methoxide) to induce cyclization to the quinazolines (E-5). Compounds of formula (E-6) may be prepared by reacting compounds (E-7) with a suitable cyanate source (such as sodium cyanate) to yield the ureas (E-6).

Scheme F: Preparation of compounds of an alternative embodiment of compounds of formula (I):

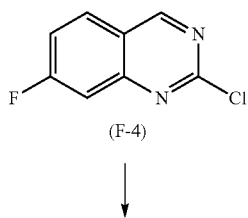

(F-4)

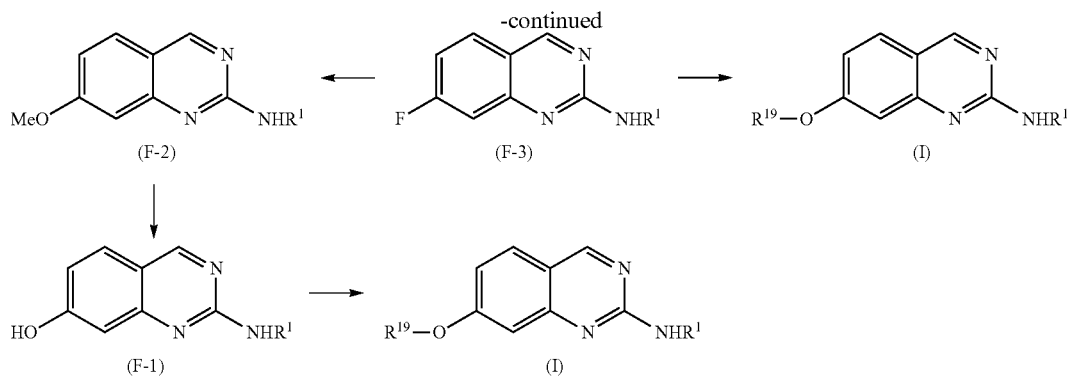

Referring to Scheme E above, the compound of formula (I) may be prepared by reacting compounds (F-1) with an alkyl halide of formula $R^{18}$—X, wherein X is halo and $R^{18}$ is $(C_1\text{-}C_6)$alkyl in a suitable solvent (such as THF) with a suitable base (such as sodium hydride). Compounds of formula (F-1) may be prepared by reacting compound (F-2) under deprotecting conditions known in the art (such as sodium ethanethiolate in DMF). Compounds of formula (F-2) may be prepared by reacting compound (F-3) with sodium methoxide in methanol. Compounds of formula (F-3) may be prepared by reacting compound 2-chloro-7-fluoro-quinazoline (F4) with various amines in a suitable solvent (such as acetonitrile) with a suitable base (such as DBU). Alternatively, the compound of formula (I) may be prepared by reacting compounds (F-3) with alcohols of formula $R^{19}$—OH, wherein $R^{19}$ is $(C_1\text{-}C_6)$alkyl, in a suitable solvent (such as THF) with a suitable base (such as sodium hydride).

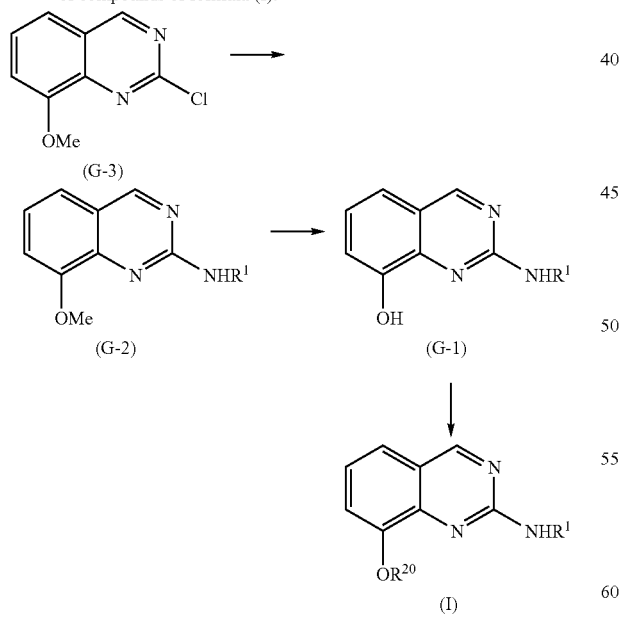

Scheme G: Preparation of compounds of an alternative embodiment of compounds of formula (I):

Referring to Scheme G above, the compound of formula (I) may be prepared by reacting compounds (G-1) with an alkyl halide of formula $R^{20}$—X, wherein X is halo and $R^{20}$ is $(C_1\text{-}C_6)$alkyl in a suitable solvent (such as THF) with a suitable base (such as sodium hydride). Compounds of formula (G-1) may be prepared by reacting compound (G-2) under deprotecting conditions known in the art (such as sodium ethanethiolate in DMF). Compounds of formula (G-2) may be prepared by reacting compound 2-chloro-8-methoxy-quinazoline (G-1) with various amines in a suitable solvent (such as acetonitrile) with a suitable base (such as DBU).

Scheme H:

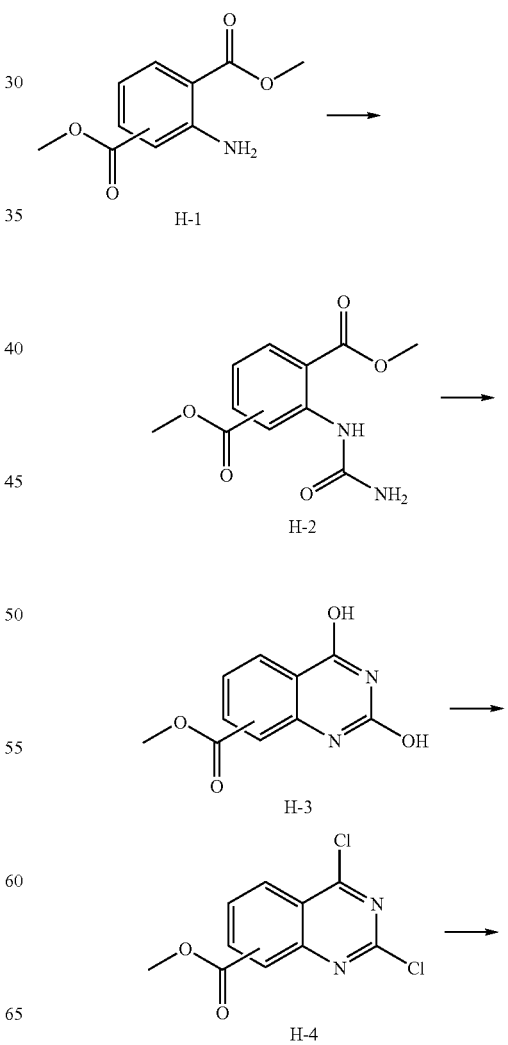

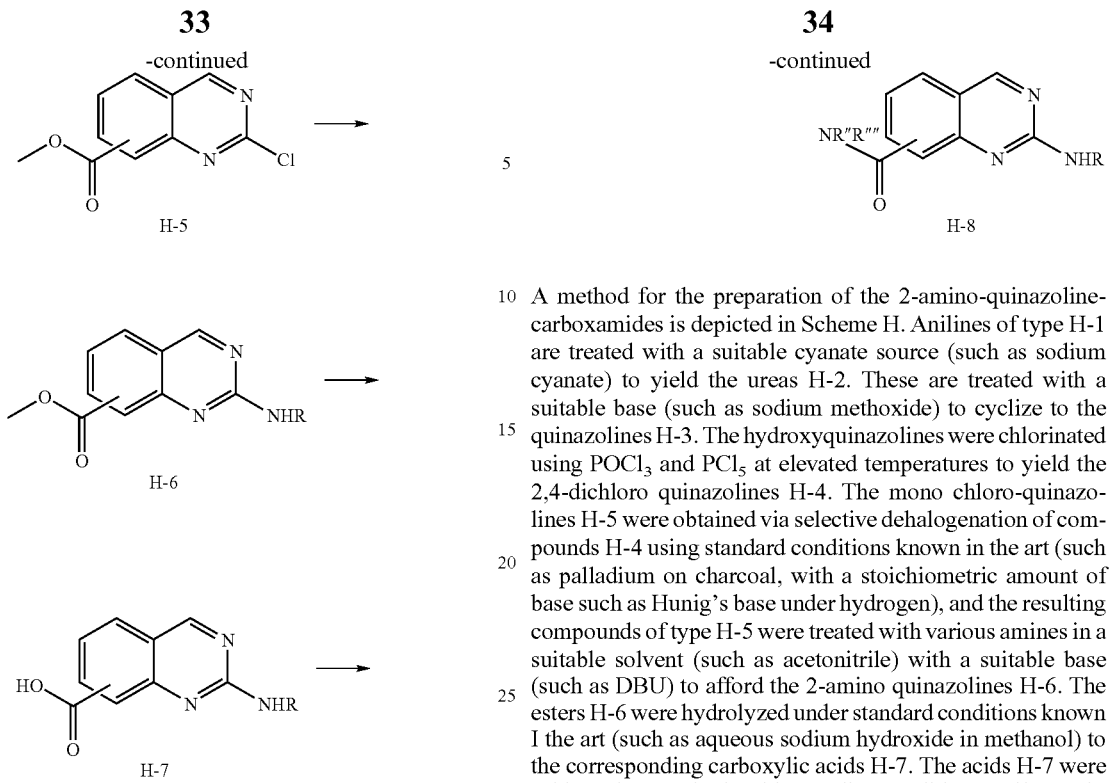

A method for the preparation of the 2-amino-quinazoline-carboxamides is depicted in Scheme H. Anilines of type H-1 are treated with a suitable cyanate source (such as sodium cyanate) to yield the ureas H-2. These are treated with a suitable base (such as sodium methoxide) to cyclize to the quinazolines H-3. The hydroxyquinazolines were chlorinated using POCl$_3$ and PCl$_5$ at elevated temperatures to yield the 2,4-dichloro quinazolines H-4. The mono chloro-quinazolines H-5 were obtained via selective dehalogenation of compounds H-4 using standard conditions known in the art (such as palladium on charcoal, with a stoichiometric amount of base such as Hunig's base under hydrogen), and the resulting compounds of type H-5 were treated with various amines in a suitable solvent (such as acetonitrile) with a suitable base (such as DBU) to afford the 2-amino quinazolines H-6. The esters H-6 were hydrolyzed under standard conditions known I the art (such as aqueous sodium hydroxide in methanol) to the corresponding carboxylic acids H-7. The acids H-7 were subjected to standard amide coupling conditions and/or methods known in the art (such as EDCl, HOBt, with a suitable base such as NMM) to afford the amides H-8.

Scheme I:

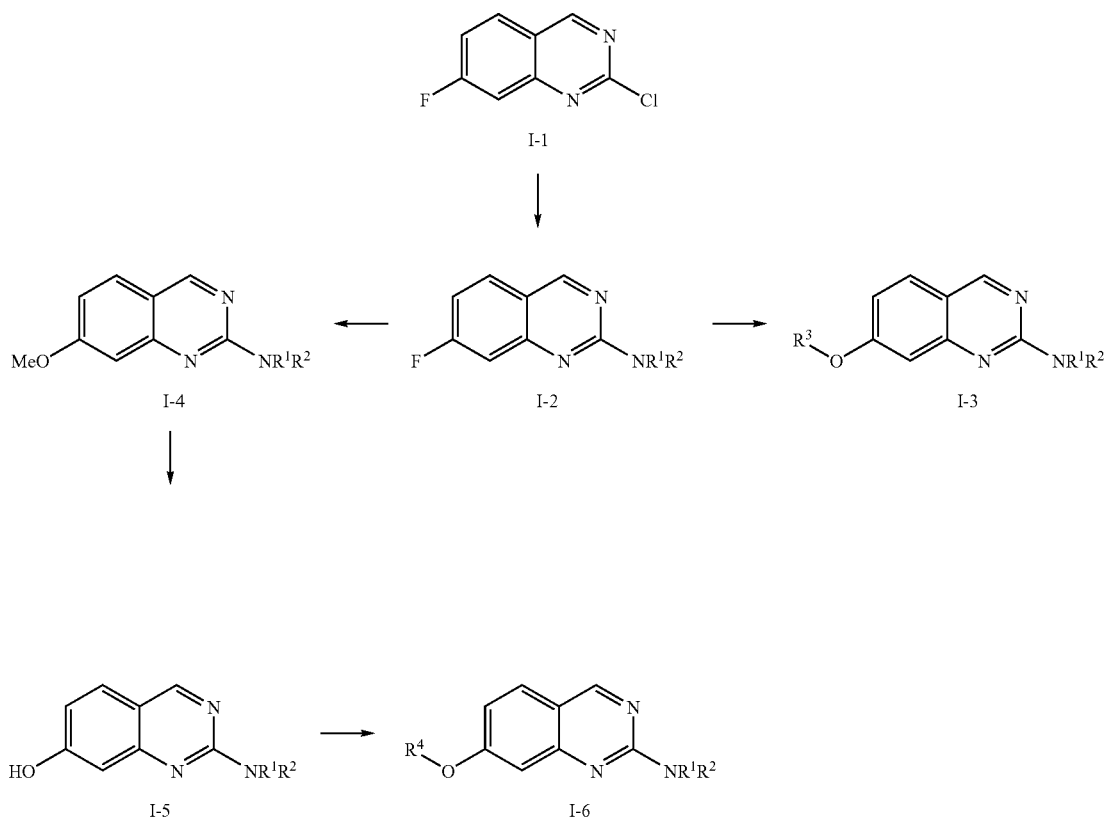

A scheme for the preparation of the 2-amino-7-alkoxyquinazolines of types I-3 and I-6 is shown in scheme I. 2-chloro-7-fluoro-quinazoline I-1 was treated with various amines in a suitable solvent (such as acetonitrile) with a suitable base (such as DBU) to afford the 2-amino quinazolines I-2. These were treated with alcohols in a suitable solvent (such as THF) with a suitable base (such as sodium hydride) to afford the ethers I-3. Alternatively, intermediate I-2 was treated with sodium methoxide in methanol to yield the methyl ether I-4. I-4 was deprotected under standard methods and/or conditions known in the art (such as sodium ethanethiolate in DMF) to yield the phenol I-5. These were treated with alkyl halides in a suitable solvent (such as THF) with a suitable base (such as sodium hydride) to afford the ethers I-6.

Scheme J:

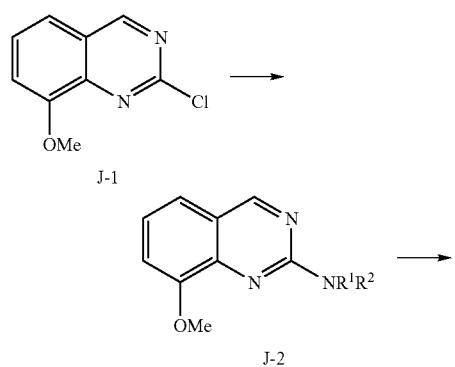

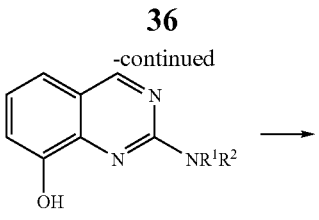

A scheme for the preparation of the 2-amino-8-alkoxyquinazolines Jo is shown in scheme J. 2-chloro-8-methoxyquinazoline J-1 was treated with various amines in a suitable solvent (such as acetonitrile) with a suitable base (such as DBU) to afford the 2-aminoquinazolines J-2. Compounds of type J-2 were deprotected under standard methods and/or conditions known in the art (such as sodium ethanethiolate in DMF) to yield the phenols J-3. These were treated with alkyl halides in a suitable solvent (such as THF) with a suitable base (such as sodium hydride) to afford the ethers J-4.

Scheme K:

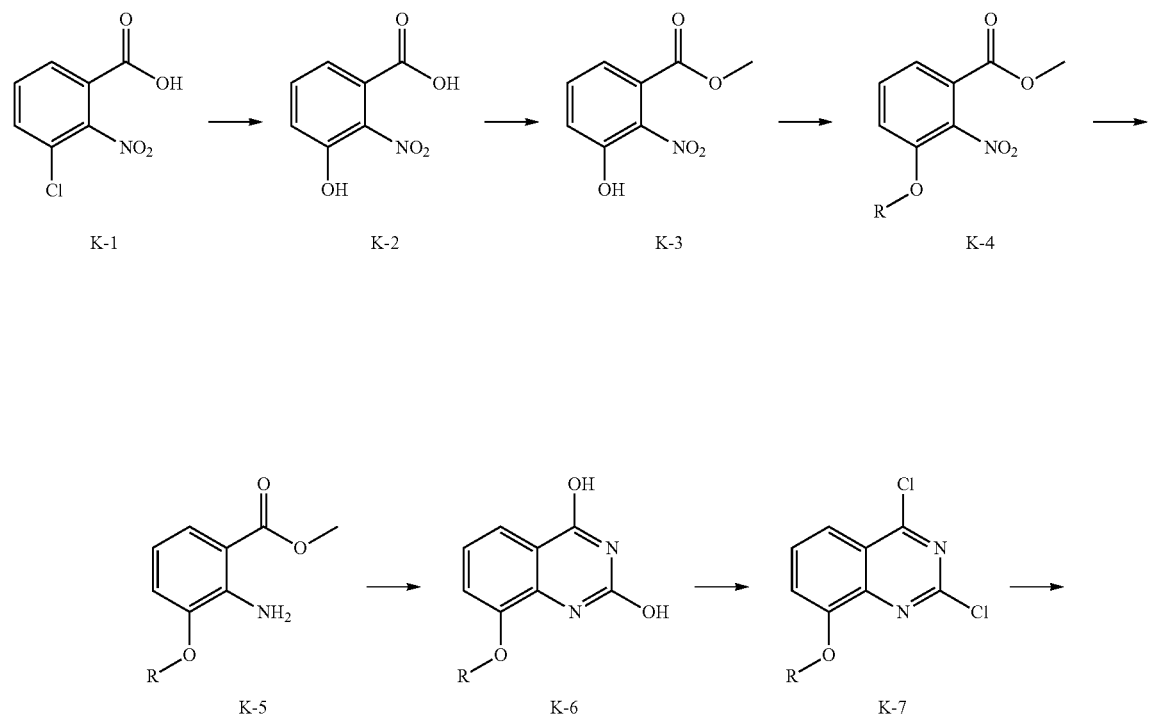

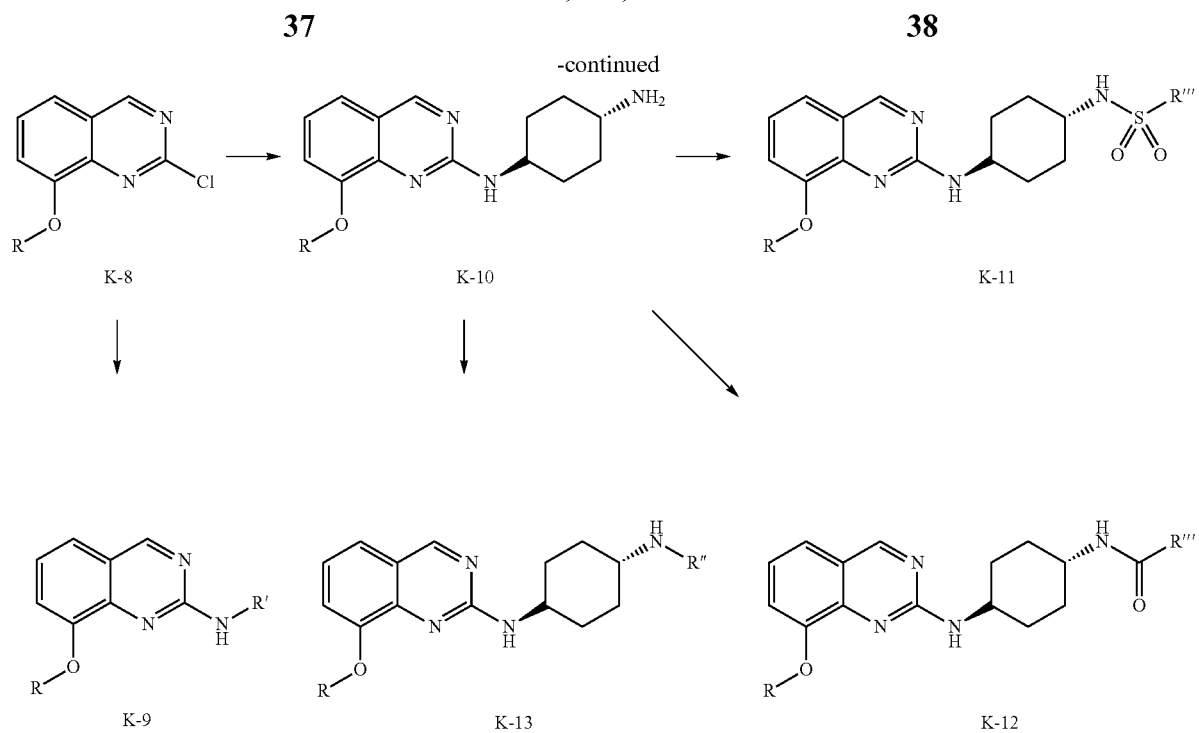

A scheme for preparation of various quinazoline-8-ethers is shown in scheme K. The 3-chlorobenzoic acid derivative K-1 was treated with a suitable hydroxide (such as potassium or sodium hydroxide) to afford the phenol K-2. K-2 was then esterified under standard conditions (such as thionyl chloride treatment followed by methanol) to afford the methyl ester K-3 which was in turn treated with a suitable alkyl mesylate and base (such as potassium carbonate) to yield the phenyl ether K-4. The nitro group was then reduced under standard conditions (such as Raney nickel under hydrogenation conditions) to give K-5, which was subsequently cyclised with sodium cyanate to afford the quinazoline core, K-6. Chlorination of K-6 was achieved using POCl$_3$ to afford K-7, which was then hydrogenated to afford the mono chloro quinazoline, K-8. K-8 was then subjected to standard nucleophillic amines together with a suitable base (such as DBU) to afford K-9 and K-10. Template K-10 was treated with a suitable alkylating agent (such as acyl chlorides or sulphonyl chlorides, in the presence of a base such as triethylamine) to afford compounds K-12 and K-11 respectively. Alternatively, template K-10 was treated with a suitable alkyl halide in the presence of a base (such as potassium carbonate) to afford the alkylamines K-13.

Scheme L:

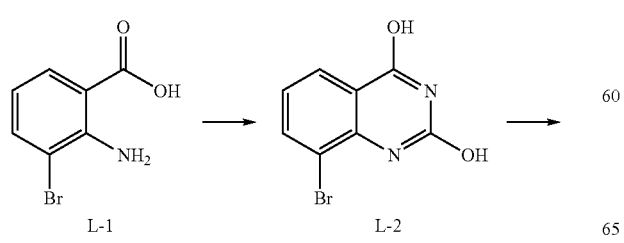

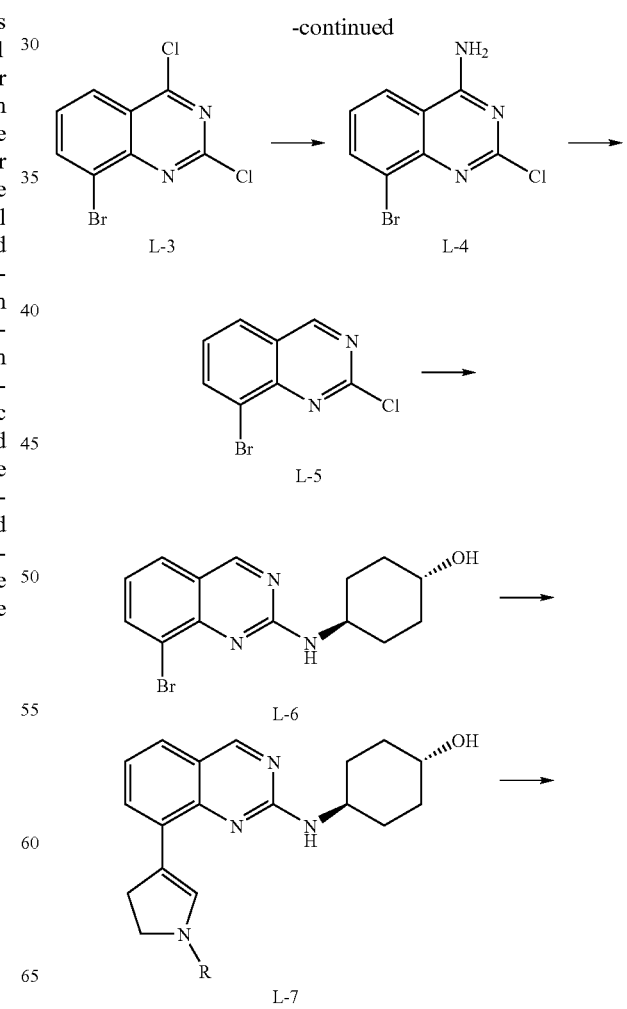

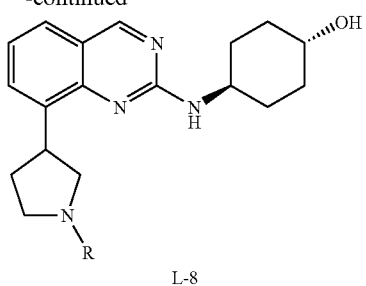

A scheme for the preparation of 8-pyrrolidine-quinazolines is shown above as scheme L. The anthranillic acid L-1 was cyclised to the quinazoline L-2 on treatment with sodium cyanate in acetic acid, followed by a suitable base (such as sodium hydroxide). Chlorination of L-2 was achieved with $POCl_3$ and $PCl_5$ to give the template L-3. Selective displacement of the 4-chloro was carried out with ammonia gas to give L-4, which in turn was treated with isoamyl nitrite to effect deamination to yield L-5. The Cl group of L-5 was displaced with an amine in the presence of a suitable base (such as DBU) to give L-6, which was subsequently subjected to Heck type coupling with a pyrroline to afford L-7. The resulting isomeric pyrrolines L-7 were hydrogenated to give the quinazoline-8-pyrrolidines L-8 under standard conditions.

Scheme M:

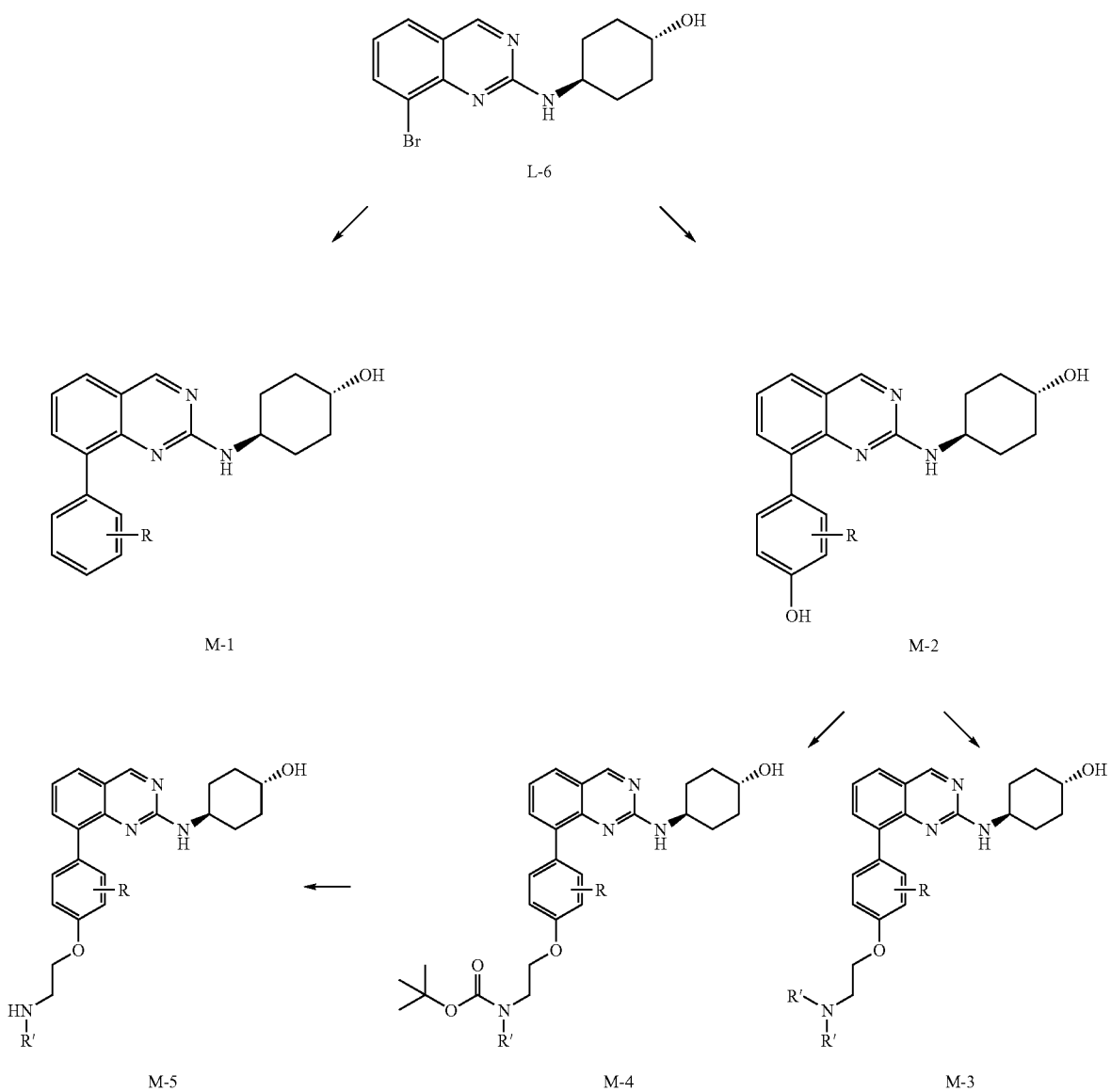

The general route for the synthesis of 8-aryl quinazolines is shown in scheme M. The 8-bromo quinazoline core L-6 was synthesised as described above in scheme E. L-6 was subjected to standard Suzuki type couplings to generate the compounds of type M-1 and M-2. The latter phenolic aryl compounds were elaborated by alkylation with alkyl halides to yield the ethers M-3 and M-4. The N-Boc amines MA were deprotected under standard conditions (such as TFA) to afford the amine ethers M-5.

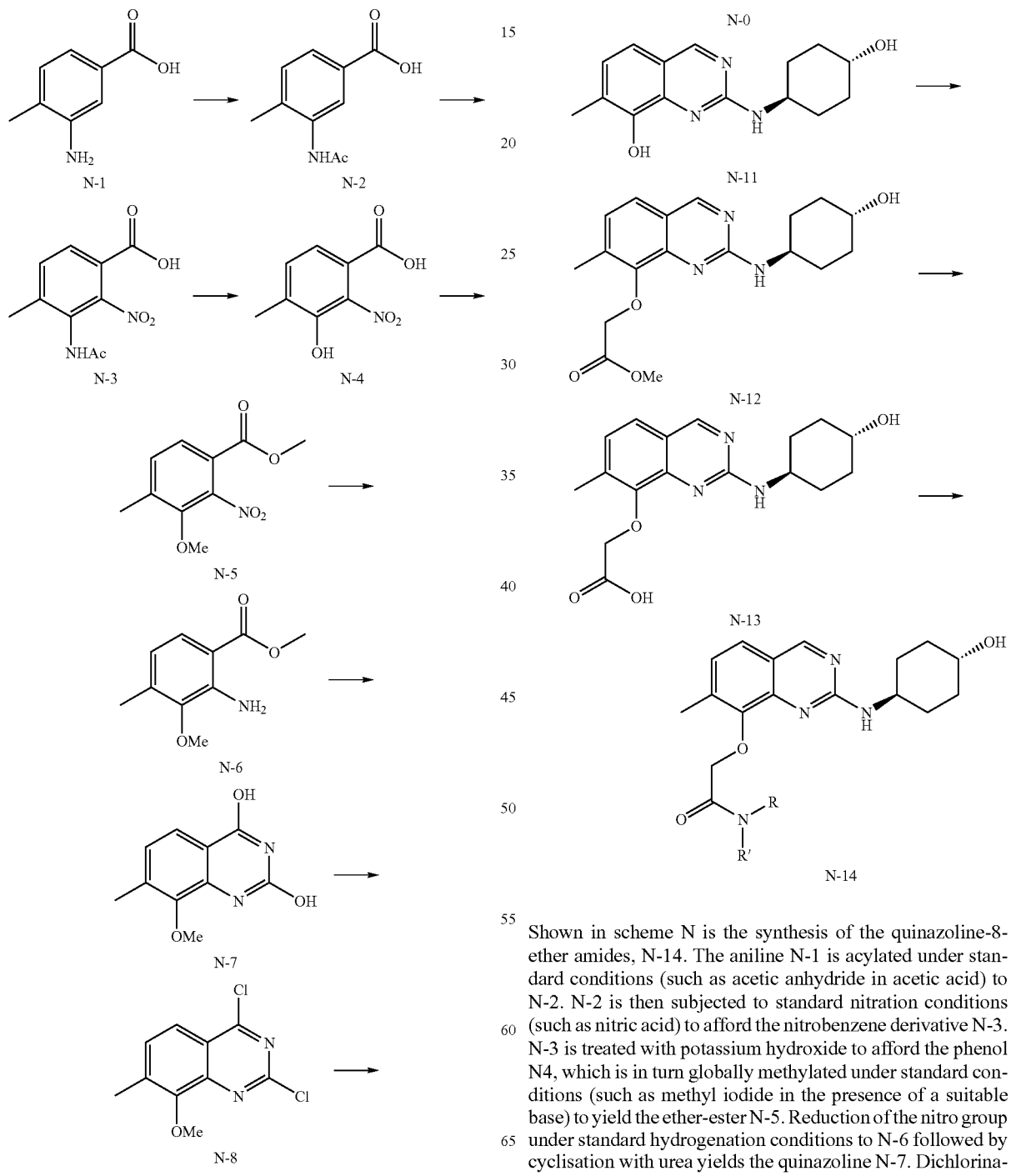

Shown in scheme N is the synthesis of the quinazoline-8-ether amides, N-14. The aniline N-1 is acylated under standard conditions (such as acetic anhydride in acetic acid) to N-2. N-2 is then subjected to standard nitration conditions (such as nitric acid) to afford the nitrobenzene derivative N-3. N-3 is treated with potassium hydroxide to afford the phenol N4, which is in turn globally methylated under standard conditions (such as methyl iodide in the presence of a suitable base) to yield the ether-ester N-5. Reduction of the nitro group under standard hydrogenation conditions to N-6 followed by cyclisation with urea yields the quinazoline N-7. Dichlorination to N-8, mono chloro-removal to N-9 and 2-chloro displacement to N-10 was performed as described in scheme A. Demethylation was achieved under standard conditions (such as sodium ethanethiolate in DMF) to give the phenol N-11. This was subsequently alkylated with methylbromoacetate in the presence of a suitable base (such as potassium carbonate) to afford the ester N-12. Hydrolysis of the ester under standard conditions (such as sodium hydroxide in water/THF) yielded the acid N-13 that was subjected to standard amide coupling conditions (such as HATU in DMF in the presence of a base such as triethylamine) to afford the amides N-14.

Scheme O:

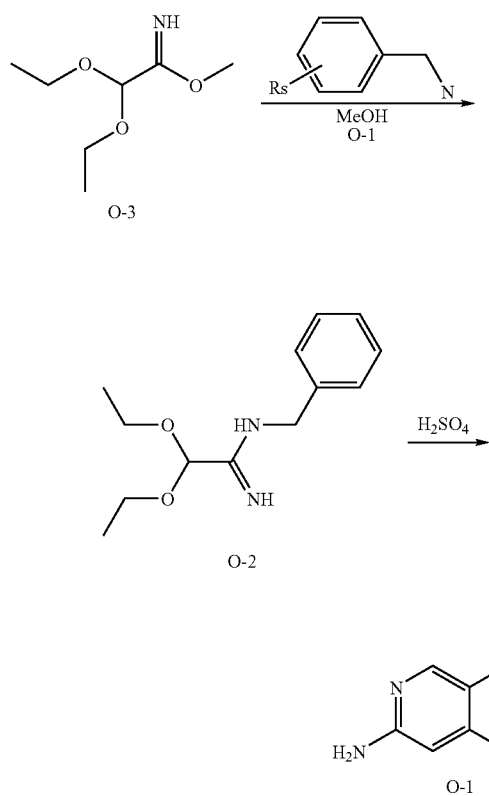

Shown in scheme O is the synthesis of intermediates compounds O-1 containing isoquinolin-3-amine. In a 250 ml of three-neck round bottom flask equipped with magnetic stir bar was charged the 2,2-diethoxyacetimidate (O-3) (6.7 g, 41.6 mmol) and MeOH (20 ml) then the phenyl methanamine hydrochloride (0.5 eq., 20.8 mmol) and MeONa (1 eq., 20.8 mmol) were added. The mixture was heated to 70° C. for 1 hr. The solution appeared dark. After the reaction finished, the MeOH solvent was removed by vacuum and the residue was dissolved in $CH_2Cl_2$ (100 ml). The organic phase washed with water (3×50 mL), then brine (1×30 mL). The organic layer was dried over magnesium sulfate, and filtered and the solvent reduced under vacuum. The product was purified by a silica gel column with 100% EA to give about 40.0% of desired product of 2,2-diethoxyacetamidine (O-2). The 2,2-diethoxyacetamidine (O-2) was dissolved in 6 ml of concentrated $H_2SO_4$ (99.9%) and the reaction was stirred at 40° C. for 72 hours. The solution was neutralized by 1M NaOH aqueous to PH 7.0. The crude was purified by silica gel column with 50:50 (petroleum ether: EA) to give final product O-1; yield from 13% to 70% depending on the substitution of phenyl methane amidine.

Scheme P:

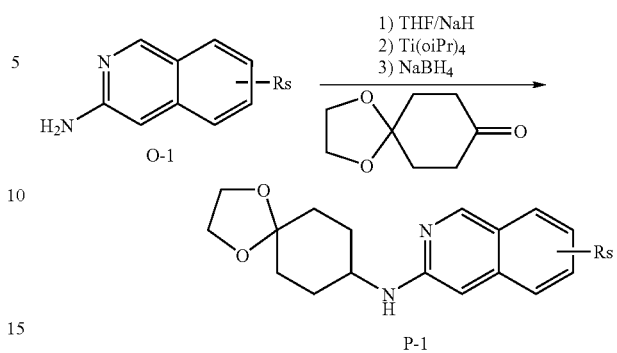

Shown in scheme P is the synthesis of intermediates compounds P-1 containing N-1,4-dioxaspiro[4.5]dec-8-yl-isoquinolin-3-amine. In the glove box, isoquinolin-3-amine (O-1) (873 mg, 3.7 mmol) was dissolved in 10 ml THF in flask and NaH (133.0 mg, 5.5 mmol) was added. The mixture was stirred at ambient temperature for 20 min. to form the N-sodium salt solution, followed by addition of $Ti(OPr)_4$ (4.2 g, 14.8 mmol) and 1,4 cyclohexanedione ethylene ketal (1.2 g, 7.2 mmol). Capped the flask and placed in an oil bath at 50° C. for 16 hours with stirring. The $NaBH_4$ was added and stirred at 50° C. for 16 hours. The solvent was removed by vacuum and the residue was dissolved in $CH_2Cl_2$ (100 ml). The organic phase washed with water (3×50 mL), and then brine (1×30 mL). The organic layer was dried over magnesium sulfate, and filtered and the solvent evaporated under vacuum. The crude material was purified by a silica gel column with 50:50 (EA/Petroleum) to give final products (P-1) with yield from 35% to 51% depending the substitutions on the isoquinoline.

Scheme Q:

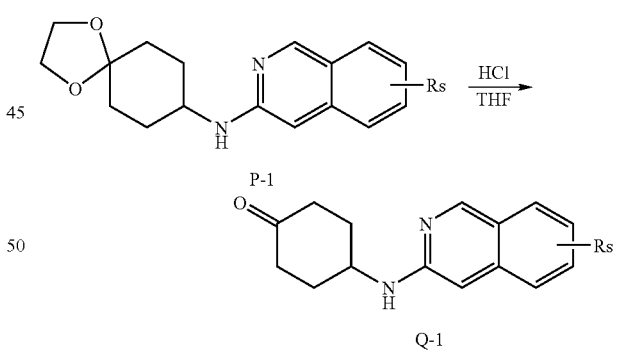

Shown in scheme Q is the synthesis of intermediates compounds Q-1 containing 4-(isoquinolin-3-ylamino)cyclohexanone. The (1,4-Dioxa-spiro[4.5]dec-8-yl)-(8-fluoro-6-methyl-isoquinolin-3-yl)-amine (P-1) (510.0 mg, 1.4 mmol) was dissolved in a solution of 20 ml of THF and 15 ml of 1 M HCl. The reaction was heated in 50° C. for 1 hour. LC/MS showed no more start material remained. The solution was neutralized by sodium carbonate (1 M $Na_2CO_3$ aqueous to neutralize the solution to pH=8), The THF was evaporated and partitioned with $CH_2Cl_2$/water. The organic layer was evaporated to give the product (Q-1) for next step without further purification.

Scheme R:

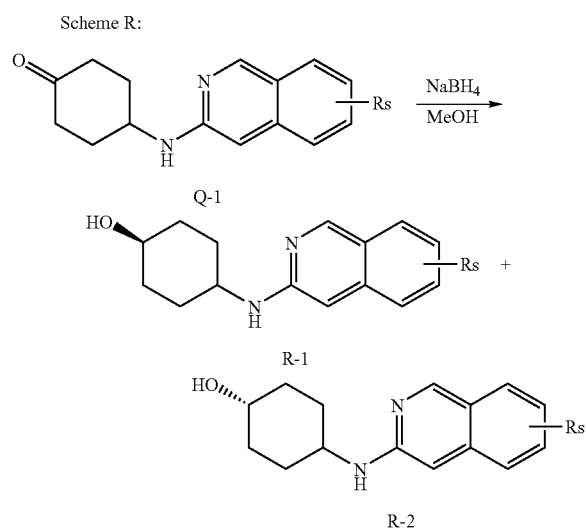

Shown in scheme R is the synthesis of intermediates compounds R-1 and R-2 containing cis and trans-4-(isoquinolin-3-ylamino)cyclohexanol. The 4-(Isoquinolin-3-ylamino)-cyclohexanones (Q-1) and $NaBH_4$ was dissolved in MeOH with stirring for 2 hrs at 50° C. LC/MS showed no more start material left and cis and trans products in about 1:1 ratio. The solvent was evaporated and partitioned with EA/water. The organic layers were evaporated. The cis (R-1) and trans (R-2) products were separated by HPLC with a combined yield ranging from 70% to 85%.

Scheme S:

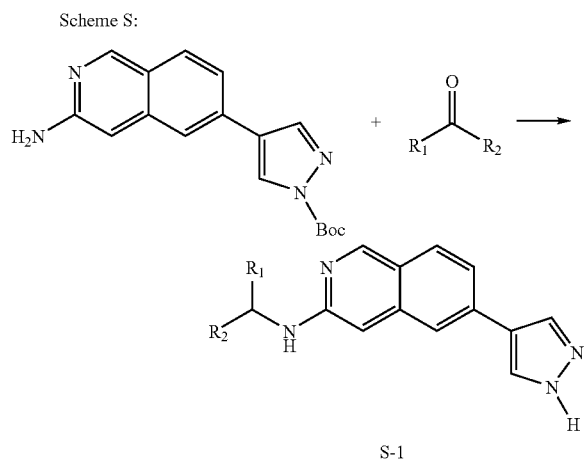

Shown in scheme S is the synthesis of intermediates compounds S-1 containing 6-(1H-pyrazol-4-yl)isoquinolin-3-alkylamines. In a glove box, treatment of tert-butyl 4-(3-aminoisoquinolin-6-yl)-1H-pyrazole-1-carboxylate with 1.5 eq. of NaH in THF at room temperature presumably formed the amino-sodium salt. This reaction accompanied a visible evolvement of $H_2$. Let the reaction go for 10 minutes before distributing the solution to four vials containing aldehydes and ketones, respectively. To these four vials 4.0 eq of Ti(O-iPr)$_4$ liquid was added. The vials were capped and placed in a 50° C. heating block in fumehood, and stirred for 14 h. After cooling to room temperature, 3.0 eq of $NaBH_4$ suspended in THF was added to the above reaction vials, respectively, and stirred for 14 h. 2-methoxylethyl ether appeared to solubilize $NaBH_4$ better and can also be used for the reduction. Carefully, 2N HCl aqueous solution was added to allow the pH to reach 1 or 2. The mixture was stirred for 1 h, and then the pH was adjusted to 8 by adding 2N aqueous NaOH. Precipitate was removed by passing the mixture through a syringe filter. The filtrate was analyzed using LCMS which showed the yields of the desired products ranging from 40 to 70%.

Any of the above compounds described in schemes A-S can be converted into another analogous compound by standard chemical manipulations. These chemical manipulations are known to those skilled in the art and include a) removal of a protecting group by methods outlined in T. W. Greene and P. G. M. Wuts, "Protective Groups in Organic Synthesis", Second Edition, John Wiley and Sons, New York, 1991; b) displacement of a leaving group (halide, mesylate, tosylate, etc) with a primary or secondary amine, thiol or alcohol to form a secondary or tertiary amine, thioether or ether, respectively; c) treatment of phenyl (or substituted phenyl) carbamates with primary of secondary amines to form the corresponding ureas as in Thavonekham, B et. al. Synthesis (1997), 10, p 1189; d) reduction of propargyl or homopropargyl alcohols or N-BOC protected primary amines to the corresponding E-allylic or E-homoallylic derivatives by treatment with sodium bis(2-methoxyethoxy)aluminum hydride (Red-Al) as in Denmark, S. E.; Jones, T. K. J. Org. Chem. (1982) 47, 4595-4597 or van Benthem, R. A. T. M.; Michels, J. J.; Speckamp, W. N. Synlett (1994), 368-370; e) reduction of alkynes to the corresponding Z-alkene derivatives by treatment hydrogen gas and a Pd catalyst as in Tomassy, B. et. al. Synth. Commun. (1998), 28, p 1201 f) treatment of primary and secondary amines with an isocyanate, acid chloride (or other activated carboxylic acid derivative), alkyl/aryl chloroformate or sulfonyl chloride to provide the corresponding urea, amide, carbamate or sulfonamide; g) reductive amination of a primary or secondary amine using $R^1CH(O)$; and h) treatment of alcohols with an isocyanate, acid chloride (or other activated carboxylic acid derivative), alkyl/aryl chloroformate or sulfonyl chloride to provide the corresponding carbamate, ester, carbonate or sulfonic acid ester.

The compounds of the present invention may have asymmetric carbon atoms. Diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomeric mixtures and pure enantiomers are considered as part of the invention.

The compounds of formulas (I) that are basic in nature are capable of forming a wide variety of different salts with various inorganic and organic acids. Although such salts must be pharmaceutically acceptable for administration to animals, it is often desirable in practice to initially isolate the compound of formula (I) from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of formula (I) that are acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of formula (I). Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The compounds of the present invention may also be useful in the treatment of other metabolic disorders associated with impaired glucose utilization and insulin resistance include major late-stage complications of NIDDM, such as diabetic angiopathy, atherosclerosis, diabetic nephropathy, diabetic neuropathy, and diabetic ocular complications such as retinopathy, cataract formation and glaucoma, and many other conditions linked to NIDDM, including dyslipidemia glucocorticoid induced insulin resistance, dyslipidemia, polycystic ovarian syndrome, obesity, hyperglycemia, hyperlipidemia, hypercholesteremia, hypertriglyceridemia, hyperinsulinemia, and hypertension. Brief definitions of these conditions are available in any medical dictionary, for instance, *Stedman's Medical Dictionary* (Xth Ed.).

Pharmaceutical Compositions/Formulations, Dosaging and Modes of Administration

Methods of preparing various pharmaceutical compositions with a specific amount of active compound are known, or will be apparent, to those skilled in this art. In addition, those of ordinary skill in the art are familiar with formulation and administration techniques. Such topics would be discussed, e.g. in Goodman and Gilman's *The Pharmaceutical Basis of Therapeutics*, current edition, Pergamon Press; and *Remington's Pharmaceutical Sciences*, current edition. Mack Publishing, Co., Easton, Pa. These techniques can be employed in appropriate aspects and embodiments of the methods and compositions described herein. The following examples are provided for illustrative purposes only and are not meant to serve as limitations of the present invention.

The amino heterocyclyl compounds of formula (I) may be provided in suitable topical, oral and parenteral pharmaceutical formulations for use in the treatment of GK mediated diseases. The compounds of the present invention may be administered orally as tablets or capsules, as oily or aqueous suspensions, lozenges, troches, powders, granules, emulsions, syrups or elixirs. The compositions for oral use may include one or more agents for flavoring, sweetening, coloring and preserving in order to produce pharmaceutically elegant and palatable preparations. Tablets may contain pharmaceutically acceptable excipients as an aid in the manufacture of such tablets. As is conventional in the art these tablets may be coated with a pharmaceutically acceptable enteric coating, such as glyceryl monostearate or glyceryl distearate, to delay disintegration and absorption in the gastrointestinal tract to provide a sustained action over a longer period.

Formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil.

Aqueous suspensions normally contain active ingredients in admixture with excipients suitable for the manufacture of an aqueous suspension. Such excipients may be a suspending agent, such as sodium carboxymethyl cellulose, methyl cellulose, hydroxypropylmethyl cellulose, sodium alginate, polyvinylpyrrolidone, gum tragacanth and gum acacia; a dispersing or wetting agent that may be a naturally occurring phosphatide such as lecithin, a condensation product of ethylene oxide and a long chain fatty acid, for example polyoxyethylene stearate, a condensation product of ethylene oxide and a long chain aliphatic alcohol such as heptadecaethylenoxycetanol, a condensation product of ethylene oxide and a partial ester derived from a fatty acid and hexitol such as polyoxyethylene sorbitol monooleate or a fatty acid hexitol anhydrides such as polyoxyethylene sorbitan monooleate.

The pharmaceutical compositions may be in the form of a sterile injectable aqueous or oleagenous suspension. This suspension may be formulated according to know methods using those suitable dispersing or wetting agents and suspending agents that have been mentioned above. The sterile injectable preparation may also be formulated as a suspension in a non toxic perenterally-acceptable diluent or solvent, for example as a solution in 1,3-butanediol. Among the acceptable vehicles and solvents that may be employed are water, Ringers solution and isotonic sodium chloride solution. For this purpose any bland fixed oil may be employed including synthetic mono- or diglycerides. In addition fatty acids such as oleic acid find use in the preparation of injectables.

The amino heterocyclyl compounds of formula (I) may also be administered in the form of suppositories for rectal administration of the drug. These compositions can be prepared by mixing the drug with a suitable non-irritating excipient that is solid at about 25 Celcius but liquid at rectal temperature and will therefore melt in the rectum to release the drug. Such materials include cocoa butter and other glycerides.

For topical use preparations, for example, creams, ointments, jellies solutions, or suspensions, containing the compounds of the present invention are employed.

The amino heterocyclyl compounds of formula (I) may also be administered in the form of liposome delivery systems such as small unilamellar vesicles, large unilamellar vesicles and multimellar vesicles. Liposomes can be formed from a variety of phospholipides, such as cholesterol, stearylamine or phosphatidylcholines.

Dosage levels of the compounds of the present invention are of the order of about 0.5 mg/kg body weight to about 100 mg/kg body weight. A preferred dosage rate is between about 30 mg/kg body weight to about 100 mg/kg body weight. It will be understood, however, that the specific dose level for any particular patient will depend upon a number of factors including the activity of the particular compound being administered, the age, body weight, general health, sex, diet, time of administration, route of administration, rate of excretion, drug combination and the severity of the particular disease undergoing therapy. To enhance the therapeutic activity of the present compounds they may be administered concomitantly with other orally active antidiabetic compounds such as the sulfonylureas, for example, tolbutamide and the like.

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

The invention will now be described in reference to the following Examples. These Examples are not to be regarded as limiting the scope of the present invention, but shall only serve in an illustrative manner.

EXAMPLES

In the examples described below, unless otherwise indicated, all temperatures are set forth in degrees Celsius and all parts and percentages are by weight. Reagents may be purchased from commercial suppliers, such as Sigma-Aldrich Chemical Company, Acros Organics, or Lancaster Synthesis Ltd. and may be used without further purification unless otherwise indicated. Tetrahydrofuran (THF), methylene chloride (CH$_2$Cl$_2$), and N,N-dimethylformamide (DMF) may be purchased from Aldrich in Sure-Seal bottles and used as received. All solvents may be purified using standard methods known to those skilled in the art, unless otherwise indicated.

The reactions set forth below were done generally under a positive pressure of argon or nitrogen or with a drying tube, at ambient temperature (unless otherwise stated), in anhydrous solvents, and the reaction flasks were fitted with rubber septa for the introduction of substrates and reagents via syringe. Glassware was oven dried and/or heat dried. Analytical thin layer chromatography (TLC) was performed using glass-backed silica gel 60 F 254 precoated plates (Merck Art 5719) and eluted with appropriate solvent ratios (v/v). Reactions were assayed by TLC or LCMS and terminated as judged by the consumption of starting material. Visualization of the TLC plates was done with UV light (254 nM wavelength) or with an appropriate TLC visualizing solvent and activated with heat. Flash column chromatography (Still et al., J. Org. Chem., 1978, 43, 2923) was performed using silica gel 60 (Merck Art 9385) or various MPLC systems, such as Biotage or ISCO purification system.

The compound structures in the examples below were confirmed by one or more of the following methods: proton magnetic resonance spectroscopy, mass spectroscopy, and elemental microanalysis. Proton magnetic resonance ($^1$H NMR) spectra were determined using a Bruker spectrometer operating at a field strength of 300 or 400 megahertz (MHz). Chemical shifts are reported in parts per million (PPM, δ) downfield from an internal tetramethylsilane standard. Alternatively, $^1$H NMR spectra were referenced to signals from residual protons in deuterated solvents as follows: CDCl$_3$=7.25 ppm; DMSO-d$_6$=2.49 ppm; C$_6$D$_6$=7.16 ppm; CD$_3$OD=3.30 ppm. Peak multiplicities are designated as follows: s, singlet; d, doublet; dd, doublet of doublets; t, triplet; dt, doublet of triplets; q, quartet; br, broadened; m, multiplet. Coupling constants are given in Hertz (Hz). Mass spectra (MS) data were obtained using Agilent mass spectrometer with APCI or ESI ionization. Elemental microanalyses were performed by Atlantic Microlab Inc. and gave results for the elements stated within ±0.4% of the theoretical values.

Preferred compounds in accordance with the invention may be prepared in manners analogous to those specifically described below.

The examples and preparations provided below further illustrate and exemplify the compounds of the present invention and methods of preparing such compounds. It is to be understood that the scope of the present invention is not limited in any way by the scope of the following examples and preparations. The skilled artisan will recognize that different acids, amines, alkyl halides, aryl halides, coupling reagents, and heterocycles may be substituted in the following descriptions to suit the preparations of a desired embodiment. The following methods may be scaled upwards or downwards to suit the amount of desired material.

In the examples and specification, "Et" means ethyl, "Ac" means acetyl, "Me" means methyl, "ETOAC" or "EtOAc" means ethyl acetate, "THF" means tetrahydrofuran, and "Bu" means butyl. Et$_2$O refers to diethyl ether. DMF refers to N,N-dimethylformamide. DMSO refers to dimethylsulfoxide. MTBE refers to tert-butyl methylether. Other abbreviations include: CH$_3$OH or MeOH (methanol), EtOH (ethanol), DME (ethylene glycol dimethyl ether), DCM or CH$_2$Cl$_2$ (dichloromethane or methylene chloride), CHCl$_3$ (chloroform), 1,2-DCE (1,2-dichloroethane), Ph (phenyl), TFA (trifluoroacetic acid), DIEA (N,N-diisopropylethylamine), TEA or Et$_3$N (triethylamine), NMM (4-methylmorpholine), HOBt (1-hydroxybenzotriazole hydrate), HATU [O-(7-azabenzotriazol-1-yl)-N,N,N',N'-tetramethyluronium hexafluorophosphate], EDCl [1-(3-dimethylaminopropyl)-3-ethylcarbodiimide hydrochloride], DCC (dicyclohexyl carbodiimide), DMAP (4-dimethylaminopyridine), NaOH (sodium hydroxide), KOH (potassium hydroxide), HCl (hydrogen chloride), MgSO$_4$ (magnesium sulfate), Na$_2$SO$_4$ (sodium sulfate), NH$_4$Cl (ammonium chloride), and NaHCO$_3$ (sodium bicarbonate).

Example 1

2-(4-methoxyphenyl)-N-[6-(1H-pyrazol-4-yl)isoquinolin-3-yl]acetamide

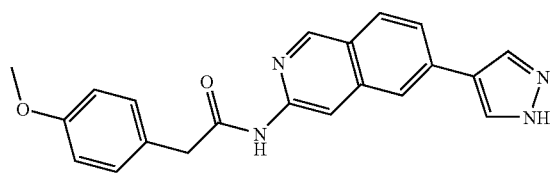

Activation of (4-Methoxy-phenyl)-acetic acid (315.6 mg, 1.9 mmol) is accomplished by treatment of the carboxylic acid in DMA (5 mL) with HATU (802.6 mg, 2.1 mmol) and triethylamine (388.2 mg, 3.8 mmol) at room temperature for 1 hour. The 6-(1H-Pyrazol-4-yl)-isoquinolin-3-ylamine (200.0 mg, 0.9 mmol) was added and the mixture was stirred at 75° C. for 24 hours. The reaction was monitored by LC/MS. Evaporation of DMA gave a residue that was washed with NaHCO$_3$ to remove the by-products from HATU. The crude residue then was dissolved in MeOH (10 mL) and was treated with K$_2$CO$_3$ (26.0 mg, 0.5 mmol) at 75° C. for 18 hrs. The solvent was evaporated and the product extracted with CH$_2$Cl$_2$ (20 mL). The extracts were washed with water (3×10 mL) and evaporated. The crude product was purified by ISCO (with petroleum ether:ethyl acetate 50:50) to give the title compound as a light yellow crystalline solid product (143.3 mg, 41.4%). $^1$H NMR (DMSO-$d_6$, 400 MHz): δ 3.68 (2H, s), 3.73 (3H, s), 6.79-6.98 (2H, m), 7.31 (2H, d, J=8.8 Hz,), 7.81 (1H, dd, J=8.6, 1.5 Hz,), 8.00 (1H, d, J=8.6 Hz), 8.08 (1H, s), 8.14 (1H, s), 8.41 (2H, d, J=8.3 Hz), 9.03 (1H, s), 10.69 (1H, s), 13.09 (1H, s). $^{13}$CNMR (DMSO-$d_6$, 100 MHz): δ 42.18, 55.01, 106.30, 113.76, 120.44, 120.56, 124.11, 124.39, 126.71, 127.87, 128.06, 130.13, 135.26, 136.96, 137.87, 147.51, 150.75, 158.14, 170.14. HRMS: m/z 359.1489, calc. 359.1503. MS m/z, (APCI); 359.2 [(M+1)$^+$100].

Preparation of intermediate 1:
N-(4-Bromobenzyl)-2,2-diethoxyethanimidamide

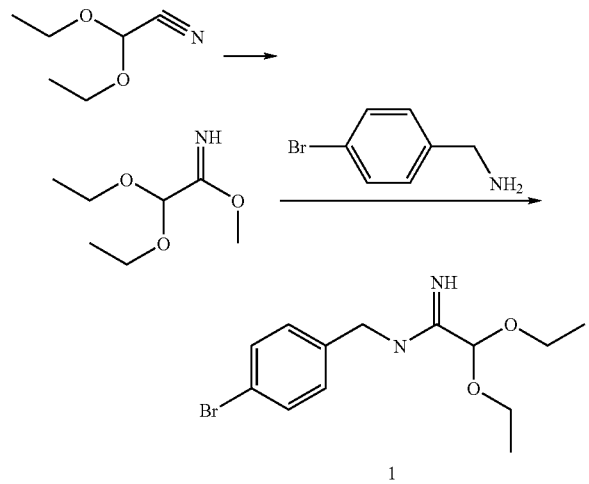

In a 2 L, three-neck round bottom flask (equipped with magnetic stir bar, thermometer, and addition funnel), charged diethoxyacetonitrile (111.1 g, 860 mmol) and methanol (620 mL, anhydrous) while under a steady nitrogen flow. Via an addition funnel, slowly charged 25 wt % solution of sodium methoxide (4.64 g, 86 mmol, 19.7 mL) in methanol. (Note: addition is slightly exothermic). The mixture was stirred for 15 h, at which point, the solvent was removed under vacuum (Note: starting material had not been completely converted according to NMR). The residue was dissolved in methanol and charged with a fresh sodium methoxide solution—same concentration/equivalents—and stirred another 15 h). The solvent was removed under vacuum and the residue was dissolved in diethyl ether (1.0 L), with the organic phase washed with water (3×500 mL), then brine (1×300 mL). The organic layer was dried over magnesium sulfate, the salts filtered and the solvent reduced under vacuum to give 89.9 g of a crude mixture of methyl 2,2-diethoxyethanimidoate and un-reacted starting material (10-12 mol % by NMR) as a thin oil. Note that best yields of the imidate are obtained when the organic layer is stripped of at 400 mbar and 45° C. because of its volatility.

The oil was dissolved in methanol (300 mL,) and placed into a 2 L round bottom flask (equipped with magnetic stir bar, reflux condenser) along with 1-(4-bromophenyl)methanamine (100.0 g, 537 mmol) and the mixture subjected to heating in a pre-heated oil bath. The mixture was stirred at 70° C. for 18 h and then allowed to cool. The solvent was removed to give 158.8 g of the desired intermediate (1) in 93.8% yield (based on 1-(4-bromophenyl)methanamine as limiting reagent).

Preparation of intermediate 2:
6-Bromoisoquinolin-3-amine

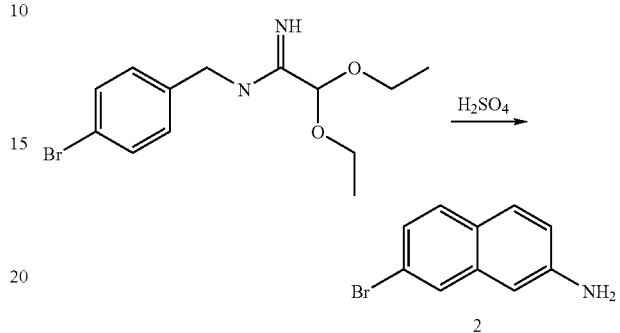

In a 3 L, three-neck round bottom flask (equipped with magnetic stir bar, thermometer, addition funnel), charged conc. sulfuric acid (1.12 L). While maintaining an internal temperature of 20-25° C. with an ice water bath, dropwise charged N-(4-bromobenzyl)-2,2-diethoxyethanimidamide (158.8 g, 504 mmol). After addition, removed bath and allowed to stir at ambient temperature for 72 h.

A 12-L, 3-necked round bottom flask, equipped with a large stirrer bar, dropping funnel and thermometer was charged with water (5 L). The flask was placed in an IPA bath and cooled externally with solid $CO_2$ to an internal temperature of 8° C. Over a period of 1¾ h, the reaction mixture was added slowly to the water, keeping the internal temperature between 0° C. and 10° C., resulting in a yellow suspension. With continued cooling, a 12 M NaOH solution was added over a 4 h period, keeping the internal temperature below 30° C. A final pH of 9-10 was reached (required 4.6 L, 12 M NaOH). Note that upon reaching neutral pH, the suspension changed to a much darker yellow. The suspension was filtered over a medium glass filter and the remaining residue was washed repeatedly with a total of 4 L of water to wash away precipitated Na-salts which resulted in a significant decrease of the amount of solids on the filter. The residue was dried in high vac at room temperature over KOH to give 143 g of a yellow powder. Elemental analysis showed 5.9 weight % of Na which corresponds to 36.4 weight % of $Na_2SO_4$. This material was used for further elaboration.

Preparation of intermediate 3:
6-(1H-Pyrazol-4-yl)isoquinolin-3-amine

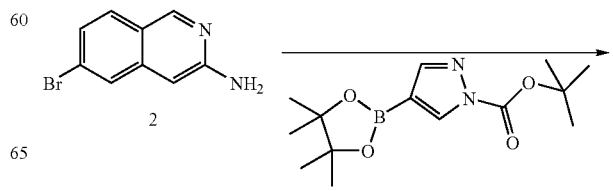

53

-continued

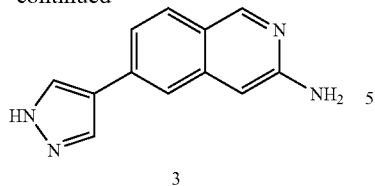

3

A 3-L, three-necked rbf, equipped with a condenser, thermometer and large stirrer bar was charged with DME (1 L) and a 2M $Cs_2CO_3$ (1 L, 10 eq). The two-phased system purged with nitrogen under vigorous stirring for 45 min, followed by the addition of 6-bromoisoquinolin-3-amine (44 g, 64 w % purity, 126 mmol), the commercially available boronate (50 g, 170 mmol), and $PdCl_2(dppf)$, $CH_2Cl_2$ complex (10.6 g, 14.2 mmol, Strem) and MeOH (2 mL). The nitrogen purge was discontinued and replaced by a nitrogen in/outlet on top of the condenser. The reaction mixture was heated to rfx (internal temperature 80° C.) for a period of 16 h and allowed to cool to room temperature. The cooled reaction mixture appeared as a two-layer system with a virtually colorless, aqueous layer and a dark organic layer in which a light brown precipitate had formed. The reaction mixture was filtered over a short path of Celite (pre-wetted with MeOH) and the Celite was subsequently washed with DME (110 mL). Removal of the solids improved visibility and the water layer could be readily separated. The organic layer was further diluted with ethyl acetate (700 mL) resulting in the separation of more solids which were remove by short-path filtration over a fresh batch of Celite (pre-wetted with MeOH). The filtrate was concentrated to a volume of 30 mL and the formed solids were isolated by filtration and washed with diethyl ether (40 mL) to give 4.8 g (11%) of the desired product as a yellow solid.

An alternative procedure for the preparation is as follows: To a 3-necked flask equipped with stirrer, nitrogen inlet and internal thermometer was charged with 3-amino, 6-bromoisoquinoline (6.0 g, 20.0 mmol), 2-(2',6'-dimethoxybiphenyl)dicyclohexylphosphine (S-Phos) (2.0 g 3.0 mmol), thoroughly freshly degassed DME (200 mL), water (40 mL), and $Cs_2CO_3$ (46.2 g, 142.0 mmol). The suspension was placed under nitrogen in a pre-heated oil bath at 86° C. Meanwhile, a solution of 1-BOC-4-(4,4,5,5-tetramethyl-1,3,2-dioxaborolan-2-yl)pyrazole (10.8 g, 36.0 mmol) in degassed DME (30 mL) was prepared and stored under nitrogen. When the internal temperature of the suspension had reached 84° C., the $Pd_2(dba)_3$ (2.8 g, 3.0 mmol) was added, and quickly followed by dropwise addition of the pyrazole boronate solution (via syringe over 5 min). The resulting bi-phasic dark orange solution was stirred at 84° C. for 20 mins. The flask was then placed in an ice bath to cool rapidly. Once at ambient temperature, the mixture was filtered to remove inorganic substance, washed with water (2×25 mL). Upon reduction of the solution volume via evaporation the solid product was filtered

54 and collected. The light yellow product was washed with ethyl ether 3 time (20 ml) to give a pale yellow solid product. Yield: 6.1 g, 98.4%.

Example 2

2-(5-methoxy-2-methyl-1H-indol-3-yl)-N-[6-(1H-pyrazol-4-yl)isoquinolin-3-yl]acetamide

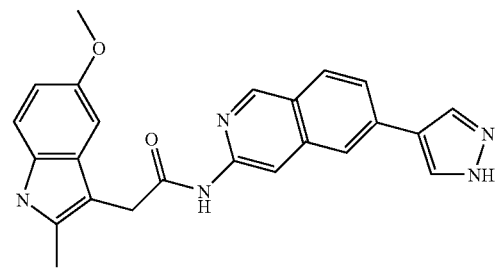

To a solution of 2-(5-methoxy-2-methyl-1H-indol-3-yl) acetic acid (219.2 mg, 0.5 mmol) in 5 mL of anhydrous THF was added oxalyl chloride (119.6 mg, 0.95 mmol), and 100 μL of DMF also was added. A effervescence occurred. Within 1-4 minutes the effervescence stopped. The mixture was stirred for 30 minute at room temperature, followed by addition of 6-(1H-Pyrazol-4-yl)-isoquinolin-3-ylamine in 5 mL of pyridine (100.0 mg, 0.5 mmol). The reaction was stirred at the ambient temperature over 16 hours as it was monitored by LC/MS. To the reaction mixture was added $K_2CO_3$ (196.7 mg, 1.4 mmol) and water (2 mL). The solution was heated to 70° C. for 5 hours. Removal of the solvents provided a crude mixture that was purified by HPLC using $H_2O/CH_3CN/0.1\%$ acetic acid as a mobile phase to give the title compound as a crystalline solid product (9.9 mg, 5.1%). $^1H$ NMR (DMSO-$d_6$, 400 MHz): δ 3.68 (2H, s), 3.73 (3H, s), 6.90 (2H, d, J=8.8 Hz), 7.31 (2H, d, J=8.6 Hz), 7.31 (1H, d, J=8.6 Hz), 7.81 (1H, dd, J=8.6, 1.5 Hz), 8.00 (1H, d, J=8.8 Hz), 8.08 (1H s), 8.10-8.22 (1H, m), 8.40 (2H, s), 9.03 (1H, s), 10.69 (1H, s), 13.09 (1H, s). $^{13}C$ NMR (DMSO-$d_6$, 100 MHz): δ 40.13, 55.00, 106.29, 113.75, 120.55, 124.10, 124.38, 127.87, 128.04, 130.12, 135.25, 137.87, 147.50, 150.75, 158.04, 170.13. HRMS: m/z 359.14959, calc 359.15025. MS m/z, (APCI); 359.1 [(M+1)⁺100].

Example 3

4,5-dimethoxy-N-[6-(1H-pyrazol-4-yl)isoquinolin-3-yl]indane-1-carboxamide

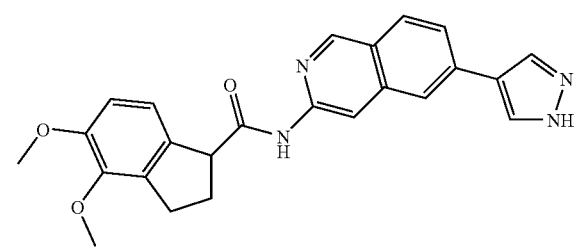

Using the method described in example 2, the title compound was obtained as a crystalline solid product (59.9 mg, 30.1%). $^1$H NMR (DMSO-$d_6$, 400 MHz): δ 2.18-2.45 (2H, m), 2.72-2.95 (1H, m), 2.98-3.18 (1H, m), 3.74 (1H, d, J=3.0 Hz), 4.25 (1H, d, J=7.3 Hz), 6.85 (1H, d, J=8.3 Hz), 7.01 (1H, d, J=8.3 Hz), 7.61 (1H, d, J=10.8 Hz), 7.82 (1H, dd, J=8.5, 1.5 Hz), 8.02 (1H, d, J=8.5 Hz), 8.07 (1H, s), 8.27 (1H, s), 8.42 (1H, s), 9.06 (1H, s), 10.83 (1H, s). $^{13}$CNMR (DMSO-$d_6$, 100 MHz): δ 28.82, 29.07, 50.78, 55.99, 59.37, 106.58, 111.80, 120.46, 124.44, 128.08, 135.28, 136.21, 136.02, 137.01, 147.35, 151.09, 172.73. HRMS: m/Z 415.1757, calc. 415.1765. MS m/z, (APCI); 415.1 [(M+1)$^+$100].

Using Chiralcel OJ-H column (50% MeOH, 120 bar, 2.5 ml/min), two single enantiomers were obtained at 4.36 minute (6.6 mg) and 8.42 minute (8.0 mg) from 40 mg of racemic compound.

Example 4

2-(4-methoxyphenyl)-N-[6-(1-methyl-1H-pyrazol-4-yl)isoquinolin-3-yl]acetamide

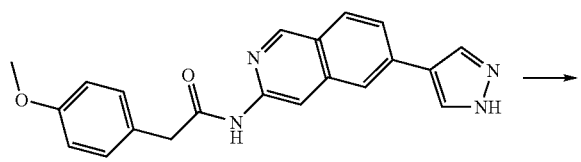

To the solution of 2-(4-Methoxy-phenyl)-N-[6-(1H-pyrazol-4-yl)-isoquinolin-3-yl]-acetamide (30.00 mg, 0.08 mmol) in 2 mL of dioxane was added Cs$_2$CO$_3$ (59.80 mg, 0.18 mmol) and CH$_3$I (13.10 mg, 0.09 mmol). The mixture was heated at 70° C. for 72 hrs. Evaporation of the solvent gave the crude product which was re-dissolved in DMSO and purified by HPLC to give the title compound as a crystalline solid product (7.5 mg, 24.0%). $^1$H NMR (DMSO-$d_6$, 400 MHz): δ 3.68 (2H, s), 3.73 (3H, s), 3.89 (3H, s), 6.89 (2H, d, J=8.5 Hz), 7.30 (2H, d, J=8.5 Hz), 7.75 (1H, dd, J=8.5, 1.5 Hz), 7.97-8.06 (2H, m), 8.08 (1H, s), 8.37 (2H, d, J=16.6 Hz), 9.03 (1H, s), 10.70 (1H, s). $^{13}$CNMR (DMSO-$d_6$, 100 MHz): δ 42.19, 55.03, 106.31, 113.77, 120.33, 121.25, 123.88, 124.41, 127.88, 128.18, 128.9, 130.16, 134.93, 136.86, 137.86, 147.56, 150.80, 158.06, 170.78. HRMS: m/z 373.1660, calc. 373.1659. MS m/z, (APCI); 373.1 [(M+1)$^+$100].

Preparation of intermediate 4: 4,5-dimethoxy-1-(tri-methylsilyloxy)-2,3-dihydro-1H-indene-1-carbonitrile

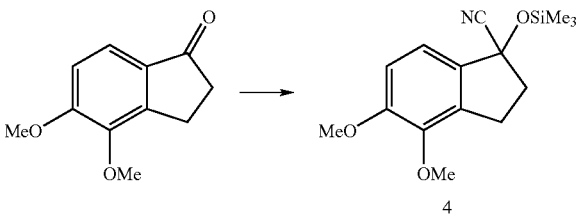

Under nitrogen, zinc iodide (1.5 g, 4.68 mmol), trimethyl-silyl cyanide (27.1 mL, 203.0 mmol) were added sequentially to the solution of 4,5-dimethoxy-1-indanone (30.0 g, 156.1 mmol) in toluene (100 mL) and acetonitrile (24 mL). The reaction mixture was heated to 50° C. for 16 h. The reaction mixture was cooled to room temperature and diluted with 100 mL of toluene and 60 mL of a saturated aqueous sodium bicarbonate solution. After the mixture was stirred for 1 h, the layers were separated. The organic layer was washed by brine (60 mL) and dried (Na$_2$SO$_4$). The organic layer was concentrated in vacuo and the residue was purified by chromatography (EtOAc/Hexanes: 5/95) to afford 1-trimethylsilanyloxy-4,5-dimethoxyindane-1-carbonitrile (33.1 g, 73%).

Preparation of intermediate 5: 4,5-dimethoxy-2,3-dihydro-1H-indene-1-carboxylic acid

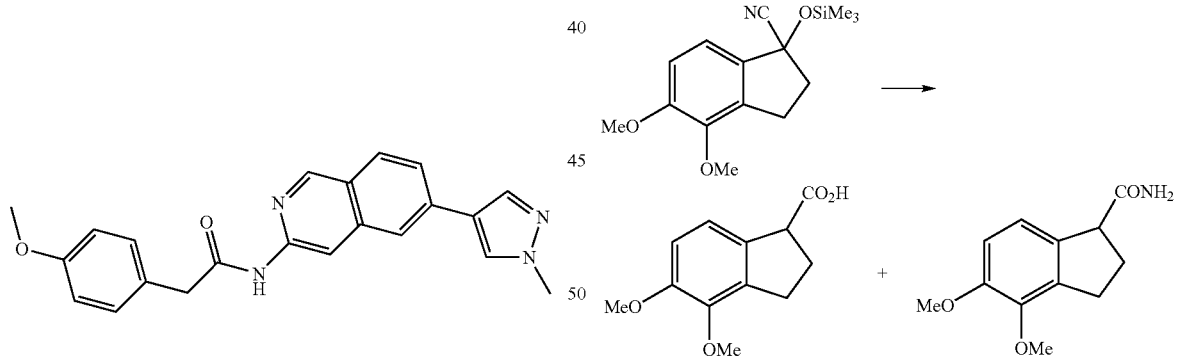

Tin (II) Chloride (28.0 g, 147.7 mmol) and concentrated HCl (10 mL) were added sequentially to the solution of 1-tri-methylanyloxy-4,5-dimethoxyindane-1-carbonitrile (33.1 g, 113.6 mmol) in acetic acid (100 mL). The reaction mixture was heated to 86° C. for 7 h. After cooled to room temperature, acetic acid was removed in vacuo. The residue was dilute by 200 mL of water, followed by addition of concentrated HCl to PH ~1. The water layer was extracted by EtOAc (300 mL×3), the combined organic layers were dried (Na$_2$SO$_4$) and concentrated in vacuo. The solid was washed by Hexanes/DCM (200 mL/5 mL) to afford 4,5-dimethoxyindane-1-carboxamide (9.1 g, 36.4%). The filtrate was concentrated in vacuo and then purified by chromatography (MeOH/DCM: 1/99) to afford 4,5-dimethoxyindane-1-carboxylic acid as off-white solid (2.7 g, 11%).

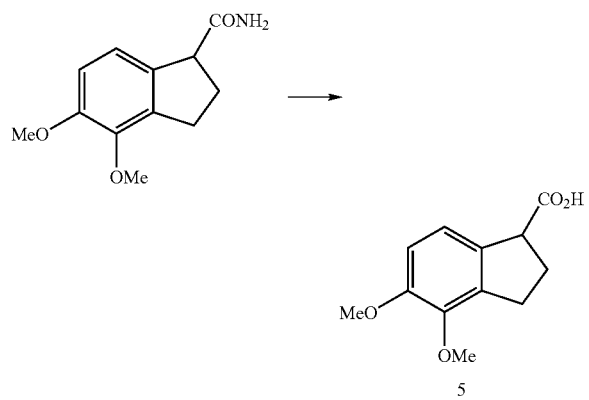

5

The mixture of 4,5-dimethoxyindane-1-carboxamide (8.4 g, 38.0 mmol), KOH (6.4 g, 114.0 mmol), MeOH (31.0 mL) and water (62 mL) was heated to reflux for 14 h. The reaction mixture was cooled to room temperature, and MeOH was removed in vacuo. The residue was diluted by 50 mL of water, and the aqueous mixture was extracted with EtOAc (50×2). The aqueous layer was added conc. HCl to adjusted pH ~1. The solid was filtered, washed by water (100 mL), and dried over $P_2O_5$ to afford 4,5-dimethoxyindane-1-carboxylic acid as off-white solid (7.7 g, 92%). M. P.: 128-130° C.

Examples 5-57 were Prepared According to the Procedure Described for Example 2

| Example Number | Structure | Compound Name | m/z | $^1$H NMR |
|---|---|---|---|---|
| 5 | 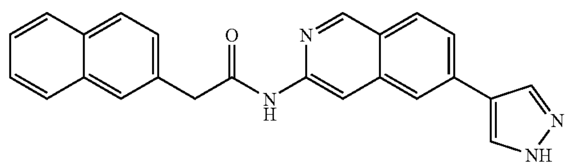 | 2-(2-naphthyl)-N-[6-(1H-pyrazol-4-yl)isoquinolin-3-yl]acetamide | 379 | (400 MHz, DMSO-$d_6$) δ: 8.02-8.13 (2H, m), 8.16 (1H, d, J = 8.1 Hz), 8.41 (1H, d, J = 8.6 Hz), 8.49 (4H, d, J = 5.5 Hz), 8.60 (1H, d, J = 8.6 Hz), 8.67 (1H, s), 9.0 (s, 1 H), 9.64 (s, 1 H), 11.45 (1H, s), 13.45 (1H, s) |
| 6 | 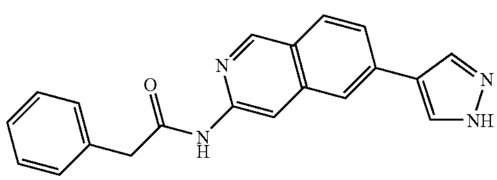 | 2-phenyl-N-[6-(1H-pyrazol-4-yl)isoquinolin-3-yl]acetamide | 329 | (400 MHz, DMSO-$d_6$) δ: 3.77 (2H, s), 7.25 (1H, t, J = 7.1 Hz), 7.33 (2H, t, J = 7.5 Hz), 7.37-7.43 (2H, m), 7.56 (1H, dd, J = 6.9, 3.1 Hz), 7.58-7.67 (1H, m), 7.81 (1H, dd, J = 8.5, 1.2 Hz), 8.00 (1H, d, J = 8.5 Hz), 8.08 (1H, s), 8.41 (1H, s), 9.04 (1H, s), 10.77 (1H, s), 13.10 (1H, s) |
| 7 | 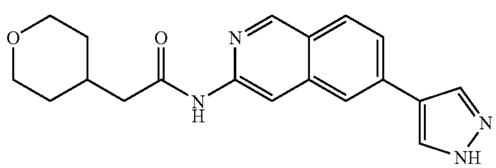 | N-[6-(1H-pyrazol-4-yl)isoquinolin-3-yl]-2-(tetrahydro-2H-pyran-4-yl)acetamide | 337 | (400 MHz, DMSO-$d_6$) δ: 1.14-1.41 (2H, m), 1.60 (2H, dd, J = 12.8, 1.7 Hz), 1.92-2.16 (1H, m), 2.38 (2H, d, J = 7.0 Hz), 2.46-2.57 (1H, m), 3.22-3.32 (2H, m), 3.83 (2H, dd, J = 11.4, 2.6 Hz), 7.81 (1H, dd, J = 8.5, 1.5 Hz), 8.00 (1H, d, J = 8.5 Hz), 8.10 (1H, s), 8.46 (1H, s), 9.02 (1H, s), 10.52 (1H, s) 13.10 (1H, s) |
| 8 | 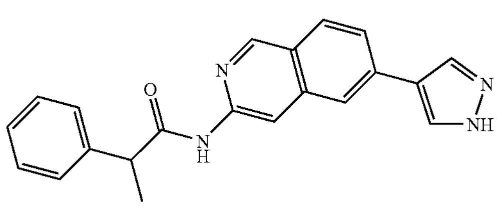 | 2-phenyl-N-[6-(1H-pyrazol-4-yl)isoquinolin-3-yl]propanamide | 343 | (400 MHz, DMSO-$d_6$) δ: 1.45 (3H, d, J = 7.0 Hz), 4.09 (1H, q, J = 7.0 Hz), 7.23 (1H, t, J = 7.3 Hz), 7.33 (2H, t, J = 7.5 Hz), 7.45 (2H, d, J = 7.8 Hz,), 7.81 (1H, dd, J = 8.5, 1.5 Hz), 7.99 (1H, d, J = 8.5 Hz), 8.08 (1H, s), 8.44 (1H, s), 9.01 (1H, s), 10.69 (1H, s), 13.11 (1H, s) |

-continued

| Example Number | Structure | Compound Name | m/z | ¹H NMR |
|---|---|---|---|---|
| 9 | 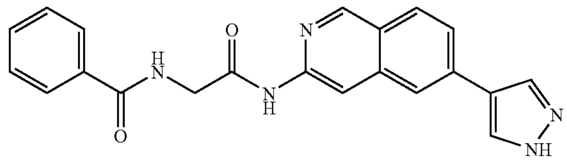 | N-(2-oxo-2-{[6-(1H-pyrazol-4-yl)isoquinolin-3-yl]amino)ethyl)benzamide | 371 | (500 MHz, DEUTERIUM OXIDE) δ: (2.4-4.2 solvent suppression), 7.47 (d, J = 7.6 Hz, 1 H), 7.51 (d, J = 7.6 Hz, 1 H), 7.78 (d, J = 7.6 Hz, 1 H), 7.87 (d, J = 7.6 Hz, 1 H), 7.98 (d, J = 8.2 Hz, 1 H), 8.05 (s, 1H), 8.23 (s, 2 H), 8.36 (s, 1 H), 8.81 (s, 1 H), 9.01 (s, 1 H), 10.52 (s, 1 H), |
| 10 | 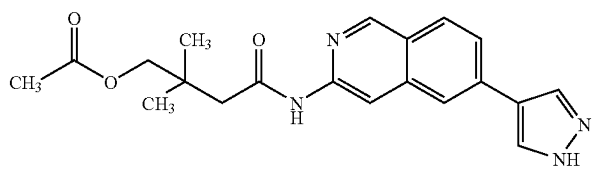 | 2,2-dimethyl-4-oxo-4-{[6-(1H-pyrazol-4-yl)isoquinolin-3-yl]amino)butyl acetate | 367 | (500 MHz, DEUTERIUM OXIDE) δ: (0.8-4.2 solvent suppression), 7.76 (d, J = 8.5 Hz, 1 H), 7.96 (d, J = 7.9 Hz, 1 H), 8.07 (s, 1 H), 8.23 (s, 2 H), 8.41 (s, 1 H), 8.98 (s, 1 H), 10.42 (s, 1 H) |
| 11 | 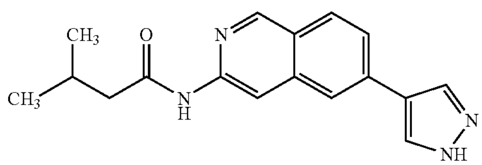 | 3-methyl-N-[6-(1H-pyrazol-4-yl)isoquinolin-3-yl]butanamide | 395 | (500 MHz, DEUTERIUM OXIDE) δ: (0.6-3.2 solvent suppression), 7.75 (d, J = 8.7 Hz, 1 H), 7.95 (d, J = 8.7 Hz, 1 H), 8.05 (s, 1 H), 8.23 (s, 2 H), 8.39 (s, 1 H), 8.97 (s, 1 H), 10.39 (s, 1 H) |
| 12 | 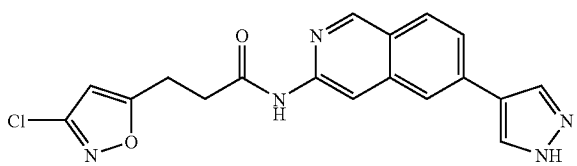 | 3-(3-chloroisoxazol-5-yl)-N-[6-(1H-pyrazol-4-yl)isoquinolin-3-yl]propanamide | 368 | (500 MHz, DEUTERIUM OXIDE) δ: (2.5-5.0 solvent suppression), 6.57 (s, 1 H), 7.77 (d, J = 8.2 Hz, 1H), 7.96 (d, J = 8.2 Hz, 1 H), 8.06 (s, 1 H), 8.23 (s, 2 H), 8.37 (s, 1 H), 8.99 (s, 1 H), 10.54-10.68 (m, 1 H) |
| 13 | 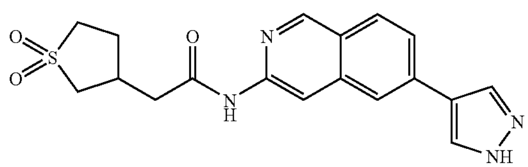 | 2-(1,1-dioxidotetrahydro-3-thienyl)-N-[6-(1H-pyrazol-4-yl)isoquinolin-3-yl]acetamide | 370 | (500 MHz, DEUTERIUM OXIDE) δ: (1.5-4.2 solvent suppression), 7.77 (d, J = 1.0 Hz, 1 H), 7.96 (d, J = 1.0 Hz, 1 H), 8.05 (s, 1 H), 8.23 (s, 2 H), 8.37 (s, 1 H), 8.99 (s, 1 H), 10.48 (s, 1 H) |
| 14 | 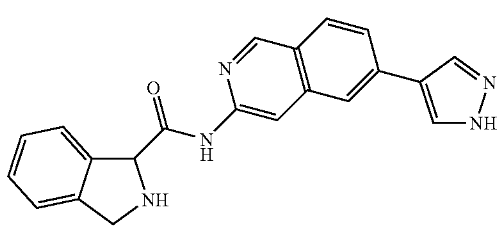 | N-[6-(1H-pyrazol-4-yl)isoquinolin-3-yl]isoindoline-1-carboxamide | 356 | (400 MHz, DMSO-d₆) δ: 7.26-7.45 (3H, m), 7.58 (1H, d, J = 7.05 Hz), 7.85 (1 H, d, J = 8.56 Hz), 8.04 (1H, d, J = 8.56 Hz), 8.14 (1 H, s), 8.29 (2 H, m), 8.40 (1H, s), 9.07 (1H, s) |
| 15 | 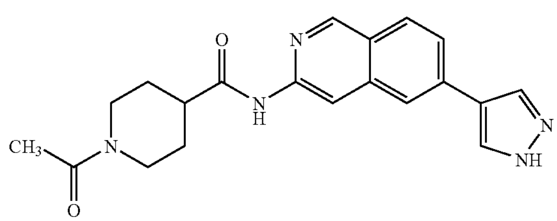 | 1-acetyl-N-[6-(1H-pyrazol-4-yl)isoquinolin-3-yl]piperidine-4-carboxamide | 397 | (500 MHz, DEUTERIUM OXIDE) δ: (1.5-4.2 solvent suppression), 7.77 (d, J = 8.7 Hz, 1 H), 7.96 (d, J = 8.7 Hz, 1 H), 8.05 (s, 1 H), 8.23 (s, 2 H), 8.37 (s, 1 H), 8.99 (s, 1 H), 10.48 (s, 1 H) |

-continued

| Example Number | Structure | Compound Name | m/z ¹H NMR |
|---|---|---|---|
| 16 | 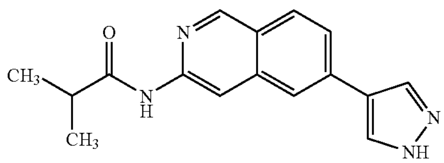 | 2-methyl-N-[6-(1H-pyrazol-4-yl)isoquinolin-3-yl]propanamide | 397 (500 MHz, DEUTERIUM OXIDE) δ: (1.5-4.2 solvent suppression), 7.76 (d, J = 9.3 Hz, 1H), 7.97 (d, J = 9.3 Hz, 1 H), 8.04 (s, 1 H), 8.23 (s, 2 H), 8.39 (s, 1 H), 8.99 (s, 1 H), 10.39 (s, 1 H), 1.08 (d, J = 6.5 Hz, 6 H) |
| 17 | 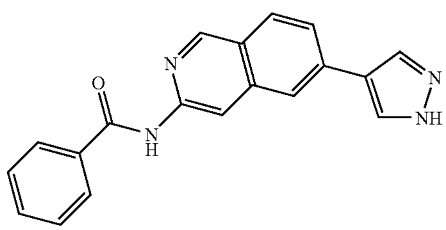 | N-[6-(1H-pyrazol-4-yl)isoquinolin-3-yl]benzamide | 315 (400 MHz, DMSO-$d_6$) δ: 7.50-7.57 (3H, m), 7.58-7.65 (2 H, m), 7.81-7.95 (1H, m), 8.07 (3H, t, J = 8.8 Hz), 8.19 (1H, s), 8.62 (1H, s), 9.12 (1H, s), 10.84 (1H, s), 13.12 (1H) |
| 18 | 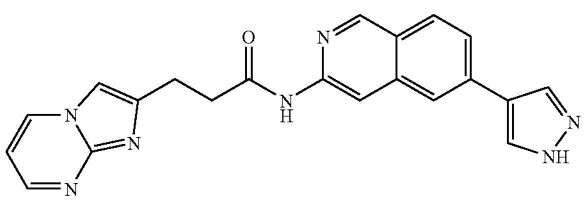 | 3-imidazo[1,2-a]pyrimidin-2-yl-N-[6-(1H-pyrazol-4-yl)isoquinolin-3-yl]propanamide | 384 |
| 19 | 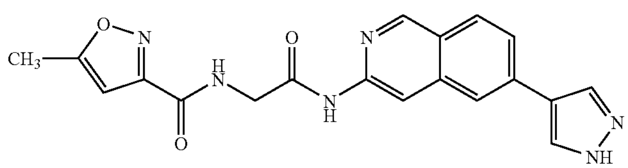 | 5-methyl-N-(2-oxo-2-{[6-(1H-pyrazol-4-yl)isoquinolin-3-yl]amino}ethyl)isoxazole-3-carboxamide | 377 |
| 20 | 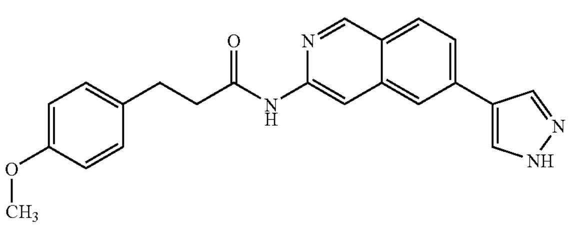 | 3-(4-methoxyphenyl)-N-[6-(1H-pyrazol-4-yl)isoquinolin-3-yl]propanamide | 373 |
| 21 | 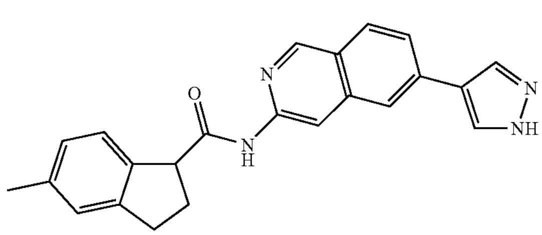 | 5-methyl-N-[6-(1H-pyrazol-4-yl)isoquinolin-3-yl]indane-1-carboxamide | 369 (400 MHz, DMSO-$d_6$) δ: 2.24 (3H, s), 2.26-2.41 (2 H, m), 2.78-2.90 (1H, m), 2.97-3.09 (1H, m), 4.30 (1H, t, J = 7.43 Hz), 7.00 (1H, d, J = 7.81 Hz), 7.11 (1H, s), 7.15 (1H, d, J = 7.81 Hz), 7.82 (1H, dd, J = 8.56, 1.01 Hz), 8.03 (1H, d, J = 8.56 Hz), 8.08 (1H, s), 8.27 (2 H, s), 8.44 (1H, s), 9.08 (1H, s), 10.87 (1H, s) |

-continued

| Example Number | Structure | Compound Name | m/z | ¹H NMR |
|---|---|---|---|---|
| 22 | 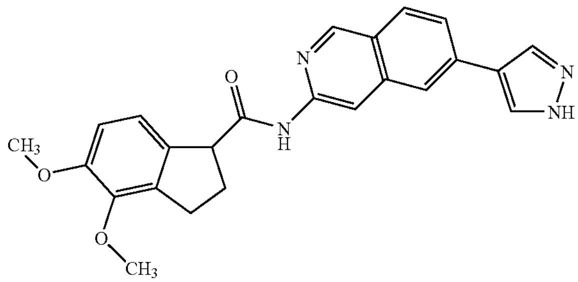 | (S)-4,5-dimethoxy-N-[6-(1H-pyrazol-4-yl)isoquinolin-3-yl]indane-1-carboxamide | 415 | (400 MHz DMSO-d6): δ 2.18-2.45 (2 H, m), 2.72-2.95 (1H, m), 2.98-3.18 (1H, m), 3.74 (1H, d, J = 3.0 Hz), 4.25 (1H, d, J = 7.3 Hz), 6.85 (1H, d, J = 8.3 Hz), 7.01 (1H, d, J = 8.3 Hz), 7.61 (1H, d, J = 10.8 Hz), 7.82 (1H, dd, J = 8.5, 1.5 Hz), 8.02 (1H, d, J = 8.5 Hz), 8.07 (1H, s), 8.27 (1H, s), 8.42 (1H, s), 9.06 (1H, s), 10.83 (1H, s) |
| 23 | 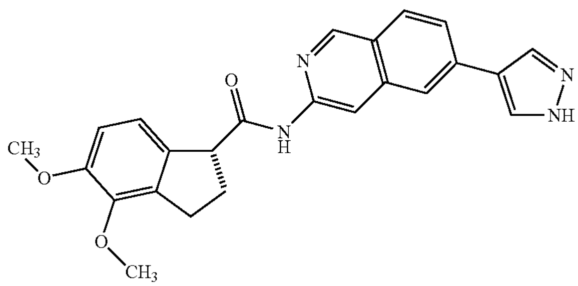 | (R)-4,5-dimethoxy-N-[6-(1H-pyrazol-4-yl)isoquinolin-3-yl]indane-1-carboxamide | 415 | (400 MHz DMSO-d6): δ 2.18-2.45 (2 H, m), 2.72-2.95 (1H, m), 2.98-3.18 (1H, m), 3.74 (1H, d, J = 3.0 Hz), 4.25 (1H, d, J = 7.3 Hz), 6.85 (1H, d, J = 8.3 Hz), 7.01 (1H, d, J = 8.3 Hz), 7.61 (1H, d, J = 10.8 Hz), 7.82 (1H, dd, J = 8.5, 1.5 Hz), 8.02 (1H, d, J = 8.5 Hz), 8.07 (1H, s), 8.27 (1H, s), 8.42 (1H, s), 9.06 (1H, s), 10.83 (1H, s) |
| 24 | 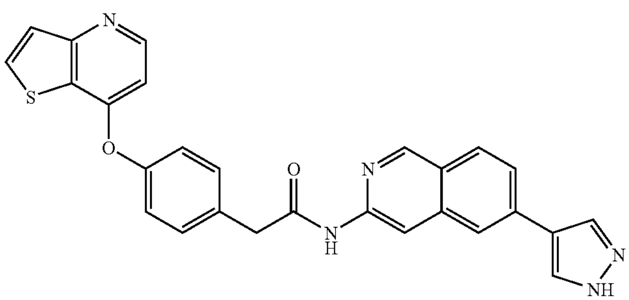 | N-[6-(1H-pyrazol-4-yl)isoquinolin-3-yl]-2-[4-(thieno[3,2-b]pyridin-7-yloxy)phenyl]acetamide | 478 | |
| 25 | 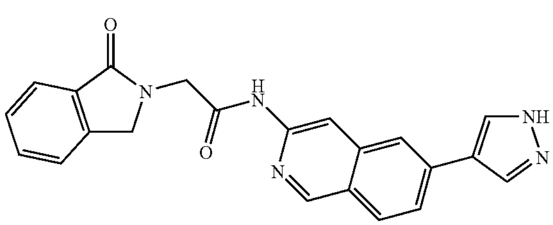 | 2-(1-oxo-1,3-dihydro-2H-isoindol-2-yl)-N-[6-(1H-pyrazol-4-yl)isoquinolin-3-yl]acetamide | 384 | |
| 26 | 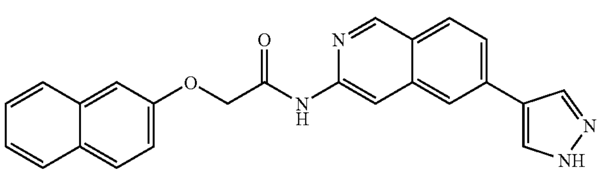 | 2-(2-naphthyloxy)-N-[6-(1H-pyrazol-4-yl)isoquinolin-3-yl]acetamide | 395 | |
| 27 | 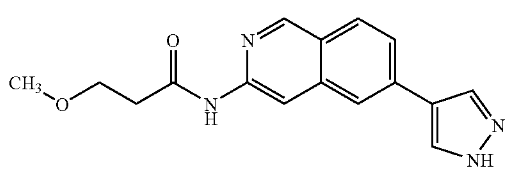 | 3-methoxy-N-[6-(1H-pyrazol-4-yl)isoquinolin-3-yl]propanamide | 297 | |

| Example Number | Structure | Compound Name | m/z $^1$H NMR |
|---|---|---|---|
| 28 | 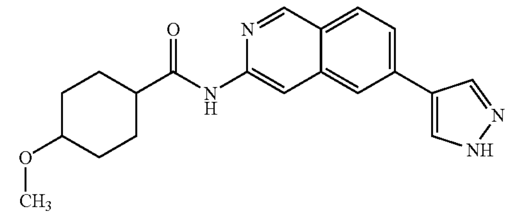 | 4-methoxy-N-[6-(1H-pyrazol-4-yl)isoquinolin-3-yl]cyclohexane-carboxamide | 351 |
| 29 | 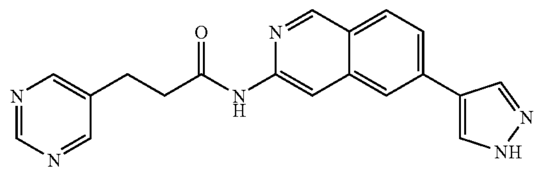 | N-[6-(1H-pyrazol-4-yl)isoquinolin-3-yl]-3-pyrimidin-5-ylpropanamide | 345 |
| 30 | 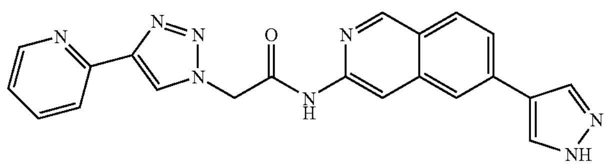 | N-[6-(1H-pyrazol-4-yl)isoquinolin-3-yl]-2-(4-pyridin-2-yl-1H-1,2,3-triazol-1-yl)acetamide | 397 |
| 31 | 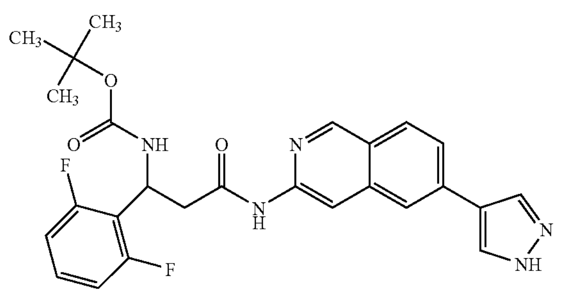 | tert-butyl (1-(2,6-difluorophenyl)-3-oxo-3-{[6-(1H-pyrazol-4-yl)isoquinolin-3-yl]amino}propyl)carbamate | 494 |
| 32 | 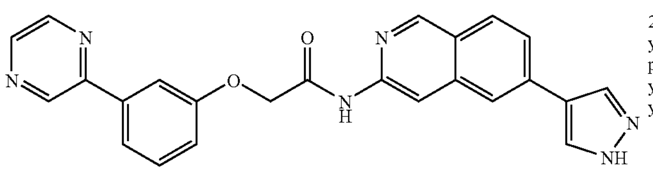 | 2-(3-pyrazin-2-ylphenoxy)-N-[6-(1H-pyrazol-4-yl)isoquinolin-3-yl]acetamide | 423 |
| 33 | 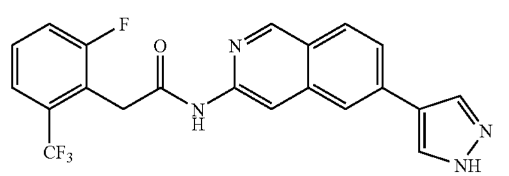 | N-[6-(1H-pyrazol-4-yl)isoquinolin-3-yl]-2-[2-(trifluoromethyl-6-fluoro)phenyl]acetamide | 415 |
| 34 | 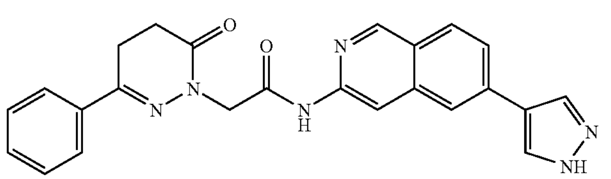 | 2-(6-oxo-3-phenyl-5,6-dihydropyridazin-1(4H)-yl)-N-[6-(1H-pyrazol-4-yl)isoquinolin-3-yl]acetamide | 425 |

-continued

| Example Number | Structure | Compound Name | m/z | ¹H NMR |
|---|---|---|---|---|
| 35 | 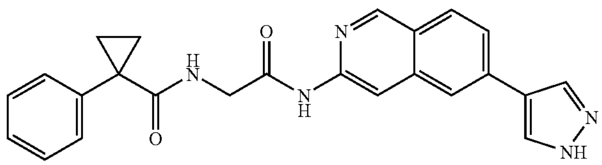 | N-(2-oxo-2-{[6-(1H-pyrazol-4-yl)isoquinolin-3-yl]amino)ethyl)-1-phenylcyclopropanecarboxamide | 412 | |
| 36 | 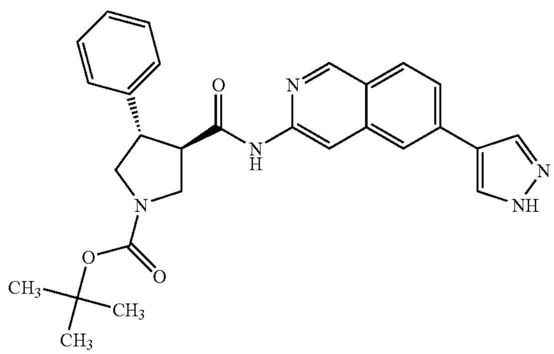 | tert-butyl (3S,4R)-3-phenyl-4-({[6-(1H-pyrazol-4-yl)isoquinolin-3-yl]aminocarbonyl)pyrrolidine-1-carboxylate | 484 | |
| 37 | 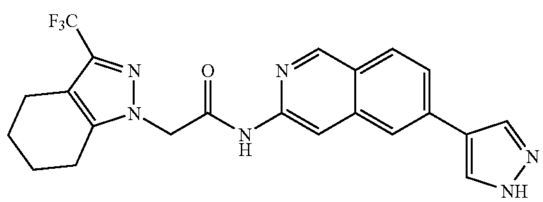 | N-[6-(1H-pyrazol-4-yl)isoquinolin-3-yl]-2-[3-(trifluoromethyl)-4,5,6,7-tetrahydro-1H-indazol-1-yl]acetamide | 441 | |
| 38 | 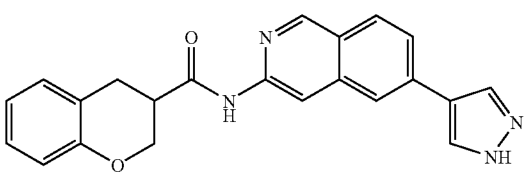 | N-[6-(1H-pyrazol-4-yl)isoquinolin-3-yl]chromane-3-carboxamide | 371 | |
| 39 | 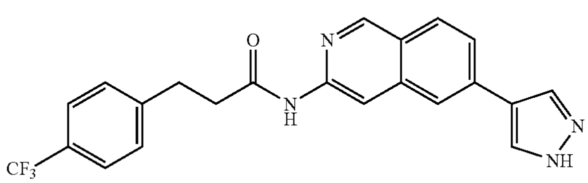 | N-[6-(1H-pyrazol-4-yl)isoquinolin-3-yl]-3-[4-(trifluoromethyl)phenyl]propanamide | 411 | |
| 40 | 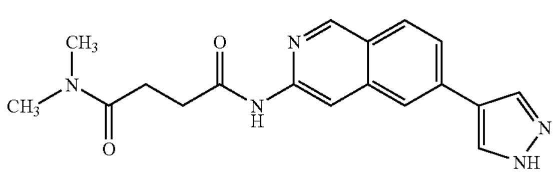 | N,N-dimethyl-N'-[6-(1H-pyrazol-4-yl)isoquinolin-3-yl]succinamide | 338 | |
| 41 | 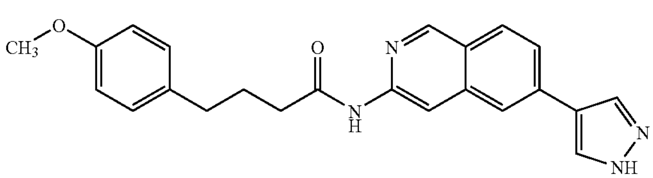 | 4-(4-methoxyphenyl)-N-[6-(1H-pyrazol-4-yl)isoquinolin-3-yl]butanamide | 386 | |

-continued

| Example Number | Structure | Compound Name | m/z ¹H NMR |
|---|---|---|---|
| 42 | 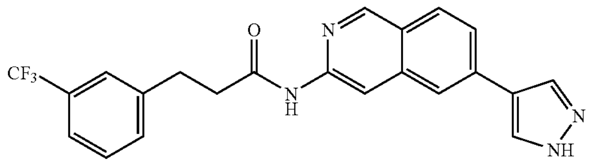 | N-[6-(1H-pyrazol-4-yl)isoquinolin-3-yl]-3-[3-(trifluoromethyl)phenyl]propanamide | 411 |
| 43 | 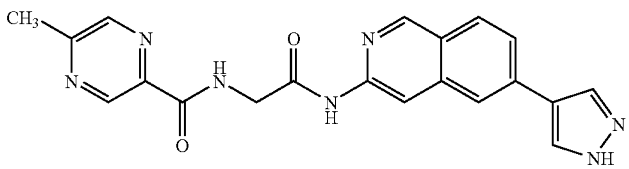 | 5-methyl-N-(2-oxo-2-{[6-(1H-pyrazol-4-yl)isoquinolin-3-yl]amino}ethyl)pyrazine-2-carboxamide | 388 |
| 44 | 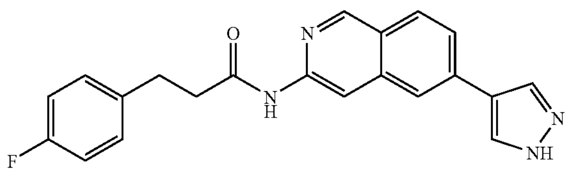 | 3-(4-fluorophenyl)-N-[6-(1H-pyrazol-4-yl)isoquinolin-3-yl]propanamide | 361 |
| 45 | 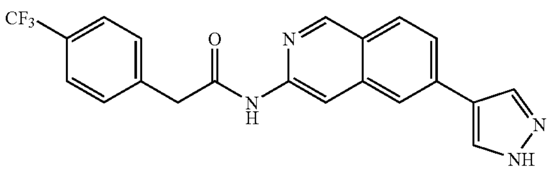 | N-[6-(1H-pyrazol-4-yl)isoquinolin-3-yl]-2-[4-(trifluoromethyl)phenyl]acetamide | 397 |
| 46 | 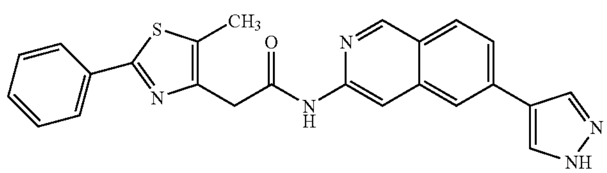 | 2-(5-methyl-2-phenyl-1,3-thiazol-4-yl)-N-[6-(1H-pyrazol-4-yl)isoquinolin-3-yl]acetamide | 426 |
| 47 | 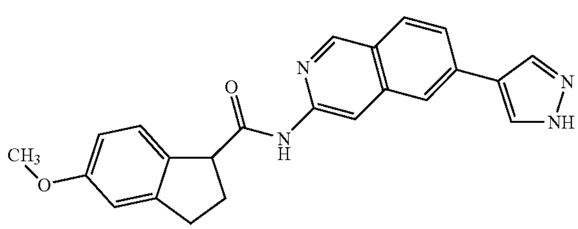 | 5-methoxy-N-[6-(1H-pyrazol-4-yl)isoquinolin-3-yl]indane-1-carboxamide | 385 (400 MHz, DMSO-$d_6$) δ: 2.23-2.45 (2 H, m), 2.71-2.89 (1H, m), 2.95-3.08 (1H, m), 3.68 (3H, s), 4.29 (1H, t, J = 7.18 Hz), 6.77 (1H, dd, J = 8.31, 2.27 Hz), 6.90 (1H, d, J = 2.01 Hz), 7.17 (1H, d, J = 8.31 Hz), 7.82 (1H, dd, J = 8.56, 1.26 Hz) 8.02, (1H, d, J = 8.56 Hz), 8.08 (1H, s), 8.28 (2 H, s), 8.43 (1H, s), 9.07 (1H, s), 10.86 (1H, s,) |
| 48 | 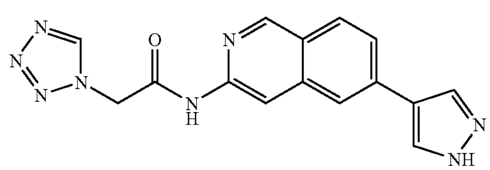 | N-[6-(1H-pyrazol-4-yl)isoquinolin-3-yl]-2-(1H-tetrazol-1-yl)acetamide | 321 |
| 49 | 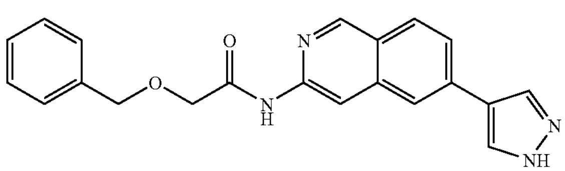 | 2-(benzyloxy)-N-[6-(1H-pyrazol-4-yl)isoquinolin-3-yl]acetamide | 359 |

-continued

| Example Number | Structure | Compound Name | m/z ¹H NMR |
|---|---|---|---|
| 50 | 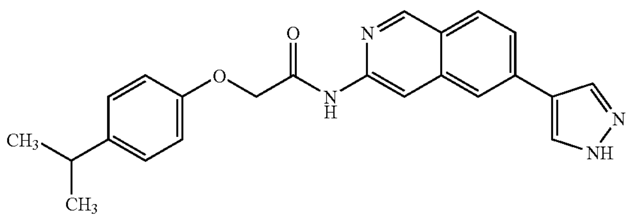 | 2-(4-isopropylphenoxy)-N-[6-(1H-pyrazol-4-yl)isoquinolin-3-yl]acetamide | 387 |
| 51 | 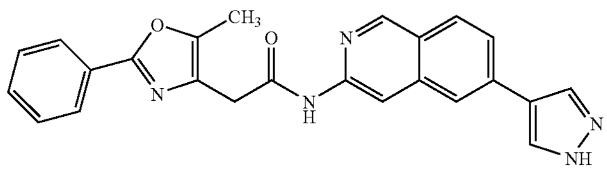 | 2-(5-methyl-2-phenyl-1,3-oxazal-4-yl)-N-[6-(1H-pyrazol-4-yl)isoquinolin-3-yl]acetamide | 410 |
| 52 | 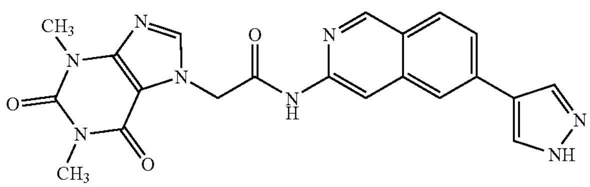 | 2-(1,3-dimethyl-2,6-dioxo-1,2,3,6-tetrahydro-7H-purin-7-yl)-N-[6-(1H-pyrazol-4-yl)isoquinolin-3-yl]acetamide | 432 |
| 53 | 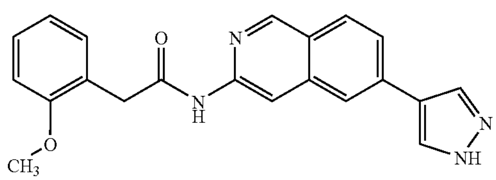 | 2-(2-methoxyphenyl)-N-[6-(1H-pyrazol-4-yl)isoquinolin-3-yl]acetamide | 459 |
| 54 | 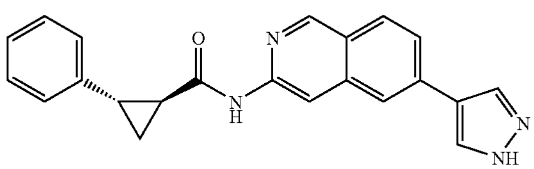 | (1S,2S)-2-phenyl-N-[6-(1H-pyrazol-4-yl)isoquinolin-3-yl]cyclopropane-carboxamide | 455 |
| 55 | 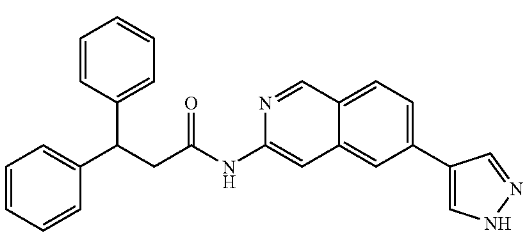 | 3,3-diphenyl-N-[6-(1H-pyrazol-4-yl)isoquinolin-3-yl]propanamide | 419 |
| 56 | 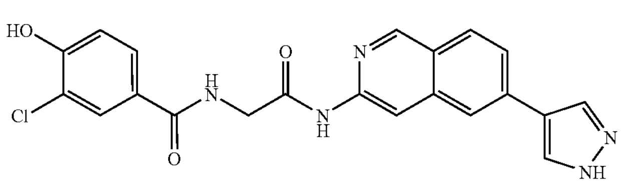 | 3-chloro-4-hydroxy-N-(2-oxo-2-{[6-(1H-pyrazol-4-yl)isoquinolin-3-yl]amino}ethyl)benzamide | 422 |

| Example Number | Structure | Compound Name | m/z | 1H NMR |
|---|---|---|---|---|
| 57 | CH3, CH3, isopropyl, cyclohexyl with OCH2C(O)NH-isoquinoline-pyrazole structure | 2-{[(1R,2S,5R)-2-isopropyl-5-methylcyclohexyl]oxy}-N-[6-(1H-pyrazol-4-yl)isoquinolin-3-yl]acetamide | 407 | |

Example 58

2-[(trans-4-hydroxycyclohexyl)amino]-N-methylquinazoline-7-carboxamide

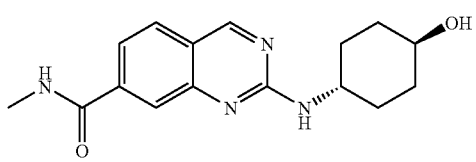

To a solution of 2-[(trans-4-hydroxycyclohexyl)amino]quinazoline-7-carboxylic acid (116 mg, 0.404 mmol) in DMF (3 mL) was added EDCl (93 mg, 0.484 mmol), HOBt (60 mg, 0.444 mmol), NMM (0.111 mL, 1.01 mmol) followed by the methylamine solution (2 M in THF, 0.303 mL, 0.606 mmol) and the mixture stirred at ambient temperature for 16 hours. The solvents were removed in vacuo and the residue azeotroped with MeOH (10 mL). The resulting yellow gum was purified directly by Biotage 25M; loaded in 2% MeOH/$CH_2Cl_2$, and eluted with 2-7% MeOH/$CH_2Cl_2$ over 520 mL. Product not fully eluted so continued over another 300 mL to 10% MeOH/$CH_2Cl_2$ to give a solid that was then triturated with EtOAc, filtered and dried in vacuo to yield the title compound as a yellow solid, 78 mg, 65%. $^1$H NMR (400 MHz, DMSO-$D_6$) δ ppm 9.11 (1H, s) 8.68 (1H, d, J=3.54 Hz) 7.90 (1H, s) 7.81 (1H, d, J=8.34 Hz) 7.57 (1H, d, J=8.34 Hz) 7.39 (1H, d, J=6.57 Hz) 4.56 (1H, d, J=4.29 Hz) 3.79 (1H, s) 3.36-3.50 (1H, m) 2.79 (3H, d, J=4.55 Hz) 1.80-2.03 (4H, m) 1.17-1.43 (4H, m); MS (API+) for $C_{16}H_{20}N_4O_2$ m/z 301.2 (M+H)$^+$.

Preparation of intermediate 1: 2-[(trans-4-hydroxycyclohexyl)amino]quinazoline-7-carboxylic acid

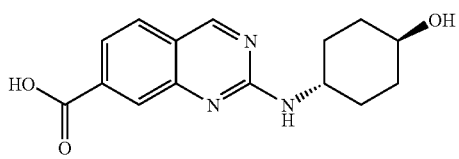

To a solution of methyl 2-[(trans-4-hydroxycyclohexyl)amino]quinazoline-7-carboxylate (3090 mg, 10.3 mmol) in THF (100 mL) was added MeOH (20 mL) followed by 2 M NaOH (20 mL, 40 mmol) and the mix stirred at R.T. for 3 hours. The solvents were stripped and the mix acidified with a stoichiometric amount of 1M HCl giving a yellow precipitate that was filtered off and washed with water and air dried to yield the title compound as a bright yellow solid, 2.7 g, 92%. $^1$H NMR (400 MHz, DMSO-$D_6$) δ ppm 13.30 (1H, s) 9.17 (1H, s) 7.96 (1H, s) 7.85 (1H, d, J=8.34 Hz) 7.64 (1H, d, J=8.34 Hz) 7.48 (1H, s) 4.57 (1H, s) 3.79 (1H, s) 1.79-2.04 (4H, m) 1.17-1.43 (4H, m); MS (API−) for $C_{15}H_{17}N_3O_3$ m/z 286.1 (M−H)$^+$.

Preparation of intermediate 2: methyl 2-[(trans-4-hydroxycyclohexyl)amino]quinazoline-7-carboxylate

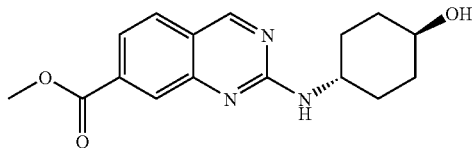

To a solution of methyl 2-chloroquinazoline-7-carboxylate (50 mg, 0.225 mmol) in acetonitrile (5 mL) was added trans-aminocyclyhexanol (52 mg, 0.449 mmol) followed by DBU (0.0672 mL, 0.449 mmol) to form a dark yellow solution that was stirred for 16 hours at 65° C. The solvents were stripped and the residue purified directly by Biotage 25M eluting with 2-9% MeOH/DCM over 600 mL. Product came off with trace impurity so re-columned using 1-6% MeOH/DCM to yield the title compound as a yellow solid, 59 mg, 87%. $^1$H NMR (400 MHz, DMSO-$D_6$) δ ppm 9.18 (1H, s) 7.97 (1H, s) 7.88 (1H, d, J=8.34 Hz) 7.65 (1H, dd, J=8.34, 1.26 Hz) 7.51 (1H, d, J=7.33 Hz) 4.56 (1H, d, J=4.55 Hz) 3.89 (3H, s) 3.78 (1H, s) 3.36-3.48 (1H, m) 1.79-2.03 (4H, m) 1.15-1.47 (4H, m); MS (API+) for $C_{16}H_{19}N_3O_3$ m/z 302.2 (M+H)+.

Preparation of intermediate 3: methyl 2-chloroquinazoline-7-carboxylate

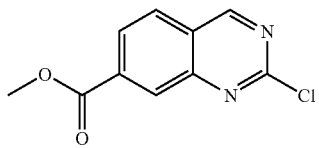

To a solution of methyl 2,4-dichloroquinazoline-7-carboxylate (1250 mg, 4.86 mmol) in EtOAc (100 mL) at R.T. was added Hunig's base (0.847 mL, 4.86 mmol) to form a pale yellow solution. The Pd catalyst was added and the mix hydrogenated with a $H_2$ balloon for 1 hour. Water (20 mL) was added to solubilize salts, and mix filtered to remove Pd. The aqueous layer separated and organics dried over MgSO4, filtered and stripped to yield a residue (yellow solid) that was purified by Biotage 40M chromatography (loaded in DCM) eluting with 15-60% EtOAc/Hex over 2000 mL to afford the title compound as a pale yellow solid, 724 mg, 67%. $^1$H NMR (400 MHz, DMSO-$D_6$) δ ppm 9.75 (1H, s) 8.45 (1H, s) 8.37 (1H, d, J=8.34 Hz) 8.13-8.30 (1H, m) 3.96 (3H, s); MS (API+) for $C_{10}H_7N_2ClO_2$ m/z 223.1 (M+H)+.

Preparation of intermediate 4: methyl 2,4-dichloroquinazoline-7-carboxylate

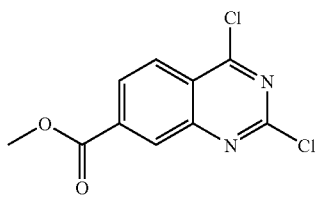

To a 250 mL flask charged with methyl 2,4-dihydroxyquinazoline-7-carboxylate was added $POCl_3$ (76 mL), $PCl_5$ (12.1 g, 58.1 mmol), and the suspension heated at reflux overnight under nitrogen. In morning a dark orange solution has formed. The $POCl_3$ was removed and the residue azeotroped with toluene to yield an orange solid that was taken into DCM (50 mL) and added slowly to stirred sat$^d$ NaHCO$_3$ (300 mL). The bi-phasic solution was then diluted with DCM (100 mL) and water (30 mL) and stirred for 1 hour at room temp. DCM (500 mL) was added and the mix transferred to a sep-funnel. The DCM layer was removed along with a large amount of ppt. The aq. was extracted with DCM (3×100 mL) and the combined organics dried over MgSO$_4$, filtered and stripped to a orange solid that was purified by Biotage 65 flash chromatography eluting with DCM –3% MeOH/DCM over 3.5 L to reveal the title compound as a white solid, 4.4 g, 59%. $^1$H NMR (400 MHz, DMSO-$D_6$) δ ppm 8.47 (1H, d, J=1.01 Hz) 8.43 (1H, d, J=8.84 Hz) 8.29 (1H, dd, J=8.72, 1.64 Hz) 3.96 (3H, s); MS (API+) for $C_{10}H_6N_2Cl_2O_2$ m/z 257.0 (M+H)+.

Preparation of intermediate 5: methyl 2,4-dihydroxyquinazoline-7-carboxylate

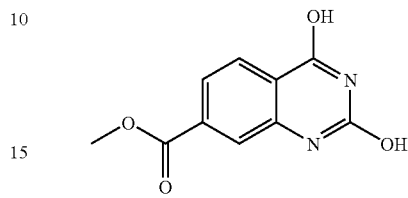

To a stirred suspension of the urea (32.5 g, 129 mmol) in methanol (500 mL) was added sodium methoxide powder (13.8 g, 248 mmol) in one portion and the suspension heated at reflux for 16 hours under nitrogen. The thick white suspension was cooled to 0° C. and acidified to pH=2 with 1M HCl and the ppt filtered off, washed with water (2×200 mL), MeOH (2×100 mL), ether (2×200 mL) and vacuum dried to yield the title compound as a white solid, 26.5 g, 94%. $^1$H NMR (400 MHz, DMSO-D6) δ ppm 11.47 (1H, s) 11.31 (1H, s) 7.99 (1H, d, J=8.08 Hz) 7.74 (1H, d, J=1.01 Hz) 7.67 (1H, dd, J=8.34, 1.52 Hz) 3.88 (3H, s); MS (API+) for $C_{10}H_8N_2O_4$ m/z 221.1 (M+H)+.

Preparation of intermediate 6: dimethyl 2-[(aminocarbonyl)amino]terephthalate

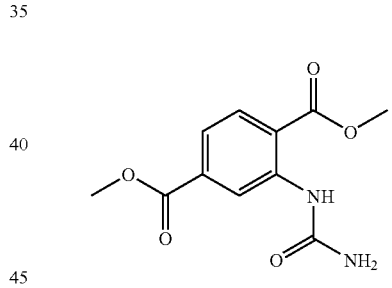

To a 1 L flask charged with 2-aminoterephthalic acid dimethyl ester (29.4 g, 141 mmol) was added AcOH (160 mL) and the suspension heated to 60° C. until a solution was formed. A solution of potassium cyanate (23.4 g, 288 mmol) in water (50 mL) was then added to the stirred solution at 60° C. Effervescence was seen and a white ppt crashed out immediately, hindering stirring. AcOH was added (70 mL) to aid stirring and the suspension was stirred at 75° C. for 7 hrs. Another 1 eq of cyanate added portion wise (dry). More effervescence was seen and the reaction left for 16 hours at 70° C. The reaction was cooled to 0° C. and the product ppt was filtered off, the flask washed with water to get all product out. The material was washed with water (150 mL) and air dried o/n under vacuum. The crude product was suspended in MeOH (300 mL) and stirred under reflux for 1 hour. The suspension was cooled to room temperature and filtered. The product was washed with cold MeOH (300 mL) and ether and dried in vacuo to afford the title compound as a white solid, 31.5 g, 89%. $^1$H NMR (400 MHz, DMSO-$D_6$) δ ppm 9.71 (1H, s) 8.97 (1H, s) 7.98 (1H, d, J=8.08 Hz) 7.46-7.57 (1H, m) 6.73 (2H, s) 3.88 (6H, s).

Examples 59-72 were Prepared According to the Procedure Described for Example 58

| Example Number | Structure | Compound Name | LRMS m/z | $^1$H NMR |
|---|---|---|---|---|
| 59 | 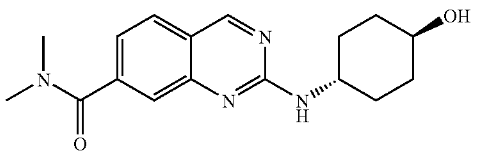 | 2-[(trans-4-hydroxycyclohexyl)amino]-N,N-dimethylquinazoline-7-carboxamide | 315.2 | $^1$H NMR (400 MHz, DMSO-D$_6$) δ ppm 9.10 (1 H, s) 7.80 (1 H, d, J = 8.08 Hz) 7.37 (2 H, d, J = 8.08 Hz) 7.13 (1 H, dd, J = 8.21, 1.39 Hz) 4.55 (1 H, d, J = 4.29 Hz) 3.69-3.87 (1 H, m) 3.34-3.53 (1 H, m) 3.00 (3 H, s) 2.89 (3 H, s) 1.71-2.03 (4 H, m) 1.19-1.43 (4 H, m). |
| 60 | 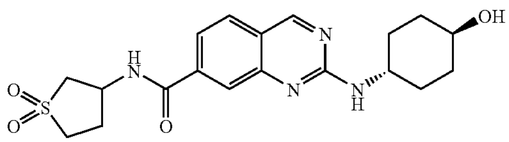 | N-(1,1-dioxidotetrahydro-3-thienyl)-2-[(trans-4-hydroxycyclohexyl)amino]quinazoline-7-carboxamide | 405.2 | $^1$H NMR (400 MHz, DMSO-D$_6$) δ ppm 9.13 (1 H, s) 9.02 (1 H, d, J = 6.82 Hz) 7.98 (1 H, s) 7.83 (1 H, d, J = 8.34 Hz) 7.59 (1 H, d, J = 8.34 Hz) 7.44 (1 H, d, J = 7.58 Hz) 4.65-4.84 (1 H, m) 4.57 (1 H, d, J = 4.29 Hz) 3.72-3.87 (1 H, m) 3.51 (1 H, dd, J = 13.39, 7.83 Hz) 3.34-3.46 (2 H, m) 3.05-3.27 (2 H, m) 2.38-2.47 (1 H, m) 2.17-2.34 (1 H, m) 1.79-2.02 (4 H, m) 1.14-1.46 (4 H, m).S) |
| 61 | 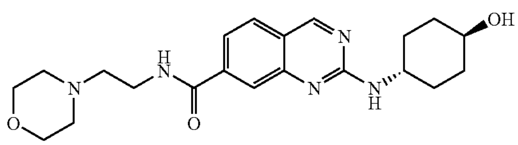 | 2-[(trans-4-hydroxycyclohexyl)amino]-N-(2-morpholin-4-ylethyl)quinazoline-7-carboxamide | 400.2 | $^1$H NMR (400 MHz, DMSO-D$_6$) δ ppm 9.12 (1 H, s) 8.68 (1 H, s) 7.92 (1 H, s) 7.81 (1 H, d, J = 8.34 Hz) 7.57 (1 H, d, J = 8.34 Hz) 7.40 (1 H, d, J = 6.82 Hz) 4.50-4.62 (1 H, m) 3.79 (1 H, s) 3.51-3.61 (4 H, m) 2.45-2.51 (2 H, m) 2.41 (4 H, s) 1.81-1.99 (4 H, m) 1.18-1.41 (4 H, m). |
| 62 | 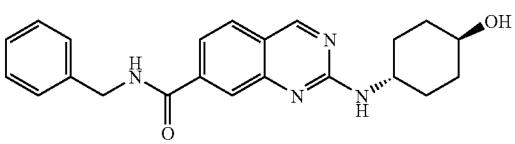 | N-benzyl-2-[(trans-4-hydroxycyclohexyl)amino]quinazoline-7-carboxamide | 377.2 | $^1$H NMR (400 MHz, DMSO-D$_6$) δ ppm 9.30 (1 H, s) 9.12 (1 H, s) 7.99 (1 H, s) 7.83 (1 H, d, J = 8.08 Hz) 7.62 (1 H, d, J = 8.34 Hz) 7.41 (1 H, d, J = 6.82 Hz) 7.29-7.36 (4 H, m) 7.18-7.27 (1 H, m) 4.56 (1 H, d, J = 4.29 Hz) 4.48 (2 H, d, J = 6.06 Hz) 3.78 (1 H, s) 3.36-3.49 (1 H, m) 1.80-1.91 (4 H, m) 1.17-1.41 (4 H, m). |
| 63 | 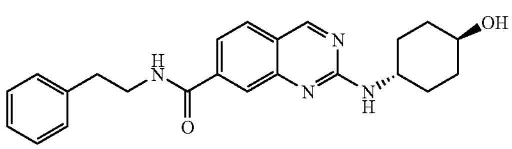 | 2-[(trans-4-hydroxycyclohexyl)amino]-N-(2-phenylethyl)quinazoline-7-carboxamide | 391.2 | $^1$H NMR (400 MHz, DMSO-D$_6$) δ ppm 8.97 (1 H, s) 7.76 (1 H, s) 7.70 (1 H, d, J = 8.08 Hz) 7.53 (1 H, dd, J = 8.21, 1.39 Hz) 7.18-7.39 (5 H, m) 6.39 (1 H, s) 5.28 (2 H, d, J = 7.83 Hz) 3.83-4.00 (1 H, m) 3.55-3.78 (3 H, m) 2.95 (2 H, t, J = 7.20 Hz) 2.19 (2 H, d, J = 11.62 Hz) 2.01 (2 H, d, J = 5.31 Hz) 1.40-1.54 (2 H, m) 1.27-1.39 (2 H, m). |
| 64 | 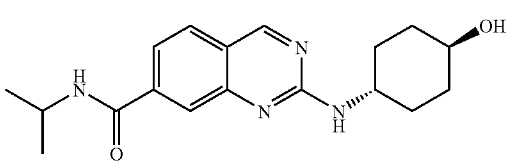 | 2-[(trans-4-hydroxycyclohexyl)amino]-N-isopropylquinazoline-7-carboxamide | 329.2 | $^1$H NMR (400 MHz, CD$_2$Cl$_2$-D$_2$) δ ppm 8.98 (1 H, s) 7.81 (1 H, s) 7.72 (1 H, d, J = 8.34 Hz) 7.59 (1 H, dd, J = 8.08, 1.52 Hz) 6.16 (1 H, s) 5.28 (1 H, d, J = 7.58 Hz) 4.19-4.32 (1 H, m) 3.86-3.99 (1 H, m) 3.61-3.73 (1 H, m) 2.20 (2 H, d, J = 11.87 Hz) 1.96-2.08 (2 H, m) 1.40-1.52 (2 H, m) 1.29-1.40 (2 H, m) 1.27 (6 H, d, J = 6.57 Hz). |

-continued

| Example Number | Structure | Compound Name | LRMS m/z | $^1$H NMR |
|---|---|---|---|---|
| 65 | 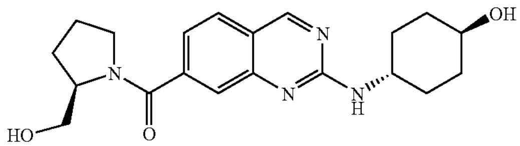 | trans-4-[(7-{[(2R)-2-(hydroxymethyl)pyrrolidin-1-yl]carbonyl}quinazolin-2-yl)amino]cyclohexanol | 371.2 | $^1$H NMR (400 MHz, CD$_2$Cl$_2$-D$_2$) δ ppm 8.97 (1 H, s) 7.71 (1 H, d, J = 8.08 Hz) 7.59 (1 H, s) 7.27 (1 H, dd, J = 8.21, 1.39 Hz) 5.21-5.30 (1 H, m) 4.71 (1 H, dd, J = 7.20, 2.40 Hz) 4.26-4.41 (1 H, m) 3.87-4.02 (1 H, m) 3.58-3.82 (3 H, m) 3.39-3.53 (2 H, m, J = 8.21, 4.93 Hz) 2.11-2.25 (3 H, m) 1.95-2.06 (2 H, m) 1.82-1.93 (1 H, m) 1.69-1.81 (1 H, m) 1.61-1.69 (1 H, m) 1.39-1.53 (2 H, m) 1.24-1.39 (2 H, m). |
| 66 | 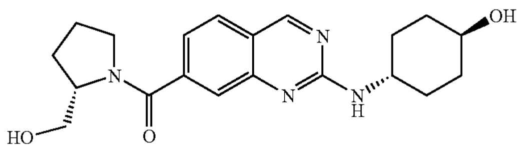 | trans-4-[(7-{[(2S)-2-(hydroxymethyl)pyrrolidin-1-yl]carbonyl}quinazolin-2-yl)amino]cyclohexanol | 371.2 | $^1$H NMR (400 MHz, CHLOROFORM-D) δ ppm 8.98 (1 H, s) 7.71 (1 H, d, J = 8.08 Hz) 7.66 (1 H, s) 7.32 (1 H, d, J = 8.08 Hz) 4.72 (1 H, s) 4.34-4.49 (1 H, m) 3.90-4.07 (1 H, m) 3.63-3.86 (3 H, m) 3.43-3.55 (2 H, m) 2.12-2.27 (3 H, m) 2.04 (2 H, dd, J = 13.01, 3.41 Hz) 1.83-1.95 (1 H, m) 1.60-1.84 (2 H, m) 1.44-1.56 (2 H, m) 1.27-1.41 (2 H, m). |
| 67 | 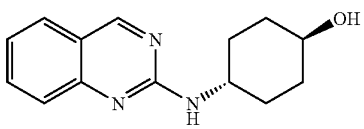 | trans-4-(quinazolin-2-ylamino)cyclohexanol | 244.2 | $^1$H NMR (400 MHz, DMSO-D$_6$) δ ppm 9.06 (1 H, s) 7.71-7.86 (1 H, m) 7.57-7.69 (1 H, m) 7.43 (1 H, d, J = 7.83 Hz) 7.19 (2 H, q, J = 6.99 Hz) 4.54 (1 H, d, J = 4.29 Hz) 3.64-3.89 (1 H, m) 3.35-3.54 (1 H, m) 1.76-1.97 (4 H, m) 1.18-1.45 (4 H, m). |
| 68 | 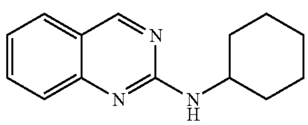 | N-[6-(1H-pyrazol-4-yl)isoquinolin-3-yl]isoindoline-1-carboxamide | 228.2 | $^1$H NMR (400 MHz, DMSO-D$_6$) δ ppm 9.06 (1 H, s) 7.74 (1 H, d, J = 7.83 Hz) 7.57-7.68 (1 H, m) 7.42 (1 H, d, J = 8.08 Hz) 7.03-7.29 (2 H, m) 3.75-3.96 (1 H, m) 1.83-2.02 (2 H, m, J = 9.85 Hz) 1.67-1.81 (2 H, m) 1.60 (1 H, d, J = 12.63 Hz) 1.20-1.44 (4 H, m) 0.98-1.20 (1 H, m). |
| 69 | 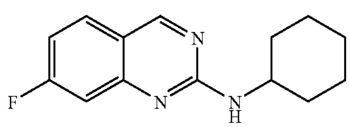 | N-cyclohexylquinazolin-2-amine | 246.2 | $^1$H NMR (400 MHz, DMSO-D$_6$) δ ppm 9.04 (1 H, s) 7.84 (1 H, dd, J = 8.59, 6.82 Hz) 7.44 (1 H, d, J = 7.58 Hz) 7.13 (1 H, d, J = 9.35 Hz) 6.85-7.10 (1 H, m) 3.82 (1 H, s) 1.90 (2 H, d, J = 7.83 Hz) 1.72 (2 H, dd, J = 9.09, 2.78 Hz) 1.59 (1 H, d, J = 12.13 Hz) 1.19-1.41 (4 H, m) 0.87-1.20 (1 H, m). |
| 70 | 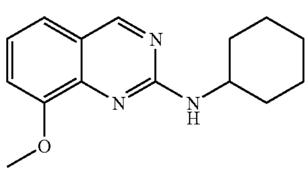 | N-cyclohexyl-7-fluoroquinazolin-2-amine | 258.2 | |
| 71 | 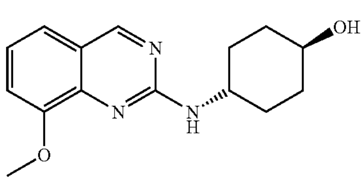 | N-cyclohexyl-8-methoxyquinazolin-2-amine | 274.3 | $^1$H NMR (400 MHz, DMSO-D$_6$) δ ppm 9.03 (1 H, s) 7.30 (1 H, dd, J = 7.58, 1.52 Hz) 7.16-7.26 (1 H, m) 7.03-7.15 (2 H, m) 4.54 (1 H, d, J = 4.29 Hz) 3.87 (3 H, s) 3.72-3.85 (1 H, m) 3.34-3.56 (1 H, m) 1.74-2.00 (4 H, m) 1.15-1.39 (4 H, m). |

| Example Number | Structure | Compound Name | LRMS m/z | $^1$H NMR |
|---|---|---|---|---|
| 72 | 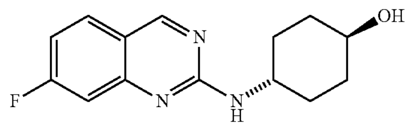 | trans-4-[(7-fluoroquinazolin-2-yl)amino]cyclohexanol | 262.1 | $^1$H NMR (400 MHz, DMSO-D$_6$) δ ppm 9.04 (1 H, s) 7.75-7.94 (1 H, m) 7.40 (1 H, d, J = 6.82 Hz) 7.15 (1 H, d, J = 6.82 Hz) 6.95-7.10 (1 H, m) 4.55 (1 H, d, J = 4.29 Hz) 3.79 (1 H, s) 3.39 (1 H, dd, J = 9.22, 4.93 Hz) 1.68-2.01 (4 H, m) 1.17-1.46 (4 H, m). |

Example 73

2-[(trans-4-hydroxycyclohexyl)amino]quinazolin-8-ol

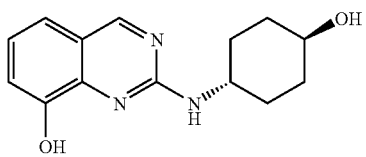

To a solution of trans-4-[(8-methoxyquinazolin-2-yl)amino]cyclohexanol (5.90 g, 21.6 mmol) in DMF (300 mL) was added sodium ethanethiolate (5.45 g, 65 mmol) and the mix heated to 11° C. for 3 hours under nitrogen. The reaction was cooled to ambient temperature and the DMF removed in-vacuo. The residue was diluted with MeOH (20 mL), DCM (200 mL) and EtOAc (100 mL) and then acidified with 1 M HCl to pH=1. The mix was concentrated in-vacuo where a yellow ppt crashed out. This was filtered off, washed with water (2×50 mL), EtOAc (100 mL) and dried to yield the title compound as a yellow solid, 4.9 g, 88%. $^1$H NMR (400 MHz, DMSO-D6) δ ppm 9.00 (2H, s) 7.21 (1H, d, J=6.32 Hz) 7.16 (1H, s) 6.98-7.09 (2H, m) 4.55 (1H, s) 3.36 (2H, d, J=23.75 Hz) 1.86 (4H, dd, J=28.30, 8.59 Hz) 1.22-1.48 (4H, m); MS (API+) for C$_{14}$H$_{17}$N$_3$O$_2$ m/z 260.2 (M+H)$^+$.

Example 74 trans-4-[(7-methoxyquinazolin-2-yl)amino]cyclohexanol

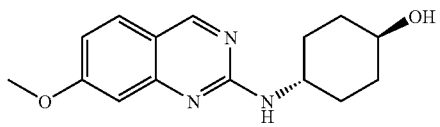

To a solution of trans-4-[(7-fluoroquinazolin-2-yl)amino]cyclohexanol (800 mg, 3.06 mmol) in MeOH (25 mL) was added sodium methoxide powder (1.65 g, 30.62 mmol) and the solution heated to reflux for 16 hours under nitrogen. The mix was cooled and the solvents evaporated. The residue was diluted with water (100 mL), brine (50 mL) and extracted with DCM (4×150 mL), and the combined organics were dried over MgSO$_4$, filtered and stripped. The residue was purified via Biotage flash chromatography (40M) eluting with 2-6% MeOH/DCM over 1300 mL to yield the title compound as an off white solid, 830 mg, 99%. $^1$H NMR (400 MHz, DMSO-D$_6$) δ ppm 8.86 (1H, s) 7.63 (1H, d, J=8.84 Hz) 7.08 (1H, d, J=6.57 Hz) 6.78 (2H, dd, J=8.72, 2.15 Hz) 4.55 (1H, d, J=4.55 Hz) 3.86 (3H, s) 3.71-3.84 (1H, m) 3.35-3.50 (1H, m) 1.76-2.02 (4H, m) 1.14-1.42 (4H, m); MS (API+) for C$_{15}$H$_{19}$N$_3$O$_2$ m/z 274.2 (M+H)$^+$.

Example 75

2-[(trans-4-hydroxycyclohexyl)amino]quinazolin-7-ol

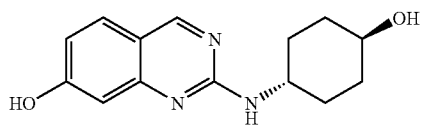

To a solution of trans-4-[(7-methoxyquinazolin-2-yl)amino]cyclohexanol (161 mg, 0.583 mmol) in DMF (10 mL) was added sodium ethanethiolate (248 mg, 2.95 mmol) and the mix heated to 110° C. for 16 hours. The reaction was cooled and the residue was purified directly via Biotage F/C eluting with 5-10% MeOH/DCM to afford the title compound as an off-white solid, 120 mg, 78%. $^1$H NMR (400 MHz, DMSO-D$_6$) δ ppm 10.28 (1H, s) 8.79 (1H, s) 7.57 (1H, d, J=8.59 Hz) 6.96 (1H, d, J=8.08 Hz) 6.54-6.79 (2H, m) 4.54 (1H, d, J=3.54 Hz) 3.74 (1H, d, J=3.28 Hz) 3.38 (1H, s) 1.67-1.93 (4H, m) 1.20-1.39 (4H, m); MS (API+) for C$_{14}$H$_{17}$N$_3$O$_2$ m/z 260.2 (M+H)$^+$.

Example 76 trans-4-{[7-(tetrahydrofuran-3-yloxy)quinazolin-2-yl]amino}cyclohexanol

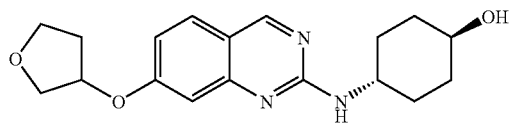

To a solution of tetrahydrofuran-3-ol (337 mg, 3.83 mmol) in THF (5 mL) was added NaH (153 mg, 60% disp. in oil, 3.83 mmol) and the mix stirred at r.t. for 20 min., forming a pale suspension. To this was added trans-4-[(7-fluoroquinazolin-2-yl)amino]cyclohexanol (100 mg, 0.383 mmol) and a yellow suspension formed almost immediately. The suspension was stirred at r.t. for 30 min then heated to 45° C. for 1 hour, then heated to 65° C. for 30 min then cooled to R.T. overnight. The liquors were concentrated and diluted with water (10 mL) and EtOAc (25 mL) and shaken vigorously. The aq. was removed and the organics washed with water (10 mL), brine (10 mL), dried over MgSO$_4$, filtered and stripped to an oil. Purified by prep TLC eluting with EtOAc to yield the title compound as a white foam, 36 mg, 29%. $^1$H NMR (400 MHz, DICHLOROMETHANE-D$_2$) δ ppm 8.75 (1H, s) 7.53 (1H, d, J=8.84 Hz) 6.62-6.88 (2H, m) 5.18 (1H, d, J=7.83 Hz) 5.05 (1H, s) 3.81-4.08 (5H, m) 3.54-3.79 (2H, m) 2.22-2.43 (1H, m) 2.08-2.21 (3H, m) 1.91-2.07 (2H, m) 1.36-1.51 (4H, m) 1.19-1.38 (4H, m); MS (API+) for C$_{18}$H$_{23}$N$_3$O$_3$ m/z 330.2 (M+H)$^+$.

Example 77

2-[(trans-4-hydroxycyclohexyl)amino]-N-methylquinazoline-7-carboxamide

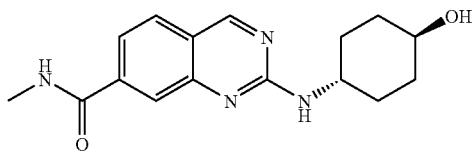

To a solution of 2-[(trans-4-hydroxycyclohexyl)amino]quinazoline-7-carboxylic acid (116 mg, 0.404 mmol) in DMF (3 mL) was added EDCl (93 mg, 0.484 mmol), HOBt (60 mg, 0.444 mmol), NMM (0.111 mL, 1.01 mmol) followed by the methylamine solution (2 M in THF, 0.303 mL, 0.606 mmol) and the mixture stirred at ambient temperature for 16 hours. The solvents were removed in vacuo and the residue azeotroped with MeOH (10 mL). The resulting yellow gum was purified directly by Biotage 25M; loaded in 2% MeOH/DCM, and eluted with 2-7% MeOH/DCM over 520 mL. Product not fully eluted so continued over another 300 mL to 10% MeOH/DCM to give a solid that was then triturated with EtOAc, filtered and dried in vacuo to yield the title compound as a yellow solid, 78 mg, 65%. $^1$H NMR (400 MHz, DMSO-D$_6$) □ ppm 9.11 (1H, s) 8.68 (1H, d, J=3.54 Hz) 7.90 (1H, s) 7.81 (1H, d, J=8.34 Hz) 7.57 (1H, d, J=8.34 Hz) 7.39 (1H, d, J=6.57 Hz) 4.56 (1H, d, J=4.29 Hz) 3.79 (1H, s) 3.36-3.50 (1H, m) 2.79 (3H, d, J=4.55 Hz) 1.80-2.03 (4H, m) 1.17-1.43 (4H, m); MS (API+) for C$_{16}$H$_{20}$N$_4$O$_2$ m/z 301.2 (M+H)$^+$.

Preparation of intermediate 77a: dimethyl 2-[(aminocarbonyl)amino]terephthalate

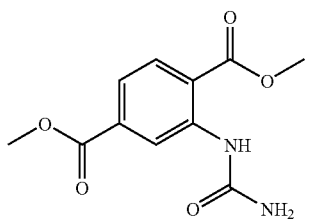

To a 1 L flask charged with 2-aminoterephthalic acid dimethyl ester (29.4 g, 141 mmol) was added AcOH (160 mL) and the suspension heated to 60° C. until a solution was formed. A solution of potassium cyanate (23.4 g, 288 mmol) in water (50 mL) was then added to the stirred solution at 60° C. Effervescence was seen and a white ppt crashed out immediately, hindering stirring. AcOH was added (70 mL) to aid stirring and the suspension was stirred at 75° C. for 7 hrs. Another 1 eq of cyanate added portion wise (dry). More effervescence was seen and the reaction left for 16 hours at 70° C. The reaction was cooled to 0° C. and the product ppt was filtered off, the flask washed with water to get all product out. The material was washed with water (150 mL) and air dried o/n under vacuum. The crude product was suspended in MeOH (300 mL) and stirred under reflux for 1 hour. The suspension was cooled to room temperature and filtered. The product was washed with cold MeOH (300 mL) and ether and dried in vacuo to afford the title compound as a white solid, 31.5 g, 89%. $^1$H NMR (400 MHz, DMSO-D$_6$) □ ppm 9.71 (1H, s) 8.97 (1H, s) 7.98 (1H, d, J=8.08 Hz) 7.46-7.57 (1H, m) 6.73 (2H, s) 3.88 (6H, s).

Preparation of intermediate 77b: methyl 2,4-dihydroxyquinazoline-7-carboxylate

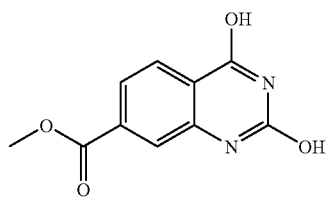

To a stirred suspension of the urea (32.5 g, 129 mmol) in methanol (500 mL) was added sodium methoxide powder (13.8 g, 248 mmol) in one portion and the suspension heated at reflux for 16 hours under nitrogen. The thick white suspension was cooled to 0° C. and acidified to pH=2 with 1 M HCl and the ppt filtered off, washed with water (2×200 mL), MeOH (2×100 mL), ether (2×200 mL) and vacuum dried to yield the title compound as a white solid, 26.5 g, 94%. $^1$H NMR (400 MHz, DMSO-D6) δ ppm 11.47 (1H, s) 11.31 (1H, s) 7.99 (1H, d, J=8.08 Hz) 7.74 (1H, d, J=1.01 Hz) 7.67 (1H, dd, J=8.34, 1.52 Hz) 3.88 (3H, s); MS (API+) for C$_{10}$H$_8$N$_2$O$_4$ m/z 221.1 (M+H)$^+$.

Preparation of intermediate 77c: methyl 2,4-dichloroquinazoline-7-carboxylate

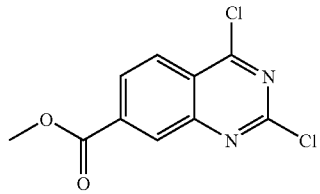

To a 250 mL flask charged with methyl 2,4-dihydroxyquinazoline-7-carboxylate was added POCl$_3$ (76 mL), PCl$_5$ (12.1 g, 58.1 mmol), and the suspension heated at reflux overnight under nitrogen. In morning a dark orange solution has formed. The POCl$_3$ was removed and the residue azeotroped with toluene to yield an orange solid that was taken into DCM (50 mL) and added slowly to stirred sat$^d$ NaHCO$_3$ (300 mL). The bi-phasic solution was then diluted with DCM (100 mL) and water (30 mL) and stirred for 1 hour at room temp. DCM (500 mL) was added and the mix transferred to a sep-funnel. The DCM layer was removed along with a large amount of ppt. The aq. was extracted with DCM (3×100 mL) and the combined organics dried over MgSO$_4$, filtered and stripped to a orange solid that was purified by Biotage 65 flash chromatography eluting with DCM −3% MeOH/DCM over 3.5 L to reveal the title compound as a white solid, 4.4 g, 59%. $^1$H NMR (400 MHz, DMSO-D$_6$) δ ppm 8.47 (1H, d, J=1.01 Hz) 8.43 (1H, d, J=8.84 Hz) 8.29 (1H, dd, J=8.72, 1.64 Hz) 3.96 (3H, s); MS (API+) for C$_{10}$H$_6$N$_2$Cl$_2$O$_2$ m/z 257.0 (M+H)$^+$.

Preparation of intermediate 77d: methyl 2-chloroquinazoline-7-carboxylate

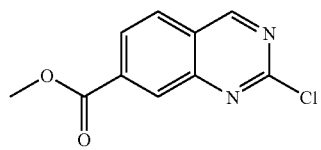

To a solution of methyl 2,4-dichloroquinazoline-7-carboxylate (1250 mg, 4.86 mmol) in EtOAc (100 mL) at R.T. was added Hunig's base (0.847 mL, 4.86 mmol) to form a pale yellow solution. The Pd catalyst was added and the mix hydrogenated with a H$_2$ balloon for 1 hour. Water (20 mL) was added to solubilize salts, and mix filtered to remove Pd. The aqueous layer separated and organics dried over MgSO$_4$, filtered and stripped to yield a residue (yellow solid) that was purified by Biotage 40M chromatography (loaded in DCM) eluting with 15-60% EtOAc/Hex over 2000 mL to afford the title compound as a pale yellow solid, 724 mg, 67%. $^1$H NMR (400 MHz, DMSO-D$_6$) δ ppm 9.75 (1H, s) 8.45 (1H, s) 8.37 (1H, d, J=8.34 Hz) 8.13-8.30 (1H, m) 3.96 (3H, s); MS (API+) for C$_{10}$H$_7$N$_2$ClO$_2$ m/z 223.1 (M+H)$^+$.

Preparation of intermediate 77e: methyl 2-[(trans-4-hydroxycyclohexyl)amino]quinazoline-7-carboxylate

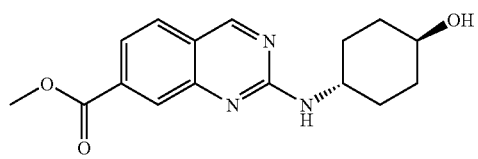

To a solution of methyl 2-chloroquinazoline-7-carboxylate (50 mg, 0.225 mmol) in acetonitrile (5 mL) was added trans-aminocyclyhexanol (52 mg, 0.449 mmol) followed by DBU (0.0672 mL, 0.449 mmol) to form a dark yellow solution that was stirred for 16 hours at 65° C. The solvents were stripped and the residue purified directly by Biotage 25M eluting with 2-9% MeOH/DCM over 600 mL. Product came off with trace impurity so re-columned using 1-6% MeOH/DCM to yield the title compound as a yellow solid, 59 mg, 87%. $^1$H NMR (400 MHz, DMSO-D$_6$) ☐ ppm 9.18 (1H, s) 7.97 (1H, s) 7.88 (1H, d, J=8.34 Hz) 7.65 (1H, dd, J=8.34, 1.26 Hz) 7.51 (1H, d, J=7.33 Hz) 4.56 (1H, d, J=4.55 Hz) 3.89 (3H, s) 3.78 (1H, s) 3.36-3.48 (1H, m) 1.79-2.03 (4H, m) 1.15-1.47 (4H, m); MS (API+) for C$_{16}$H$_{19}$N$_3$O$_3$ m/z 302.2 (M+H)$^+$.

Preparation of intermediate 77f: 2-[(trans-4-hydroxycyclohexyl)amino]quinazoline-7-carboxylic acid

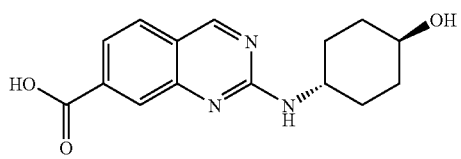

To a solution of methyl 2-[(trans-4-hydroxycyclohexyl)amino]quinazoline-7-carboxylate (3090 mg, 10.3 mmol) in THF (100 mL) was added MeOH (20 mL) followed by 2 M NaOH (20 mL, 40 mmol) and the mix stirred at R.T. for 3 hours. The solvents were stripped and the mix acidified with a stoichiometric amount of 1 M HCl giving a yellow precipitate that was filtered off and washed with water and air dried to yield the title compound as a bright yellow solid, 2.7 g, 92%. $^1$H NMR (400 MHz, DMSO-D$_6$) δ ppm 13.30 (1H, s) 9.17 (1H, s) 7.96 (1H, s) 7.85 (1H, d, J=8.34 Hz) 7.64 (1H, d, J=8.34 Hz) 7.48 (1H, s) 4.57 (1H, s) 3.79 (1H, s) 1.79-2.04 (4H, m) 1.17-1.43 (4H, m); MS (API−) for C$_{15}$H$_{17}$N$_3$O$_3$ m/z 286.1 (M−H)$^+$.

The following examples nos. 78-142 were prepared with non-critical substitutions and/or method changes in an analogous way to example 77:

| Example Number | Structure | Compound Name | LRMS m/z | $^1$H NMR |
|---|---|---|---|---|
| 78 | 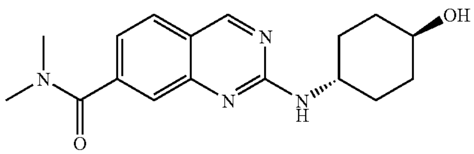 | 2-[(trans-4-hydroxycyclohexyl)amino]-N,N-dimethylquinazoline-7-carboxamide | 315.2 | $^1$H NMR (400 MHz, DMSO-D$_6$) δ ppm 9.10 (1 H, s) 7.80 (1 H, d, J = 8.08 Hz) 7.37 (2 H, d, J = 8.08 Hz) 7.13 (1 H, dd, J = 8.21, 1.39 Hz) 4.55 (1 H, d, J = 4.29 Hz) 3.69-3.87 (1 H, m) 3.34-3.53 (1 H, m) 3.00 (3 H, s) 2.89 (3 H, s) 1.71-2.03 (4 H, m) 1.19-1.43 (4 H, m) |
| 79 | 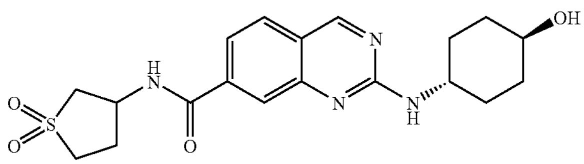 | N-(1,1-dioxidotetrahydro-3-thienyl)-2-[(trans-4-hydroxycyclohexyl)amino]quinazoline-7-carboxamide | 405.2 | $^1$H NMR (400 MHz, DMSO-D$_6$) δ ppm 9.13 (1 H, s) 9.02 (1 H, d, J = 6.82 Hz) 7.98 (1 H, s) 7.83 (1 H, d, J = 8.34 Hz) 7.59 (1 H, d, J = 8.34 Hz) 7.44 (1 H, d, J = 7.58 Hz) 4.65-4.84 (1 H, m) 4.57 (1 H, d, J = 4.29 Hz) 3.72-3.87 (1 H, m) 3.51 (1 H, dd, J = 13.39, 7.83 Hz) 3.34-3.46 (2 H, m) 3.05-3.27 (2 H, m) 2.38-2.47 (1 H, m) 2.17-2.34 (1 H, m) 1.79-2.02 (4 H, m) 1.14-1.46 (4 H, m). |
| 80 | 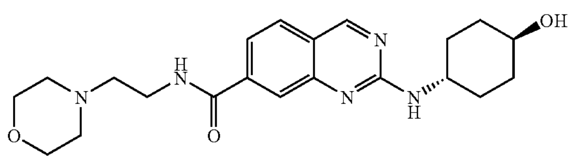 | 2-[(trans-4-hydroxycyclohexyl)amino]-N-(2-morpholin-4-ylethyl)quinazoline-7-carboxamide | 400.2 | $^1$H NMR (400 MHz, DMSO-D$_6$) δ ppm 9.12 (1 H, s) 8.68 (1 H, s) 7.92 (1 H, s) 7.81 (1 H, d, J = 8.34 Hz) 7.57 (1 H, d, J = 8.34 Hz) 7.40 (1 H, d, J = 6.82 Hz) 4.50-4.62 (1 H, m) 3.79 (1 H, s) 3.51-3.61 (4 H, m) 2.45-2.51 (2 H, m) 2.41 (4 H, s) 1.81-1.99 (4 H, m) 1.18-1.41 (4 H, m) |
| 81 | 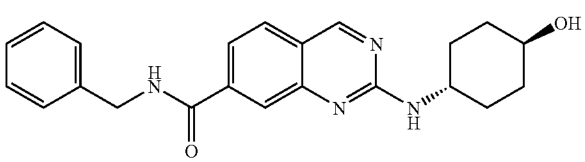 | N-benzyl-2-[(trans-4-hydroxycyclohexyl)amino]quinazoline-7-carboxamide | 377.2 | $^1$H NMR (400 MHz, DMSO-D$_6$) δ ppm 9.30 (1 H, s) 9.12 (1 H, s) 7.99 (1 H, s) 7.83 (1 H, d, J = 8.08 Hz) 7.62 (1 H, d, J = 8.34 Hz) 7.41 (1 H, d, J = 6.82 Hz) 7.29-7.36 (4 H, m) 7.18-7.27 (1 H, m) 4.56 (1 H, d, J = 4.29 Hz) 4.48 (2 H, d, J = 6.06 Hz) 3.78 (1 H, s) 3.36-3.49 (1 H, m) 1.80-1.91 (4 H, m) 1.17-1.41 (4 H, m). |
| 82 | 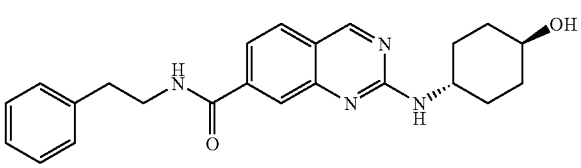 | 2-[(trans-4-hydroxycyclohexyl)amino]-N-(2-phenylethyl)quinazoline-7-carboxamide | 391.2 | $^1$H NMR (400 MHz, DMSO-D$_6$) δ ppm 8.97 (1 H, s) 7.76 (1 H, s) 7.70 (1 H, d, J = 8.08 Hz) 7.53 (1 H, dd, J = 8.21, 1.39 Hz) 7.18-7.39 (5 H, m) 6.39 (1 H, s) 5.28 (2 H, d, J = 7.83 Hz) 3.83-4.00 (1 H, m) 3.55-3.78 (3 H, m) 2.95 (2 H, t, J = 7.20 Hz) 2.19 (2 H, d, J = 11.62 Hz) 2.01 (2 H, d, J = 5.31 Hz) 1.40-1.54 (2 H, m) 1.27-1.39 (2 H, m). |

-continued

| Example Number | Structure | Compound Name | LRMS m/z | $^1$H NMR |
|---|---|---|---|---|
| 83 | 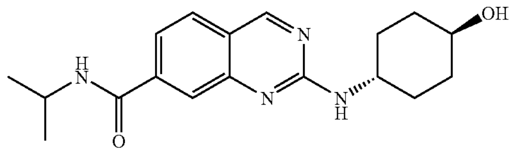 | 2-[(trans-4-hydroxycyclohexyl)amino]-N-isopropylquinazoline-7-carboxamide | 329.2 | $^1$H NMR (400 MHz, CD$_2$Cl$_2$-D$_2$) δ ppm 8.98 (1 H, s) 7.81 (1 H, s) 7.72 (1 H, d, J = 8.34 Hz) 7.59 (1 H, dd, J = 8.08, 1.52 Hz) 6.16 (1 H, s) 5.28 (1 H, d, J = 7.58 Hz) 4.19-4.32 (1 H, m) 3.86-3.99 (1 H, m) 3.61-3.73 (1 H, m) 2.20 (2 H, d, J = 11.87 Hz) 1.96-2.08 (2 H, m) 1.40-1.52 (2 H, m) 1.29-1.40 (2 H, m) 1.27 (6 H, d, J = 6.57 Hz). |
| 84 | 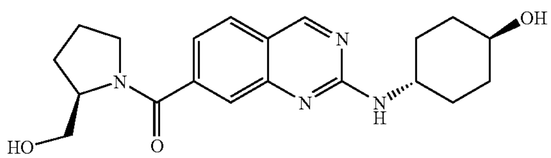 | trans-4-[(7-{[(2R)-2-(hydroxymethyl)pyrrolidin-1-yl]carbonyl}quinazolin-2-yl)amino]cyclohexanol | 371.2 | $^1$H NMR (400 MHz, CD$_2$Cl$_2$-D$_2$) δ ppm 8.97 (1 H, s) 7.71 (1 H, d, J = 8.08 Hz) 7.59 (1 H, s) 7.27 (1 H, dd, J = 8.21, 1.39 Hz) 5.21-5.30 (1 H, m) 4.71 (1 H, dd, J = 7.20, 2.40 Hz) 4.26-4.41 (1 H, m) 3.87-4.02 (1 H, m) 3.58-3.82 (3 H, m) 3.39-3.53 (2 H, m, J = 8.21, 4.93 Hz) 2.11-2.25 (3 H, m) 1.95-2.06 (2 H, m) 1.82-1.93 (1 H, m) 1.69-1.81 (1 H, m) 1.61-1.69 (1 H, m) 1.39-1.53 (2 H, m) 1.24-1.39 (2 H, m). |
| 85 | 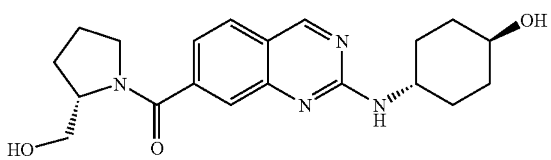 | trans-4-[(7-{[(2S)-2-(hydroxymethyl)pyrrolidin-1-yl]carbonyl}quinazolin-2-yl)amino]cyclohexanol | 371.2 | $^1$H NMR (400 MHz, CHLOROFORM-D) δ ppm 8.98 (1 H, s) 7.71 (1 H, d, J = 8.08 Hz) 7.66 (1 H, s) 7.32 (1 H, d, J = 8.08 Hz) 4.72 (1 H, s) 4.34-4.49 (1 H, m) 3.90-4.07 (1 H, m) 3.63-3.86 (3 H, m) 3.43-3.55 (2 H, m) 2.12-2.27 (3 H, m) 2.04 (2 H, dd, J = 13.01, 3.41 Hz) 1.83-1.95 (1 H, m) 1.60-1.84 (2 H, m) 1.44-1.56 (2 H, m) 1.27-1.41 (2 H, m). |
| 86 | 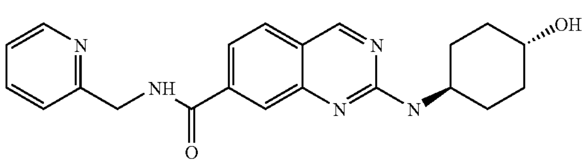 | 2-[(trans-4-hydroxycyclohexyl)amino]-N-(pyridin-2-ylmethyl)quinazoline-7-carboxamide | 378.2 | 1H NMR (400 MHz, CHLOROFORM-D) d ppm 9.00 (1 H, s) 8.54 (1 H, d, J = 4.29 Hz) 8.01 (1 H, s) 7.63-7.81 (3 H, m) 7.45 (1 H, d, J = 7.83 Hz) 7.27 (1 H, dd, J = 7.33, 5.05 Hz) 4.75 (2 H, s) 3.86-4.07 (1 H, m) 3.52-3.74 (1 H, m) 2.20 (2 H, d, J = 11.37 Hz) 2.04 (2 H, d, J = 11.12 Hz) 1.42-1.60 (2 H, m) 1.28-1.41 (2 H, m) |
| 87 | 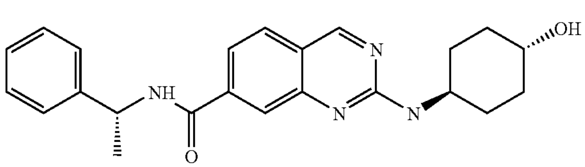 | 2-[(trans-4-hydroxycyclohexyl)amino]-N-[(1R)-1-phenylethyl]quinazoline-7-carboxamide | 391.1 | 1H NMR (400 MHz, CHLOROFORM-D) d ppm 8.98 (1 H, s) 7.83 (1 H, s) 7.61-7.74 (2 H, m) 7.34-7.47 (4 H, m) 7.27-7.34 (1 H, m) 6.48 (1 H, d, J = 7.33 Hz) 5.31-5.43 (1 H, m) 5.18 (1 H, d, J = 7.83 Hz) 3.86-4.05 (1 H, m) 3.71 (1 H, t, J = 9.60 Hz) 2.23 (2 H, d, J = 10.86 Hz) 2.05 (2 H, d, J = 9.09 Hz) 1.64 (3 H, d, J = 6.82 Hz) 1.44-1.62 (4 H, m) 1.28-1.42 (2 H, m) |

| Example Number | Structure | Compound Name | LRMS m/z | $^1$H NMR |
|---|---|---|---|---|
| 88 | 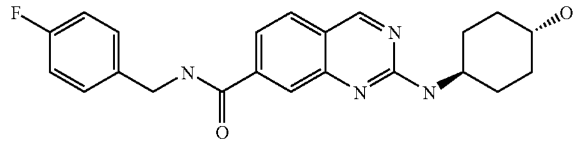 | N-(4-fluorobenzyl)-2-[(trans-4-hydroxycyclohexyl)amino]quinazoline-7-carboxamide | 395.1 | 1H NMR (400 MHz, CHLOROFORM-D) d ppm 8.99 (1 H, s) 7.86 (1 H, s) 7.57-7.80 (2 H, m) 7.35 (2 H, dd, J = 8.21, 5.43 Hz) 7.06 (2 H, t, J = 8.59 Hz) 6.56 (1 H, s) 5.18 (1 H, d, J = 7.83 Hz) 4.65 (2 H, d, J = 5.56 Hz) 3.83-4.05 (1 H, m) 3.51-3.81 (1 H, m) 2.22 (2 H, d, J = 11.12 Hz) 1.93-2.12 (2 H, m) 1.42-1.58 (2 H, m) 1.30-1.42 (2 H, m) |
| 89 | 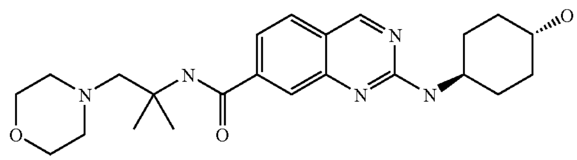 | N-(1,1-dimethyl-2-morpholin-4-ylethyl)-2-[(trans-4-hydroxycyclohexyl)amino]quinazoline-7-carboxamide | 428.1 | 1H NMR (400 MHz, CHLOROFORM-D) d ppm 8.99 (1 H, s) 7.81 (1 H, s) 7.67-7.74 (1 H, m) 7.61 (1 H, dd, J = 8.21, 1.39 Hz) 6.91 (1 H, s) 5.17 (1 H, d, J = 7.83 Hz) 3.88-4.05 (1 H, m) 3.63-3.80 (5 H, m) 2.58-2.70 (6 H, m) 2.25 (2 H, d, J = 11.12 Hz) 2.06 (2 H, d, J = 10.11 Hz) 1.44-1.57 (8 H, m) 1.27-1.42 (2 H, m) |
| 90 | 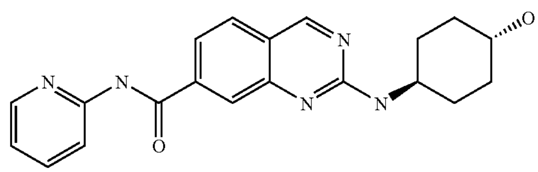 | 2-[(trans-4-hydroxycyclohexyl)amino]-N-pyridin-2-ylquinazoline-7-carboxamide | 364.2 | 1H NMR (400 MHz, DMSO-D6) d ppm 11.00 (1 H, s) 9.16 (1 H, s) 8.34-8.46 (1 H, m) 8.18 (1 H, d, J = 8.34 Hz) 8.09 (1 H, s) 7.79-7.90 (2 H, m) 7.69 (1 H, d, J = 8.34 Hz) 7.43 (1 H, d, J = 7.83 Hz) 7.11-7.24 (1 H, m) 4.56 (1 H, d, J = 4.30 Hz) 3.74-3.88 (1 H, m) 3.35-3.47 (1 H, m) 1.76-2.08 (4 H, m) 1.19-1.45 (4 H, m) |
| 91 | 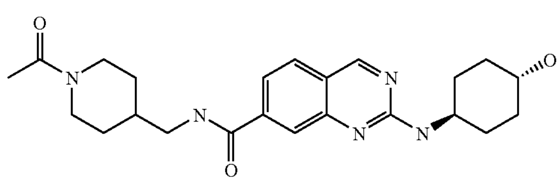 | N-[(1-acetylpiperidin-4-yl)methyl]-2-[(trans-4-hydroxycyclohexyl)amino]quinazoline-7-carboxamide | 426.2 | 1H NMR (400 MHz, DMSO-D6) d ppm 9.12 (1 H, s) 8.76 (1 H, s) 7.93 (1 H, s) 7.81 (1 H, d, J = 8.34 Hz) 7.58 (1 H, d, J = 8.08 Hz) 7.38 (1 H, s) 4.56 (1 H, d, J = 4.29 Hz) 4.34 (1 H, d, J = 13.14 Hz) 3.79 (2 H, d, J = 12.88 Hz) 3.36-3.48 (1 H, m) 3.17 (2 H, q, J = 6.23 Hz) 2.98 (1 H, t, J = 11.75 Hz) 2.37-2.46 (1 H, m) 1.97 (3 H, s) 1.61-1.94 (7 H, m) 1.19-1.41 (4 H, m) 1.05-1.18 (1 H, m) 0.90-1.04 (1 H, m) |
| 92 | 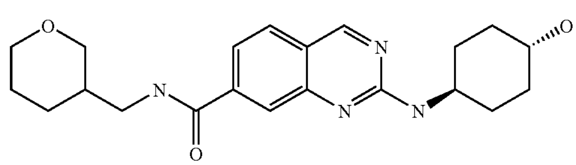 | 2-[(trans-4-hydroxycyclohexyl)amino]-N-(tetrahydro-2H-pyran-3-ylmethyl)quinazoline-7-carboxamide | 385.2 | 1H NMR (400 MHz, CHLOROFORM-D) d ppm 8.98 (1 H, s) 7.83 (1 H, s) 7.68-7.76 (1 H, m) 7.55-7.68 (1 H, m) 6.36 (1 H, s) 5.19 (1 H, d, J = 8.08 Hz) 3.90-4.04 (2 H, m) 3.80-3.89 (1 H, m) 3.72 (1 H, s) 3.35-3.52 (3 H, m) 3.31 (1 H, dd, J = 11.24, 8.97 Hz) 2.22 (2 H, s) 2.01-2.11 (2 H, m) 1.86-2.01 (2 H, m) 1.30-1.75 (6 H, m) |

-continued

| Example Number | Structure | Compound Name | LRMS m/z | ¹H NMR |
|---|---|---|---|---|
| 93 | 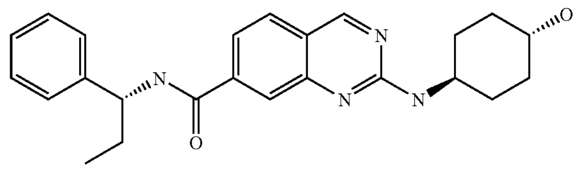 | 2-[(trans-4-hydroxycyclohexyl)amino]-N-[(1R)-1-phenylpropyl]quinazoline-7-carboxamide | 405.2 | 1H NMR (400 MHz, CHLOROFORM-D) d ppm 8.99 (1 H, s) 7.83 (1 H, s) 7.69 (2 H, q, J = 8.08 Hz) 7.33-7.50 (4 H, m) 7.26-7.33 (1 H, m) 6.49 (1 H, d, J = 7.83 Hz) 5.27 (1 H, s) 5.10 (1 H, q, J = 7.49 Hz) 3.90-4.05 (1 H, m) 3.60-3.79 (1 H, m) 2.22 (2 H, d, J = 10.11 Hz) 1.85-2.15 (4 H, m) 1.44-1.65 (3 H, m) 1.28-1.44 (2 H, m) 0.97 (3 H, t, J = 7.33 Hz) |
| 94 | 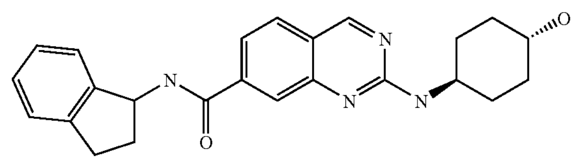 | N-(2,3-dihydro-1H-inden-1-yl)-2-[(trans-4-hydroxycyclohexyl)amino]quinazoline-7-carboxamide | 403.2 | 1H NMR (400 MHz, CHLOROFORM-D) d ppm 8.99 (1 H, s) 7.84 (1 H, s) 7.65-7.79 (2 H, m) 7.37 (1 H, d, J = 6.82 Hz) 7.26-7.33 (3 H, m, J = 5.05 Hz) 6.49 (1 H, d, J = 7.83 Hz) 5.71 (1 H, q, J = 7.41 Hz) 5.31 (1 H, s) 3.96 (1 H, s) 3.69 (1 H, s) 3.00-3.18 (1 H, m) 2.86-3.01 (1 H, m) 2.58-2.81 (1 H, m) 2.20 (2 H, d, J = 11.62 Hz) 1.89-2.14 (3 H, m) 1.41-1.60 (3 H, m) 1.33 (2 H, q, J = 11.12 Hz) |
| 95 | 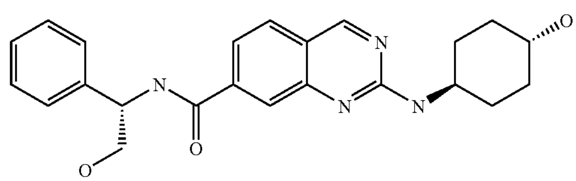 | 2-[(trans-4-hydroxycyclohexyl)amino]-N-[(1S)-2-hydroxy-1-phenylethyl]quinazoline-7-carboxamide | 407.2 | 1H NMR (400 MHz, DMSO-D6) d ppm 9.12 (1 H, s) 8.93-9.05 (1 H, m) 8.07 (1 H, s) 7.81 (1 H, d, J = 7.83 Hz) 7.59 (1 H, d, J = 7.33 Hz) 7.40 (3 H, s) 7.32 (2 H, s) 7.24 (1 H, d, J = 7.07 Hz) 5.07 (1 H, s) 4.96 (1 H, s) 4.56 (1 H, s) 3.81 (1 H, s) 3.74 (1 H, s) 3.65 (1 H, s) 3.41 (1 H, s) 1.75-2.06 (4 H, m) 1.18-1.44 (4 H, m) |
| 96 | 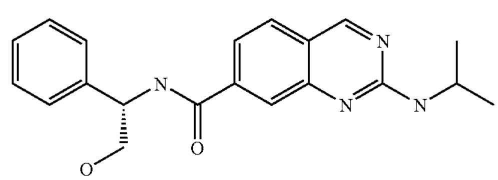 | N-[(1S)-2-hydroxy-1-phenylethyl]-2-(isopropylamino)quinazoline-7-carboxamide | 351.2 | 1H NMR (400 MHz, DMSO-D6) d ppm 9.13 (1 H, s) 8.97 (1 H, d, J = 8.08 Hz) 8.05 (1 H, s) 7.82 (1 H, d, J = 8.34 Hz) 7.59 (1 H, dd, J = 8.34, 1.52 Hz) 7.37-7.47 (3 H, m, J = 7.07 Hz) 7.32 (2 H, t, J = 7.58 Hz) 7.23 (1 H, t, J = 7.20 Hz) 5.02-5.14 (1 H, m) 4.96 (1 H, t, J = 5.94 Hz) 4.13-4.24 (1 H, m) 3.69-3.80 (1 H, m) 3.60-3.69 (1 H, m) 1.21 (6 H, d, J = 6.32 Hz) |

-continued

| Example Number | Structure | Compound Name | LRMS m/z | ¹H NMR |
|---|---|---|---|---|
| 97 | 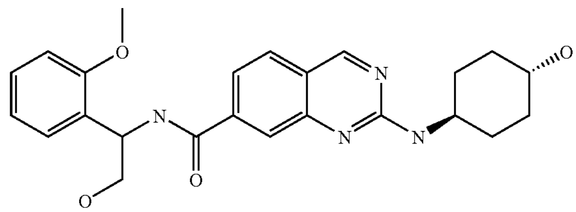 | 2-[(trans-4-hydroxycyclohexyl)amino]-N-[2-hydroxy-1-(2-methoxyphenyl)ethyl]quinazoline-7-carboxamide | 437.2 | 1H NMR (400 MHz, DMSO-D6) d ppm 9.12 (1 H, s) 8.89 (1 H, d, J = 7.83 Hz) 8.10 (1 H, s) 7.82 (1 H, d, J = 8.34 Hz) 7.59 (1 H, dd, J = 8.34, 1.26 Hz) 7.37 (2 H, dd, J = 7.58, 1.52 Hz) 7.16-7.27 (1 H, m) 6.98 (1 H, d, J = 7.83 Hz) 6.90 (1 H, t, J = 7.45 Hz) 5.47 (1 H, q, J = 7.07 Hz) 4.93 (1 H, t, J = 5.94 Hz) 4.57 (1 H, d, J = 4.55 Hz) 3.76-3.92 (4 H, m) 3.58 (2 H, t, J = 6.32 Hz) 3.37-3.48 (1 H, m) 1.91 (4 H, dd, J = 34.36, 10.61 Hz) 1.16-1.45 (4 H, m) |
| 98 | 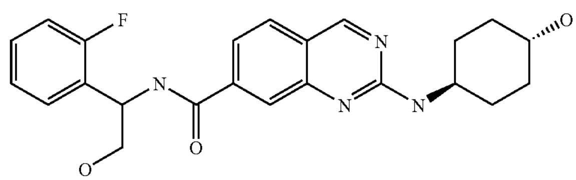 | N-[1-(2-fluorophenyl)-2-hydroxyethyl]-2-[(trans-4-hydroxycyclohexyl)amino]quinazoline-7-carboxamide | 425.2 | 1H NMR (400 MHz, DMSO-D6) d ppm 9.12 (1 H, s) 9.04 (1 H, d, J = 7.07 Hz) 8.08 (1 H, s) 7.82 (1 H, d, J = 8.08 Hz) 7.58 (1 H, d, J = 8.34 Hz) 7.52 (1 H, t, J = 6.69 Hz) 7.39 (1 H, s) 7.23-7.35 (1 H, m) 7.12-7.22 (2 H, m) 5.39 (1 H, d, J = 4.80 Hz) 5.07 (1 H, t, J = 5.56 Hz) 4.56 (1 H, d, J = 3.79 Hz) 3.59-3.91 (3 H, m) 3.42 (1 H, d, J = 4.04 Hz) 1.78-2.01 (4 H, m) 1.19-1.45 (4 H, m) |
| 99 | 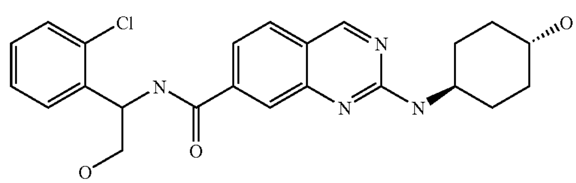 | N-[1-(2-chlorophenyl)-2-hydroxyethyl]-2-[(trans-4-hydroxycyclohexyl)amino]quinazoline-7-carboxamide | 441.2 | 1H NMR (400 MHz, DMSO-D6) d ppm 9.01-9.28 (2 H, m) 8.11 (1 H, s) 7.82 (1 H, d, J = 8.08 Hz) 7.58 (2 H, dd, J = 7.58, 3.79 Hz) 7.37-7.49 (2 H, m, J = 7.83 Hz) 7.20-7.37 (2 H, m) 5.36-5.57 (1 H, m) 5.12 (1 H, t, J = 5.81 Hz) 4.57 (1 H, d, J = 4.04 Hz) 3.74-3.91 (1 H, m) 3.57-3.73 (2 H, m) 3.36-3.50 (1 H, m) 1.61-2.13 (4 H, m) 1.10-1.47 (4 H, m) |
| 100 | 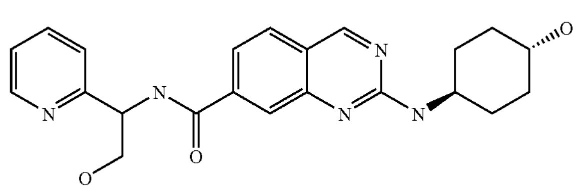 | 2-[(trans-4-hydroxycyclohexyl)amino]-N-(2-hydroxy-1-pyridin-2-ylethyl)quinazoline-7-carboxamide | 408.1 | 1H NMR (400 MHz, DMSO-D6) d ppm 9.13 (1 H, s) 8.99 (1 H, d, J = 7.33 Hz) 8.53 (1 H, d, J = 3.79 Hz) 8.09 (1 H, s) 7.83 (1 H, d, J = 8.34 Hz) 7.68-7.79 (1 H, m) 7.61 (1 H, dd, J = 8.34, 1.52 Hz) 7.33-7.48 (2 H, m, J = 7.07, 7.07 Hz) 7.26 (1 H, dd, J = 6.95, 5.43 Hz) 5.08-5.24 (1 H, m) 4.98 (1 H, s) 4.57 (1 H, d, J = 4.04 Hz) 3.66-3.95 (3 H, m) 3.42 (1 H, s) 1.91 (4 H, dd, J = 36.00, 10.74 Hz) 1.17-1.43 (4 H, m) |

-continued

| Example Number | Structure | Compound Name | LRMS m/z | ¹H NMR |
|---|---|---|---|---|
| 101 | 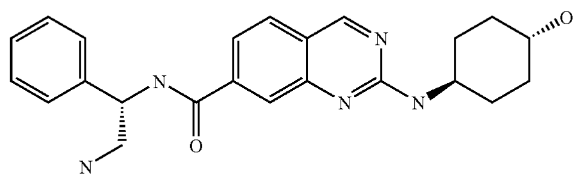 | N-[(1S)-2-amino-1-phenylethyl]-2-[(trans-4-hydroxycyclohexyl)amino]quinazoline-7-carboxamide | 406.2 | N/A |
| 102 | 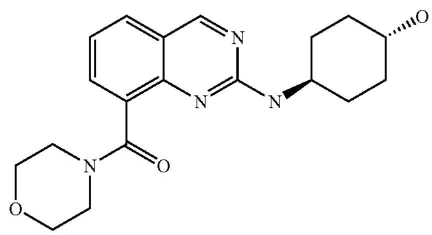 | trans-4-{[8-(morpholin-4-ylcarbonyl)quinazolin-2-yl]amino}cyclohexanol | 357.1 | 1H NMR (400 MHz, DMSO-D6) d ppm 9.10 (1 H, s) 7.80 (1 H, dd, J = 8.08, 1.26 Hz) 7.58 (1 H, dd, J = 7.07, 1.52 Hz) 7.47 (1 H, d, J = 7.58 Hz) 7.22 (1 H, t, J = 7.58 Hz) 4.58 (1 H, d, J = 4.29 Hz) 3.63-3.84 (5 H, m) 3.48-3.59 (1 H, m) 3.35-3.48 (2 H, m) 3.06 (2 H, s) 1.71-2.11 (4 H, m) 1.12-1.45 (4 H, m) |
| 103 | 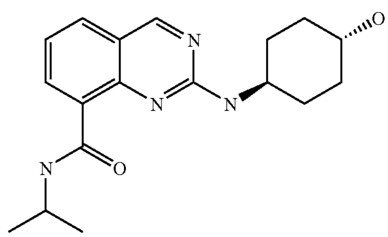 | 2-[(trans-4-hydroxycyclohexyl)amino]-N-isopropylquinazoline-8-carboxamide | 329.1 | 1H NMR (400 MHz, DMSO-D6) d ppm 10.53 (1 H, d, J = 7.83 Hz) 9.18 (1 H, s) 8.51 (1 H, dd, J = 7.45, 1.64 Hz) 7.95 (1 H, dd, J = 7.83, 1.52 Hz) 7.85 (1 H, d, J = 8.08 Hz) 7.32 (1 H, t, J = 7.58 Hz) 4.65 (1 H, d, J = 4.04 Hz) 4.18-4.31 (1 H, m) 3.71 (1 H, d, J = 7.83 Hz) 3.38-3.52 (1 H, m) 1.84-2.04 (4 H, m) 1.36-1.50 (2 H, m) 1.23-1.36 (8 H, m) |
| 104 | 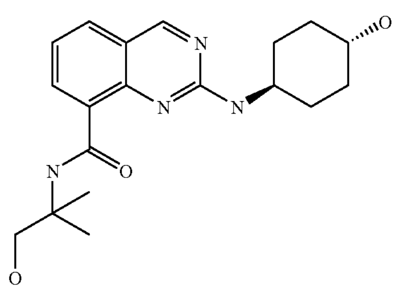 | 2-[(trans-4-hydroxycyclohexyl)amino]-N-(2-hydroxy-1,1-dimethylethyl)quinazoline-8-carboxamide | 359.2 | 1H NMR (400 MHz, DMSO-D6) d ppm 10.20 (1 H, s) 9.15 (1 H, s) 8.48 (1 H, dd, J = 7.45, 1.64 Hz) 7.85-8.03 (1 H, m) 7.72 (1 H, d, J = 8.59 Hz) 7.30 (1 H, t, J = 7.58 Hz) 4.99 (1 H, t, J = 5.31 Hz) 4.60 (1 H, d, J = 4.04 Hz) 3.81-3.98 (1 H, m) 3.61 (2 H, d, J = 5.56 Hz) 3.36-3.49 (1 H, m) 1.76-1.97 (4 H, m) 1.22-1.47 (10 H, m) |
| 105 | 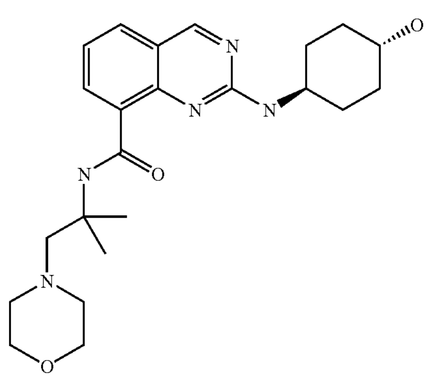 | N-(1,1-dimethyl-2-morpholin-4-ylethyl)-2-[(trans-4-hydroxycyclohexyl)amino]quinazoline-8-carboxamide | 428.2 | 1H NMR (400 MHz, DMSO-D6) d ppm 10.27 (1 H, s) 9.15 (1 H, s) 8.48 (1 H, dd, J = 7.58, 1.52 Hz) 7.92 (1 H, dd, J = 7.83, 1.77 Hz) 7.78 (1 H, d, J = 8.84 Hz) 7.29 (1 H, t, J = 7.71 Hz) 4.64 (1 H, d, J = 4.04 Hz) 3.84-3.97 (1 H, m) 3.42-3.53 (5 H, m) 2.74 (2 H, s) 2.39-2.47 (4 H, m) 1.81-2.03 (4 H, m) 1.38-1.52 (8 H, m) 1.24-1.37 (2 H, m) |

-continued

| Example Number | Structure | Compound Name | LRMS m/z | ¹H NMR |
|---|---|---|---|---|
| 106 | 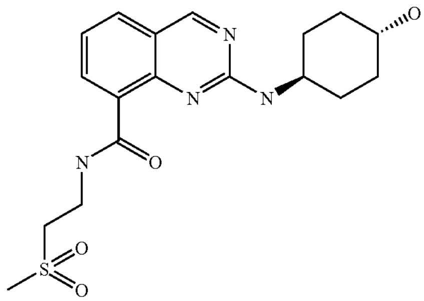 | 2-[(trans-4-hydroxycyclohexyl)amino]-N-[2-(methylsulfonyl)ethyl]quinazoline-8-carboxamide | 393.1 | 1H NMR (400 MHz, DMSO-D6) d ppm 11.02 (1 H, s) 9.19 (1 H, s) 8.43-8.67 (1 H, m) 7.97 (1 H, dd, J = 7.83, 1.26 Hz) 7.90 (1 H, d, J = 7.58 Hz) 7.33 (1 H, t, J = 7.58 Hz) 4.60 (1 H, d, J = 4.04 Hz) 3.70 (1 H, s) 3.54-3.66 (2 H, m) 3.49 (2 H, t, J = 5.18 Hz) 3.44 (1 H, dd, J = 7.96, 3.66 Hz) 3.28 (3 H, s) 1.76-2.11 (4 H, m) 1.26-1.51 (4 H, m) |
| 107 | 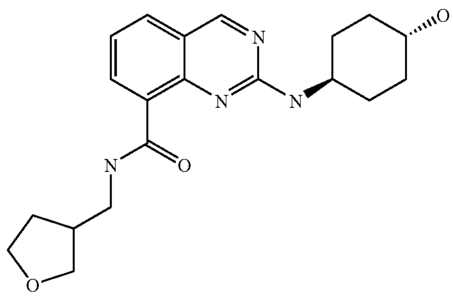 | 2-[(trans-4-hydroxycyclohexyl)amino]-N-(tetrahydrofuran-3-ylmethyl)quinazoline-8-carboxamide | 371.2 | 1H NMR (400 MHz, DMSO-D6) d ppm 11.02 (1 H, s) 9.19 (1 H, s) 8.43-8.67 (1 H, m) 7.97 (1 H, dd, J = 7.83, 1.26 Hz) 7.90 (1 H, d, J = 7.58 Hz) 7.33 (1 H, t, J = 7.58 Hz) 4.60 (1 H, d, J = 4.04 Hz) 3.70 (1 H, s) 3.54-3.66 (2 H, m) 3.49 (2 H, t, J = 5.18 Hz) 3.44 (1 H, dd, J = 7.96, 3.66 Hz) 3.28 (3 H, s) 1.76-2.11 (4 H, m) 1.26-1.51 (4 H, m) |
| 108 | 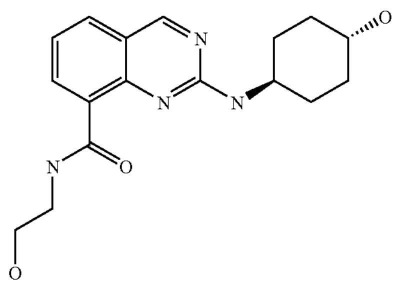 | 2-[(trans-4-hydroxycyclohexyl)amino]-N-(2-hydroxyethyl)quinazoline-8-carboxamide | 331.2 | N/A |
| 109 | 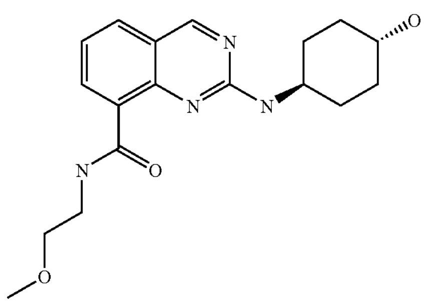 | 2-[(trans-4-hydroxycyclohexyl)amino]-N-(2-methoxyethyl)quinazoline-8-carboxamide | 345.1 | 1H NMR (400 MHz, DMSO-D6) d ppm 11.02 (1 H, s) 9.19 (1 H, s) 8.43-8.67 (1 H, m) 7.97 (1 H, dd, J = 7.83, 1.26 Hz) 7.90 (1 H, d, J = 7.58 Hz) 7.33 (1 H, t, J = 7.58 Hz) 4.60 (1 H, d, J = 4.04 Hz) 3.70 (1 H, s) 3.54-3.66 (2 H, m) 3.49 (2 H, t, J = 5.18 Hz) 3.44 (1 H, dd, J = 7.96, 3.66 Hz) 3.28 (3 H, s) 1.76-2.11 (4 H, m) 1.26-1.51 (4 H, m) |
| 110 | 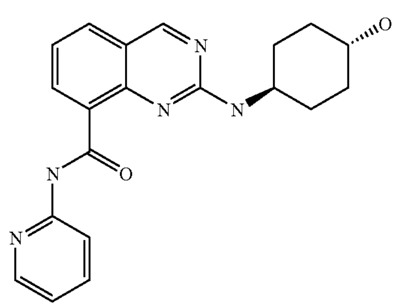 | 2-[(trans-4-hydroxycyclohexyl)amino]-N-pyridin-2-ylquinazoline-8-carboxamide | 364 | 1H NMR (400 MHz, DMSO-D6) δ ppm 13.86 (1 H, s) 9.23 (1 H, s) 8.64 (1 H, dd, J = 7.58, 1.52 Hz) 8.28-8.51 (2 H, m) 7.97-8.17 (2 H, m) 7.79-7.92 (1 H, m) 7.39 (1 H, t, J = 7.71 Hz) 7.19 (1 H, dd, J = 6.82, 5.05 Hz) 4.60 (1 H, d, J = 4.04 Hz) 4.30-4.53 (1 H, m) 3.36-3.68 (1 H, m) 1.97 (2 H, d, J = 10.86 Hz) 1.82 (2 H, d, J = 9.85 Hz) 1.49-1.68 (2 H, m) 1.27-1.49 (2 H, m) |

-continued

| Example Number | Structure | Compound Name | LRMS m/z | ¹H NMR |
|---|---|---|---|---|
| 111 | 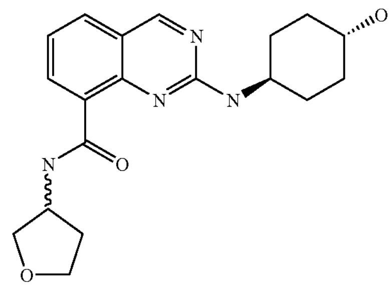 | 2-[(trans-4-hydroxycyclohexyl)amino]-N-(tetrahydrofuran-3-yl)quinazoline-8-carboxamide | 357 | 1H NMR (400 MHz, DMSO-D6) d ppm 10.87 (1 H, s) 9.20 (1 H, s) 8.51 (1 H, d, J = 7.07 Hz) 7.96 (2 H, t, J = 7.58 Hz) 7.33 (1 H, t, J = 7.58 Hz) 4.63 (1 H, d, J = 3.03 Hz) 3.50-3.72 (7 H, m, J = 4.29 Hz) 3.37-3.50 (1 H, m) 2.37-2.60 (6 H, m) 1.75-2.13 (4 H, m) 1.20-1.53 (4 H, m) |
| 112 | 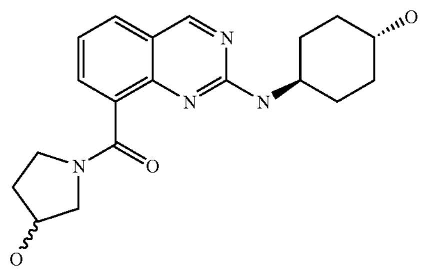 | 1-({2-[(trans-4-hydroxycyclohexyl)amino]quinazolin-8-yl}carbonyl)pyrrolidin-3-ol | 357 | N/A |
| 113 | 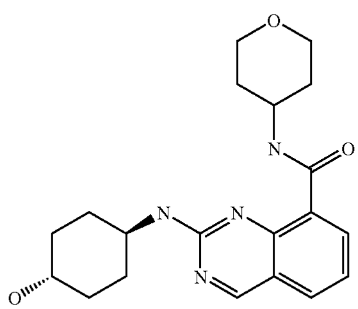 | 2-[(trans-4-hydroxycyclohexyl)amino]-N-(tetrahydro-2H-pyran-4-yl)quinazoline-8-carboxamide | 371 | N/A |
| 114 | 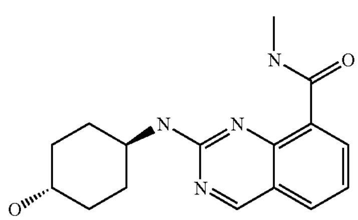 | 2-[(trans-4-hydroxycyclohexyl)amino]-N-methylquinazoline-8-carboxamide | 301 | N/A |
| 115 | 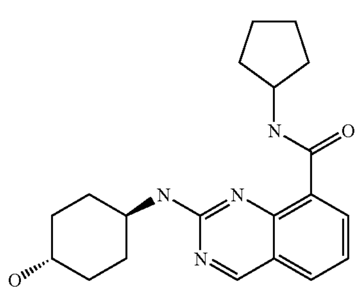 | N-cyclopentyl-2-[(trans-4-hydroxycyclohexyl)amino]quinazoline-8-carboxamide | 355 | N/A |

-continued

| Example Number | Structure | Compound Name | LRMS m/z | ¹H NMR |
|---|---|---|---|---|
| 116 | 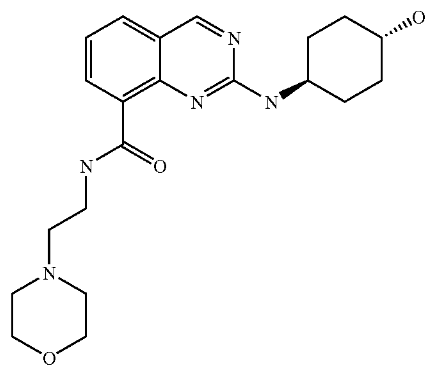 | 2-[(trans-4-hydroxycyclohexyl)amino]-N-(2-morpholin-4-ylethyl)quinazoline-8-carboxamide | 400.2 | 1H NMR (400 MHz, DMSO-D6) d ppm 10.87 (1 H, s) 9.20 (1 H, s) 8.51 (1 H, d, J = 7.07 Hz) 7.96 (2 H, t, J = 7.58 Hz) 7.33 (1 H, t, J = 7.58 Hz) 4.63 (1 H, d, J = 3.03 Hz) 3.50-3.72 (7 H, m, J = 4.29 Hz) 3.37-3.50 (1 H, m) 2.37-2.60 (6 H, m) 1.75-2.13 (4 H, m) 1.20-1.53 (4 H, m) |
| 117 | 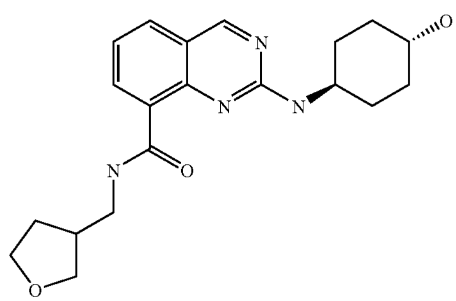 | 2-[(trans-4-hydroxycyclohexyl)amino]-N-(tetrahydrofuran-3-ylmethyl)quinazoline-8-carboxamide | 371.2 | 1H NMR (400 MHz, DMSO-D6) d ppm 11.02 (1 H, s) 9.19 (1 H, s) 8.43-8.67 (1 H, m) 7.97 (1 H, dd, J = 7.83, 1.26 Hz) 7.90 (1 H, d, J = 7.58 Hz) 7.33 (1 H, t, J = 7.58 Hz) 4.60 (1 H, d, J = 4.04 Hz) 3.70 (1 H, s) 3.54-3.66 (2 H, m) 3.49 (2 H, t, J = 5.18 Hz) 3.44 (1 H, dd, J = 7.96, 3.66 Hz) 3.28 (3 H, s) 1.76-2.11 (4 H, m) 1.26-1.51 (4 H, m) |
| 118 | 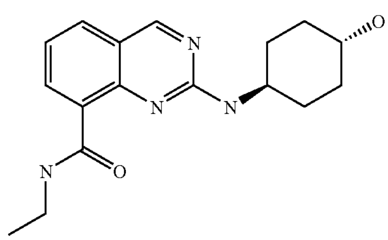 | N-ethyl-2-[(trans-4-hydroxycyclohexyl)amino]quinazoline-8-carboxamide | 315.3 | 1H NMR (400 MHz, DMSO-D6) d ppm 10.82-11.09 (1 H, m) 9.18 (1 H, s) 8.43-8.61 (1 H, m) 7.96 (1 H, dd, J = 7.83, 1.77 Hz) 7.85 (1 H, d, J = 7.83 Hz) 7.32 (1 H, t, J = 7.71 Hz) 4.86 (1 H, d, J = 4.29 Hz) 4.57 (1 H, d, J = 4.04 Hz) 3.62-3.94 (2 H, m, J = 10.74, 5.43 Hz) 3.28-3.55 (3 H, m) 1.76-2.09 (4 H, m) 1.26-1.50 (4 H, m) 1.10 (3 H, d, J = 6.06 Hz) |
| 119 | 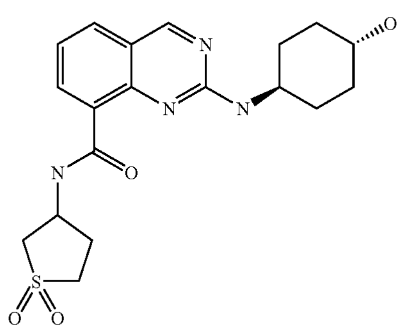 | N-(1,1-dioxidotetrahydro-3-thienyl)-2-[(trans-4-hydroxycyclohexyl)amino]quinazoline-8-carboxamide | 405.1 | 1H NMR (400 MHz, DMSO-D6) d ppm 10.82-11.09 (1 H, m) 9.18 (1 H, s) 8.43-8.61 (1 H, m) 7.96 (1 H, dd, J = 7.83, 1.77 Hz) 7.85 (1 H, d, J = 7.83 Hz) 7.32 (1 H, t, J = 7.71 Hz) 4.86 (1 H, d, J = 4.29 Hz) 4.57 (1 H, d, J = 4.04 Hz) 3.62-3.94 (2 H, m, J = 10.74, 5.43 Hz) 3.28-3.55 (3 H, m) 1.76-2.09 (4 H, m) 1.26-1.50 (4 H, m) 1.10 (3 H, d, J = 6.06 Hz) |

-continued

| Example Number | Structure | Compound Name | LRMS m/z | $^1$H NMR |
|---|---|---|---|---|
| 120 | 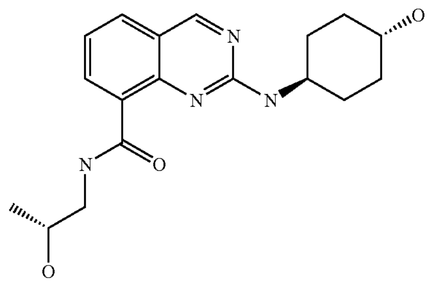 | 2-[(trans-4-hydroxycyclohexyl)amino]-N-[(2R)-2-hydroxypropyl]quinazoline-8-carboxamide | 345.2 | 1H NMR (400 MHz, DMSO-D6) d ppm 10.97 (1 H, t, J = 5.43 Hz) 9.20 (1 H, s) 8.54 (1 H, d, J = 6.32 Hz) 7.98 (1 H, dd, J = 7.71, 1.64 Hz) 7.87 (1 H, d, J = 7.83 Hz) 7.34 (1 H, t, J = 7.71 Hz) 4.88 (1 H, d, J = 4.04 Hz) 4.59 (1 H, d, J = 3.79 Hz) 3.84 (2 H, dd, J = 10.99, 5.43 Hz) 3.28-3.56 (3 H, m) 2.01 (2 H, d, J = 7.83 Hz) 1.86 (2 H, s) 1.28-1.55 (4 H, m) 1.12 (3 H, d, J = 6.06 Hz) |
| 121 | 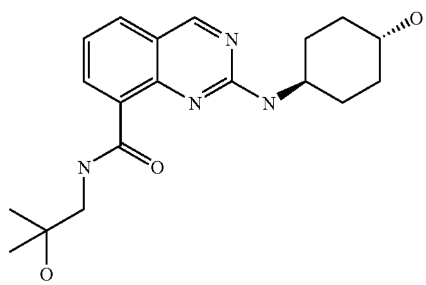 | 2-[(trans-4-hydroxycyclohexyl)amino]-N-(2-hydroxy-2-methylpropyl)quinazoline-8-carboxamide | 359.2 | 1H NMR (400 MHz, DMSO-D6) d ppm 9.05 (1 H, s) 7.38 (1 H, s) 7.26 (1 H, d, J = 7.83 Hz) 7.18 (1 H, s) 7.08 (1 H, t, J = 7.71 Hz) 5.24 (1 H, s) 4.53 (1 H, d, J = 4.55 Hz) 3.89 (3 H, s) 3.69-3.84 (2 H, m) 3.34-3.51 (1 H, m) 1.78-2.28 (6 H, m) 1.18-1.46 (4 H, m) |
| 122 | 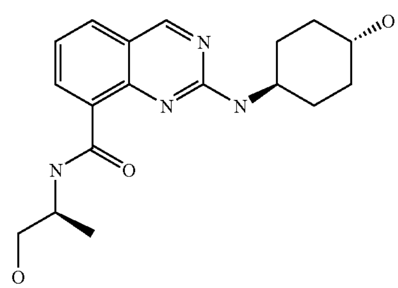 | 2-[(trans-4-hydroxycyclohexyl)amino]-N-[(1S)-2-hydroxy-1-methylethyl]quinazoline-8-carboxamide | 345.2 | 1H NMR (400 MHz, DMSO-D6) d ppm 10.59 (1 H, d, J = 8.34 Hz) 9.17 (1 H, s) 8.52 (1 H, dd, J = 7.45, 1.64 Hz) 7.94 (1 H, dd, J = 7.83, 1.52 Hz) 7.79 (1 H, d, J = 8.59 Hz) 7.31 (1 H, t, J = 7.71 Hz) 4.92 (1 H, t, J = 5.31 Hz) 4.60 (1 H, d, J = 4.04 Hz) 4.13-4.31 (1 H, m) 3.84 (1 H, s) 3.49-3.64 (1 H, m) 3.35-3.50 (2 H, m) 1.74-2.05 (4 H, m) 1.30-1.57 (4 H, m) 1.26 (3 H, d, J =6.57 Hz) |
| 123 | 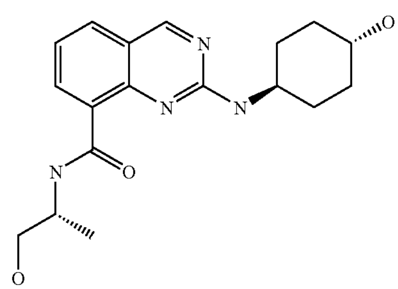 | 2-[(trans-4-hydroxycyclohexyl)amino]-N-[(1R)-2-hydroxy-1-methylethyl]quinazoline-8-carboxamide | 345.2 | 1H NMR (400 MHz, DMSO-D6) d ppm 10.59 (1 H, d, J = 8.34 Hz) 9.17 (1 H, s) 8.52 (1 H, dd, J = 7.45, 1.64 Hz) 7.94 (1 H, dd, J = 7.83, 1.52 Hz) 7.79 (1 H, d, J = 8.59 Hz) 7.31 (1 H, t, J = 7.71 Hz) 4.92 (1 H, t, J = 5.31 Hz) 4.60 (1 H, d, J = 4.04 Hz) 4.13-4.31 (1 H, m) 3.84 (1 H, s) 3.49-3.64 (1 H, m) 3.35-3.50 (2 H, m) 1.74-2.05 (4 H, m) 1.30-1.57 (4 H, m) 1.26 (3 H, d, J = 6.57 Hz) |

-continued

| Example Number | Structure | Compound Name | LRMS m/z | ¹H NMR |
|---|---|---|---|---|
| 124 | 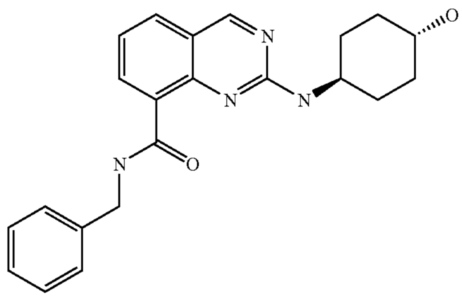 | N-benzyl-2-[(trans-4-hydroxycyclohexyl)amino]quinazoline-8-carboxamide | 377.2 | 1H NMR (400 MHz, DMSO-D6) d ppm 10.59 (1 H, d, J = 8.34 Hz) 9.17 (1 H, s) 8.52 (1 H, dd, J = 7.45, 1.64 Hz) 7.94 (1 H, dd, J = 7.83, 1.52 Hz) 7.79 (1 H, d, J = 8.59 Hz) 7.31 (1 H, t, J = 7.71 Hz) 4.92 (1 H, t, J = 5.31 Hz) 4.60 (1 H, d, J = 4.04 Hz) 4.13-4.31 (1 H, m) 3.84 (1 H, s) 3.49-3.64 (1 H, m) 3.35-3.50 (2 H, m) 1.74-2.05 (4 H, m) 1.30-1.57 (4 H, m) 1.26 (3 H, d, J = 6.57 Hz) |
| 125 | 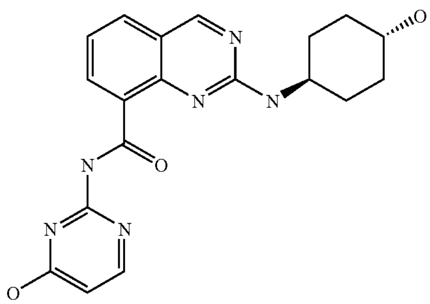 | 2-[(trans-4-hydroxycyclohexyl)amino]-N-(4-hydroxypyrimidin-2-yl)quinazoline-8-carboxamide | 381.1 | 1H NMR (400 MHz, DMSO-D6) d ppm 14.71 (1 H, s) 12.05 (1 H, s) 9.26 (1 H, s) 8.59 (1 H, dd, J = 7.58, 1.52 Hz) 8.25 (1 H, d, J = 9.10 Hz) 8.13 (1 H, dd, J = 7.83, 1.52 Hz) 7.85 (1 H, d, J = 6.57 Hz) 7.42 (1 H, t, J = 7.71 Hz) 6.13 (1 H, d, J = 6.57 Hz) 4.53 (1 H, s) 4.11-4.29 (1 H, m) 3.35-3.49 (1 H, m) 1.93 (2 H, d, J = 11.37 Hz) 1.81 (2 H, d, J = 9.60 Hz) 1.59 (2 H, s) 1.31-1.47 (2 H, m) |
| 126 | 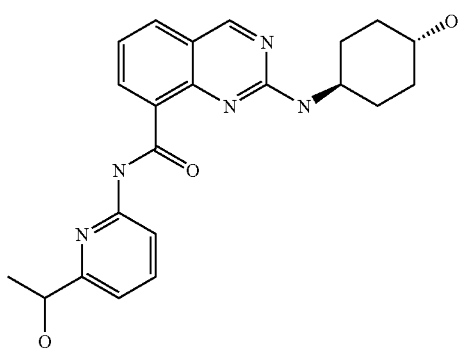 | 2-[(trans-4-hydroxycyclohexyl)amino]-N-[6-(1-hydroxyethyl)pyridin-2-yl]quinazoline-8-carboxamide | 408.2 | 1H NMR (400 MHz, DMSO-D6) d ppm 13.20 (1 H, s) 9.25 (1 H, s) 8.65 (1 H, dd, J = 7.58, 1.52 Hz) 8.21 (1 H, d, J = 8.34 Hz) 8.06 (1 H, dd, J = 7.71, 1.64 Hz) 8.00 (1 H, d, J = 7.58 Hz) 7.84 (1 H, t, J = 7.96 Hz) 7.40 (1 H, t, J = 7.58 Hz) 7.32 (1 H, d, J = 7.58 Hz) 5.37 (1 H, d, J = 4.55 Hz) 4.75-4.97 (1 H, m) 4.54 (1 H, d, J = 3.28 Hz) 4.00-4.28 (1 H, m) 3.48 (1 H, d, J = 3.28 Hz) 1.97-2.21 (2 H, m, J = 24.00, 11.37 Hz) 1.80-1.94 (1 H, m) 1.62-1.79 (1 H, m, J = 10.36 Hz) 1.19-1.59 (7 H, m) |
| 127 | 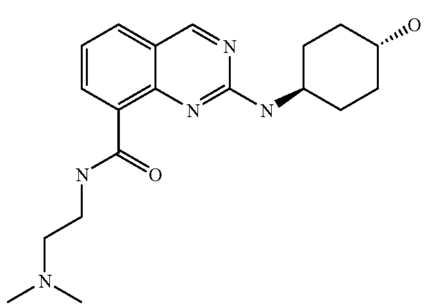 | N-[2-(dimethylamino)ethyl]-2-[(trans-4-hydroxycyclohexyl)amino]quinazoline-8-carboxamide | 358.3 | 1H NMR (400 MHz, DMSO-D6) d ppm 10.82 (1 H, s) 9.20 (1 H, s) 8.51 (1 H, d, J = 7.58 Hz) 7.82-8.13 (2 H, m) 7.33 (1 H, t, J = 7.58 Hz) 4.64 (1 H, d, J = 3.54 Hz) 3.28-4.02 (6 H, m) 2.38-2.58 (1 H, m) 2.13-2.23 (6 H, m) 1.96 (4 H, dd, J = 42.57, 10.74 Hz) 1.20-1.56 (4 H, m) |

| Example Number | Structure | Compound Name | LRMS m/z | ¹H NMR |
|---|---|---|---|---|
| 128 | 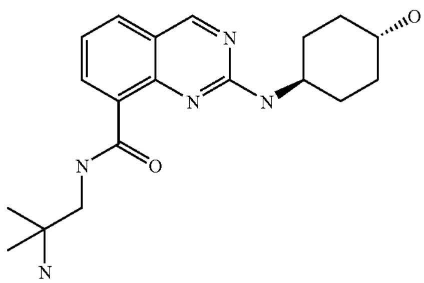 | N-(2-amino-2-methylpropyl)-2-[(trans-4-hydroxycyclohexyl)amino]quinazoline-8-carboxamide | 358.2 | 1H NMR (400 MHz, DMSO-D6) d ppm 11.43 (0.4 H, s) 11.07 (0.6 H, s) 9.29 (0.4 H, s) 9.23 (0.6 H, s) 8.54 (1 H, d) 7.79-8.23 (4 H, m) 7.21-7.47 (1 H, m) 4.52-4.70 (1 H, m), 3.89 (0.4 H, s) 3.62 (2.4 H, s) 3.44 (1 H, s) 1.77-2.09 (4 H, m) 1.21-1.54 910 H, m) |
| 129 | 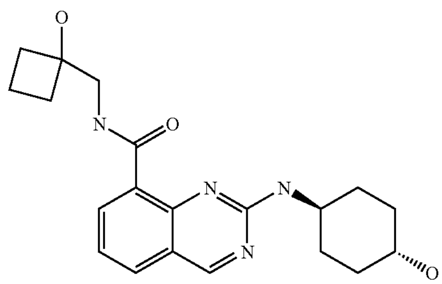 | N-[(1-hydroxycyclobutyl)methyl]-2-[(trans-4-hydroxycyclohexyl)amino]quinazoline-8-carboxamide | 371.2 | 1H NMR (400 MHz, DMSO-D6) d ppm 10.98 (1 H, t, J = 5.81 Hz) 9.18 (1 H, s) 8.49-8.63 (1 H, m) 7.96 (1 H, dd, J = 7.71, 1.64 Hz) 7.80 (1 H, d, J = 8.08 Hz) 7.32 (1 H, t, J = 7.58 Hz) 4.55 (1 H, d, J = 3.54 Hz) 3.79-3.97 (1 H, m) 3.57 (2 H, d, J = 6.06 Hz) 3.34-3.47 (1 H, m) 1.89-2.05 (7 H, m) 1.79 (2 H, d, J = 10.61 Hz) 1.61 (1 H, d, J = 11.62 Hz) 1.24-1.54 (5 H, m) |
| 130 | 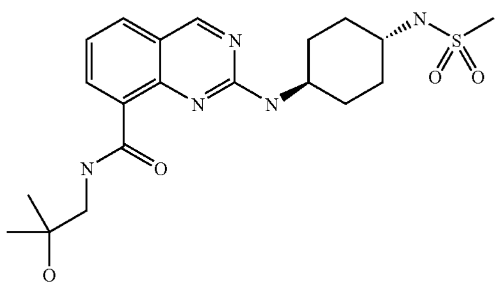 | N-(2-hydroxy-2-methylpropyl)-2-({trans-4-[(methylsulfonyl)amino]cyclohexyl}amino)quinazoline-8-carboxamide | 436.1 | 1H NMR (400 MHz, DMSO-D6) d ppm 10.88 (1 H, t, J = 6.06 Hz) 9.19 (1 H, s) 8.44-8.72 (1 H, m) 7.96 (1 H, dd, J = 7.71, 1.39 Hz) 7.88 (1 H, d, J = 7.83 Hz) 7.32 (1 H, t, J = 7.58 Hz) 7.04 (1 H, d, J = 7.07 Hz) 4.56 (1 H, s) 3.79-3.97 (1 H, m) 3.41 (2 H, d, J = 6.06 Hz) 3.04-3.21 (1 H, m) 2.92 (3 H, s) 1.84-2.10 (4 H, m) 1.31-1.59 (4 H, m) 1.15 (6 H, s) |
| 131 | 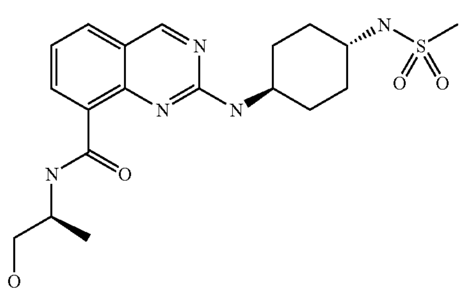 | N-[(1S)-2-hydroxy-1-methylethyl]-2-({trans-4-[(methylsulfonyl)amino]cyclohexyl}amino)quinazoline-8-carboxamide | 422.2 | 1H NMR (400 MHz, DMSO-D6) d ppm 10.56 (1 H, d, J = 8.34 Hz) 9.18 (1 H, s) 8.52 (1 H, dd, J = 7.45, 1.64 Hz) 7.95 (1 H, dd, J = 7.83, 1.52 Hz) 7.85 (1 H, d, J = 8.34 Hz) 7.32 (1 H, t, J = 7.58 Hz) 7.06 (1 H, d, J = 7.07 Hz) 4.88 (1 H, t, J = 5.18 Hz) 4.14-4.32 (1 H, m) 3.76-3.93 (1 H, m) 3.41-3.64 (2 H, m) 3.03-3.20 (1 H, m) 2.92 (3 H, s) 1.85-2.13 (4 H, m) 1.32-1.57 (4 H, m) 1.26 (3 H, d, J = 6.82 Hz) |

-continued

| Example Number | Structure | Compound Name | LRMS m/z | ¹H NMR |
|---|---|---|---|---|
| 132 | 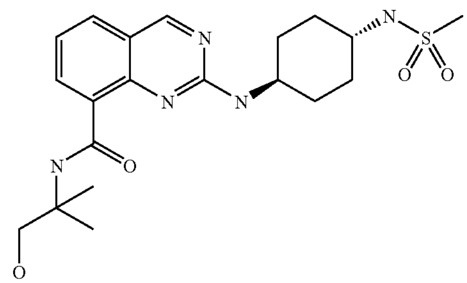 | N-(2-hydroxy-1,1-dimethylethyl)-2-({trans-4-[(methylsulfonyl)amino]cyclohexyl}amino)quinazoline-8-carboxamide | 436.2 | 1H NMR (400 MHz, DMSO-D6) d ppm 10.19 (1 H, s) 9.16 (1 H, s) 8.48 (1 H, dd, J = 7.58, 1.77 Hz) 7.93 (1 H, d, J = 7.58 Hz) 7.79 (1 H, d, J = 8.84 Hz) 7.30 (1 H, t, J = 7.71 Hz) 7.08 (1 H, d, J = 7.07 Hz) 4.97 (1 H, t, J = 4.93 Hz) 3.81-3.99 (1 H, m) 3.61 (2 H, d, J = 5.31 Hz) 3.04-3.20 (1 H, m) 2.92 (3 H, s) 1.84-2.08 (4 H, m) 1.32-1.53 (10 H, m) |
| 133 | 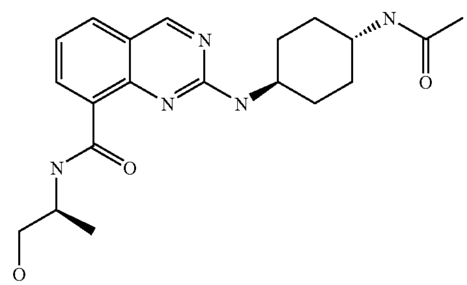 | 2-{[trans-4-(acetylamino)cyclohexyl]amino}-N-[(1S)-2-hydroxy-1-methylethyl]quinazoline-8-carboxamide | 386.2 | 1H NMR (400 MHz, DMSO-D6) d ppm 10.59 (1 H, d, J = 8.08 Hz) 9.18 (1 H, s) 8.52 (1 H, dd, J = 7.33, 1.52 Hz) 7.95 (1 H, dd, J = 7.83, 1.52 Hz) 7.79 (2 H, t, J = 7.58 Hz) 7.32 (1 H, t, J = 7.71 Hz) 4.89 (1 H, t, J = 5.18 Hz) 4.14-4.35 (1 H, m) 3.75-3.95 (1 H, m) 3.40-3.63 (3 H, m) 1.91-2.10 (2 H, m) 1.71-1.88 (5 H, m) 1.30-1.57 (4 H, m) 1.27 (3 H, d, J = 6.82 Hz) |
| 134 | 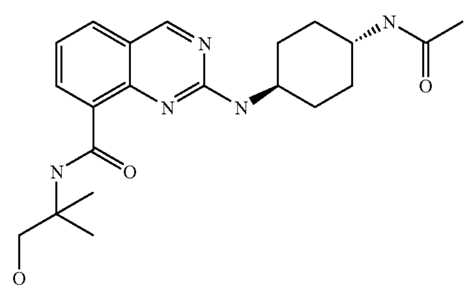 | 2-{[trans-4-(acetylamino)cyclohexyl]amino}-N-(2-hydroxy-1,1-dimethylethyl)quinazoline-8-carboxamide | 400.2 | 1H NMR (400 MHz, DMSO-D6) d ppm 10.22 (1 H, s) 9.16 (1 H, s) 8.48 (1 H, dd, J = 7.58, 1.52 Hz) 7.93 (1 H, d, J = 6.82 Hz) 7.67-7.84 (2 H, m) 7.30 (1 H, t, J = 7.58 Hz) 4.98 (1 H, t, J = 5.31 Hz) 3.84-4.00 (1 H, m) 3.61 (2 H, d, J = 5.56 Hz) 3.41-3.54 (1 H, m) 1.92-2.03 (2 H, m) 1.72-1.86 (5 H, m) 1.23-1.52 (10 H, m) |
| 135 | 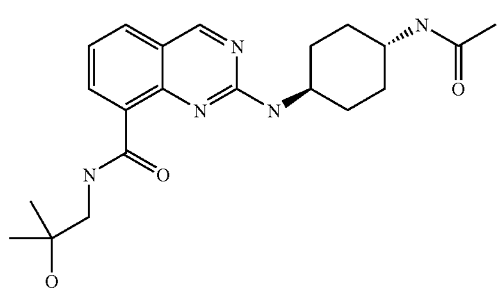 | 2-{[trans-4-(acetylamino)cyclohexyl]amino}-N-(2-hydroxy-2-methylpropyl)quinazoline-8-carboxamide | 400.2 | 1H NMR (400 MHz, DMSO-D6) d ppm 10.89 (1 H, t, J = 5.68 Hz) 9.19 (1 H, s) 8.41-8.68 (1 H, m) 7.96 (1 H, dd, J = 7.83, 1.52 Hz) 7.84 (1 H, d, J = 7.83 Hz) 7.76 (1 H, d, J = 7.58 Hz) 7.32 (1 H, t, J = 7.58 Hz) 4.60 (1 H, s) 3.91 (1 H, s) 3.47 (1 H, s) 3.41 (2 H, d, J =6.32 Hz) 2.01 (2 H, s) 1.69-1.86 (5 H, m) 1.27-1.52 (4 H, m) 1.15 (6 H, s) |

-continued

| Example Number | Structure | Compound Name | LRMS m/z | $^1$H NMR |
|---|---|---|---|---|
| 136 | 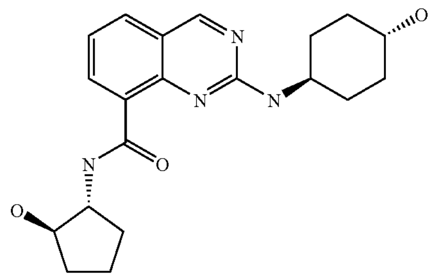 | 2-[(trans-4-hydroxycyclohexyl)amino]-N-[(trans)-2-hydroxycyclopentyl]quinazoline-8-carboxamide | 371.4 | 1H NMR (400 MHz, DMSO-D6) d ppm 10.59 (1 H, d, J = 7.33 Hz) 9.18 (1 H, s) 8.51 (1 H, d, J = 7.58 Hz) 7.95 (1 H, d, J = 7.58 Hz) 7.85 (1 H, d, J = 8.08 Hz) 7.32 (1 H, t, J = 7.58 Hz) 4.98 (1 H, d, J = 3.54 Hz) 4.64 (1 H, d, J = 3.28 Hz) 4.07-4.25 (1 H, m) 3.96-4.07 (1 H, m) 3.73 (1 H, s) 3.38-3.51 (1 H, m) 2.09-2.25 (1 H, m) 1.83-2.03 (5 H, m) 1.62-1.82 (2 H, m) 1.15-1.61 (6 H, m) |
| 137 | 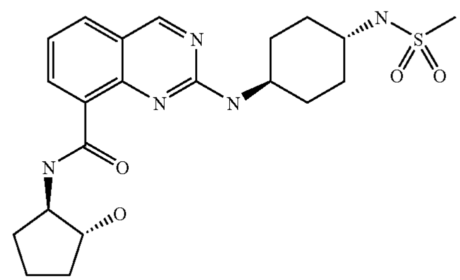 | N-[(trans)-2-hydroxycyclopentyl]-2-({trans-4-[(methylsulfonyl)amino]cyclohexyl}amino)quinazoline-8-carboxamide | 448.4 | 1H NMR (400 MHz, DMSO-D6) d ppm 10.56 (1 H, d, J = 7.33 Hz) 9.19 (1 H, s) 8.51 (1 H, dd, J = 7.58, 1.77 Hz) 7.96 (1 H, dd, J = 7.83, 1.77 Hz) 7.90 (1 H, d, J = 7.83 Hz) 7.33 (1 H, t, J = 7.58 Hz) 7.18 (1 H, d, J = 6.82 Hz) 4.96 (1 H, d, J = 4.29 Hz) 4.05-4.23 (1 H, m) 3.88-4.04 (1 H, m) 3.58-3.82 (1 H, m) 3.04-3.19 (1 H, m) 2.93 (3 H, s) 2.09-2.25 (1 H, m) 1.87-2.07 (5 H, m) 1.61-1.84 (2 H, m) 1.26-1.62 (6 H, m) |
| 138 | 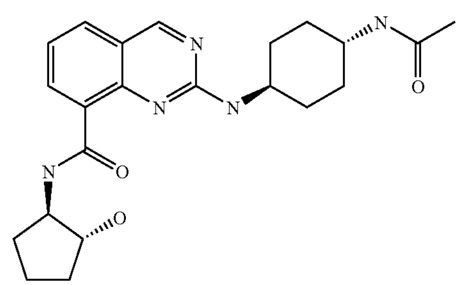 | 2-{[trans-4-(acetylamino)cyclohexyl]amino}-N-[(trans)-2-hydroxycyclopentyl]quinazoline-8-carboxamide | 412.3 | 1H NMR (400 MHz, DMSO-D6) d ppm 10.57 (1 H, d, J = 7.07 Hz) 9.19 (1 H, s) 8.51 (1 H, dd, J = 7.58, 1.77 Hz) 7.96 (1 H, dd, J = 7.83, 1.77 Hz) 7.84 (2 H, dd, J = 16.04, 7.96 Hz) 7.32 (1 H, t, J = 7.58 Hz) 4.97 (1 H, d, J = 4.04 Hz) 4.06-4.23 (1 H, m) 3.93-4.05 (1 H, m) 3.65-3.80 (1 H, m) 3.43-3.55 (1 H, m) 2.08-2.24 (1H, m) 1.91-2.09 (3 H, m) 1.85 (2 H, d, J = 9.60 Hz) 1.79 (3 H, s) 1.65-1.77 (2 H, m) 1.35-1.64 (4 H, m) 1.16-1.34 (2 H, m) |
| 139 | 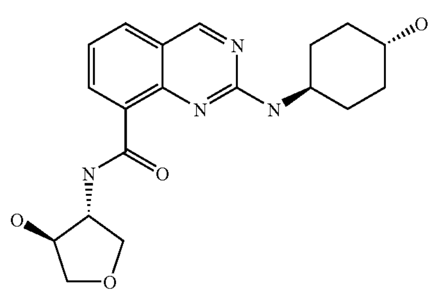 | 2-[(trans-4-hydroxycyclohexyl)amino]-N-[(trans)-4-hydroxytetrahydrofuran-3-yl]quinazoline-8-carboxamide | 373.3 | 1H NMR (400 MHz, DMSO-D6) d ppm 10.73 (1 H, d, J = 6.82 Hz) 9.17 (1 H, s) 8.52 (1 H, d, J = 7.07 Hz) 7.92-8.11 (1 H, m) 7.79 (1 H, d, J = 8.34 Hz) 7.32 (1 H, t, J = 7.58 Hz) 5.46 (1 H, s) 4.57 (1 H, d, J = 3.79 Hz) 4.36 (1 H, s) 4.22 (1 H, s) 4.07 (1 H, dd, J = 8.72, 5.18 Hz) 3.95 (1 H, dd, J = 9.35, 4.55 Hz) 3.66-3.84 (2 H, m) 3.58 (1 H, d, J = 9.35 Hz) 3.35-3.49 (1 H, m) 1.74-2.05 (4 H, m) 1.25-1.56 (4 H, m) |

| Example Number | Structure | Compound Name | LRMS m/z | $^1$H NMR |
|---|---|---|---|---|
| 140 | 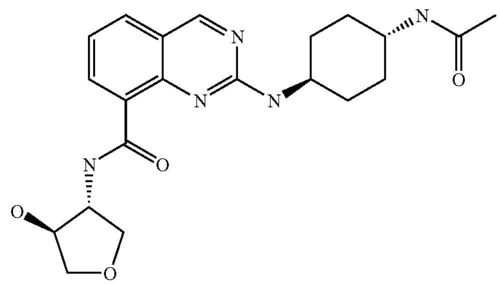 | 2-{[trans-4-(acetylamino)cyclohexyl]amino}-N-[(trans)-4-hydroxytetrahydrofuran-3-yl]quinazoline-8-carboxamide | 414.2 | 1H NMR (400 MHz, DMSO-D6) d ppm 10.76 (1 H, d, J = 6.82 Hz) 9.18 (1 H, s) 8.52 (1 H, d, J = 7.33 Hz) 7.96 (1 H, d, J = 7.58 Hz) 7.80 (2 H, s) 7.32 (1 H, t, J = 7.71 Hz) 5.47 (1 H, s) 4.36 (1 H, s) 4.21 (1 H, s) 4.07 (1 H, dd, J = 8.72, 4.93 Hz) 3.98 (1 H, dd, J = 9.35, 4.29 Hz) 3.71-3.90 (2 H, m) 3.60 (1 H, d, J = 9.09 Hz) 3.46 (1 H, s) 1.85-2.03 (2 H, m) 1.78 (5 H, s) 1.29-1.56 (4 H, m) |
| 141 | 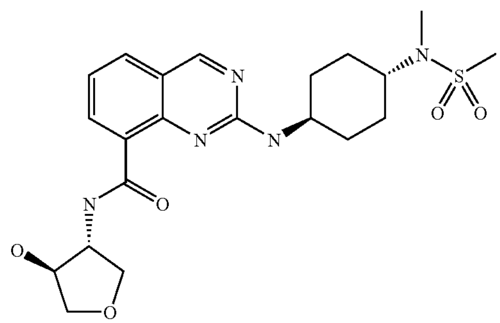 | N-[(trans)-4-hydroxytetrahydrofuran-3-yl]-2-({trans-4-[methyl(methylsulfonyl)amino]cyclohexyl}amino)quinazoline-8-carboxamide | 464.2 | 1H NMR (400 MHz, DMSO-D6) d ppm 10.73 (1 H, d, J = 5.56 Hz) 9.18 (1 H, s) 8.54 (1 H, d, J = 6.82 Hz) 7.94-8.06 (1 H, m) 7.91 (1 H, d) 7.22-7.44 (1 H, m) 5.50 (1 H, s) 4.41 (1 H, s) 4.20 (1 H, s) 4.04-4.16 (1 H, m) 3.90-4.03 (1 H, m) 3.70-3.86 (2 H, m) 3.49-3.68 (2 H, m) 2.85-3.00 (3 H, m) 2.65-2.78 (3 H, m) 1.88-2.10 (2 H, m) 1.74-1.89 (2 H, m) 1.61-1.74 (2 H, m) 1.36-1.62 (2 H, m) |
| 142 | 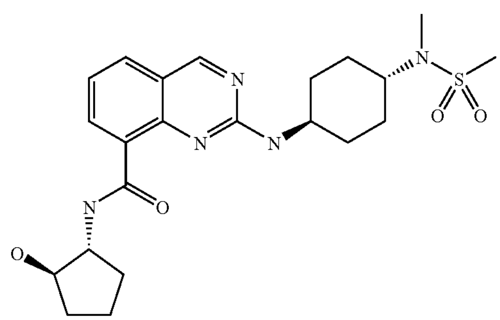 | N-[(trans)-2-hydroxycyclopentyl]-2-({trans-4-[methyl(methylsulfonyl)amino]cyclohexyl}amino)quinazoline-8-carboxamide | 462.2 | 1H NMR (400 MHz, DMSO-D6) d ppm 10.55 (1 H, d, J = 6.06 Hz) 9.20 (1 H, s) 8.51 (1 H, d, J = 7.33 Hz) 7.86-8.02 (2 H, m) 7.33 (1 H, t, J = 7.45 Hz) 5.05 (1 H, s) 3.97-4.18 (2 H, m) 3.74 (1 H, s) 3.63 (1 H, t, J = 10.99 Hz) 2.92 (3 H, s) 2.71 (3 H, s) 2.14-2.26 (1 H, m) 2.04 (2 H, t, J = 12.13 Hz) 1.85-1.97 (1 H, m) 1.42-1.82 (10 H, m) |

Preparation of Example 143: trans-4-[(7-fluoro-quinazolin-2-yl)amino]cyclohexanol

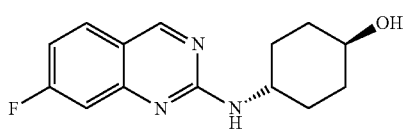

To a solution of 2-chloro, 7-fluoroquinazoline (150 mg, 0.82 mmol) in MeCN (5 mL) was added trans-aminocyclyhexanol (188 mg, 1.65 mmol) followed by DBU (244 uL, 1.65 mmol) and the mixture heated to 80° C. for 18 hours. The reaction was cooled to ambient temperature, the volatiles removed in vacuo, and the residue taken into minimum DCM. Purified by Biotage flash chromatography, eluting with 1-7% MeOH/DCM to afford the title compound as a white solid, 130 mg, 61%. $^1$H NMR (400 MHz, DMSO-D$_6$) δ ppm 9.04 (1H, s) 7.75-7.94 (1H, m) 7.40 (1H, d, J=6.82 Hz) 7.15 (1H, d, J=6.82 Hz) 6.95-7.10 (1H, m) 4.55 (1H, d, J=4.29 Hz) 3.79 (1H, s) 3.39 (1H, dd, J=9.22, 4.93 Hz) 1.68-2.01 (4H, m) 1.17-1.46 (4H, m).

Preparation of Example 144: trans-4-{[7-(tetrahydro-furan-3-yloxy)quinazolin-2-yl]amino}cyclohexanol

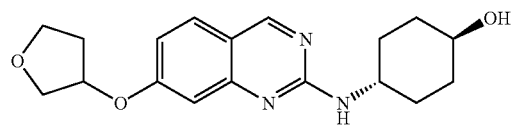

To a solution of tetrahydrofuran-3-ol (337 mg, 3.83 mmol) in THF (5 mL) was added NaH (153 mg, 60% disp. in oil, 3.83 mmol) and the mix stirred at r.t. for 20 min., forming a pale suspension. To this was added trans-4-[(7-fluoroquinazolin- 2-yl)amino]cyclohexanol (100 mg, 0.383 mmol) and a yellow suspension formed almost immediately. The suspension was stirred at r.t. for 30 min then heated to 45° C. for 1 hour, then heated to 65° C. for 30 min then cooled to R.T. overnight. The liquors were concentrated and diluted with water (10 mL) and EtOAc (25 mL) and shaken vigorously. The aq. was removed and the organics washed with water (10 mL), brine (10 mL), dried over MgSO$_4$, filtered and stripped to an oil. Purified by prep TLC eluting with EtOAc to yield the title compound as a white foam, 36 mg, 29%. $^1$H NMR (400 MHz, DICHLOROMETHANE-D$_2$) δ ppm 8.75 (1H, s) 7.53 (1H, d, J=8.84 Hz) 6.62-6.88 (2H, m) 5.18 (1H, d, J=7.83 Hz) 5.05 (1H, s) 3.81-4.08 (5H, m) 3.54-3.79 (2H, m) 2.22-2.43 (1H, m) 2.08-2.21 (3H, m) 1.91-2.07 (2H, m) 1.36-1.51 (4H, m) 1.19-1.38 (4H, m); MS (API+) for C$_{18}$H$_{23}$N$_3$O$_3$ m/z 330.2 (M+H)$^+$.

Preparation of Example 145: trans-4-[(7-methoxyquinazolin-2-yl)amino]cyclohexanol

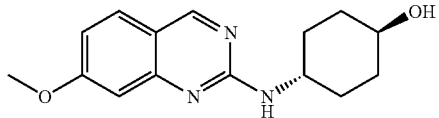

To a solution of trans-4-[(7-fluoroquinazolin-2-yl)amino]cyclohexanol (800 mg, 3.06 mmol) in MeOH (25 mL) was added sodium methoxide powder (1.65 g, 30.62 mmol) and the solution heated to reflux for 16 hours under nitrogen. The mix was cooled and the solvents evaporated. The residue was diluted with water (100 mL), brine (50 mL) and extracted with DCM (4×150 mL), and the combined organics were dried over MgSO$_4$, filtered and stripped. The residue was purified via Biotage flash chromatography (40M) eluting with 2-6% MeOH/DCM over 1300 mL to yield the title compound as an off white solid, 830 mg, 99%. $^1$H NMR (400 MHz, DMSO-D$_6$) δ ppm 8.86 (1H, s) 7.63 (1H, d, J=8.84 Hz) 7.08 (1H, d, J=6.57 Hz) 6.78 (2H, dd, J=8.72, 2.15 Hz) 4.55 (1H, d, J=4.55 Hz) 3.86 (3H, s) 3.71-3.84 (1H, m) 3.35-3.50 (1H, m) 1.76-2.02 (4H, m) 1.14-1.42 (4H, m); MS (API+) for C$_{15}$H$_{19}$N$_3$O$_2$ m/z 274.2 (M+H)$^+$.

Preparation of Example 146: 2-[(trans-4-hydroxycyclohexyl)amino]quinazolin-7-ol

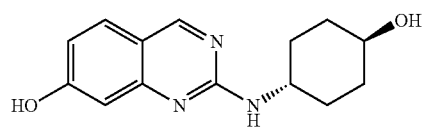

To a solution of trans-4-[(7-methoxyquinazolin-2-yl)amino]cyclohexanol (161 mg, 0.583 mmol) in DMF (10 mL) was added sodium ethanethiolate (248 mg, 2.95 mmol) and the mix heated to 110° C. for 16 hours. The reaction was cooled and the residue was purified directly via Biotage F/C eluting with 5-10% MeOH/DCM to afford the title compound as an off-white solid, 120 mg, 78%. $^1$H NMR (400 MHz, DMSO-D$_6$) ☐ ppm 10.28 (1H, s) 8.79 (1H, s) 7.57 (1H, d, J=8.59 Hz) 6.96 (1H, d, J=8.08 Hz) 6.54-6.79 (2H, m) 4.54 (1H, d, J=3.54 Hz) 3.74 (1H, d, J=3.28 Hz) 3.38 (1H, s) 1.67-1.93 (4H, m) 1.20-1.39 (4H, m); MS (API+) for C$_{14}$H$_{17}$N$_3$O$_2$ m/z 260.2 (M+H)$^+$.

The following examples nos. 147-152 were prepared with non-critical substitutions and/or method changes in an analogous way to example 146:

| Example Number | Structure | Compound Name | LRMS m/z | $^1$H NMR |
|---|---|---|---|---|
| 147 | 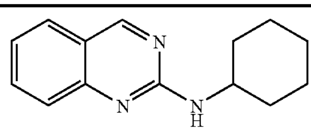 | N-[6-(1H-pyrazol-4-yl)isoquinolin-3-yl]isoindoline-1-carboxamide | 228.2 | $^1$H NMR (400 MHz, DMSO-D$_6$) δ ppm 9.06 (1 H, s) 7.74 (1 H, d, J = 7.83 Hz) 7.57-7.68 (1 H, m) 7.42 (1 H, d, J = 8.08 Hz) 7.03-7.29 (2 H, m) 3.75-3.96 (1 H, m) 1.83-2.02 (2 H, m, J = 9.85 Hz) 1.67-1.81 (2 H, m) 1.60 (1 H, d, J = 12.63 Hz) 1.20-1.44 (4 H, m) 0.98-1.20 (1 H, m). |
| 148 | 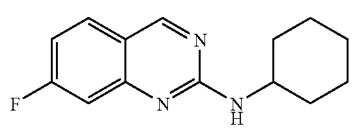 | N-cyclohexylquinazolin-2-amine | 246.2 | $^1$H NMR (400 MHz, DMSO-D$_6$) δ ppm 9.04 (1 H, s) 7.84 (1 H, dd, J = 8.59, 6.82 Hz) 7.44 (1 H, d, J = 7.58 Hz) 7.13 (1 H, d, J = 9.35 Hz) 6.85-7.10 (1 H, m) 3.82 (1 H, s) 1.90 (2 H, d, J = 7.83 Hz) 1.72 (2 H, dd, J = 9.09, 2.78 Hz) 1.59 (1 H, d, J = 12.13 Hz) 1.19-1.41 (4 H, m) 0.87-1.20 (1 H, m). |
| 149 | 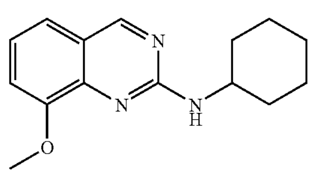 | N-cyclohexyl-7-fluoroquinazolin-2-amine | 258.2 | N/A |
| 150 | 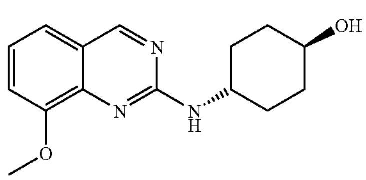 | N-cyclohexyl-8-methoxyquinazolin-2-amine | 274.3 | $^1$H NMR (400 MHz, DMSO-D$_6$) δ ppm 9.03 (1 H, s) 7.30 (1 H, dd, J = 7.58, 1.52 Hz) 7.16-7.26 (1 H, m) 7.03-7.15 (2 H, m) 4.54 (1 H, d, J = 4.29 Hz) 3.87 (3 H, s) 3.72-3.85 (1 H, m) 3.34-3.56 (1 H, m) 1.74-2.00 (4 H, m) 1.15-1.39 (4 H, m). |

| Example Number | Structure | Compound Name | LRMS m/z | ¹H NMR |
|---|---|---|---|---|
| 151 | 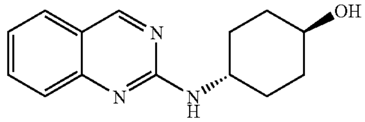 | trans-4-(quinazolin-2-ylamino) cyclohexanol | 244.2 | ¹H NMR (400 MHz, DMSO-D$_6$) δ ppm 9.06 (1 H, s) 7.71-7.86 (1 H, m) 7.57-7.69 (1 H, m) 7.43 (1 H, d, J = 7.83 Hz) 7.19 (2 H, q, J = 6.99 Hz) 4.54 (1 H, d, J = 4.29 Hz) 3.64-3.89 (1 H, m) 3.35-3.54 (1 H, m) 1.76-1.97 (4 H, m) 1.18-1.45 (4 H, m). |
| 152 | 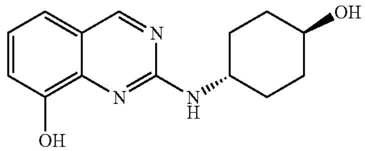 | 2-[(trans-4-hydroxycyclohexyl) amino]quinazolin-8-ol | 260.2 | ¹H NMR (400 MHz, DMSO-D$_6$) d ppm 9.00 (2 H, s) 7.21 (1 H, d, J = 6.32 Hz) 7.16 (1 H, s) 6.98-7.09 (2 H, m) 4.55 (1 H, s) 3.36 (2 H, d, J = 23.75 Hz) 1.86 (4 H, dd, J = 28.30, 8.59 Hz) 1.22-1.48 (4 H, m) |

The following examples nos. 154-169 were prepared with non-critical substitutions and/or method changes in an analogous way to example 68:

| Example Number | Structure | Compound Name | LRMS m/z | ¹H NMR |
|---|---|---|---|---|
| 153 | 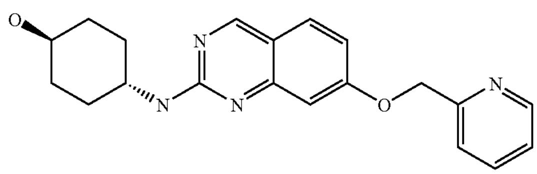 | trans-4-{[7-(pyridin-2-ylmethoxy) quinazolin-2-yl]amino} cyclohexanol | 351.2 | 1H NMR (400 MHz, DMSO-D6) d ppm 8.88 (1 H, s) 8.60 (1 H, d, J = 4.04 Hz) 7.80-7.87 (1 H, m) 7.67 (1 H, d, J = 8.84 Hz) 7.53 (1 H, d, J = 7.83 Hz) 7.36 (1 H, dd, J = 6.82, 5.31 Hz) 7.09 (1 H, d, J = 5.81 Hz) 6.90 (2 H, dd, J = 8.84, 2.02 Hz) 5.30 (2 H, s) 4.53 (1 H, d, J = 4.55 Hz) 3.69-3.85 (1 H, m) 3.34-3.46 (1 H, m) 1.76-1.94 (4 H, m) 1.19-1.39 (4 H, m) |
| 154 | 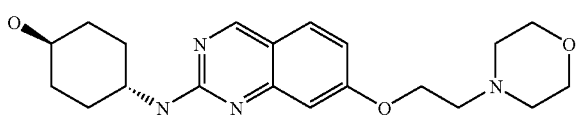 | trans-4-{[7-(2-morpholin-4-ylethoxy)quinazolin-2-yl]amino} cyclohexanol | 373.3 | 1H NMR (400 MHz, CHLOROFORM-D) d ppm 8.78 (1 H, s) 7.52 (1 H, d, J = 8.84 Hz) 6.76-6.94 (2 H, m) 5.03 (1 H, d, J = 7.58 Hz) 4.12-4.36 (2 H, m) 3.85-4.05 (1 H, m) 3.57-3.82 (5 H, m) 2.75-3.01 (2 H, m) 2.60 (4 H, s) 2.22 (2 H, d, J = 11.87 Hz) 2.04 (2 H, d, J = 11.12 Hz) 1.43-1.58 (2 H, m) 1.19-1.40 (2 H, m) |
| 155 | 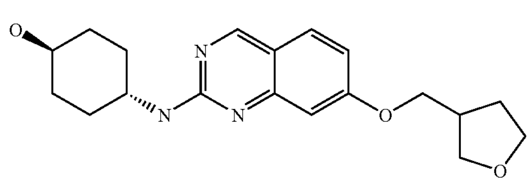 | trans-4-{[7-(tetrahydrofuran-3-ylmethoxy)quinazolin-2-yl]amino} cyclohexanol | 344.2 | 1H NMR (400 MHz, CHLOROFORM-D) d ppm 8.78 (1 H, s) 7.52 (1 H, d, J = 8.84 Hz) 6.72-6.95 (2 H, m) 5.02 (1 H, d, J = 8.08 Hz) 3.58-4.19 (8 H, m) 2.63-3.09 (1 H, m) 1.96-2.36 (5 H, m) 1.68-1.85 (1 H, m) 1.43-1.59 (2 H, m) 1.17-1.40 (2 H, m) |

-continued

| Example Number | Structure | Compound Name | LRMS m/z | ¹H NMR |
|---|---|---|---|---|
| 156 | 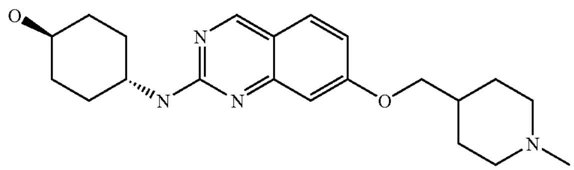 | trans-4-({7-[(1-methylpiperidin-4-yl)methoxy]quinazolin-2-yl}amino)cyclohexanol | 371.2 | 1H NMR (400 MHz, DMSO-D6) d ppm 8.85 (1 H, s) 7.62 (1 H, d, J = 8.84 Hz) 7.06 (1 H, s) 6.73-6.83 (2 H, m) 4.55 (1 H, d, J = 4.29 Hz) 3.93 (2 H, d, J = 5.81 Hz) 3.65-3.83 (1 H, m) 3.35-3.49 (1 H, m) 2.77 (2 H, d, J = 11.37 Hz) 2.14 (3 H, s) 1.62-1.95 (10 H, m) 1.20-1.41 (5 H, m) |
| 157 | 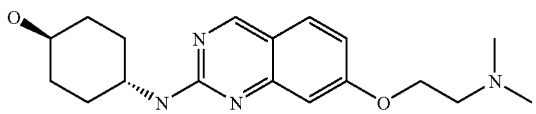 | trans-4-({7-[2-(dimethylamino)ethoxy]quinazolin-2-yl}amino)cyclohexanol | 331.2 | 1H NMR (400 MHz, DMSO-D6) d ppm 8.86 (1 H, s) 7.62 (1 H, d, J = 8.84 Hz) 7.06 (1 H, s) 6.80-6.89 (1 H, m) 6.77 (1 H, dd, J = 8.72, 2.15 Hz) 4.55 (1 H, d, J = 4.29 Hz) 4.15 (2 H, t, J = 5.68 Hz) 3.69-3.87 (1 H, m) 3.34-3.48 (1 H, m) 2.64 (2 H, t, J = 5.68 Hz) 2.21 (6 H, s) 1.76-1.95 (4 H, m) 1.18-1.40 (4 H, m) |
| 158 | 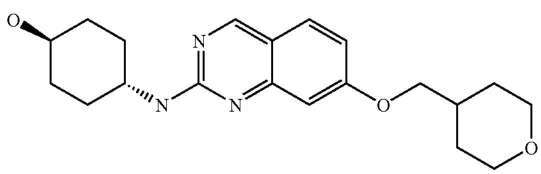 | trans-4-{[7-(tetrahydro-2H-pyran-4-ylmethoxy)quinazolin-2-yl]amino}cyclohexanol | 358.2 | 1H NMR (400 MHz, CHLOROFORM-D) d ppm 8.76 (1 H, s) 7.51 (1 H, d, J = 8.84 Hz) 6.85 (1 H, s) 6.64-6.84 (1 H, m) 5.01 (1 H, d, J = 7.83 Hz) 3.87-4.13 (4 H, m) 3.56-3.80 (1 H, m) 3.45 (2 H, t, J = 11.24 Hz) 1.95-2.32 (4 H, m) 1.77 (2 H, d, J = 12.13 Hz) 1.39-1.58 (6 H, m) 1.15-1.37 (2 H, m) |
| 159 | 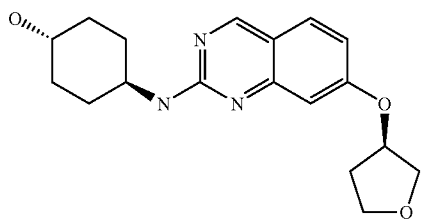 | trans-4-({7-[(3R)-tetrahydrofuran-3-yloxy]quinazolin-2-yl}amino)cyclohexanol | 330.2 | 1H NMR (400 MHz, DMSO-D6) d ppm 8.87 (1 H, s) 7.64 (1 H, d, J = 9.09 Hz) 7.06 (1 H, s) 6.76 (2 H, d, J = 7.07 Hz) 5.20 (1 H, s) 4.53 (1 H, d, J = 4.29 Hz) 3.71-3.95 (5 H, m) 3.34-3.47 (1 H, m) 2.18-2.37 (1 H, m) 1.94-2.07 (1 H, m) 1.73-1.94 (4 H, m) 1.18-1.38 (4 H, m) |
| 160 | 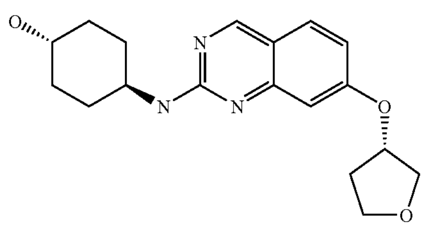 | trans-4-({7-[(3S)-tetrahydrofuran-3-yloxy]quinazolin-2-yl}amino)cyclohexanol | 330.2 | 1H NMR (400 MHz, DMSO-D6) d ppm 8.87 (1 H, s) 7.64 (1 H, d, J = 9.09 Hz) 7.06 (1 H, s) 6.76 (2 H, d, J = 7.07 Hz) 5.20 (1 H, s) 4.53 (1 H, d, J = 4.29 Hz) 3.71-3.95 (5 H, m) 3.34-3.47 (1 H, m) 2.18-2.37 (1 H, m) 1.94-2.07 (1 H, m) 1.73-1.94 (4 H, m) 1.18-1.38 (4 H, m) |

| Example Number | Structure | Compound Name | LRMS m/z | $^1$H NMR |
|---|---|---|---|---|
| 161 | 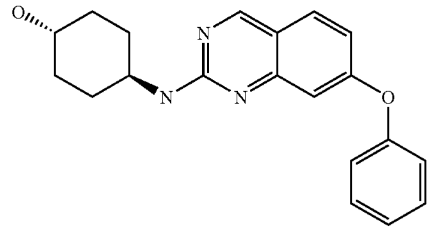 | trans-4-[(7-phenoxyquinazolin-2-yl)amino]cyclohexanol | 336.2 | 1H NMR (400 MHz, DMSO-D6) d ppm 8.95 (1 H, s) 7.77 (1 H, d, J = 8.59 Hz) 7.48 (2 H, t, J = 7.96 Hz) 7.27 (1 H, t, J = 7.45 Hz) 7.05-7.23 (3 H, m, J = 7.83 Hz) 6.81-7.05 (1 H, m) 6.58 (1 H, d, J = 2.27 Hz) 4.52 (1 H, d, J = 4.29 Hz) 3.70 (1 H, s) 3.30-3.47 (1 H, m) 1.83 (4 H, dd, J = 21.73, 10.61 Hz) 1.05-1.44 (4 H, m) |
| 162 | 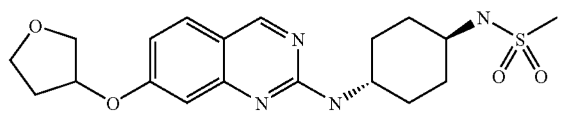 | N-(trans-4-{[7-(tetrahydrofuran-3-yloxy)quinazolin-2-yl]amino}cyclohexyl)methanesulfonamide | 407.3 | 1H NMR (400 MHz, DMSO-D6) d ppm 8.87 (1 H, s) 7.65 (1 H, d, J = 8.84 Hz) 7.15 (1 H, s) 7.03 (1 H, d, J = 7.07 Hz) 6.77 (2 H, d, J = 7.58 Hz) 5.20 (1 H, s) 3.69-3.97 (5 H, m) 3.09 (1 H, s) 2.92 (3 H, s) 2.18-2.37 (1 H, m, J = 13.77, 6.44 Hz) 1.79-2.06 (5 H, m) 1.25-1.52 (4 H, m) |
| 163 | 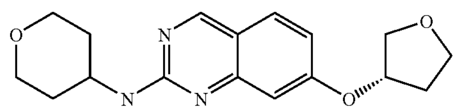 | 7-[(3S)-tetrahydrofuran-3-yloxy]-N-(tetrahydro-2H-pyran-4-yl)quinazolin-2-amine | 316.0 | 1H NMR (CDCl$_3$): 8.74 (1 H, s), 7.48 (1 H, d), 6.77 (1 H, dd), 6.72 (1 H, s), 5.21 (1 H, bs), 4.98 (1 H, m), 4.15 (1 H, m), 3.97 (5 H, m), 3.86 (1 H, m), 3.53 (2 H, m), 2.20 (2 H, m), 2.04 (2 H, m), 1.53 (2 H, m) |
| 164 | 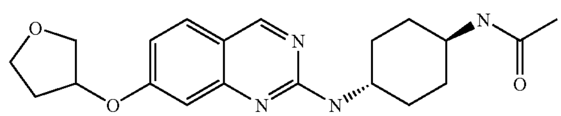 | N-(trans-4-{[7-(tetrahydrofuran-3-yloxy)quinazolin-2-yl]amino}cyclohexyl)acetamide | 371.3 | 1H NMR (400 MHz, DMSO-D6) d ppm 8.87 (1 H, s) 7.74 (1 H, d, J = 7.58 Hz) 7.65 (1 H, d, J = 9.09 Hz) 7.12 (1 H, s) 6.69-6.84 (2 H, m) 5.20 (1 H, s) 3.70-3.97 (5 H, m) 3.39-3.58 (1 H, m) 2.20-2.37 (1 H, m) 1.86-2.07 (3 H, m) 1.71-1.85 (5 H, m) 1.16-1.46 (4 H, m) |
| 165 | 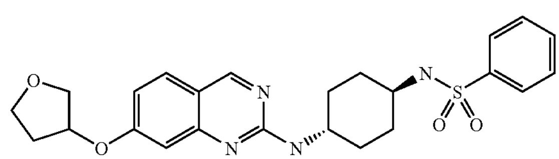 | N-(trans-4-{[7-(tetrahydrofuran-3-yloxy)quinazolin-2-yl]amino}cyclohexyl)benzenesulfonamide | 469.3 | 1H NMR (400 MHz, DMSO-D6) d ppm 8.85 (1 H, s) 7.82 (2 H, dd, J = 7.96, 1.39 Hz) 7.72 (1 H, d, J = 7.33 Hz) 7.52-7.66 (4 H, m) 7.05 (1 H, s) 6.69-6.80 (2 H, m) 5.19 (1 H, s) 3.64-3.95 (5 H, m) 2.92 (1 H, s) 2.20-2.33 (1 H, m) 1.92-2.05 (1 H, m) 1.85 (2 H, d, J = 9.85 Hz) 1.64 (2 H, d, J = 10.86 Hz) 1.11-1.36 (4 H, m) |
| 166 | 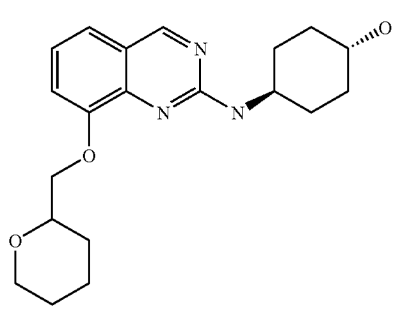 | trans-4-{[8-(tetrahydro-2H-pyran-2-ylmethoxy)quinazolin-2-yl]amino}cyclohexanol | 358.3 | 1H NMR (400 MHz, DICHLOROMETHANE-D2) d ppm 8.94 (1 H, s) 7.27 (1 H, dd, J = 7.71, 1.39 Hz) 6.98-7.17 (2 H, m) 5.27 (1 H, s) 3.88-4.21 (4 H, m) 3.75-3.87 (1 H, m) 3.60-3.73 (1 H, m) 3.47-3.58 (1 H, m) 2.11-2.43 (2 H, m) 2.00 (2 H, t, J = 3.54 Hz) 1.92 (1 H, dd, J = 5.43, 2.91 Hz) 1.75 (1 H, d, J = 11.87 Hz) 1.26-1.71 (9 H, m) |

| Example Number | Structure | Compound Name | LRMS m/z | $^1$H NMR |
|---|---|---|---|---|
| 167 | 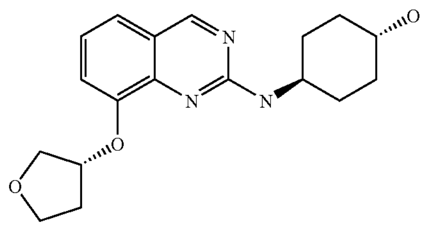 | trans-4-({8-[(3R)-tetrahydrofuran-3-yloxy]quinazolin-2-yl}amino)cyclohexanol | 330.3 | 1H NMR (400 MHz, DMSO-D6) d ppm 9.05 (1 H, s) 7.39 (1 H, d, J = 6.57 Hz) 7.26 (1 H, s) 7.19 (1 H, s) 7.09 (1 H, t, J = 7.58 Hz) 5.24 (1 H, s) 4.53 (1 H, s) 3.89 (3 H, s) 3.62-3.83 (2 H, m) 3.34-3.49 (1 H, m) 1.77-2.27 (6 H, m) 1.12-1.47 (4 H, m) |
| 168 | 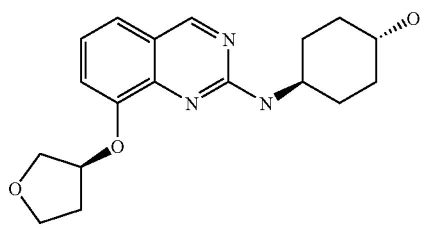 | trans-4-({8-[(3S)-tetrahydrofuran-3-yloxy]quinazolin-2-yl}amino)cyclohexanol | 330.3 | 1H NMR (400 MHz, DMSO-D6) d ppm 9.05 (1 H, s) 7.39 (1 H, d, J = 6.57 Hz) 7.26 (1 H, s) 7.19 (1 H, s) 7.09 (1 H, t, J = 7.58 Hz) 5.24 (1 H, s) 4.53 (1 H, s) 3.89 (3 H, s) 3.62-3.83 (2 H, m) 3.34-3.49 (1 H, m) 1.77-2.27 (6 H, m) 1.12-1.47 (4 H, m) |

Preparation of example 169: trans-4-{[8-(tetrahydro-2H-pyran-4-yloxy)quinazolin-2-yl]amino}cyclohexanol

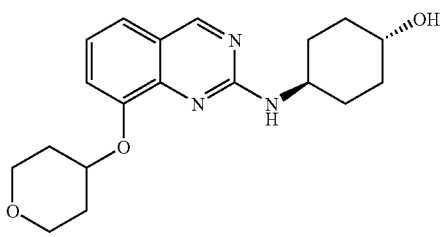

2-chloro-8-(tetrahydro-2H-pyran-4-yloxy)quinazoline (1 g, 3.8 mmol), trans-4-amino-cyclohexanol (0.524 g, 4.56 mmol) and DBU (0.69 g, 4.56 mmol) were suspended in MeCN (10 mL). The mixture was heated at reflux for 10 h. TLC showed the reaction was complete. The mixture was concentrated in vacuo, the residue was purified by HPLC to yield the title compound (0.373 g, 28%) as a yellow solid. $^1$H NMR (400 MHz, CDCl$_3$): δ 10.817 (d, 1H), 9.120 (s, 1H), 7.351 (m, 2H), 7.210 (m, 1H), 4.630 (m, 1H), 4.118 (m, 1H), 4.041 (m, 2H), 3.712 (m, 1H), 3.524 (m, 2H), 2.001 (m, 8H), 1.620 (q, 2H), 1.419 (q, 2H)

Preparation of intermediate 169a: 3-hydroxy-2-nitrobenzoic acid

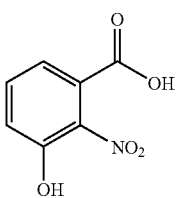

3-chloro-2-nitrobenzoic acid (30 g, 0.15 mol) and KOH (120 g, 2.14 mol) were dissolved in water (150 mL). The mixture was heated at reflux for 12 h. TLC (petroleum ether:ethyl acetate=1:1) showed the reaction was complete. The pH of mixture was adjusted to 3. The resulting mixture was extracted with ethyl acetate (2×300 mL). The combined organic layers were washed with brine, dried over Na$_2$SO$_4$ and concentrated in vacuo to give the title compound (40 g, 100%) as a brown solid. $^1$H NMR (400 MHz, DMSO): δ 11.193 (s, 1H), 7.476 (t, 1H), 7.367 (d, 1H), 7.268 (d, 1H).

Preparation of intermediate 169b: methyl 3-hydroxy-2-nitrobenzoate

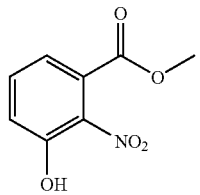

SOCl$_2$ (0.6 mL) was added dropwise to anhydrous MeOH (10 mL) at 0° C. The mixture was stirred at this temperature for 0.5 h, then 3-hydroxy-2-nitrobenzoic acid (0.6 g, 3.2 mmol) was added to the mixture. The resulting mixture was heated at reflux for 4 h. TLC (petroleum ether:ethyl acetate=1:1) showed the reaction was complete. The resulting mixture was concentrated in vacuo to give the title compound (0.63 g 100%) as a brown solid.

Preparation of intermediate 169c: methyl 2-nitro-3-(tetrahydro-2H-pyran-4-yloxy)benzoate

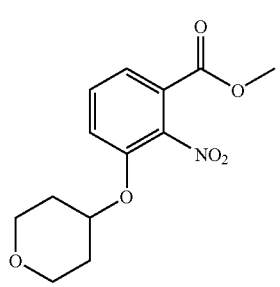

Methyl 3-hydroxy-2-nitrobenzoate (95 g, 0.52 mol), tetrahydro-2H-pyran-4-yl methanesulfonate (234 g, 1.3 mol) and K$_2$CO$_3$ (358 g, 2.6 mol) was suspend in MeCN (2 L). The mixture was heated at reflux for 20 h. TLC (petroleum ether: ethyl acetate=1:1) showed the reaction was complete. The mixture was filtered; the filtrate was concentrated in vacuo. The residue was purified by chromatography (petroleum ether: ethyl acetate=10:1, 5:1, 2:1) to give the title compound (200 g 100%) as a yellow oil.

Preparation of intermediate 169d: methyl 2-amino-3-(tetrahydro-2H-pyran-4-yloxy)benzoate

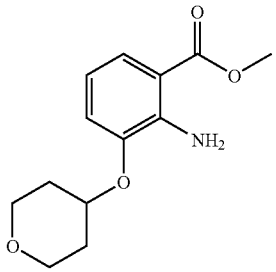

A mixture of methyl 2-nitro-3-(tetrahydro-2H-pyran-4-yloxy)benzoate (1.3 g, 4.8 mmol) and Raney Ni (0.5 g) in MeOH (30 mL) was stirred under 1 atm of H$_2$ at room temperature for 24 h. TLC (petroleum ether:ethyl acetate=1:1) showed the reaction was complete. The mixture was filtered, the filtrate was concentrated in vacuo. The residue was purified by chromatography (petroleum ether:ethyl acetate=20:1) to give the title compound (0.8 g, 72%) as a colorless oil.

Preparation of intermediate 169e: 8-(tetrahydro-2H-pyran-4-yloxy)quinazoline-2,4-diol

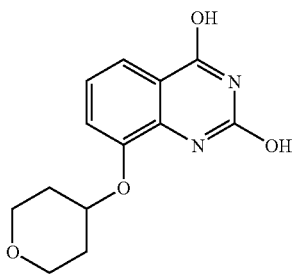

To a solution of methyl 2-amino-3-(tetrahydro-2H-pyran-4-yloxy)benzoate (18 g, 0.071 mol) in AcOH (180 mL) was added a solution of KOCN (11.47 g, 142 mmol) in water (22 mL) at 60° C. Then the mixture was heated at 80° C. for 40 h. TLC (petroleum ether:ethyl acetate=1:1) showed the reaction was complete. Then the mixture was concentrated in vacuo. The residue was diluted with water (200 mL). The precipitate was filtered to give the title compound (9 g, 42%) as a white solid. $^1$H NMR (400 MHz, DMSO): δ 11.354 (s, 1H), 10.491 (s, 1H), 7.539 (d, 1H), 7.455 (d, 1H), 7.191 (t, 1H), 4.732 (m, 1H), 4.006 (m, 2H), 3.535 (m, 3H), 2.023 (m, 2H), 1.842 (m, 2H)

Preparation of intermediate 169f: 2,4-dichloro-8-(tetrahydro-2H-pyran-4-yloxy)quinazoline

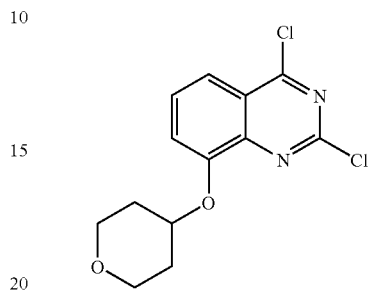

8-(tetrahydro-2H-pyran-4-yloxy)quinazoline-2,4-diol (0.3 g, 1.14 mmol) and DMA (1.16 g, 9.5 mmol) was suspended in POCl$_3$ (9 mL). The mixture was heated at reflux for 2.5 h. TLC (petroleum ether:ethyl acetate=1:1) showed the reaction was complete. The mixture was concentrated in vacuo. The residue was purified by chromatography (CH$_2$Cl$_2$) to give the title compound (0.16 g, 50%) as a light yellow solid. $^1$H NMR (400 MHz, CDCl$_3$): δ 8.280 (s, 1H), 7.441 (s, 1H), 7.266-7.234 (dd, 1H), 7.195-7.167 (d, 1H), 3.290-3.192 (m, 1H), 1.659-1.570 (m, 2H), 1.520-1.464 (m, 2H), 1.423-1.330 (m, 1H), 1.190-1.030 (m, 2H), 1.030-0.860 (m, 3H)

Preparation of intermediate 169g: 2-chloro-8-(tetrahydro-2H-pyran-4-yloxy)quinazoline

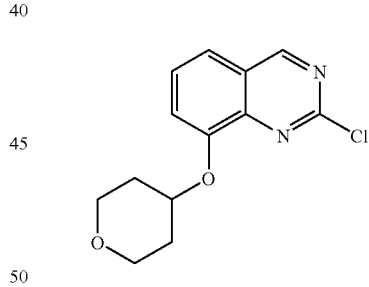

To a mixture of 2,4-dichloro-8-(tetrahydro-2H-pyran-4-yloxy)quinazoline (4 g, 13.4 mmol), DIPEA (2.07 g, 16.8 mmol) and Pd/C (0.4 g, 10%) in ethyl acetate (10 mL) was stirred under 1 atm of H$_2$ for 4 h. TLC (petroleum ether:ethyl acetate=1:1) showed the reaction was complete. The mixture was filtered through a Celite pad, and the filtrate was concentrate in vacuo. The residue was purified by chromatography (petroleum ether:ethyl acetate=20:1, 10:1) to give the title compound (2 g, 57%) as a light yellow solid. $^1$H NMR (300 MHz, CDCl$_3$): δ 7.789 (d, 1H), 7.551 (t, 1H), 7.317 (d, 1H), 4.723 (m, 1H), 4.038 (m, 2H), 3.556 (m, 2H), 2.068 (m, 2H), 1.950 (m, 2H)

The following examples nos. 170-178 were prepared with non-critical substitutions and/or method changes in an analogous way to example 169:

| Example Number | Structure | Compound Name | LRMS m/z | ¹H NMR |
|---|---|---|---|---|
| 170 | 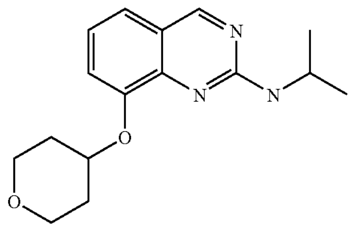 | N-isopropyl-8-(tetrahydro-2H-pyran-4-yloxy)quinazolin-2-amine | 288.3 | ¹H NMR (CDCl₃, 400 Hz): 10.635 (s, 1H), 9.117 (s, 1H), 7.319 (m, 2H), 7.206 (d, 1H), 4.598 (m, 1H), 4.462 (m, 1H), 4.028 (m, 2H), 3.524 (m, 2H), 2.012 (t, 4H), 1.299 (d, 6H). |
| 171 | 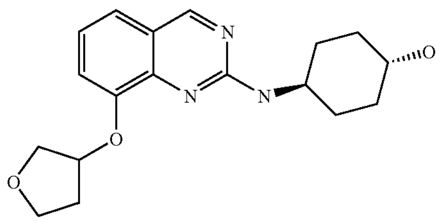 | trans-4-{[8-(tetrahydrofuran-3-yloxy)quinazolin-2-yl]amino}cyclohexanol | 330.5 | ¹H NMR (400 MHz, CDCl₃): δ 11.331 (s, 1H), 9.195 (s, 1H), 7.371 (m, 2H), 7.048 (d, 1H), 5.001 (m, 1H), 4.071 (m, 4H), 3.905 (m, 1H), 3.678 (m, 1H), 2.567 (m, 1H), 2.231 (m, 1H), 1.992 (m, 4H), 1.614 (q, 2H), 1.410 (q, 2H). |
| 172 | 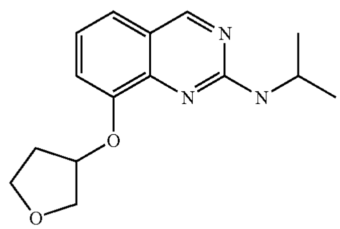 | N-isopropyl-8-(tetrahydrofuran-3-yloxy)quinazolin-2-amine | 274.5 | ¹H NMR (CDCl₃, 400 Hz): 11.342 (s, 1H), 9.171 (s, 1H), 7.379 (m, 2H), 7.107 (d, 1H), 5.076 (m, 1H), 4.508 (m, 1H), 4.136 (m, 3H), 3.969 (m, 2H), 2.645 (m, 1H), 2.292 (m, 1H), 1.371 (d, 6H) |
| 173 | 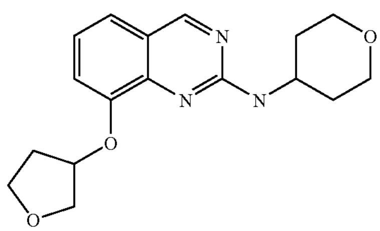 | 8-(tetrahydrofuran-3-yloxy)-N-(tetrahydro-2H-pyran-4-yl)quinazolin-2-amine | 316.3 | ¹H NMR (CDCl₃, 400 Hz): 11.580 (s, 1H), 9.179 (s, 1H), 7.401 (m, 2H), 7.146 (d, 1H), 5.082 (s, 1H), 4.386 (m, 1H), 4.031 (m, 4H), 3.508 (m, 1H), 2.636 (m, 1H), 2.263 (m, 1H), 1.945 (m, 4H) |
| 174 | 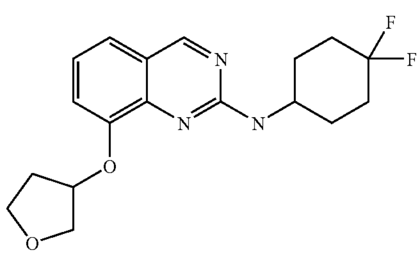 | N-(4,4-difluorocyclohexyl)-8-(tetrahydrofuran-3-yloxy)quinazolin-2-amine | 350.4 | ¹H NMR (CDCl₃, 400 Hz): 11.617 (s, 1H), 9.191 (s, 1H), 7.410 (m, 2H), 7.153 (d, 1H), 5.086 (s, 1H), 3.997 (m, 2H), 2.637 (m, 1H), 1.960 (m, 9H). |
| 175 | 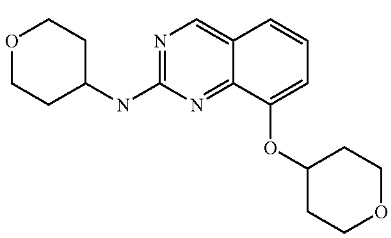 | N-(tetrahydro-2H-pyran-4-yl)-8-(tetrahydro-2H-pyran-4-yloxy)quinazolin-2-amine | 330.5 | ¹H NMR (CDCl₃, 400 Hz): 11.369 (s, 1H), 9.109 (s, 1H), 7.324 (m, 2H), 7.213 (d, 1H), 4.636 (m, 1H), 4.302 (m, 1H), 4.005 (m, 4H), 3.493 (m, 4H), 2.024 (t, 4H), 1.887 (m, 4H) |

| Example Number | Structure | Compound Name | LRMS m/z | $^1$H NMR |
|---|---|---|---|---|
| 176 | 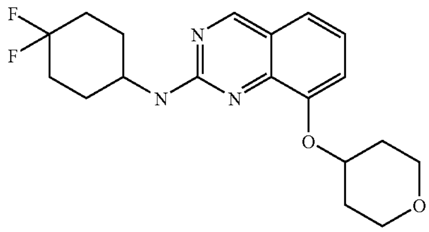 | N-(4,4-difluorocyclohexyl)-8-(tetrahydro-2H-pyran-4-yloxy)quinazolin-2-amine | 364.5 | $^1$H NMR (CDCl$_3$, 400 Hz): 11.384 (s, 1H), 9.128 (s, 1H), 7.289 (m, 3H), 4.623 (s, 1H), 4.209 (s, 1H), 4.016 (m, 2H), 3.522 (m, 2H), 1.922 (m, 12H) |
| 177 | 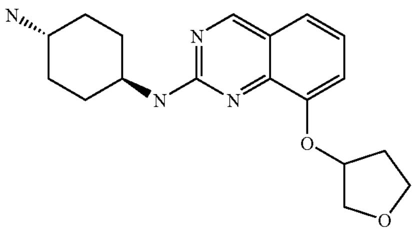 | trans-N-[8-(tetrahydrofuran-3-yloxy)quinazolin-2-yl]cyclohexane-1,4-diamine | 329.6 | $^1$H NMR (CDCl$_3$, 400 Hz): 8.881 (s, 1H), 7.247 (d, 1H), 7.047 (m, 2H), 5.127 (s, 1H), 4.027 (m, 5H), 3.157 (s, 1H), 2.212 (m, 7H), 1.623 (m, 3H), 1.305 (m, 3H) |
| 178 | 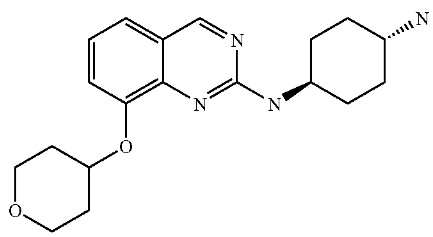 | trans-N-[8-(tetrahydro-2H-pyran-4-yloxy)quinazolin-2-yl]cyclohexane-1,4-diamine | 343.2 | $^1$H NMR (CDCl$_3$, 400 Hz): 8.912 (s, 1H), 7.321 (d, 1H), 7.301 (d, 1H), 7.071 (t, 1H), 4.750 (m, 1H), 3.965 (m, 3H), 3.495 (m, 2H), 3.050 (m, 1H), 2.210 (d, 2H), 2.004 (m, 4H), 1.773 (m, 2H), 1.400 (m, 4H) |

Preparation of example 179: N-(trans-4-{[8-(tetrahydro-2H-pyran-4-yloxy)quinazolin-2-yl]amino}cyclohexyl)acetamide

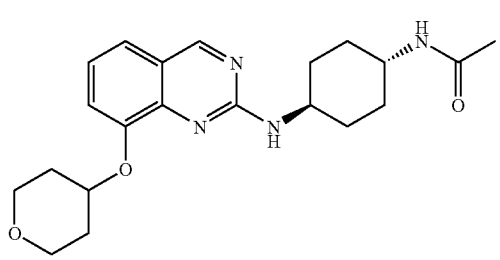

To a solution of trans-N-[8-(tetrahydro-2H-pyran-4-yloxy)quinazolin-2-yl]cyclohexane-1,4-diamine (0.3 g, 0.876 mmol) and acetyl chloride (0.0825 g, 1.05 mmol) in CH$_2$Cl$_2$ (10 mL) was added Et$_3$N (0.106 g, 1.05 mmol). The resulting mixture was stirred at room temperature overnight. TLC (DCM:MeOH=10:1) showed the reaction was complete. CH$_2$Cl$_2$ (30 mL) was added to the solution. The solution was washed with H$_2$O (3×20 mL) and brine (30 mL), dried over Na$_2$SO$_4$ and concentrated in vacuo to give crude solid, which was washed with ethyl acetate to give the title compound (0.180 g, 54.5%) as a white solid. $^1$H NMR (CDCl$_3$, 400 Hz): 8.875 (s, 1H), 7.255 (d, 2H), 7.132 (d, 1H), 7.050 (t, 1H), 5.245 (d, 1H), 5.133 (d, 1H), 4.002 (m, 2H), 3.869 (m, 1H), 3.709 (m, 1H), 3.507 (m, 2H), 2.178 (d, 2H), 1.979 (t, 4H), 1.893 (m, 5H), 1.249 (m, 4H).

The following examples nos. 180-188 were prepared with non-critical substitutions and/or method changes in an analogous way to example 179:

| Example Number | Structure | Compound Name | LRMS m/z | $^1$H NMR |
|---|---|---|---|---|
| 180 | 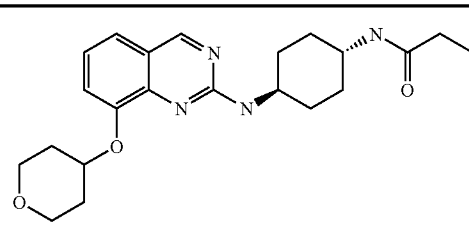 | N-(trans-4-{[8-(tetrahydro-2H-pyran-4-yloxy)quinazolin-2-yl]amino}cyclohexyl)propanamide | 399.5 | $^1$H NMR (CDCl$_3$, 400 Hz): 11.350 (s, 1H), 9.094 (s, 1H), 7.330 (m, 2H), 7.218 (d, 1H), 5.155 (d, 1H), 4.610 (d, 1H), 4.016 (t, 3H), 3.746 (d, 1H), 3.504 (m, 2H), 2.069 (m, 10H), 1.683 (m, 2H), 1.197 (m, 2H), 1.065 (t, 3H) |

-continued

| Example Number | Structure | Compound Name | LRMS m/z | ¹H NMR |
|---|---|---|---|---|
| 181 | 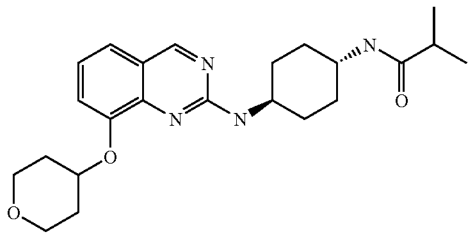 | 2-methyl-N-(trans-4-{[8-(tetrahydro-2H-pyran-4-yloxy)quinazolin-2-yl]amino}cyclohexyl)propanamide | 413.5 | ¹H NMR (CDCl₃, 400 Hz): 8.870 (s, 1H), 7.252 (d, 1H), 7.148 (d, 1H), 7.046 (t, 1H), 5.194 (d, 1H), 5.109 (d, 1H), 4.695 (s, 1H), 4.001 (m, 2H), 3.762 (m, 2H), 3.528 (t, 2H), 2.226 (m, 3H), 1.992 (d, 4H), 1.884 (m, 2H), 1.267 (m, 4H), 1.082 (d, 6H) |
| 182 | 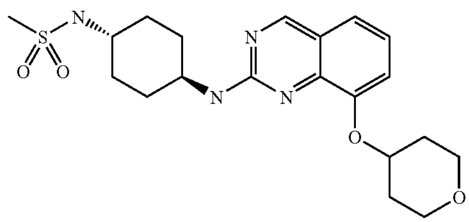 | N-(trans-4-{[8-(tetrahydro-2H-pyran-4-yloxy)quinazolin-2-yl]amino}cyclohexyl)methanesulfonamide | 421.4 | ¹H NMR (CDCl₃, 400 Hz): 8.884 (s, 1H), 7.277 (d, 1H), 7.194 (m, 2H), 5.132 (s, 1H) 4.695 (s, 1H), 4.141 (d, 1H), 4.041 (d, 2H), 3.879 (d, 1H), 2.943 (s, 3H), 2.096 (m, 8H), 1.345 (m, 4H) |
| 183 | 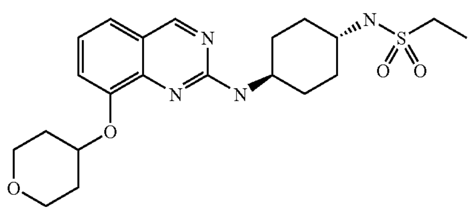 | N-(trans-4-{[8-(tetrahydro-2H-pyran-4-yloxy)quinazolin-2-yl]amino}cyclohexyl)ethanesulfonamide | 435.7 | ¹H NMR (CDCl₃, 400 Hz): 11.234 (d, 1H), 9.130 (s, 1H), 7.322 (m, 2H), 7.208 (t, 1H), 4.614 (t, 1H), 4.001 (m, 4H), 3.520 (t, 2H), 3.246 (s, 1H), 2.981 (m, 2H), 2.104 (d, 2H), 2.005 (d, 6H), 1.700 (m, 2H), 1.290 (m, 5H) |
| 184 | 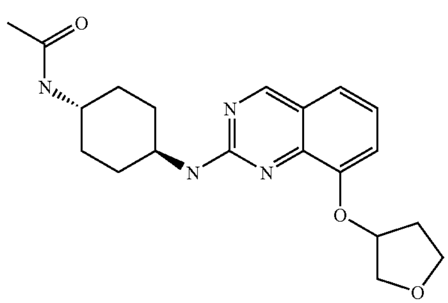 | N-(trans-4-{[8-(tetrahydrofuran-3-yloxy)quinazolin-2-yl]amino}cyclohexyl)acetamide | 371.3 | ¹H NMR (CDCl₃, 400 Hz): 8.878 (s, 1H), 7.257 (d, 1H), 7.052 (m, 2H), 5.231 (d, 1H), 5.143 (s, 1H), 4.021 (m, 3H), 3.908 (m, 2H), 3.769 (m, 1H), 2.213 (m, 4H), 2.304 (d, 1H), 1.911 (s, 3H), 1.271 (m, 4H) |
| 185 | 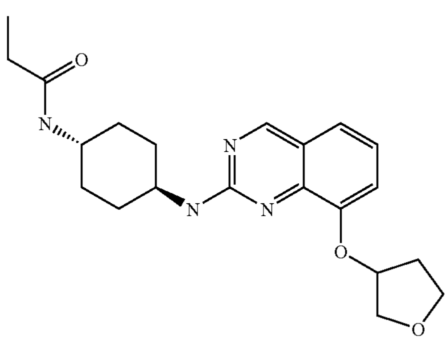 | N-(trans-4-{[8-(tetrahydrofuran-3-yloxy)quinazolin-2-yl]amino}cyclohexyl)propanamide | 385.4 | ¹H NMR (CDCl₃, 400 Hz): 8.876 (s, 1H), 7.256 (s, 1H), 7.051 (m, 2H), 5.201 (m, 3H), 4.014 (m, 3H), 3.878 (m, 2H), 3.769 (m, 1H), 2.177 (m, 6H), 2.029 (d, 2H), 1.311 (m, 4H), 1.115 (t, 3H) |

| Example Number | Structure | Compound Name | LRMS m/z | $^1$H NMR |
|---|---|---|---|---|
| 186 | 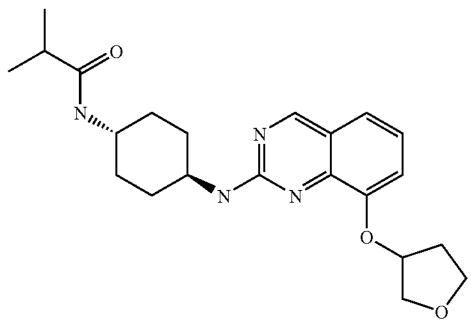 | 2-methyl-N-(trans-4-{[8-(tetrahydrofuran-3-yloxy)quinazolin-2-yl]amino}cyclohexyl)propanamide | 399.5 | $^1$H NMR (CDCl$_3$, 400 Hz): 8.875 (s, 1H), 7.255 (d, 1H), 7.051 (m, 2H), 5.197 (m, 3H), 3.990 (m, 3H), 3.890 (m, 2H), 3.748 (m, 1H), 2.227 (m, 5H), 2.022 (d, 2H), 1.263 (m, 4H), 1.082 (d, 6H) |
| 187 | 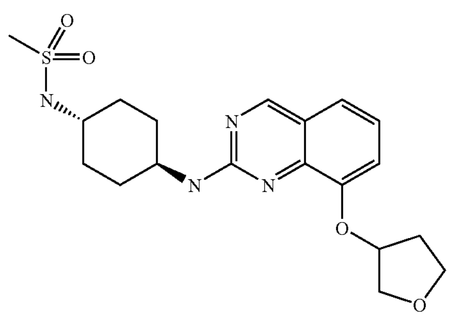 | N-(trans-4-{[8-(tetrahydrofuran-3-yloxy)quinazolin-2-yl]amino}cyclohexyl)methanesulfonamide | 407.7 | $^1$H NMR (CDCl$_3$, 400 Hz): 8.883 (s, 1H), 7.264 (d, 1H), 7.042 (m, 2H), 5.134 (s, 2H), 4.187 (d, 1H), 4.056 (m, 3H), 3.878 (m, 2H), 3.310 (m, 1H), 2.940 (s, 3H), 2.204 (m, 6H), 1.357 (m, 4H) |
| 188 | 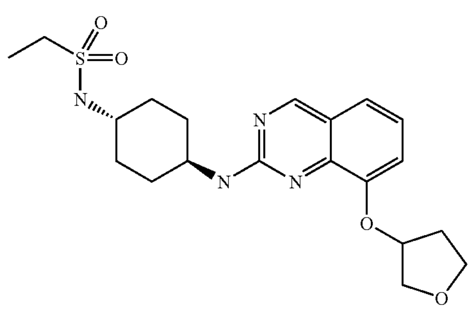 | N-(trans-4-{[8-(tetrahydrofuran-3-yloxy)quinazolin-2-yl]amino}cyclohexyl)ethanesulfonamide | 421.4 | $^1$H NMR (CDCl$_3$, 400 Hz): 8.887 (s, 1H), 7.269 (d, 1H), 7.068 (m, 2H), 5.138 (s, 2H), 4.044 (m, 4H), 3.980 (m, 2H), 3.280 (m, 1H), 3.010 (m, 2H), 2.175 (m, 6H), 1.215 (m, 6H) |

Preparation of example 189: trans-N-(2-fluoroethyl)-N'-[8-(tetrahydro-2H-pyran-4-yloxy)quinazolin-2-yl]cyclohexane-1,4-diamine

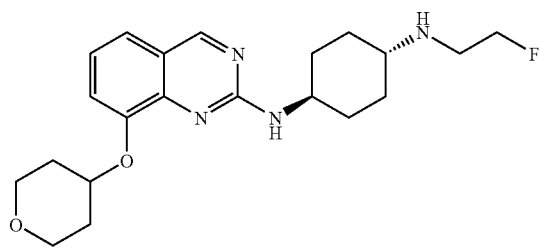

To a solution of trans-N-[8-(tetrahydro-2H-pyran-4-yloxy)quinazolin-2-yl]cyclohexane-1,4-diamine (0.4 g, 1.168 mmol) and 1-bromo-2-fluoro-ethane (0.178 g, 1.4 mmol) in anhydrous DMF (10 mL) were added anhydrous K$_2$CO$_3$ (0.4035 g, 2.92 mmol) and NaI (0.0174 g, 0.1168). The resulting mixture was stirred at room temperature for 72 h. The mixture was concentrated and CH$_2$Cl$_2$ (40 mL) was added to the residue. The mixture was washed with H$_2$O (3×30 mL) and brine (30 mL), dried over Na$_2$SO$_4$ and concentrated in vacuo to give crude solid, which was purified by chromatography (CH$_2$Cl$_2$: MeOH=40:1) to give the title compound (0.150 g, 33.3%) as a yellow solid. $^1$H NMR (CDCl$_3$, 400 Hz): 8.872 (s, 1H), 7.273 (d, 1H), 7.130 (d, 1H), 7.038 (t, 1H), 5.129 (s, 1H), 4.568 (s, 1H), 4.556 (t, 1H), 4.449 (t, 1H), 3.995 (m, 2H), 3.897 (m, 1H), 3.493 (m, 2H), 2.925 (t, 1H), 2.854 (t, 1H), 2.491 (m, 1H), 2.201 (s, 2H), 1.970 (m, 6H), 1.214 (m, 5H).

The following examples nos. 190-194 were prepared with non-critical substitutions and/or method changes in an analogous way to example 189:

| Example Number | Structure | Compound Name | LRMS m/z | ¹H NMR |
|---|---|---|---|---|
| 190 | 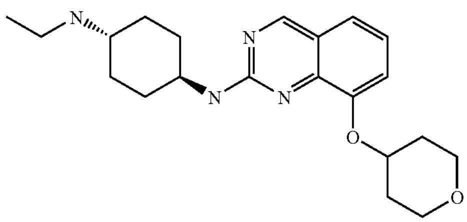 | trans-N-ethyl-N'-[8-(tetrahydro-2H-pyran-4-yloxy)quinazolin-2-yl]cyclohexane-1,4-diamine | 371.2 | ¹H NMR (CDCl₃, 400 Hz): 8.876 (s, 1H), 7.270 (d, 1H), 7.147 (d, 1H), 7.033 (t, 1H), 5.120 (d, 1H), 4.723 (s, 1H), 3.981 (m, 2H), 3.889 (m, 1H), 3.476 (m, 2H), 2.628 (m, 2H), 2.469 (s, 1H), 2.187 (s, 2H), 1.875 (m, 6H), 1.358 (m, 5H), 1.069 (t, 3H) |
| 191 | 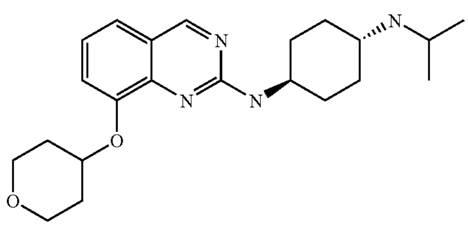 | trans-N-isopropyl-N'-[8-(tetrahydro-2H-pyran-4-yloxy)quinazolin-2-yl]cyclohexane-1,4-diamine | 385.3 | ¹H NMR (CDCl₃, 400 Hz): 8.839 (s, 1H), 7.244 (d, 1H), 7.189 (d, 1H), 7.036 (t, 1H), 5.097 (d, 1H), 4.676 (s, 1H), 3.989 (m, 3H), 3.475 (t, 2H), 3.332 (d, 1H), 2.977 (s, 1H), 2.226 (m, 4H), 1.989 (m, 2H), 1.842 (m, 3H), 1.405 (m, 6H), 1.285 (m, 4H) |
| 192 | 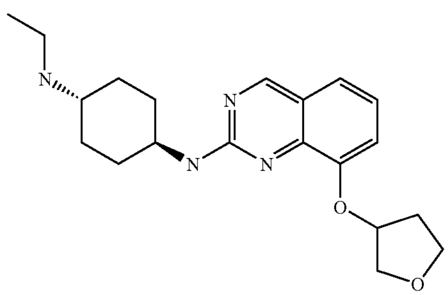 | trans-N-ethyl-N'-[8-(tetrahydrofuran-3-yloxy)quinazolin-2-yl]cyclohexane-1,4-diamine | 357.2 | ¹H NMR (CDCl₃, 400 Hz): 8.874 (s, 1H), 7.248 (d, 1H), 7.055 (m, 2H), 5.186 (m, 2H), 3.970 (m, 5H), 2.646 (m, 2H), 2.460 (m, 1H), 2.240 (m, 4H), 1.947 (m, 2H), 1.290 (m, 2H), 1.068 (t, 3H) |
| 193 | 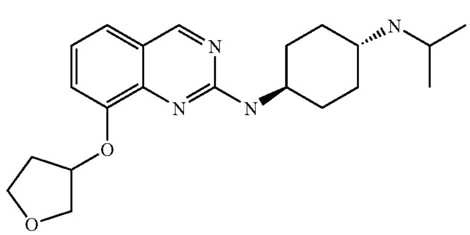 | trans-N-isopropyl-N'-[8-(tetrahydrofuran-3-yloxy)quinazolin-2-yl]cyclohexane-1,4-diamine | 371.3 | ¹H NMR (CDCl₃, 400 Hz): 8.873 (s, 1H), 7.235 (d, 1H), 7.21 (m, 2H), 5.124 (s, 2H), 4.026 (m, 4H), 3.868 (m, 1H), 3.390 (m, 1H), 3.035 (m, 1H), 2.189 (m, 6H), 1.939 (m, 2H), 1.452 (d, 6H), 1.205 (m, 3H) |
| 194 | 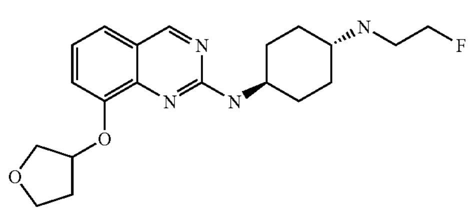 | trans-N-(2-fluoroethyl)-N'-[8-(tetrahydrofuran-3-yloxy)quinazolin-2-yl]cyclohexane-1,4-diamine | 375.2 | ¹H NMR (CDCl₃, 400 Hz): 8.877 (s, 1H), 7.259 (d, 1H), 7.042 (m, 2H), 5.185 (m, 2H), 4.567 (t, 1H), 4.448 (t, 1H), 3.917 (m, 5H), 2.936 (t, 1H), 2.854 (t, 1H), 2.485 (m, 1H), 2.253 (m, 4H), 1.966 (m, 2H), 1.215 (m, 4H) |

Preparation of example 195: trans-4-({8-[1-(methyl-sulfonyl)pyrrolidin-3-yl]quinazolin-2-yl}amino)cyclohexanol

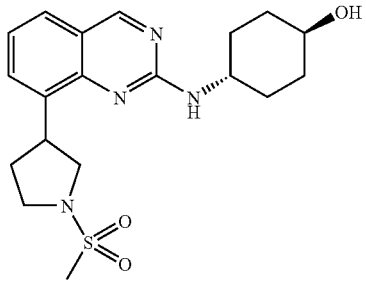

To the solution of trans-4-({8-[1-(methylsulfonyl)-4,5-dihydro-1H-pyrrol-3-yl]quinazolin-2-yl}amino)cyclohexanol (88 mg, 0.23 mmol) in methanol (8 mL) was added 20 mg of Pd/C (dry, 10%). The mixture was hydrogenated with a $H_2$ balloon at RT for 48 h. The catalyst was filtered off and washed with methanol (15 mL). The filtrate was concentrated in vacuo, and the residue was purified by chromatography (eluting with DCM, then DCM/EA=2/1) to give the title compound as off white solid (52 mg, 62%). 1H-NMR (CDCl$_3$, 400 MHz): δ 8.97 (s, 1H), 7.61 (d, J=7.6 Hz, 1H), 7.59 (d, J=7.6 Hz, 1H), 7.21 (dd, J=7.6, 7.6 Hz, 1H), 5.17 (d, J=6.8 Hz, 1H), 4.30-4.25 (m, 1H), 4.01 (dd, J=9.2, 7.6 Hz, 1H), 4.01-3.98 (m, 1H), 3.71-3.67 (m, 2H), 3.54-3.50 (m, 1H), 2.92 (s, 3H), 2.49-2.29 (m, 2H), 2.28-2.24 (m, 2H), 2.12-2.06 (m, 2H), 1.57-1.50 (m, 2H), 1.45-1.30 (m, 2H). MS (m/e) 391.3 (M+1).

Preparation of intermediate 195a: 8-bromoquinazoline-2,4-diol

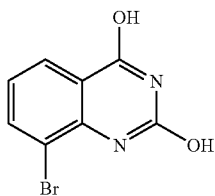

To a 2000 mL flask charged with 2-amino-3-bromobenzoic acid (67.0 g, 310 mmol) was added water (750 mL) and AcOH (18.8 mL). The suspension was heated to 35° C. A solution of NaOCN (30.82 g, 403 mmol, 85% purity) in water (250 mL) was added dropwise at 35° C. The reaction mixture was stirred at 35° C. for 2 hrs. NaOH (415 g, 10.38 mol) was added in portions, the reaction temperature was kept below 40° C. during the addition. The mixture turned clear for a short time, then an off-white suspension was formed. The reaction mixture was cooled to room temperature, and filtered. The obtained solid was dissolved in hot water, pH was adjusted to 5 by addition of 6 N HCl. The resulting mixture was cooled to room temperature, and the precipitate was collected by filtration, rinsed with a small amount of DCM, cold MeOH, ether, then dried in vacuo to yield the title compound as a off-white solid (43.32 g, 58%). 1HNMR (DMSO-d6, 400 MHz): δ 11.60-11.40 (br s, 1H), 10.40-10.20 (br s, 1H), 7.92 (d, J=7.6 Hz, 1H), 7.90 (d, J=8.0 Hz, 1H), 7.12 (dd, J=7.6, 8.0 Hz, 1H).

Preparation of intermediate 195b: 8-bromo-2,4-dichloroquinazoline

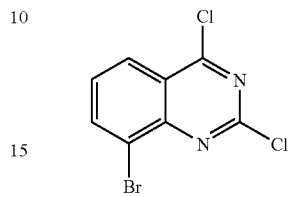

To a flask charged with 8-bromoquinazoline-2,4-diol 2 (39.61 g, 164 mmol) was added PCl$_5$ (68.4 g, 328 mmol) and POCl$_3$, (250 mL). The mixture was refluxed at 110-120° C. overnight with a drying tube attached. POCl$_3$ was stripped off under vacuum. Toluene was added to azeotroped the remaining POCl$_3$. The residue was taken into DCM (300 mL), washed with sat NaHCO$_3$ (500 mL), filtered and dried over Na$_2$SO$_4$. The organic layer was concentrated in vacuo and the residue was purified by chromatography to give the title compound as white solid (34.67 g, 76%). 1HNMR (CDCl$_3$, 400 MHz): δ 8.31 (dd, J=1.2, 7.6 Hz, 1H), 8.27 (dd, J=1.2, 8.4 Hz, 1H), 7.62 (dd, J=7.6, 8.4 Hz, 1H).

Preparation of intermediate 195c: 8-bromo-2-chloroquinazolin-4-amine

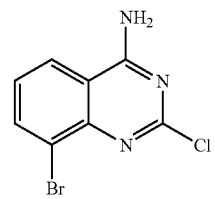

8-bromo-2,4-dichloroquinazoline (13.90 g, 50 mmol) was dissolved in DCM (60 mL) and ammonia was bubbled through the reaction solution with stirring overnight at room temperature. A suspension was formed, and the precipitate was collected by filtration to give crude title compound as a white solid (12.93 g, 99%).

Preparation of intermediate 195d: 8-bromo-2-chloroquinazoline

To a stirred mixture of 8-bromo-2-chloroquinazolin-4-amine (12.93 g, 50 mmol) in THF (500 mL) was added isoamyl nitrite (23.43 g, 200 mmol) over 3 hours and 40 mins at 60° C. The mixture was stirred for another 5 hours. TLC (PE:EA, 1:1) showed reaction complete. After cooling to room temperature, the solvent was stripped and the residue was taken into DCM (300 mL). The organic layer was washed with brine (100 mL), water (100 mL), then dried over anhydrous $Na_2SO_4$ and purified by chromatography (DCM:PE, 1:1) to give the title compound as a yellow solid (8.21 g, 67%). $^1$HNMR (DMSO-$d_6$, 400 MHz): δ 9.66 (s, 1H), 8.45 (dd, J=0.8, 7.6 Hz, 1H), 8.26 (dd, J=0.8, 8.0 Hz, 7.73 (dd, J=7.6, 8.0 Hz, 1H).

Preparation of intermediate 195e: trans-4-[(8-bromo-quinazolin-2-yl)amino]cyclohexanol

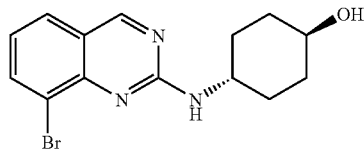

To a solution of 8-bromo-2-chloroquinazoline (7.3 g, 30 mmol) in acetonitrile (150 mL) was added trans-4-aminocyclohexanol (6.9 g, 60 mmol) to form a suspension. DBU (9.1 g, 60 mmol) was added. The reaction mixture was stirred at 45° C. overnight. A light yellow suspension was formed. The solvent was removed under reduced pressure, and the residue was taken into DCM (100 mL) and washed with water (100 mL). The organic layer was dried over $Na_2SO_4$ and purified by chromatography (eluting with DCM) to give the title compound as a light yellow solid (3.36 g, 35%). $^1$HNMR (DMSO-$d_6$, 400 MHz): δ 9.10 (s, 1H), 8.02 (dd, J=1.2, 7.6 Hz, 1H), 7.81 (dd, J=1.2, 7.6 Hz, 1H), 7.62-7.60 (m, 1H), 7.12 (dd, J=7.6, 7.6 Hz, 1H), 4.62-4.60 (m, 1H), 3.85-3.82 (m, 1H), 2.05-2.02 (m, 2H), 1.89-1.86 (m, 2H), 1.36-1.26 (m, 4H).

Preparation of intermediate 195f: trans-4-({8-[1-(methylsulfonyl)-4,5-dihydro-1H-pyrrol-3-yl]quinazolin-2-yl}amino)cyclohexanol

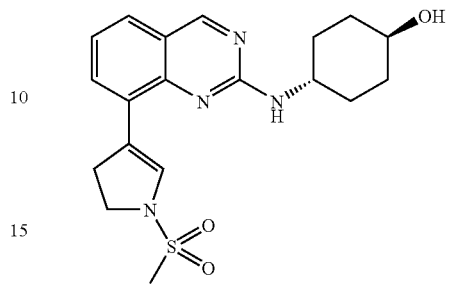

To a shlenk tube was added trans-4-[(8-bromoquinazolin-2-yl)amino]cyclohexanol (322 mg, 1 mmol), followed by $Pd(OAc)_2$ (48 mg, 0.2 mmol), (o-Tol)$_3$P (60 mg, 0.2 mg), $Ag_2CO_3$ (192 mg, 0.7 mmol), toluene (8 mL) and $^iPr_2NEt$ (516 mg, 4 mmol), followed by 1-(methylsulfonyl)-2,5-dihydro-1H-pyrrole (560 mg, 3.8 mmol). The mixture was refluxed overnight under Ar. TLC showed that several new spots were formed with small amount of starting material remaining. The reaction mixture was diluted with water (30 mL) and extracted with EtOAc (4×15 mL). The combined organic layers were washed with water, brine, dried over anhydrous $Na_2SO_4$, and concentrated in vacuo. The residue was purified by chromatography (eluting with DCM, then DCM/EA 3/1, then DCM/EA=2/1) to afford the title compound (88 mg, 23%) as an off white solid. $^1$H-NMR (CDCl$_3$, 400 MHz): δ 8.97 (s, 1H), 7.59 (d, J=8.8 Hz, 1H), 7.55 (d, J=7.2 Hz, 1H), 7.21 (dd, J=8.8, 7.2 Hz, 1H), 6.60-6.58 (m, 1H), 5.51-5.49 (m, 1H), 5.22-5.19 (m, 1H), 5.16-5.11 (m, 1H), 4.36 (t, J=10.8 Hz, 1H), 3.99-3.94 (m, 1H), 3.58 (dd, J=10.8, 6.0 Hz, 1H), 2.85 (s, 3H), 2.30-2.24 (m, 2H), 2.12-2.08 (m, 2H), 1.41-1.26 (m, 4H).

The following examples nos. 196-197 were prepared with non-critical substitutions and/or method changes in an analogous way to example 195:

| Example Number | Structure | Compound Name | LRMS m/z | $^1$H NMR |
|---|---|---|---|---|
| 196 | 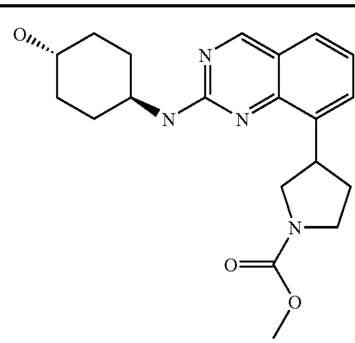 | methyl 3-{2-[(trans-4-hydroxycyclohexyl)amino]quinazolin-8-yl}pyrrolidine-1-carboxylate | 371.4 | 1H-NMR (CDCl3, 400 MHz): δ 8.97 (s, 1H), 7.61 (d, J = 7.6 Hz, 1H), 7.55 (d, J = 7.2 Hz, 1H), 7.21 (dd, J = 7.6, 7.2 Hz, 1H), 5.15 (d, J = 7.2 Hz, 1H), 4.24-4.17 (m, 1H), 4.07-4.00 (m, 1H), 3.98-3.90 (m, 1H), 3.76 (s, 3H), 3.70-3.49 (m, 4H), 2.40-2.24 (m, 4H), 2.11-2.07 (m, 2H), 1.57-1.48 (m, 2H), 1.45-1.30 (m, 2H). |

| Example Number | Structure | Compound Name | LRMS m/z | $^1$H NMR |
|---|---|---|---|---|
| 197 | 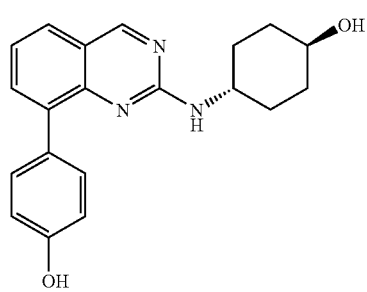 | trans-4-{[8-(1-acetyl-4,5-dihydro-1H-pyrrol-3-yl)quinazolin-2-yl]amino}cyclohexanol | 355.3 | $^1$H-NMR (CDCl$_3$, 400 MHz, two isomers): δ 8.973 (s, 0.55H), 8.969 (s, 0.47H), 7.61-7.52 (m, 2H), 7.23-7.17 (m, 1H), 5.21-5.16 (m, 1H), 4.27-4.22 (m, 1H), 4.12-4.06 (m, 1H), 3.95-3.58 (m, 5H), 2.35-2.23 (m, 4H), 2.15-2.08 (m, 5H), 1.55-1.27 (m, 4H). |

Preparation of example 198: 4-{2-[(trans-4-hydroxycyclohexyl)amino]quinazolin-8-yl}phenol Preparation of example 199: trans-4-[(8-{4-[2-(methylamino)ethoxy]phenyl}quinazolin-2-yl)amino]cyclohexanol

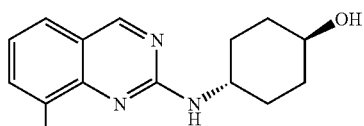

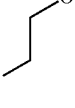

To a flask charged with trans-4-[(8-bromoquinazolin-2-yl)amino]cyclohexanol (1.3 g, 4.035 mmol) was added Pd(PPh$_3$)$_4$ (233 mg, 0.202 mmol), K$_3$PO$_4$·3H$_2$O (2.686 mg, 10.09 mmol), 4-hydroxybenzeneboronic acid (1.113 g, 8.07 mmol) and DMF (16 mL) under argon. The mixture was heated at 80-90° C. under argon overnight, then cooled to room temperature and filtered. The filtrate was concentrated under vacuum and purified by silica gel chromatography (eluted with EA:PE=2:1) to give the title compound as a yellow solid (1 g, 74%). 1 HNMR (DMSO-d6, 400 MHz): δ 9.50 (s, 1H), 9.01 (s, 1H), 7.72-7.61 (m, 3H), 7.31-7.20 (m, 2H), 6.83 (t, 2H, J=7.6 Hz), 4.53 (d, 1H, J=4 Hz), 3.70-3.55 (m, 1H), 3.45-3.36 (m, 1H), 1.99-1.84 (m, 4H), 1.35-1.14 (m, 4H).

To the flask were added 4-{2-[(trans-4-hydroxycyclohexyl)amino]quinazolin-8-yl}phenol (110 mg, 0.33 mmol), Cs$_2$CO$_3$ (1345 mg, 4.13 mmol), tert-butyl (2-chloroethyl)methylcarbamate (290 mg, 1.45 mmol) and DMF (5 mL). The mixture was stirred for 3 hours at 85° C. The reaction was completed as judged by TLC. The mixture was concentrated in vacuo to afford crude tert-butyl [2-(4-{2-[(trans-4 hydroxycyclohexyl)amino]quinazolin-8-yl}phenoxy)ethyl]methylcarbamate This crude material was diluted with MeOH. The solid was removed by filtration. The filtrate was reacted with HCl gas for 30 min at RT. Then Na$_2$CO$_3$ was added into the reaction mixture to remove HCl. The reaction mixture was filtered to remove the salt and the filtrate was concentrated in vacuo to give a crude product (95 mg). The crude product was purified by chromatography on silica gel (eluted with EA:PE, 3:1 then DCM:MeOH, 10:1) to afford the title compound (65 mg, 50%). 1HNMR (DMSO-d6, 400 MHz): δ 9.12 (s, 1H), 8.45 (br, s, 1H), 7.82 (t, 2H, J=5.8 Hz), 7.75 (t, 2H, J=5.2 Hz, 6.8 Hz), 7.28 (m, 2H), 7.06 (d, 2H, J=8.8 Hz), 4.61 (br, s, 1H), 4.30-4.27 (m, 2H), 4.10 (s, 1H), 3.58 (s, 1H), 3.32 (s, 1H), 3.17 (t, 2H), 2.62 (s, 3H), 1.97-1.96 (m, 2H), 1.89-1.85 (m, 2H), 1.30-1.19 (m, 4H).

The following examples nos. 200-205 were prepared with non-critical substitutions and/or method changes in an analogous way to example 199:

| Example Number | Structure | Compound Name | LRMS m/z | $^1$H NMR |
|---|---|---|---|---|
| 200 | 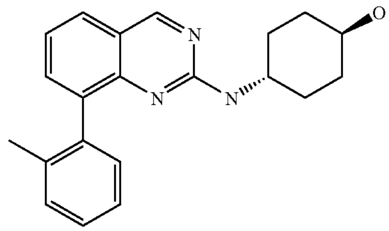 | trans-4-{[8-(2-methylphenyl)quinazolin-2-yl]amino}cyclohexanol | 334.6 | 1HNMR CDCl3, 400 MHz): δ 9.00 (s, 1H), 7.67 (dd, 1H, J = 0.8, 8 Hz), 7.60 (d, 1H, J = 13.6 Hz), 7.33-7.28 (m, 3H), 7.26-7.23 (m, 2H), 5.06 (d, 1H, J = 6.8 Hz), 3.61 (s, 1H), 2.15-2.10 (s, 3H), 2.08 (d, 2H, J = 15 Hz), 1.94 (d, 2H, J = 8 Hz), 1.64 (s, 1H), 1.46 (s, 1H), 1.30-1.15 (m, 4H). |
| 201 | 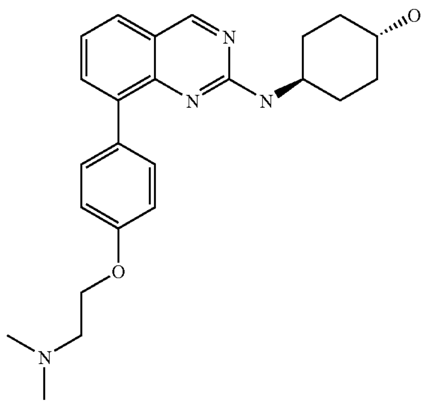 | trans-4-[(8-{4-[2-(dimethylamino)ethoxy]phenyl}quinazolin-2-yl)amino]cyclohexanol | 407.9 | 1HNMR (DMSO-d6, 400 MHz): δ 9.07 (s, 1H), 7.74-7.69 (m, 4H), 7.23 (t, 2H, J = 7.2 Hz), 6.96 (d, 2H, J = 8.8 Hz), 4.08 (t, 2H, J = 5.6 Hz), 3.55 (s, 1H), 2.69 (t, 2H, J = 5.2 Hz), 2.24 (s, 6H), 1.91 (d, 2H, J = 10.4 Hz), 1.82 (d, 2H, J = 11.2 Hz), 1.34-1.10 (m, 4H). |
| 202 | 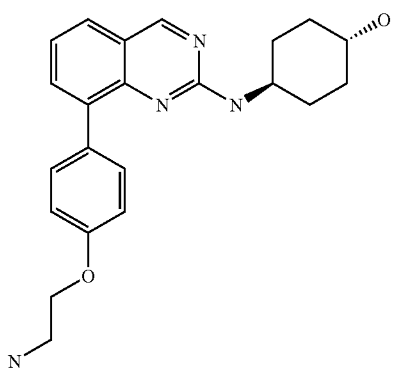 | trans-4-({8-[4-(2-aminoethoxy)phenyl]quinazolin-2-yl}amino)cyclohexanol | 379.5 | 1HNMR (CDCl3, 400 MHZ): δ 5.01 (br, s, 1H), 3.59 (t, 2H, J = 5.4 Hz), 3.46 (t, 2H, J = 5.4 Hz), 1.44 (s, 9H). |
| 203 | 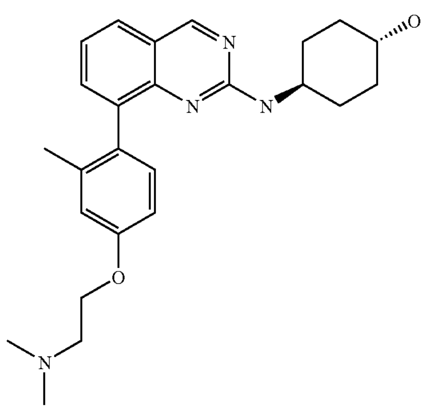 | trans-4-[(8-{4-[2-(dimethylamino)ethoxy]-2-methylphenyl}quinazolin-2-yl)amino]cyclohexanol | 444.5 | 1HNMR (DMSO-d6, 400 MHz): δ 9.11 (s, 1H), 7.76 (d, 1H, J = 8 Hz), 7.5 (d, 1H, J = 12.4 Hz), 7.24 (t, 1H, J = 7.6 Hz) 7.16 (br, 1H), 7.08 (d, 1H, J = 8 Hz), 6.89 (s, 1H), 6.79 (m, 1H), 4.52 (t, 1H, J = 8 Hz), 4.10 (t, 2H, J = 5.6 Hz), 2.73 (d, 2H, J = 8 Hz), 2.28 (s, 6H), 2.05 (s, 3H), 1.80 (t, 4H, J = 9.6 Hz), 1.38-0.98 (m, 4H). |

| Example Number | Structure | Compound Name | LRMS m/z | $^1$H NMR |
|---|---|---|---|---|
| 204 | 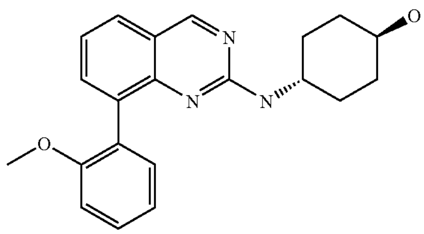 | trans-4-{(8-(2-methoxyphenyl)quinazolin-2-yl]amino} cyclohexanol | 350.5 | 1HNMR (CDCl3, 400 MHz): δ 8.98 (s, 1H), 7.73 (d, 1H, J = 7.6 Hz), 7.66 (d, 1H, J = 8 Hz), 7.48-7.35 (m, 2H), 7.27 (t, 1H, J = 4 Hz), 7.10-6.98 (m, 2H), 5.03 (d, 1H, J = 6.8 Hz), 3.74 (s, 3H), 3.64 (t, 2H, J = 3.2 Hz), 2.12 (d, 2H, J = 12 Hz), 1.96 (d, 2H, J = 12 Hz), 1.37-1.20 (m, 4H). |
| 205 | 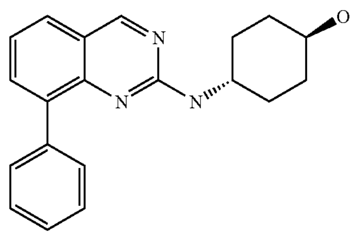 | trans-4-[(8-phenylquinazolin-2-yl)amino] cyclohexanol | 320.5 | 1HNMR (CDCl3, 400 MHz): δ 9.00 (s, 1H), 7.79 (d, 3H, J = 7.2 Hz), 7.68-7.65 (m, 1H), 7.48-7.45 (m, 2H), 7.41-7.37 (m, 1H), 7.32-7.28 (m, 1H), 5.11 (d, 1H, J = 7.2 Hz), 3.78 (br, 1H), 3.72-3.67 (m, 1H), 2.20 (d, 2H, J = 11.6 Hz), 2.04 (t, 2H, J = 4.8, 6.4 Hz), 1.57-1.32 (m, 4H) |

Preparation of example 206: 2-({2-[(trans-4-hydroxycyclohexyl)amino]-7-methylquinazolin-8-yl}oxy) N-methylacetamide

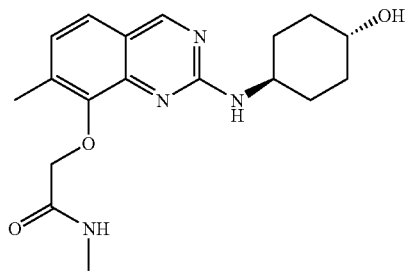

To a solution of ({2-[(trans-4-hydroxycyclohexyl)amino]-7-methylquinazolin-8-yl}oxy)acetic acid (1.8 g, 5.4 mmol) in the mixed solvents of DMF (36 mL) and THF (36 mL) were added NMM (2.3 g, 21 mmol), methylamine hydrochloride (0.44 g, 6.5 mmol), HOBt (1.47 g, 11 mmol) and EDCl (2.08 g, 11 mmol) at room temperature. The reaction mixture was stirred at room temperature overnight. TLC(CH$_2$Cl$_2$/MeOH=2:1) indicated the reaction was complete. The mixture was concentrated in vacuo. The residue was taken up with CH$_2$Cl$_2$ (100 mL), washed with 5% aq. Na$_2$CO$_3$ (30 mL×2) and brine. The organic layer was dried over anhydrous Na$_2$SO$_4$ and concentrated in vacuo to give the crude product. The crude product was purified by silica gel chromatography (CH$_2$Cl$_2$~CH$_2$Cl$_2$/MeOH=100:1 to CH$_2$Cl$_2$/MeOH=80:1) to give the title compound (1.2 g, 63.2%) as a light yellow solid.
$^1$H NMR (MeOD) δ (ppm) 8.90 (1H, s), 7.39 (1H, d), 7.40 (1H, m), 4.689 (2H, s), 3.84 (1H, m), 3.67 (1H, m), 2.94 (3H, s), 2.40 (3H, s), 2 54 (4H, m), 1.39 (4H, m).

Preparation of intermediate 206a: 3-(acetylamino)-4-methylbenzoic acid

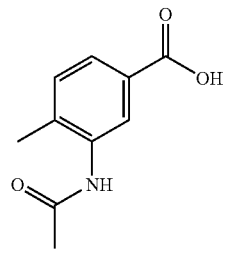

To a solution of 3-amino-4-methylbenzoic acid (375 g, 2.48 mol) in glacial acetic acid (2500 mL) was added dropwise Ac$_2$O (1547.7 g, 15.2 mol). After the addition, the reaction mixture was stirred at room temperature overnight. The solid formed was collected by filtration, and washed with acetic acid (500 mL×2) and ether (500 mL×2). Then the solid was dried in vacuo to give the title compound (420 g, 87.6%) as an off-white solid.

Preparation of intermediate 206b: 3-(acetylamino)-4-methyl-2-nitrobenzoic acid

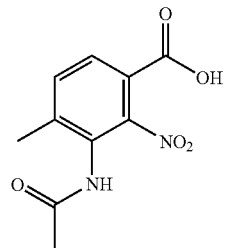

3-(acetylamino)-4-methylbenzoic acid (300 g, 1.55 mol) was added portionwise to fuming nitric acid (1200 mL) with stirring over a period of 1 h at 0~5° C. The solution gradually turned into a heavy slurry during the addition. At the end of addition, an additional fuming nitric acid (200 mL) was added. The reaction mixture was stirred for an additional hour at 5° C., then allowed to warm to room temperature and poured into ice water. The solid formed was collected and washed with water (450 mL×3). The crude product was re-crystallized from acetic acid (1800 mL) to give the title compound (191.5 g, 51.8%) as a white solid.

Preparation of intermediate 206c:
3-hydroxy-4-methyl-2-nitrobenzoic acid

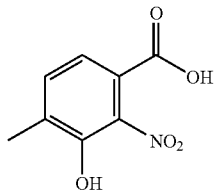

A solution of 3-(acetylamino)-4-methyl-2-nitrobenzoic acid (237.5 g, 0.997 mol) and KOH (451.2 g, 8.04 mol) in water (2830 mL) was refluxed for 48 h. The dark red solution was cooled and acidified to pH 1 with concentrated HCl. The yellow solid was filtered and re-crystallized from water (1800 mL) to give the title compound (183 g, 93.4%) as a yellow solid.

Preparation of intermediate 206d: methyl
3-methoxy-4-methyl-2-nitrobenzoate

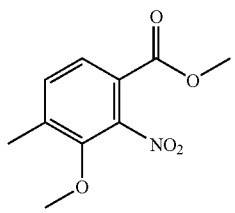

To a solution of 3-hydroxy-4-methyl-2-nitrobenzoic acid (365 g, 1.85 mol) in DMF (3280 mL) were added $K_2CO_3$ (524.4 g, 3.80 mol) and MeI (788 g, 5.55 mol) in one portion. Then the reaction mixture was stirred at room temperature overnight. TLC($CH_2Cl_2$/MeOH=3:1) indicated the reaction was complete. Water (9 L) was added to the reaction mixture and the mixture was extracted with EtOAc (3 L×2). The combined organic layers were washed with 1 N aq. NaOH (1 L×2) and brine, dried over anhydrous $Na_2SO_4$ and concentrated in vacuo to give the title compound (395 g, 94.7%) as a light yellow solid.

Preparation of intermediate 206e: methyl
2-amino-3-methoxy-4-methylbenzoate

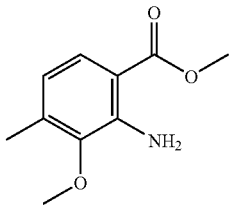

To a solution of methyl 3-methoxy-4-methyl-2-nitrobenzoate (395 g, 1.75 mol) in ethanol (6700 mL) was added Pd/C (39.5 g) in one portion. The reaction mixture was stirred at room temperature under 50 psi of hydrogen overnight. TLC (petroleum ether/ethyl acetate=3:1) indicated the reaction was complete. The mixture was filtered and the filtrate was evaporated in vacuo to give the crude product, which was re-crystallized from ethanol (1.6 L) to give the title compound (321 g, 93.8%) as a white solid.

Preparation of intermediate 206f:
8-methoxy-7-methylquinazoline-2,4-diol

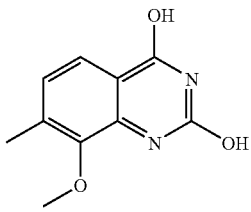

A mixture of methyl 2-amino-3-methoxy-4-methylbenzoate (139.3 g, 0.714 mol) and urea (214.3 g, 3.57 mol) was heated in an oil bath at 110~120° C. for 30 minutes. The temperature was then raised to 150-160° C. and the reaction mixture was stirred at this temperature for 8 h. TLC (petroleum ether/ethyl acetate=3:1) indicated the reaction was complete. The mixture was washed with EtOH (1.5 L) and water (1 L×6) and dried in vacuo to give the title compound (123 g, 83.7%) as a light brown solid.

Preparation of intermediate 206g:
2,4-dichloro-8-methoxy-7-methylquinazoline

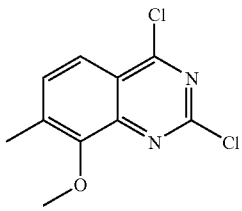

A mixture of 8-methoxy-7-methylquinazoline-2,4-diol (93 g, 0.45 mol), phosphorus oxychloride (783.1 g, 5.1 mol) and N,N-dimethylaniline (46.5 g, 0.363 mol) was refluxed with stirring overnight. The excess POCl₃ was removed in vacuo. The residue was poured into crushed ice. The precipitate was filtered and washed with water (400 mL×2). Then the solid was taken up with dichloromethane (2.5 L). The solution was dried over anhydrous Na₂SO₄ and concentrated in vacuo to give the crude product. The crude product was purified by silica gel chromatography (dichloromethane/petroleum ether=1:1) to give the title compound (58 g, 53%) as a white solid.

Preparation of intermediate 206h: 2-chloro-8-methoxy-7-methylquinazoline

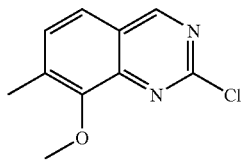

To a solution of 2,4-dichloro-8-methoxy-7-methylquinazoline (43 g, 0.177 mol) in EtOAc (2580 mL) were added DIPEA (22.9 g, 0.177 mol) and Pd/C (8.6 g) in one portion. The reaction mixture was stirred at room temperature for 6 h under 20 psi of hydrogen. Water (800 mL) was added and the mixture was filtered. The filtrate was separated, the organic layer was washed with water (500 mL). The combined aqueous layers were re-extracted with EtOAc (700 mL). The combined organic layers were washed with brine, dried over anhydrous Na₂SO₄ and concentrated in vacuo to give the crude product. The crude product was re-crystallized from EtOAc (64 mL)/petroleum ether (192 mL) to give the title compound (24.9 g, 67.5%) as a white solid.

Preparation of intermediate 206i: trans-4-[(8-methoxy-7-methylquinazolin-2-yl)amino]cyclohexanol

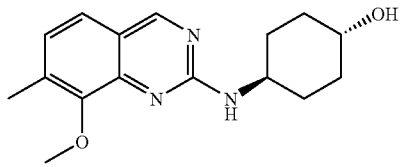

To a solution of 2-chloro-8-methoxy-7-methylquinazoline (20.4 g, 0.098 mol) in CH₃CN (800 mL) were added trans-4-amino-cyclohexanol (22.5 g, 0.195 mol) and DBU (29.7 g, 0.195 mol) in one portion. The reaction mixture was refluxed with stirring overnight. TLC (ethyl acetate/petroleum ether=1:1) indicated the reaction was complete. The solvent was removed in vacuo. The residue was taken up with CHCl₃ (550 mL), the solution was washed with water (150 mL×2). The aqueous layer was re-extracted with CHCl₃ (150 mL). The combined organic layers were washed with brine, dried over anhydrous Na₂SO₄ and concentrated in vacuo to give the crude product. The crude product was re-crystallized from EtOH (130 mL)/water (200 mL) to give the title compound (17 g, 60.5%) as an off-white solid.

Preparation of intermediate 206j: 2-[(trans-4-hydroxycyclohexyl)amino]-7-methylquinazolin-8-ol

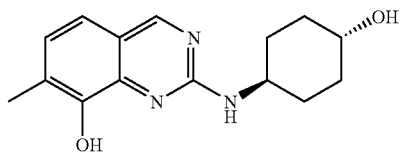

To a solution of trans-4-[(8-methoxy-7-methylquinazolin-2-yl)amino]cyclohexanol (16.7 g, 0.058 mol) in DMF (280 mL) was added NaSEt (11.9 g, 0.142 mol) in one portion at room temperature. The reaction mixture was stirred at 120° C. for 3 h. TLC (EtOAc) indicated the reaction was complete. DMF was removed in vacuo. The residue was taken up with water (200 mL), and the aqueous solution was adjusted to pH 6 with 1 N aq. HCl. The precipitate was filtered, washed with water (60 mL×2) and dried in vacuo to give the title compound (15.1 g, 95%) as an off-white solid.

Preparation of intermediate 206k: methyl ({2-[(trans-4-hydroxycyclohexyl)amino]-7-methylquinazolin-8-yl}oxy)acetate

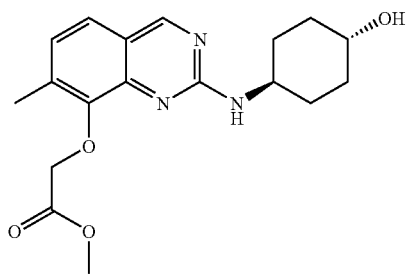

To a solution of 2-[(trans-4-hydroxycyclohexyl)amino]-7-methylquinazolin-8-ol (20 g, 0.073 mol) in DMF (160 mL) was added K₂CO₃ (10.6 g, 0.077 mol) in one portion at room temperature. Then a solution of bromoacetic acid methyl ester (11.5 g, 0.075 mol) in DMF (40 mL) was added dropwise. After the addition, the reaction mixture was stirred at room temperature overnight. The mixture was diluted with water (400 mL) and extracted with EtOAc (200 mL×3). The combined organic layers were washed with water (150 mL), dried over anhydrous Na₂SO₄ and evaporated in vacuo to give the crude product. The crude product was re-crystallized from EtOH (150 mL) to give the title compound (13 g, 51.4%) as an off-white solid.

Preparation of intermediate 206l: ({2-[(trans-4-hydroxycyclohexyl)amino]-7-methylquinazolin-8-yl}oxy)acetic acid

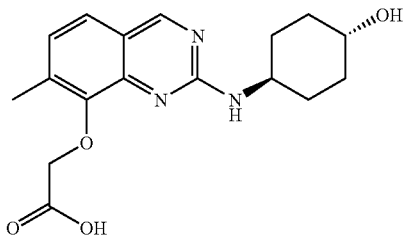

To a solution of methyl ({2-[(trans-4-hydroxycyclohexyl)amino]-7-methylquinazolin-8-yl}oxy)acetate (11 g, 0.032 mol) in MeOH (210 mL) was added 2 N aq. NaOH (81.4 mL, 0.163 mol) in one portion. The reaction mixture was stirred at room temperature overnight. TLC (EtOAc) indicated the reaction was complete. The solvent was removed in vacuo. The residue was adjusted to pH 6 with 1 N aq. HCl. The precipitate was filtered, washed with ether (30 mL×2) and dried in vacuo to give the title compound (9.8 g, 92.4%) as an off-white solid. m/e 332.2 (MH+).

The following examples nos. 207-214 were prepared with non-critical substitutions and/or method changes in an analogous way to example 206:

| Example Number | Structure | Compound Name | LRMS m/z | $^1$H NMR |
|---|---|---|---|---|
| 207 | 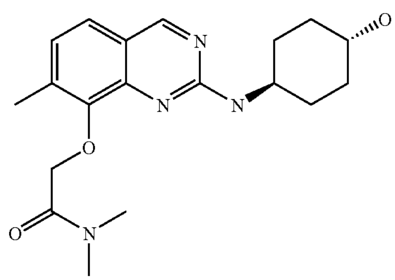 | 2-({2-[(trans-4-hydroxycyclohexyl)amino]-7-methylquinazolin-8-yl}oxy)-N,N-dimethylacetamide | 359.2 | 1HNMR (MeOD, 400 MHz): δ 8.90 (1H, s) 7.39 (1H, d), 7.05 (1H, d), 5.10 (2H, s), 3.89 (1H, m), 3.60 (1H, m), 3.13 (3H, s), 3.02 (3H, s), 2.42 (3H, a), 2.56 (4H, m), 1.39 (4H, m). |
| 208 | 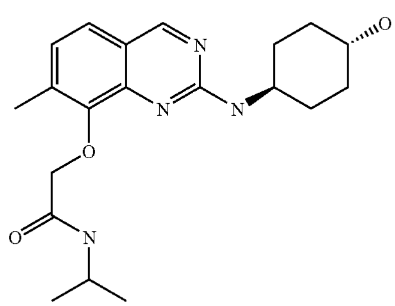 | 2-({2-[(trans-4-hydroxycyclohexyl)amino]-7-methylquinazolin-8-yl}oxy)-N-isopropylacetamide | 373.2 | 1H NMR (400 MHz, DMSO-D6) d ppm 9.01 (1H, s) 7.80 (1H, s) 7.43 (1H, d, J = 8.08 Hz) 7.24 (1H, s) 7.03 (1H, d, J = 8.08 Hz) 4.65 (2H, s) 4.53 (1H, d, J = 4.29 Hz) 4.01 (1H, m) 3.73 (1H, s) 3.34-3.47 (1H, m) 2.36 (3H, s) 1.75-2.06 (4H, m) 1.19-1.40 (4H, m) 1.13 (6H, d = 6.57 Hz) |
| 209 | 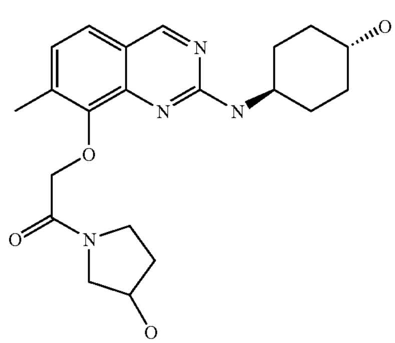 | 1-[({2-[(trans-4-hydroxycyclohexyl)amino]-7-methylquinazolin-8-yl}oxy)acetyl]pyrrolidin-3-ol | 401.1 | 1H NMR (400 MHz, DMSO-D6) d ppm 9.01 (1H, s) 7.41 (1H, d, J = 7.33 Hz) 7.26 (1H, s) 7.03 (1H, d, J = 7.33 Hz) 4.85-5.28 (3H, m) 4.54 (1H, s) 4.18-4.38 (1H, m, J = 27.79 Hz) 3.75 (1H, s) 3.21-3.60, (6H, m) 2.40 (3H, s) 1.65-2.06 (5H, m) 1.20-1.47 (4H, m) |

| Example Number | Structure | Compound Name | LRMS m/z | ¹H NMR |
|---|---|---|---|---|
| 210 | 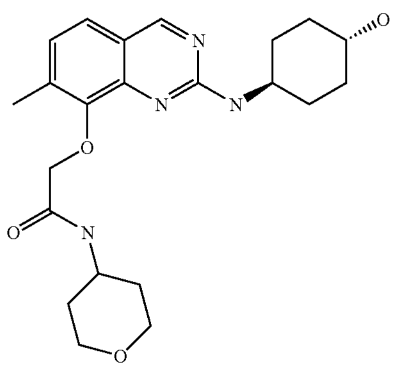 | 2-({2-[(trans-4-hydroxycyclohexyl)amino]-7-methylquinazolin-8-yl}oxy)-N-(tetrahydro-2H-pyran-4-yl)acetamide | 415.2 | 1H NMR (400 MHz, DMSO-D6) d ppm 9.01 (1H, s) 8.04 (1H, s) 7.43 (1H, d, J = 8.08 Hz) 7.29 (1H, s) 7.03 (1H, d, J = 8.34 Hz) 4.69 (2H, s) 4.55 (1H, d, J = 4.29 Hz) 3.92 (1H, a) 3.83 (2H, d, J = 10.86 Hz) 3.72 (1H, s) 3.27-3.48 (3H, m) 2.36 (3H, s) 1.77-2.00 (3H, m) 1.50-1.73 (4H, m) 1.15-1.39 (4H, m) |
| 211 | 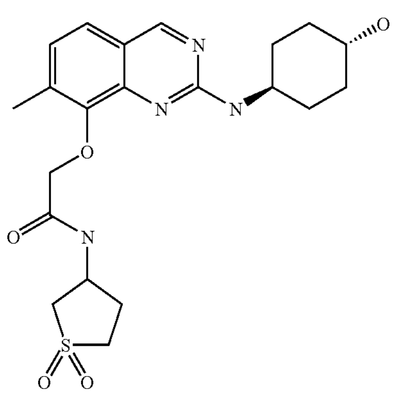 | N-(1,1-dioxidotetrahydro-3-thienyl)-2-({2-[(trans-4-hydroxycyclohexyl)amino]-7-methylquinazolin-8-yl}oxy)acetamide | 449.1 | 1H NMR (400 MHz, DMSO-D6) d ppm 9.01 (1H, s) 8.54 (1H, s) 7.44 (1H, d, J = 8.08 Hz) 7.30 (1H, s) 7.04 (1H, d, J = 8.08 Hz) 4.76 (2H, s) 4.66 (1H, s 4.56 (1H, d, J = 4.55 Hz) 3.69 (1H, s 3.28-3.46 (4H, m) 3.05-3.23 (2H, m 2.37 (3H, s) 2.12-2.26 (1H, m) 1.78-2.02 (4H, m) 1.15-1.39 (4H, m) |
| 212 | 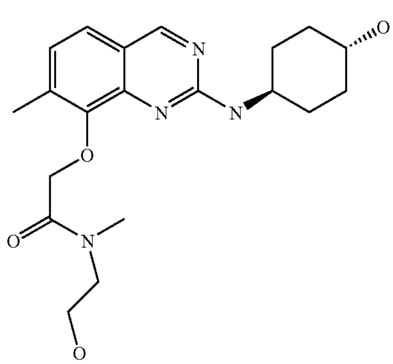 | 2-({2-[(trans-4-hydroxycyclohexyl)amino]-7-methylquinazolin-8-yl}oxy)-N-(2-hydroxyethyl)-N-methylacetamide | 389.2 | 1H NMR (400 MHz, DMSO-D6) d ppm 8.99 (1H, s) 7.39 (1H, dd, J = 7.96, 2.15 Hz) 7.28 (1H, s) 7.01 (1H, dd, J = 8.21, 3.16 Hz) 5.23 (1H, s) 5.17 (1H, s) 4.83 (0.5H, s) 4.68 (0.5H, t, J = 5.43 Hz) 4.56 (1H, dd, J = 8.59, 4.29 Hz) 3.74 (1H, s 3.44-3.61 (2H, m) 3.25-3.44 (3H, m) 3.05 (1.5H, s) 2.83 (1.5H, s) 2.38 (3H, d, J = 3.79 Hz) 1.79-2.04 (4H, m) 1.20-1.42 (4H, m) |

| Example Number | Structure | Compound Name | LRMS m/z | $^1$H NMR |
|---|---|---|---|---|
| 213 | 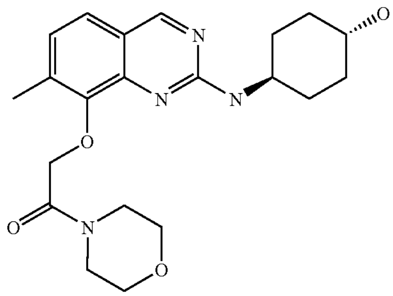 | trans-4-{[7-methyl-8-(2-morpholin-4-yl-2-oxoethoxy)quinazolin-2-yl]amino}cyclohexanol | 401.2 | 1H NMR (400 MHz, DMSO-d6) d ppm 9.00 (1H, s) 7.41 (1H, d, J = 8.08 Hz) 7.28 (1H, s) 7.03 (1H, d, J = 8.08 Hz) 5.18 (2H, s) 4.57 (1H, d, J = 4.04 Hz) 3.73 (1H, d) 3.37-3.62 (9H, m) 2.38 (3H, s) 1.80-2.03 (4H, m) 1.20-1.41 (4H, m) |
| 214 | 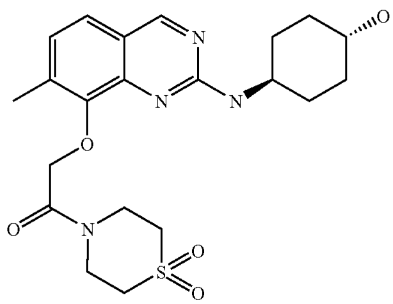 | trans-4-({8-[2-(1,1-dioxidothiomorpholin-4-yl)-2-oxoethoxyl]-7-methylquinazolin-2-yl}amino)cyclohexanol | 449.1 | 1H NMR (400 MHz, DMSO-D6) d ppm 9.00 (1H, s) 7.41 (1H, d, J = 8.34 Hz 7.31 (1H, s) 7.02 (1H, d, J = 8.34 Hz) 5.26 (2H, s) 4.57 (1H, d, J = 4.29 Hz) 3.90 (4H, s) 3.71 (1H, s) 3.35-3.50 (1H, m) 3.25 (2H, s) 3.14 (2H, s) 2.38 (3H, s) 1.91-2.00 (2H, m) 1.81-1.89 (2H) 1.19-1.40 (4H, m) |

Examples of preparation of compounds O-1 as described above in Scheme O:

1. Preparation of intermediate: 5-fluoro-8-methylisoquinolin-3-amine

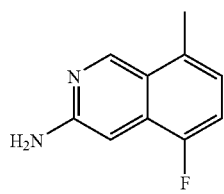

Scheme O was used for the preparation of 5-fluoro-8-methylisoquinolin-3-amine from 11.6 g of methyl 2,2-dimethoxyethanimidoate to give 860.0 mg, yield 13.6%. 1H NMR (400 MHz, DMSO-d6) ppm 2.57 (s, 3H), 6.17 (s, 2H), 6.68 (s, 1H), 6.87 (dd, J=7.05, 5.79 Hz, 1H), 7.14 (dd, J=11.20, 7.68 Hz, 1H), 8.96 (s, 1H).

2. Preparation of intermediate: 7-fluoro-5-(trifluoromethyl)isoquinolin-3-amine

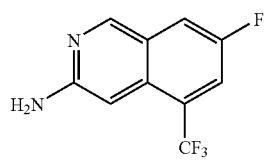

Scheme O was used for the preparation of 5-fluoro-8-methylisoquinolin-3-amine from 12.0 g of 5-ethoxy-4-(ethoxymethyl)-1-[3-fluoro-5-(trifluoromethyl)phenyl]pentane-2,3-diimine start material to give 5.9 g, yield 69.4%. 1H NMR (400 MHz, DMSO-d6) ppm 6.39 (s, 2H), 6.77 (d, J=1.01 Hz, 1H), 7.91 (dd, J 9.06, 2.52 Hz, 1H), 7.97 (dd, J=8.81, 2.27 Hz, 1H), 8.94 (s, 1H).

3. Preparation of intermediate: 6-bromo-8-methylisoquinolin-3-amine

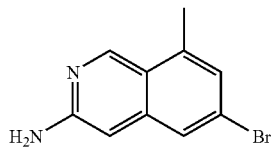

6-bromo-8-methylisoquinolin-3-amine was also prepared using the Scheme 0.4.1 g of SM provided 2.8 g of crude product. 0.87 g of pure product was obtained using a silica gel column purification. 1H NMR (400 MHz, DMSO-d6) ppm, 2.58 (s, 3H), 6.09 (s, 2H), 6.55 9 s, 1H), 7.63 (s, 1H), 8.91 (s, 1H). MS m/z, (APCI) 273 (M+H), 279 (M$^+$+3).

Examples of preparation of compounds O-1=>P-1=>Q-1=>R-1+R-2 according to the above described Schemes O-R:

1. Preparation of N-benzyl-3-[(trans-4-hydroxycyclohexyl)amino]-8-methylisoquinoline-6-carboxamide

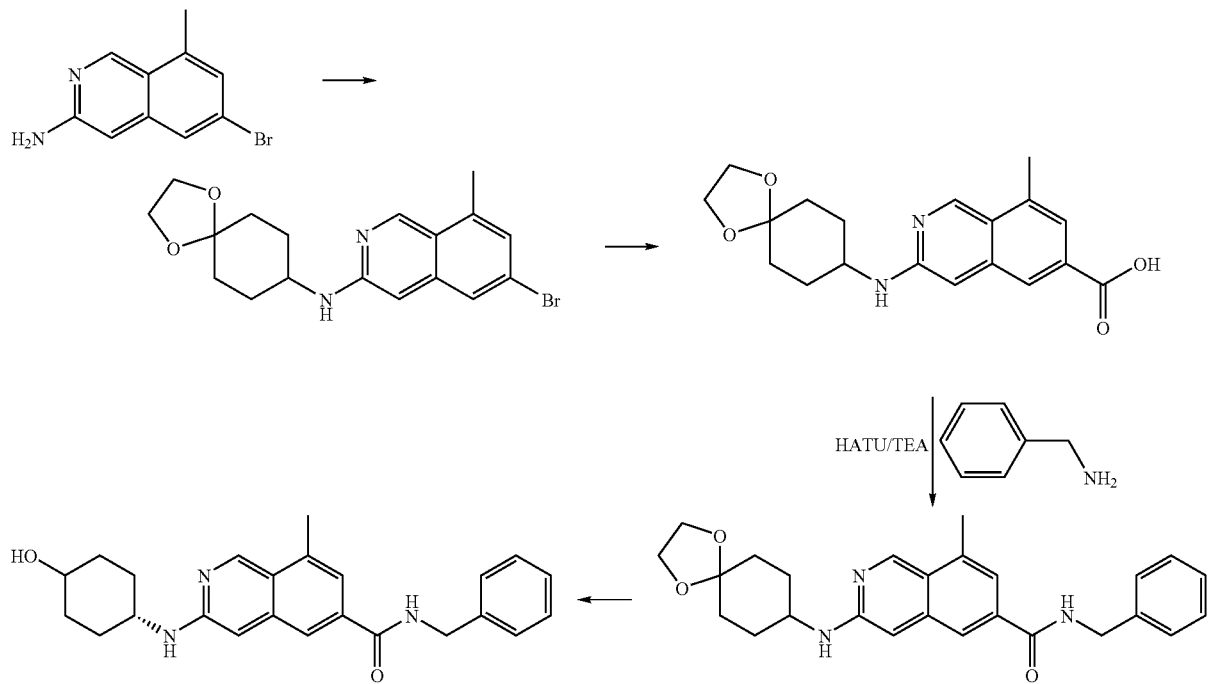

1a. Preparation of intermediate: 3-(1,4-dioxaspiro[4.5]dec-8-ylamine)-8-methyl-6-bromo-isoquinoline

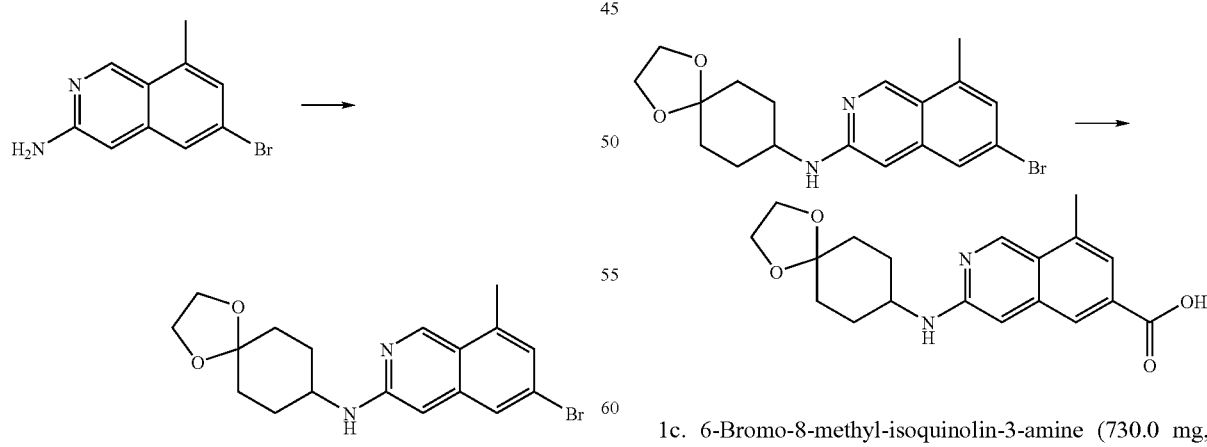

Scheme P was used in the preparation of 3-(1,4-dioxaspiro[4.5]dec-8-ylamine)-8-methyl-6-bromo-isoquinoline. The crude material was purified by a silica gel column with 50:50 (EtAc/Petroleum) to give 730.0 mg of the desired product (yield 52.1%). 1H NMR (400 MHz, DMSO-d6) ppm, 2.58 (s, 3H), 6.09 (s, 2H), 6.55 9 s, 1H), 7.63 (s, 1H), 8.91 (s, 1H). MS m/z, (APCI) 273 (M+H), 279 (M$^+$+3).

1b. Preparation of intermediate: 3-(1,4-dioxaspiro[4.5]dec-8-ylamino)-8-methylisoquinoline-6-carboxylic acid 1c. 6-Bromo-8-methyl-isoquinolin-3-amine (730.0 mg, 1.93 mmol) in 20 ml THF was added to a solution of 4 eq. BuLi in Hexane (7.7 ml of 2.0 M solution in pentane) at −75° C. After 45 min, the mixture was poured with excess of carbon dioxide (source from a $CO_2$ tank). The solvents were evaporated and the residue was partitioned between 1.0 M aq solution of NaOH and $Et_2O$. The combined organic layer were dried and evaporated. The aqueous layer was acidified to pH 6 and extracted with Et₂O (3×25 ml). The combined organic layers were evaporated and the crude was purified by a silica gel column to give 740.0 mg (70.1%) of the desired product. MS m/z, (APCI); 343.2 ([M+H]⁺).

1d. Preparation of intermediate: N-benzyl-3-(1,4-dioxaspiro[4.5]dec-8-ylamino)-8-methyl-isoquinoline-6-carboxamide

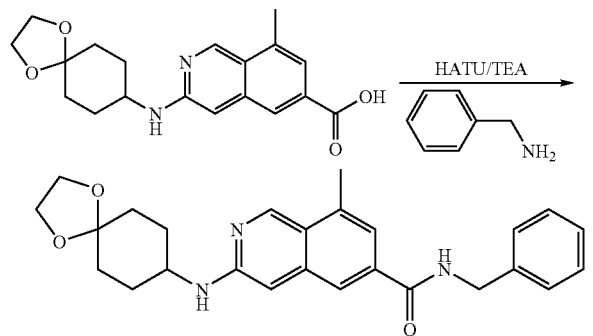

3-(1,4-Dioxa-spiro[4.5]dec-8-ylamino)-8-methyl-isoquinoline-6-carboxylic acid (100.0 mg, 0.29 mmol) in 5 ml DMA was treated with a HATU (240.0 mg, 0.63 mmol) and triethylamine (192.0 mg, 1.89 mmol) for 1 hour at room temperature. After 1 hour, benzylamine (74.5 mg, 0.69 mmol) was added and the mixture was heated to 50° C. for 2 hours. The reaction was completed by LC/MS monitoring. The solvent DMA was evaporated under vacuum, and the crude was dissolved in CH₂Cl₂ and washed with NaHCO₃ aqueous (10%) to remove the by-products from HATU. The crude residue was purified by a silica gel column to give 119.0 mg (94.4%). 1H NMR (400 MHz, CHLOROFORM-d) ppm 1.59-1.75 (m, 2H), 1.78-1.95 (m, 4H), 2.01-2.12 (m, 2H), 2.64 (s, 3H), 3.39-3.55 (m, J=4.28 Hz, 1H), 3.91-4.04 (m, 4H), 4.69 (d, J=5.54 Hz, 2H), 6.62 (s, 1H), 6.94 (s, 1H), 7.34-7.46 (m, 5H), 7.87 (s, 1H), 8.85 (s, 1H).

1e. Preparation of N-benzyl-3-[(trans-4-hydroxycyclohexyl)amino]-8-methylisoquinoline-6-carboxamide

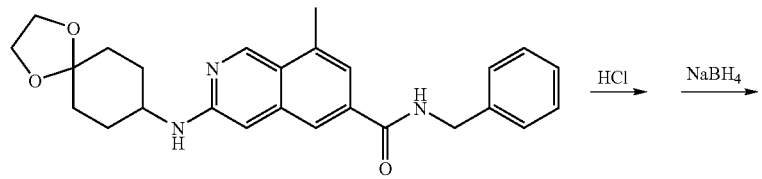

Preparation of 3-(4-Hydroxy-cyclohexylamino)-8-methyl-isoquinoline-6-carboxylic acid benzylamide was used the Schemes Q and R to give the design product 35.0 mg, yield 20.1%. 1H NMR (400 MHz, DMSO-d6) ppm 1.15-1.34 (m, 4H), 1.77-1.88 (m, 2H), 1.92-2.02 (m, 2H), 2.63 (s, 3H), 3.57 (m, 1H), 4.49 (d, J=5.79 Hz, 1H), 6.35 (d, J=8.06 Hz, 1H), 6.66 (s, 1H), 7.34 (d, J=4.53 Hz, 5H), 7.91 (s, 1H), 9.01 (s, 1H). HRMS: m/z 390.21697 [M+H]⁺), calc. 390.21760, MS m/z, (APCI); 390.2 ([M+H]⁺).

2. Preparation of 3-[(trans-4-hydroxycyclohexyl)amino]-N,8-dimethylisoquinoline-6-carboxamide

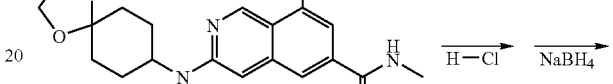

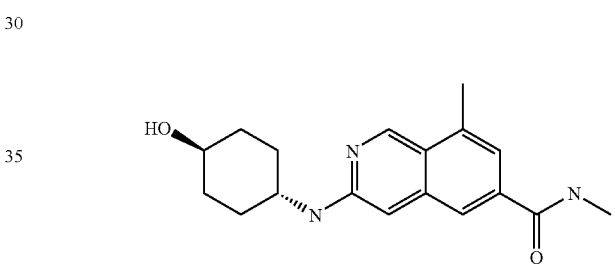

3-[(trans-4-hydroxycyclohexyl)amino]-N,8-dimethylisoquinoline-6-carboxamide was prepared by using the Schemes Q and R. The crude was separated by SFC to afford 24.0 mg of the product with yield of 17.0%. ¹H NMR (400 MHz, MeOD) ppm 1.23-1.55 (m, 4H), 2.06 (m, 4H), 2.65 (s, 3H), 2.94 (s, 3H), 3.44-3.79 (m, 2H), 6.68 (s, 1H), 7.28 (s, 1H),

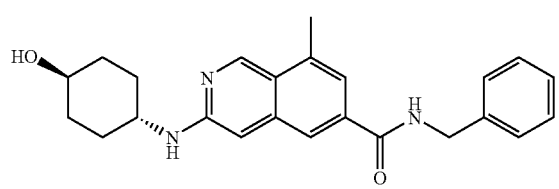

7.80 (s, 1H), 8.94 (s, 1H). HRMS: m/z 314.18688 [M+H]+, calc. 314.18630. MS m/z, (APCI); 314.2 ([M+H]+).

2a. Preparation of intermediate: 3-(1,4-dioxaspiro[4.5]dec-8-ylamino)-N-8-dimethylisoquinoline-6-carboxamide

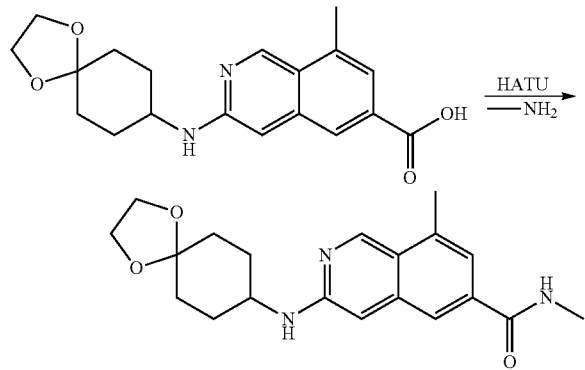

3-(1,4-Dioxa-spiro[4.5]dec-8-ylamino)-8-methyl-isoquinoline-6-carboxylic acid (200.0 mg, 0.58 mmol) in 5 ml DMA was treated with a HATU (222.0 mg, 0.58 mmol) and triethylamine (177.0 mg, 1.75 mmol) for 1 hour at room temperature. Then, methylamine was added and the mixture was heated to 50° C. for 2 hours. The reaction was completed by LC/MS monitoring. The solvent DMA was evaporated under vacuum, and the crude was dissolved in $CH_2Cl_2$ and washed with $NaHCO_3$ aqueous (10%) to remove the by-products from HATU. The crude after removal of the organic solvent was purified by a silica gel column to give 140 mg of the product with yield of 67.4%. MS m/z, (APCI); 356.2 ([M+H]+).

3. Preparation of N-(6-methoxyisoquinolin-3-yl)-2-(4-methoxyphenyl)acetamide

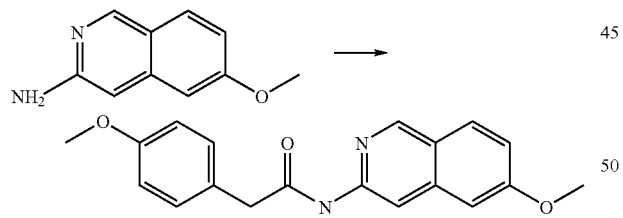

To a solution of (4-methoxyphenyl)acetic acid (166.2 mg, 0.86 mmol) in 5 ml of anhydrous THF were added oxalyl chloride (126.9 mg, 4.3 mmol) and 100 ul of DMF. A vigorous effervescence occurred. Within 1-4 minutes the effervescence stopped and the mixture was stirred for 30 minutes at room temperature. Then the 6-methoxyisoquinolin-3-amine (150.0 mg, 0.86 mmol) and $Et_3N$ (0.86 mmol) were added. The reaction was stirred at the ambient temperature over 16 hours. The reaction was monitored by LC/MS that showed no more start material left. The reaction crude was purified by a silica gel column to give product 75.7 mg (yield 27.3%). 1H NMR (400 MHz, DMSO-d6) ppm 3.68 (s, 2H), 3.72 (s, 3H), 3.89 (s, 3H), 6.89 (d, J=8.81 Hz, 2H), 7.14 (dd, J=8.94, 2.39 Hz, 1H), 7.26 (d, J=2.27 Hz, 1H), 7.30 (d, J=8.81 Hz, 2H), 7.95 (d, J=9.06 Hz, 1H), 8.32 (s, 1H), 8.98 (s, 1H), 10.73 (s, 1H). HRMS: m/z 323.13882 [M+H]+, calc. 323.13902. MS m/z, (APCI); 323.2 ([M+H]+).

3a. Preparation of intermediate: 6-methoxyisoquinolin-3-amine

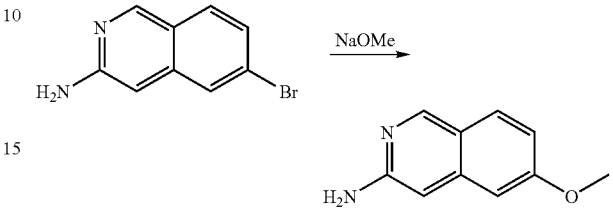

In a dry box, to the microwave test tube (20 ml volume) was added the 6-bromoisoquinolin-3-amine (1.0 g, 4.5 mmol) and the NaOMe (242.0 mg, 4.5 mmol) in 10 ml of DMSO. The microwave test tube was capped and moved from the dry box. The test tube was place into Microwave station to heat at 150° C. for 30 min. The crude residue was purified by a silica gel column to give 420 mg (yield 53.8%). 1H NMR (400 MHz, DMSO-d6) ppm 2.44 (s, 3H), 7.94-8.11 (m, 2H), 8.17 (d, J=8.56 Hz, 2H), 8.82 (s, 1H). MS m/z, (APCI); 175.1 ([M+H]+).

4. Preparation of trans- and cis-4-{[5-(cyclopentyloxy)-8-methylisoquinolin-3-yl]amino}cyclohexanol

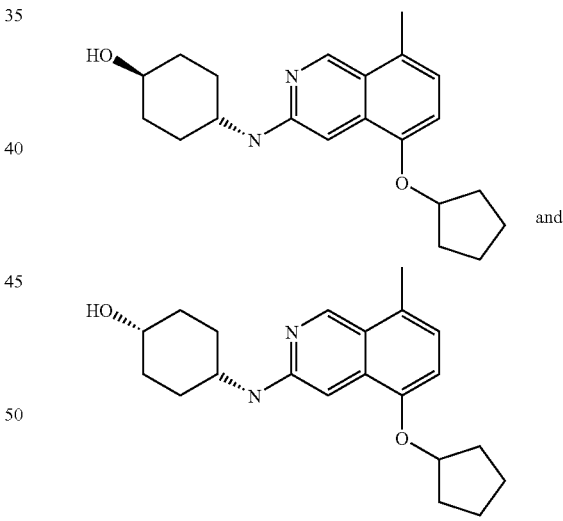

The trans-4-{[5-(cyclopentyloxy)-8-methylisoquinolin-3-yl]amino}cyclohexanol was prepared 5-(cyclopentyloxy)-N-1,4-dioxaspiro[4.5]dec-8-yl-8-methylisoquinolin-3-amine by using the Schemes Q and R described above. The crude product was purified by prepHPLC to give 84.0 mg, yield 39.4%, and the cis-isomer described below. 1H NMR (400 MHz, MeOD) ppm 0.09-0.29 (m, 4H), 0.38-0.51 (m, 2H), 0.51-0.92 (m, 12H), 1.28 (s, 3H), 2.28-2.52 (m, 1H), 3.67-3.82 (m, 1H), 5.57-5.74 (dd, J=7.55, 1.01 Hz, 1H), 5.81 (dd, J=7.55, 1.01 Hz, 1H), 6.22 (s, 1H), 7.47 (s, 1H). HRMS: m/z 341.22300 ([M+H]+), calc. 341.22235, MS m/z, (APCI); 341.2 [(M+1)+100].

Preparation of cis-4-{[5-(cyclopentyloxy)-8-methyl-isoquinolin-3-yl]amino}cyclohexanol cis-4-{[5-(cyclopentyloxy)-8-methylisoquinolin-3-yl]amino}cyclohexanol was obtained from prepHPLC to give 63.6 mg, yield 31.2%. 1H NMR (400 MHz, MeOD) ppm 1.63-2.11 (m, 16H), 2.55 (s, 3H), 3.68 (d, J=4.53 Hz, 1H), 3.93 (d, J=3.27 Hz, 1H), 4.95-5.08 (m, 1H), 6.94 (d, J=7.81 Hz, 1H), 7.01-7.12 (m, 1H), 7.51 (s, 1H), 8.77 (s, 1H). HRMS: m/z 341.22300 ([M+H]$^+$), calc. 341.22235, MS m/z, (APCI); 341.2 [(M+1)$^+$100].

4a. Preparation of intermediate: N-1,4-dioxaspiro[4.5]dec-8-yl-5-fluoro-8-methylisoquinolin-3-amine

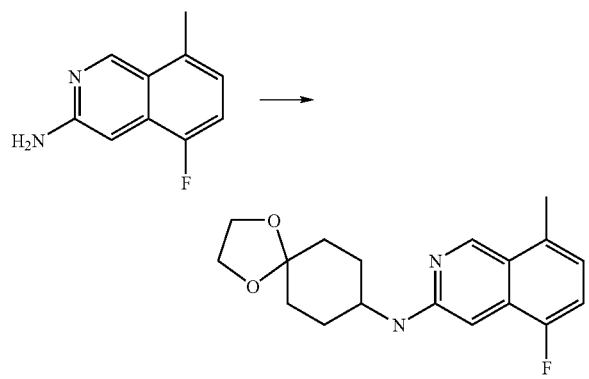

N-1,4-dioxaspiro[4.5]dec-8-yl-5-fluoro-8-methylisoquinolin-3-amine was prepared by using the Scheme P. The crude residue was purified by a silica gel column to give product 1.3 g. 1H NMR (400 MHz, CHLOROFORM-d) ppm 1.55-1.79 (m, 4H), 1.78-1.94 (m, 2H), 1.99-2.20 (m, 2H), 3.39-3.72 (m, 1H), 3.88-4.09 (m, 4H), 4.86-5.04 (m, 1H), 6.37 (s, 1H), 6.91 (dd, J=9.82, 1.51 Hz, 1H), 7.48 (s, 1H), 9.01 (s, 1H). 317.2 ([M+H]$^+$).

4b. Preparation of intermediate: 5-(cyclopentyloxy)-N-1,4-dioxaspiro[4.5]dec-8-yl-8-methylisoquinolin-3-amine

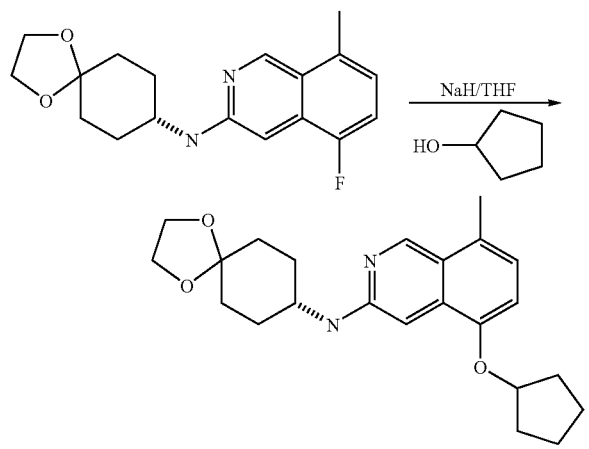

In a dry box, in a microwave test tube cyclopentanol (600.0 mg, 7.0 mmol) was dissolved in 5 ml of THF. To this solution was added the NaH (273.0 mg, 11.4 mmol) at room temperature and the mixture was stirred for 30 min. N-1,4-dioxaspiro[4.5]dec-8-yl-5-fluoro-8-methylisoquinolin-3-amine (1.8 g, 5.7 mmol) mixed with 15-crown-5 ether (0.13 g, 0.57 mmol) in 15 ml of DMSO was added to above solution. The microwave test tube was capped and moved out from the dry box. The tube was placed into Microwave apparatus and heated to 140° C. for 2 hours. The crude product was purified using a silica gel column to give 263.0 mg (yield 53%). 1H NMR (400 MHz, CHLOROFORM-d) ppm 0.89 (m, 1H), 1.17-1.40 (m, 2H), 1.57-2.02 (m, 10H), 2.05-2.29 (m, 2H), 2.47-2.63 (m, 3H), 3.54-3.78 (m, 1H), 3.90-4.06 (m, 4H), 4.64-5.02 (m, 2H), 6.46-6.77 (m, 1H), 6.79-6.98 (m, 2H), 7.20-7.43 (m, 1H), 8.91 (s, 1H). MS m/z, (APCI); 383.2 ([M+H]$^+$).

5. Preparation of 7-fluoro-3-[(trans-4-hydroxycyclohexyl)amino]-N-(2-hydroxyethyl) isoquinoline-5-carboxamide

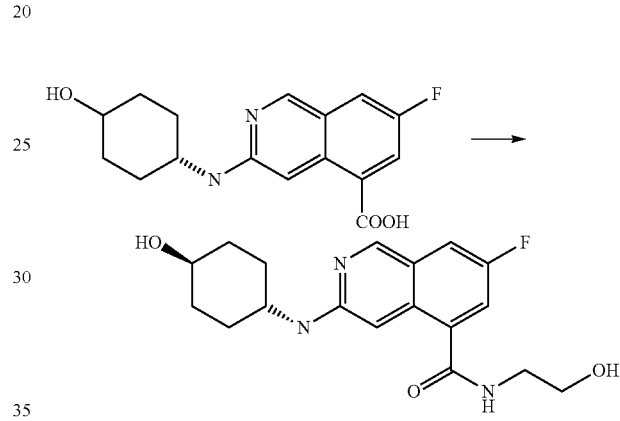

7-fluoro-3-[(trans-4-hydroxycyclohexyl)amino]isoquinoline-5-carboxylic acid (23.0 mg, 0.076 mmol) in 5 ml DMA was treated with HATU (62.1 mg, 0.16 mmol) and triethylamine (49.5 mg, 0.49 mmol). After 1 hour, 2-aminoethanol (15.0 mg, 0.25 mmol) was added and the solution was heated to 50° C. for 2 hours. The reaction was monitored by LC/MS to show no start acid left. The solvent was removed under vacuum and the crude was dissolved in CH$_2$Cl$_2$ and washed with 1 M NaHCO$_3$ aqueous. The organic layers were dried over MgSO$_4$. The crude material after removal of the solvent was purified by prepHPLC to give 5.8 mg (yield 19.3%). $^1$H NMR (400 MHz, MeOD) ppm 1.21-1.56 (m, 4H), 1.87-2.20 (m, 4H), 3.48-3.67 (m, 4H), 3.77 (m, 2H), 7.02 (s, 1H), 7.46-7.69 (m, 2H), 8.78 (s, 1H). HRMS: m/z 348.17226[M+H]$^+$), calc. 348.17180. MS m/z, (APCI); 348.2 ([M+H]$^+$).

5a. Preparation of intermediate: N-1,4-dioxaspiro[4.5]dec-8-yl-7-fluoro-5-(trifluoromethyl)isoquinolin-3-amine

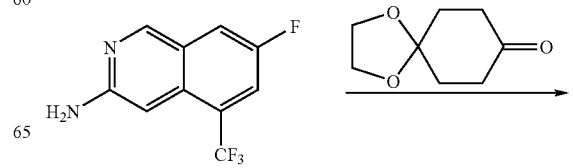

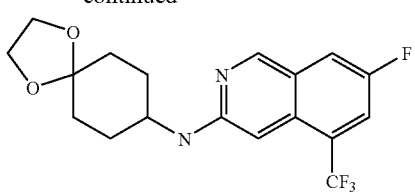

N-1,4-dioxaspiro[4.5]dec-8-yl-7-fluoro-5-(trifluoromethyl)isoquinolin-3-amine was prepared by using the Scheme P. The crude material was purified by a silica gel column to give 1.3 g, yield of 13.0% from 6.2 g of 7-fluoro-5-(trifluoromethyl)isoquinolin-3-amine. 1H NMR (400 MHz, CHLOROFORM-d) ppm 1.55-1.79 (m, 4H), 1.78-1.94 (m, 2H), 1.99-2.20 (m, 2H), 3.39-3.72 (m, 1H), 3.88-4.09 (m, 4H), 4.86-5.04 (m, 1H), 6.37 (s, 1H), 6.91 (dd, J=9.82, 1.51 Hz, 1H), 7.48 (s, 1H), 9.01 (s, 1H). MS m/z, (APCI); 371.2 ([M+H]+), 5b. Preparation of intermediate: 4-{[7-fluoro-5-(trifluoromethyl)isoquinolin-3-yl]amino}cyclohexanone

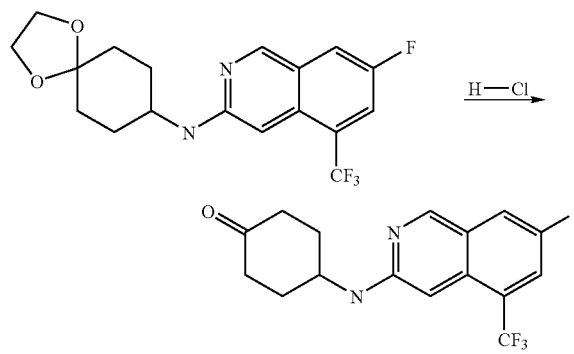

4-{[7-fluoro-5-(trifluoromethyl)isoquinolin-3-yl]amino}cyclohexanone was prepared by using the Scheme Q to give the product with no need for purification for next step. (APCI); 327.2 ([M+H]+), 5c. Preparation of Trans- and cis-4-{[7-fluoro-5-(trifluoromethyl)isoquinolin-3-yl]amino}cyclohexanol

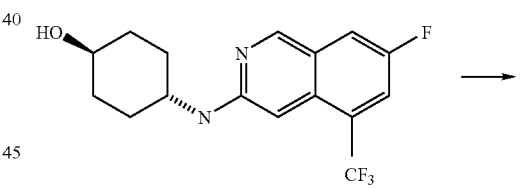

Scheme R was used for the preparation of both trans and cis products. The crude product was purified by SFC to give Trans-4-{[7-fluoro-5-(trifluoromethyl)isoquinolin-3-yl]amino}cyclohexanol 37.1 mg, 30.1%, and cis-isomer described below. 1H NMR (400 MHz, DMSO-d6) ppm 1.09-1.40 (m, 4H), 1.73-2.02 (m, 4H), 3.43 (d, J=4.78 Hz, 1H), 3.66 (s, 1H), 4.55 (d, J=4.28 Hz, 1H), 6.70 (s, 1H), 6.81 (d, J=7.81 Hz, 1H), 7.70-8.03 (m, 2H), 8.97 (s, 1H). HRMS: m/z 329.12794 [M+H]+), calc. 329.12715, MS m/z, (APCI); 329.1 ([M+H]+), Preparation of cis-4-{[7-fluoro-6-(trifluoromethyl)isoquinolin-3-yl]amino}cyclohexanol The SFC separation also afforded 8.1 mg of cis-4-{[7-fluoro-5-(trifluoromethyl)isoquinolin-3-yl]amino}cyclohexanol (yield 6.6%). 1H NMR (400 MHz, DMSO-d6) ppm 1.42-1.81 (m, 8H), 3.61-3.89 (m, 2H), 4.41 (d, J=2.77 Hz, 1H), 6.78 (s, 1H), 6.87 (d, J=7.55 Hz, 1H), 7.77-7.98 (m, 2H), 8.96 (s, 1H). HRMS: m/z 329.12796 [M+H]+), calc. 329.12715, MS m/z, (APCI); 329.1 ([M+H]+).

5d. Preparation of intermediate: 7-fluoro-3-[(trans-4-hydroxycyclohexyl)amino]isoquinoline-5-carboxylic acid

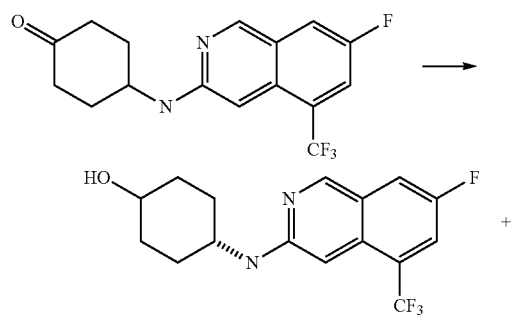

A mixture of Trans-4-{[7-fluoro-5-(trifluoromethyl)isoquinolin-3-yl]amino}cyclohexanol (150.0 mg, 0.46 mmol) and sodium hydroxide (183.0, 4.6 mmol) in 4 ml DMSO/THF (50:50) was placed into a microwave test tube and was heated in Microwave Apparatus to 160° C. for 2 hours. The crude material was purified by prepHPLC to give 23 mg (yield 16.5%). 1H NMR (400 MHz, MeOD) ppm 1.26-1.61 (m, 4H), 1.95-2.25 (m, 4H), 3.49-3.78 (m, 2H), 7.83 (dd, J=7.93, 2.64 Hz, 1H), 8.28 (dd, J=9.32, 2.77 Hz, 1H), 8.37 (s, 1H), 8.92 (s, 1H). MS m/z, (APCI); 305.1 ([M+H]⁺).

6. Preparation of trans-4-{[6-(cyclopentyloxy)-7-methoxyquinazolin-2-yl]amino}cyclohexanol

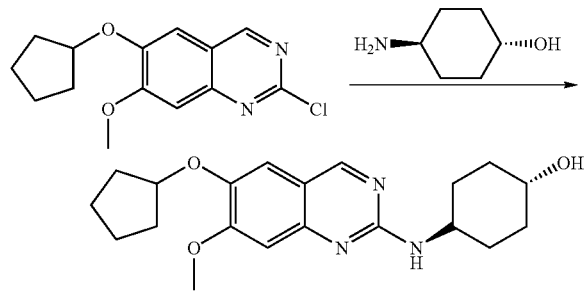

To a suspension of 2-chloro-6-(cyclopentyloxy)-7-methoxyquinazoline (100.0 mg, 0.36 mmol) (obtained from the company compound collection) in 20 ml of CH₃CN at room temperature was added the trans-4-aminocyclohexanol (207.0 mg, 1.79 mmol). The resulting mixture was heated to 60° C. for 5 hours. The reaction was cooled and partitioned with EA and water. The organics layer was washed with water (2×20 mL) and brine (20 mL), combined and dried over MgSO₄, Removal of the solvent provided a yellow solid. The crude material was purified using silica gel eluting with 95/5 EA/MeOH to afford 45.9 mg of the desired product with 35.9% yield. 1H NMR (400 MHz, DMSO-d6) ppm 1.14-1.40 (m, 4H), 1.51-2.06 (m, 12H), 3.36-3.52 (m, 1H), 3.66-3.80 (m, 1H), 3.82-3.95 (m, 3H), 4.54 (s, 1H), 4.75-4.88 (m, 1H), 6.74 (d, J=8.06 Hz, 1H), 6.83 (s, 1H), 7.12 (s, 1H), 8.80 (s, 1H). HRMS: m/z 358.21218 [M+H]⁺), calc. 358.21252. MS m/z, (APCI); 358.2 ([M+H]⁺).

7. Preparation of N-benzyl2({trans4-[(cyclopropylsulfonyl)amino]cyclohexyl}amino) quinazoline-7-carboxamide

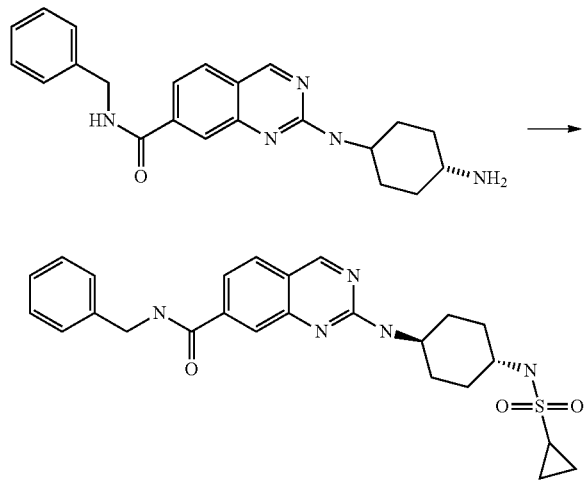

A solution of 2-[(trans-4-aminocyclohexyl)amino]-N-benzylquinazoline-7-carboxamide (200.0 mg, 0.53 mmol), cyclopropanesulfonyl chloride (37.4 mg, 0.53 mmol) and triethylamine (162.0 mg, 1.6 mmol) in 7 ml of a mixed solvents of dichloroethane:dimethoxyethane (1:2) was stirred at room temperature for 16 hours. The crude material was purified by prepHPLC to give 13.0 mg of the product (yield 10.2%). 1H NMR (400 MHz, DMSO-d6) ppm 0.78-1.06 (m, 6H), 1.39 (t, J=9.82 Hz, 4H), 1.99 (d, J=4.28 Hz, 3H), 2.37-2.48 (m, 1H), 2.54-2.64 (m, 1H), 3.13 (s, 1H), 3.78 (s, 1H), 4.18 (d, J=6.55 Hz, 1H), 4.50 (d, J=6.04 Hz, 1H), 7.08 (d, J=7.81 Hz, 1H), 7.22-7.30 (m, 1H), 7.31-7.37 (m, 6H), 7.43-7.50 (m, 1H), 7.64 (d, J=6.80 Hz, 1H), 7.85 (d, J=8.31 Hz, 1H), 8.00 (s, 1H), 9.14 (s, 1H), 9.29 (t, J=5.92 Hz, 1H). HRMS: m/z 480.20484 [M+H]⁺), calc. 480.20638. MS m/z, (APCI); 480.2 ([M+H]⁺).

7a. Preparation of intermediate: 2-({trans-4-[(tert-butoxycarbonyl)amino]cyclohexyl}amino)-quinazoline-7-carboxylic acid

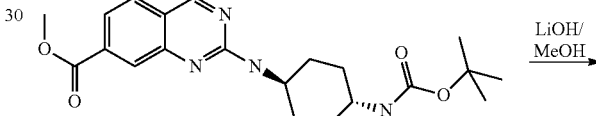
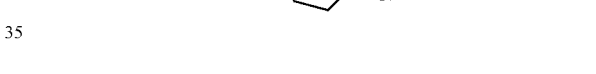

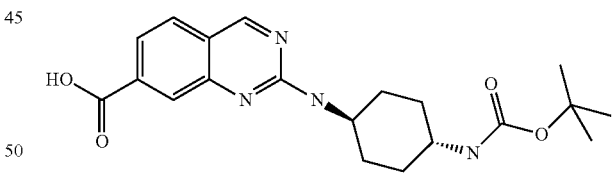

The methyl 2-({trans-4-[(tert-butoxycarbonyl)amino]cyclohexyl}amino)quinazoline-7-carboxylate (1.0 g, 4.0 mmol) was dissolved in MeOH (20 ml). To this solution LiOH (538.0 mg, 22.5 mmol) was added and then heated to 50° C. for 16 hours. Evaporation of the solvent and partition with EtAc/H₂O, followed by separation of the organic layers and evaporation provided the crude product. Purification using a silica gel column with 40% EA in heptane to give 780.0 mg of the desired product (yield 81.3%). 1H NMR (400 MHz, DMSO-d₆) ppm 1.23-1.36 (m, 4H), 1.38 (s, 9H), 1.82 (s, 2H), 1.93-2.05 (m, 2H), 3.18-3.27 (m, 1H), 3.77 (s, 1H), 6.76 (d, J=8.06 Hz, 1H), 7.27 (d, J=8.06 Hz, 1H), 7.63-7.71 (m, 1H), 7.71-7.78 (m, 1H), 7.93 (s, 1H), 9.10 (s, 1H). (APCI); 387.5 ([M+H]⁺).

7b. Preparation of intermediate: tert-butyl [trans-4-({7-[(benzylamino)carbonyl]quinazolin-2-yl}amino)cyclohexyl]carbamate

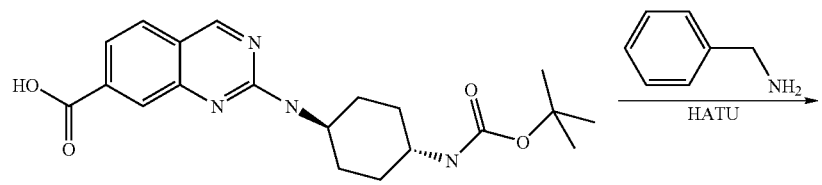

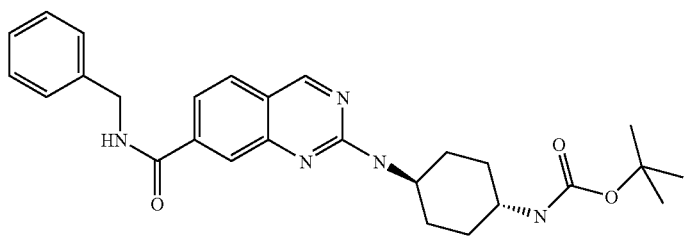

2-({trans-4-[(tert-butoxycarbonyl)amino]cyclohexyl}amino)quinazoline-7-carboxylic acid (780.0 mg, 2.0 mmol) was treated with HATU (767.0 mg, 2.0 mmol) and triethylamine (613.0 mg, 6.1 mmol) in 10 ml of acetonitrile. After 1 hour the benzylamine was added and heated to 50° C. for 2 hours. The solvent was removed and the crude was dissolved in EA and washed with NaHCO$_3$ aqueous to remove the by-products form HATU. The crude was purified using a silica gel column to give 930.0 mg of desired product with yield of 96.7%. MS m/z, (APCI); 476.2 ([M+H]$^+$).

7c. Preparation of intermediate: 2-[(trans-4-aminocyclohexyl)amino]-N-benzylquinazoline-7-carboxamide

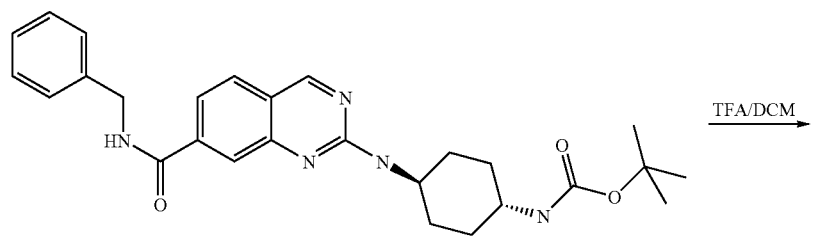

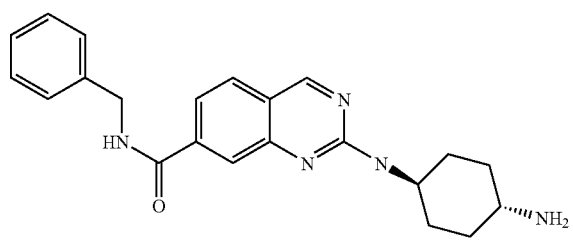

The tert-butyl [trans-4-({7-[(benzylamino)carbonyl] quinazolin-2-yl}amino)cyclohexyl]carbamate (780.0 mg, 2.0 mmol) was treated with TFA (2.3 g, 20.0 mmol) in DCM (15 ml) at 50° C. for 2 hours. Removal of solvent and TFA gave 758.0 mg of product without further purification. MS m/z, (APCI); 378.5 ([M+H]$^+$).

8. Preparation of 2-[([trans-4-(acetylamino)cyclohexyl]amino]-N-benzylquinazoline-7-carboxamide

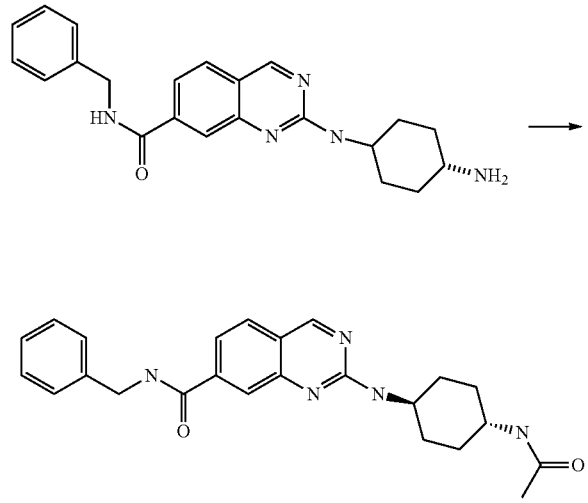

A solution of 2-[(trans-4-aminocyclohexyl)amino]-N-benzylquinazoline-7-carboxamide (prepared as described in preparation 7c above) (200.0 mg, 0.53 mmol), acetyl chloride (27.3 mg, 0.53 mmol) and triethylamine (162.0 mg, 1.6 mmol) in 7 ml of a mixed solvents of dichloroethane: dimethoxyethane (1:2) was stirred at room temperature for 16 hours. The crude material was purified by HPLC to give product 15.1 mg, 13.6%. 1H NMR (400 MHz, DMSO-d6) ppm 1.13-1.49 (m, 4H), 1.79 (s, 3H), 1.82 (s, 3H), 1.98 (s, 1H), 3.22-3.41 (m, 4H), 3.43-3.59 (m, 1H), 3.90 (s, 1H), 4.50 (d, J=6.04 Hz, 1H), 7.17-7.29 (m, 1H), 7.31-7.37 (m, 4H), 7.44 (d, J=8.31 Hz, 1H), 7.63 (dd, J=8.18, 1.38 Hz, 1H), 7.75 (d, J=7.81 Hz, 1H), 7.84 (d, J=8.31 Hz, 1H), 7.99 (s, 1H), 9.14 (s, 1H), 9.30 (t, J=5.79 Hz, 1H). HRMS: m/z 418.22213 [M+H]$^+$), calc. 418.22375. MS m/z, (APCI); 418.2 ([M+H]$^+$).

9. Preparation of N-benzyl-2-([trans-4-(isobutyrylamino)cyclohexyl]amino)quinazoline-7-carboxamide

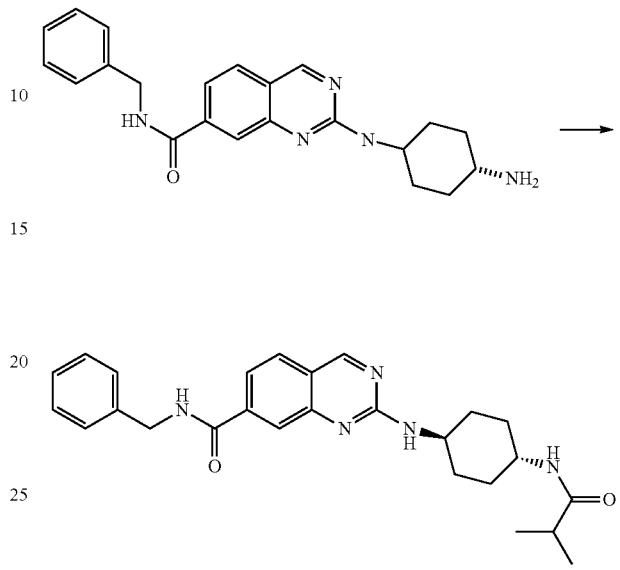

A solution of 2-[(trans-4-aminocyclohexyl)amino]-N-benzylquinazoline-7-carboxamide (prepared as described in preparation 7c above) (200.0 mg, 0.53 mmol), acetyl chloride (56.8 mg, 0.53 mmol) and triethylamine (162.0 mg, 1.6 mmol) in 7 ml of a mixed solvents of dichloroethane: dimethoxyethane (1:2) was stirred at room temperature for 16 hours. The crude material was purified by HPLC to give product 21.0 mg, 9.5%. 1H NMR (400 MHz, DMSO-d6) ppm 0.86-0.90 (m, 1H), 0.94 (s, 3H), 0.96 (s, 3H), 0.97-1.00 (m, 1H), 1.16-1.42 (m, 4H), 1.64-1.99 (m, 8H), 2.15-2.39 (m, 2H), 2.45-2.56 (m, 1H), 4.36-4.62 (m, 4H), 7.19-7.30 (m, 1H), 7.30-7.41 (m, 6H), 7.60 (d, J=7.81 Hz, 1H), 8.26 (dd, J=8.56, 1.51 Hz, 1H), 8.37 (d, J=8.56 Hz, 1H), 8.45-8.67 (m, 1H), 9.54 (t, J=5.79 Hz, 1H), 9.66-10.04 (m, 1H). HRMS: m/z 446.25321 [M+H]$^+$), calc. 446.25505. MS m/z, (APCI); 446.2 ([M+H]$^+$).

The following examples nos. 216-239 were prepared based on Scheme S as described above:

| ID | Structure | Name | LRMS m/z |
|---|---|---|---|
| 215 | 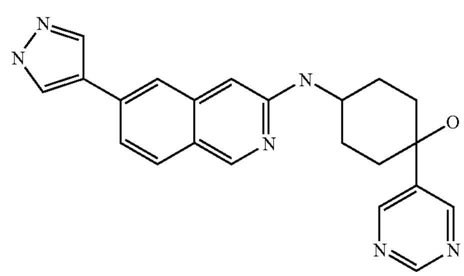 | 4-{[6-(1H-pyrazol-4-yl)isoquinolin-3-yl]amino}-1-pyrimidin-5-ylcyclohexanol | 387 |

-continued

| ID | Structure | Name | LRMS m/z |
|---|---|---|---|
| 216 | 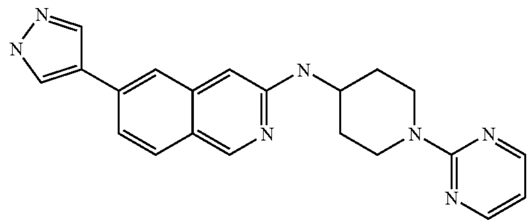 | 6-(1H-pyrazol-4-yl)-N-(1-pyrimidin-2-ylpiperidin-4-yl)isoquinolin-3-amine | 372 |
| 217 | 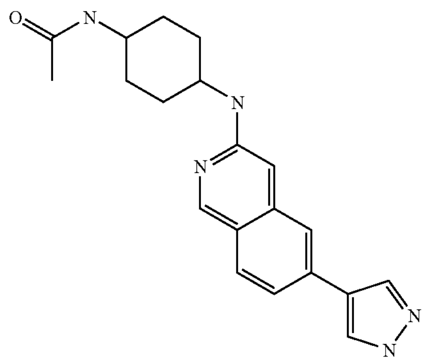 | N-(4-{[6-(1H-pyrazol-4-yl)isoquinolin-3-yl]amino}cyclohexyl)acetamide | 350 |
| 218 | 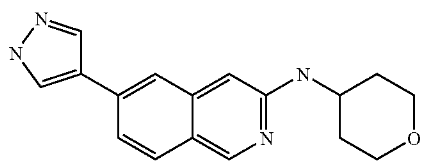 | 6-(1H-pyrazol-4-yl)-N-(tetrahydro-2H-pyran-4-yl)isoquinolin-3-amine | 295 |
| 219 | 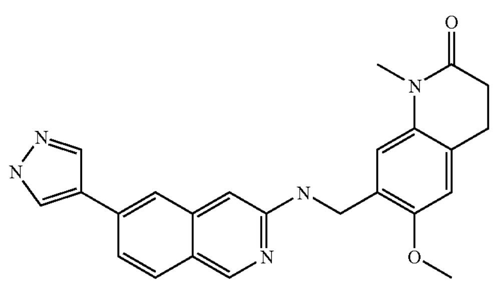 | 6-methoxy-1-methyl-7-({[6-(1H-pyrazol-4-yl)isoquinolin-3-yl]amino}methyl)-3,4-dihydroquinolin-2(1H)-one | 414 |
| 220 | 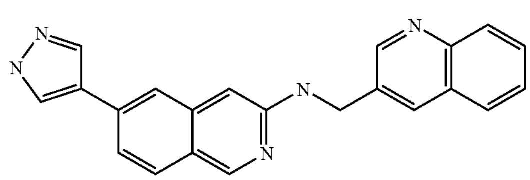 | 6-(1H-pyrazol-4-yl)-N-(quinolin-3-ylmethyl)isoquinolin-3-amine | 352 |
| 221 | 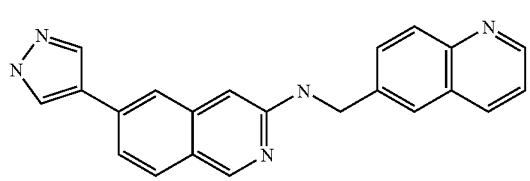 | 6-(1H-pyrazol-4-yl)-N-(quinolin-6-ylmethyl)isoquinolin-3-amine | 352 |
| 222 | 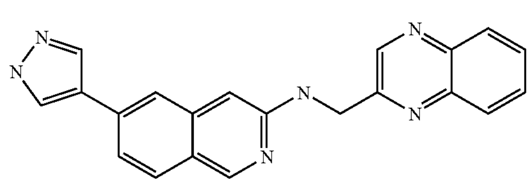 | 6-(1H-pyrazol-4-yl)-N-(quinoxalin-2-ylmethyl)isoquinolin-3-amine | 353 |

| ID | Structure | Name | LRMS m/z |
|---|---|---|---|
| 223 | 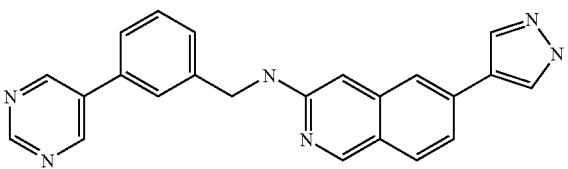 | 6-(1H-pyrazol-4-yl)-N-(3-pyrimidin-5-ylbenzyl)isoquinolin-3-amine | 379 |
| 224 | 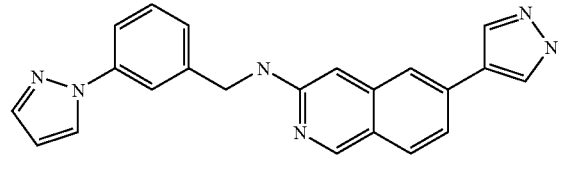 | 6-(1H-pyrazol-4-yl)-N-[3-(1H-pyrazol-1-yl)benzyl]isoquinolin-3-amine | 367 |
| 225 | 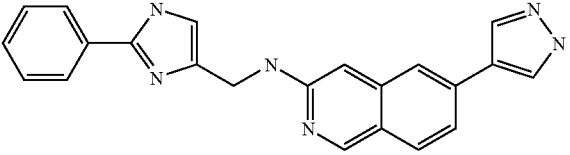 | N-[(2-phenyl-1H-imidazol-4-yl)methyl]-6-(1H-pyrazol-4-yl)isoquinolin-3-amine | 367 |
| 226 | 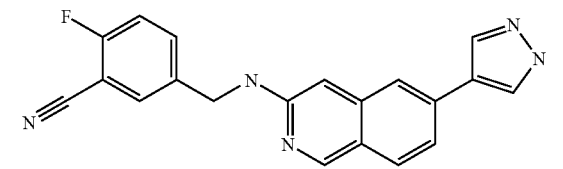 | 2-fluoro-5-({[6-(1H-pyrazol-4-yl)isoquinolin-3-yl]amino}methyl)benzonitrile | 344 |
| 227 | 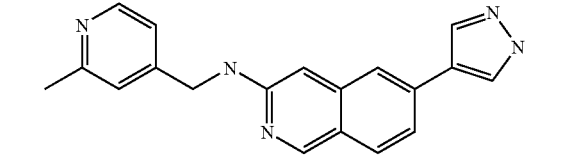 | N-[(2-methylpyridin-4-yl)methyl]-6-(1H-pyrazol-4-yl)isoquinolin-3-amine | 316 |
| 228 | 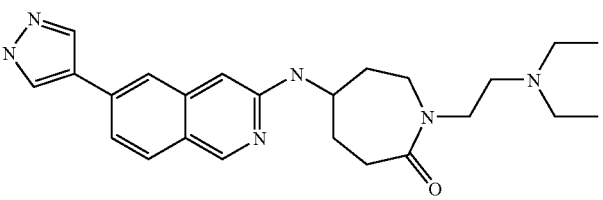 | 1-[2-(diethylamino)ethyl]-5-{[6-(1H-pyrazol-4-yl)isoquinolin-3-yl]amino}azepan-2-one | 422 |
| 229 | 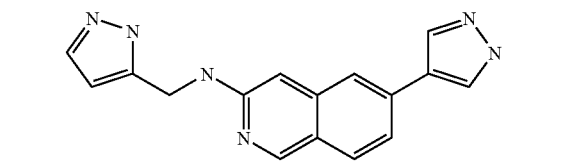 | 6-(1H-pyrazol-4-yl)-N-(1H-pyrazol-5-ylmethyl)isoquinolin-3-amine | 291 |
| 230 | 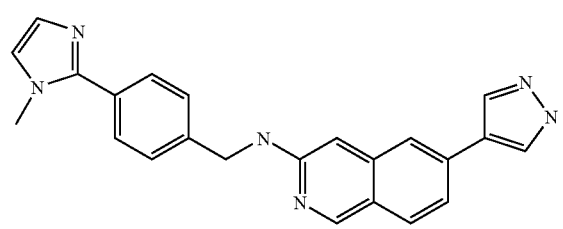 | N-[4-(1-methyl-1H-imidazol-2-yl)benzyl]-6-(1H-pyrazol-4-yl)isoquinolin-3-amine | 381 |

| ID | Structure | Name | LRMS m/z |
|---|---|---|---|
| 231 | 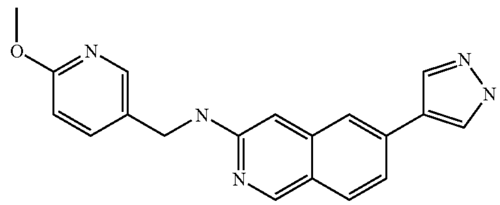 | N-[(6-methoxypyridin-3-yl)methyl]-6-(1H-pyrazol-4-yl)isoquinolin-3-amine | 332 |
| 232 | 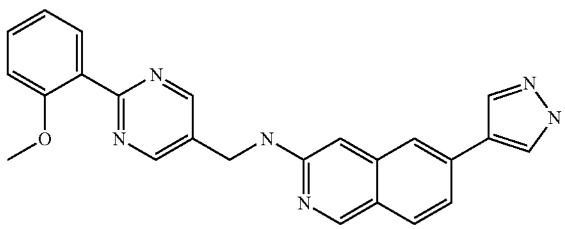 | N-{[2-(2-methoxyphenyl)pyrimidin-5-yl]methyl}-6-(1H-pyrazol-4-yl)isoquinolin-3-amine | 409 |
| 233 | 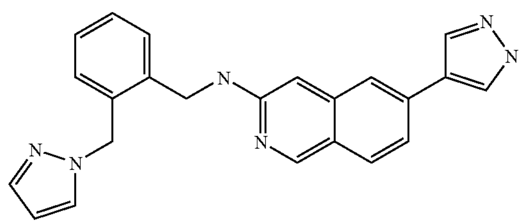 | 6-(1H-pyrazol-4-yl)-N-[2-(1H-pyrazol-1-ylmethyl)benzyl]isoquinolin-3-amine | 381 |
| 234 | 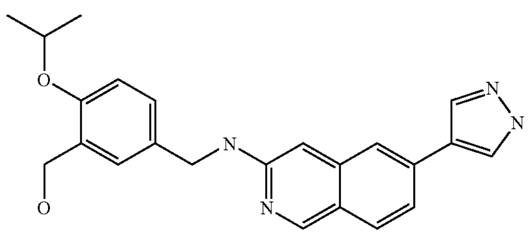 | [2-isopropoxy-5-({[6-(1H-pyrazol-4-yl)isoquinolin-3-yl]amino}methyl)phenyl]methanol | 389 |
| 235 | 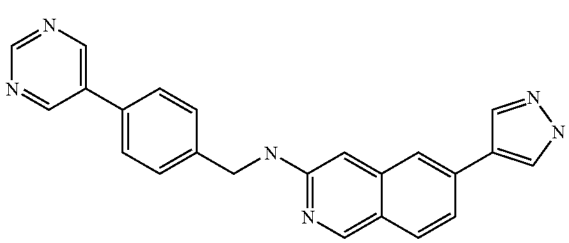 | 6-(1H-pyrazol-4-yl)-N-(4-pyrimidin-5-ylbenzyl)isoquinolin-3-amine | 379 |
| 236 | 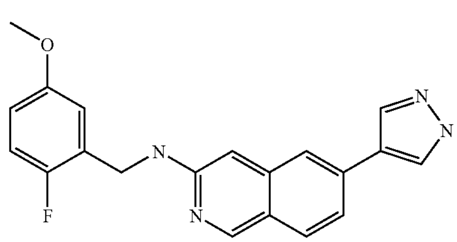 | N-(2-fluoro-5-methoxybenzyl)-6-(1H-pyrazol-4-yl)isoquinolin-3-amine | 349 |

-continued

| ID | Structure | Name | LRMS m/z |
|---|---|---|---|
| 237 | 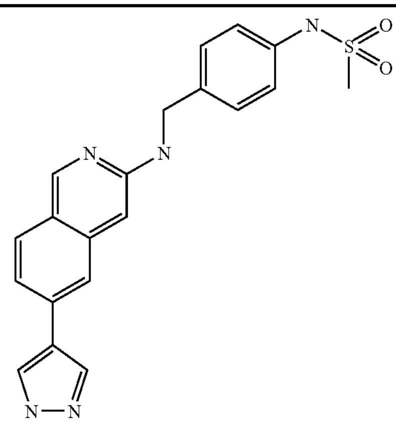 | N-[4-({[6-(1H-pyrazol-4-yl)isoquinolin-3-yl]amino}methyl)phenyl]methanesulfon-amide | 394 |
| 238 | 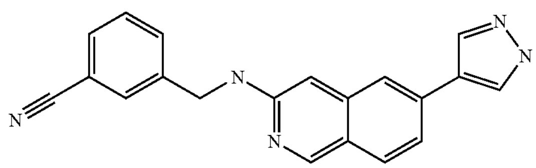 | 3-({[6-(1H-pyrazol-4-yl)isoquinolin-3-yl]amino}methyl)benzonitrile | 326 |

The following examples nos. 239-267 were prepared with non-critical substitutions and/or method changes in an analogous way to example 144:

| ID | Structure | Name | LC/MS m/z |
|---|---|---|---|
| 239 | 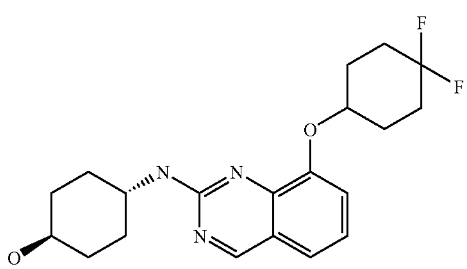 | trans-4-({8-[(4,4-difluorocyclohexyl)oxy]quinazolin-2-yl}amino)cyclohexanol | 378.43 |
| 240 | 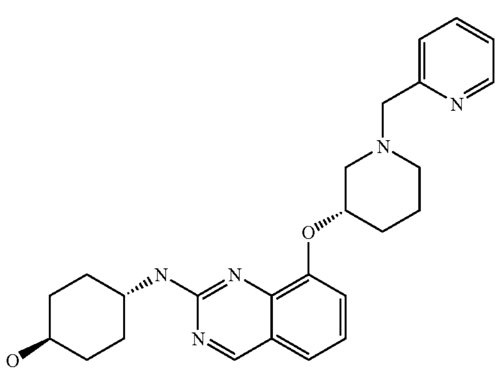 | trans-4-[(8-{[1-(pyridin-2-ylmethyl)piperidin-3-yl]oxy}quinazolin-2-yl)amino]cyclohexanol | 434.55 |

-continued

| ID | Structure | Name | LC/MS m/z |
|---|---|---|---|
| 241 | 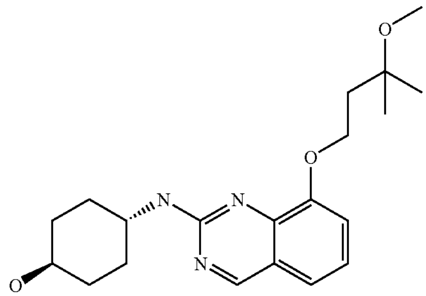 | trans-4-{[8-(3-methoxy-3-methylbutoxy)quinazolin-2-yl]amino}cyclohexanol | 360.47 |
| 242 | 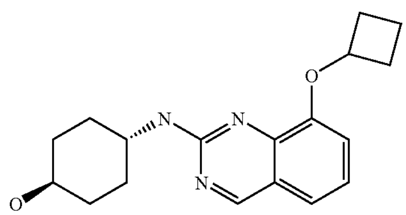 | trans-4-{[8-(cyclobutyloxy)quinazolin-2-yl]amino}cyclohexanol | 314.4 |
| 243 | 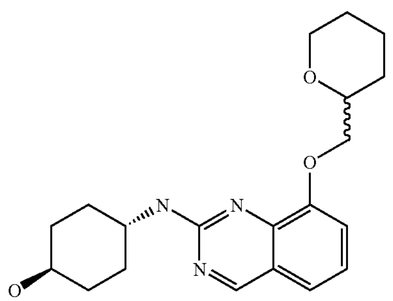 | trans-4-{[8-(tetrahydro-2H-pyran-2-ylmethoxy)quinazolin-2-yl]amino}cyclohexanol | 358.45 |
| 244 | 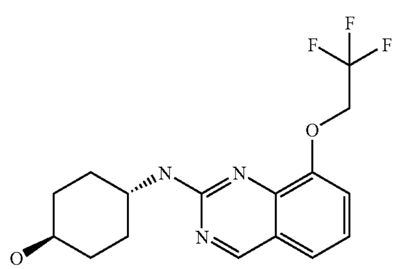 | trans-4-{[8-(2,2,2-trifluoroethoxy)quinazolin-2-yl]amino}cyclohexanol | 342.33 |
| 245 | 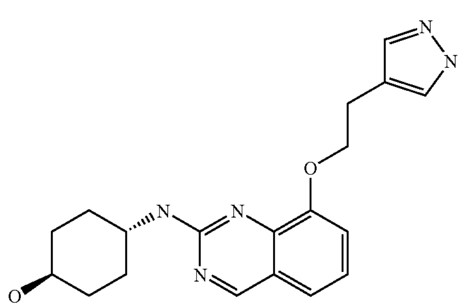 | trans-4-({8-[2-(1H-pyrazol-4-yl)ethoxy]quinazolin-2-yl}amino)cyclohexanol | 354.42 |

-continued

| ID | Structure | Name | LC/MS m/z |
|---|---|---|---|
| 246 | 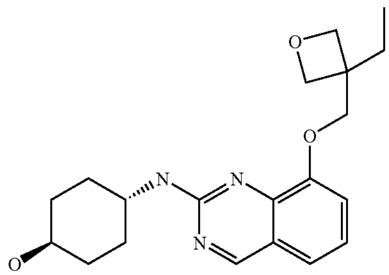 | trans-4-({8-[(3-ethyloxetan-3-yl)methoxy]quinazolin-2-yl}amino)cyclohexanol | 358.45 |
| 247 | 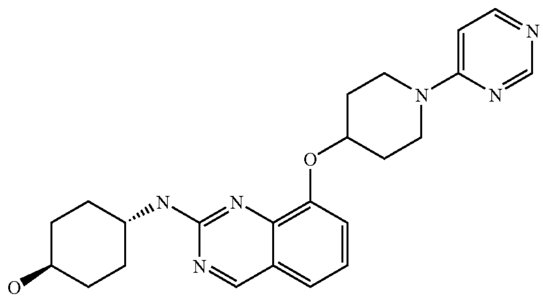 | trans-4-({8-[(1-pyrimidin-4-ylpiperidin-4-yl)oxy]quinazolin-2-yl}amino)cyclohexanol | 421.51 |
| 248 | 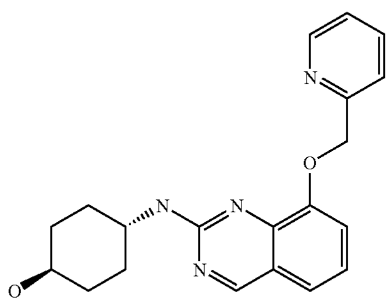 | trans-4-{[8-(pyridin-2-ylmethoxy)quinazolin-2-yl]amino}cyclohexanol | 351.42 |
| 249 | 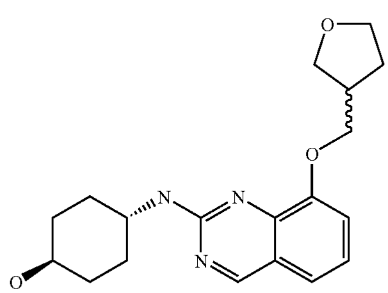 | trans-4-{[8-(tetrahydrofuran-3-ylmethoxy)quinazolin-2-yl]amino}cyclohexanol | 344.42 |
| 250 | 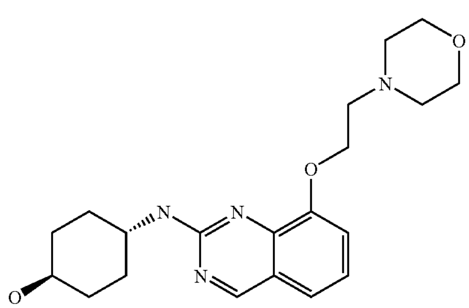 | trans-4-{[8-(2-morpholin-4-ylethoxy)quinazolin-2-yl]amino}cyclohexanol | 373.47 |

-continued

| ID | Structure | Name | LC/MS m/z |
|---|---|---|---|
| 251 | 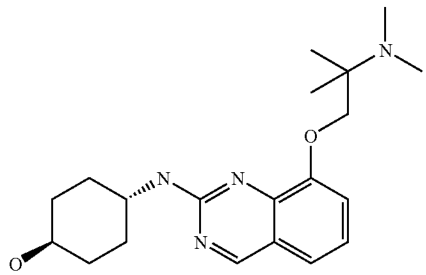 | trans-4-({8-[2-(dimethylamino)-2-methylpropoxy]quinazolin-2-yl}amino)cyclohexanol | 359.48 |
| 252 | 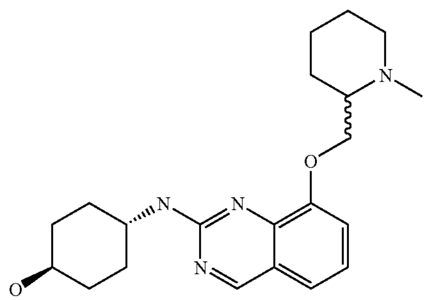 | trans-4-({8-[(1-methylpiperidin-2-yl)methoxy]quinazolin-2-yl}amino)cyclohexanol | 371.49 |
| 253 | 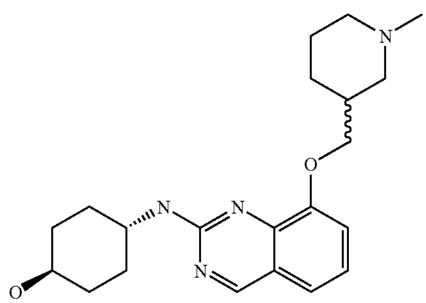 | trans-4-({8-[(1-methylpiperidin-3-yl)methoxy]quinazolin-2-yl}amino)cyclohexanol | 371.49 |
| 254 | 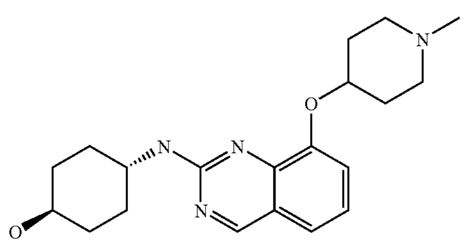 | trans-4-({8-[(1-methylpiperidin-4-yl)oxy]quinazolin-2-yl}amino)cyclohexanol | 357.47 |
| 255 | 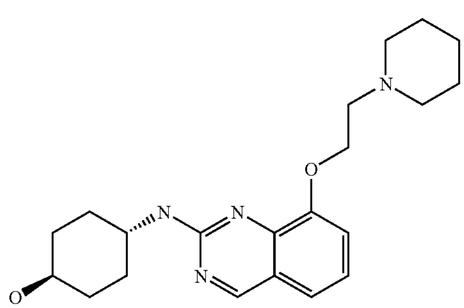 | trans-4-{[8-(2-piperidin-1-ylethoxy)quinazolin-2-yl]amino}cyclohexanol | 371.49 |

-continued

| ID | Structure | Name | LC/MS m/z |
|---|---|---|---|
| 256 | 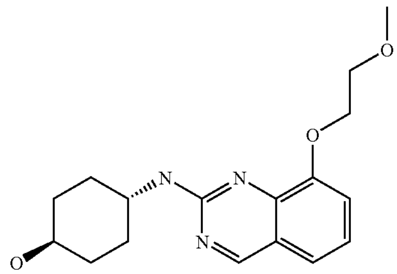 | trans-4-{[8-(2-methoxyethoxy)quinazolin-2-yl]amino}cyclohexanol | 318.39 |
| 257 | ABS | trans-4-[(8-{[(2S)-1-methylpyrrolidin-2-yl]methoxy}quinazolin-2-yl)amino]cyclohexanol | 357.47 |
| 258 | 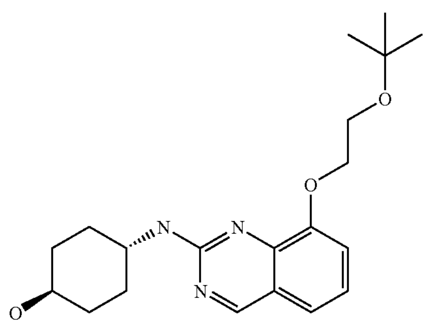 | trans-4-{[8-(2-tert-butoxyethoxy)quinazolin-2-yl]amino}cyclohexanol | 360.47 |
| 259 | 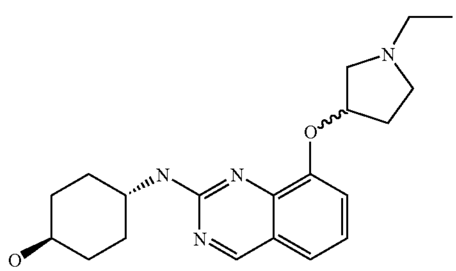 | trans-4-({8-[(1-ethylpyrrolidin-3-yl)oxy]quinazolin-2-yl}amino)cyclohexanol | 357.47 |
| 260 | 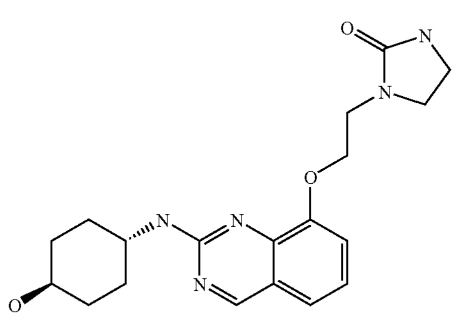 | 1-[2-({2-[(trans-4-hydroxycyclohexyl)amino]quinazolin-8-yl}oxy)ethyl]imidazolidin-2-one | 372.44 |

| ID | Structure | Name | LC/MS m/z |
|---|---|---|---|
| 261 | 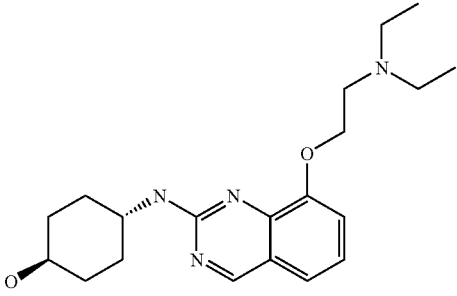 | trans-4-({8-[2-(diethylamino)ethoxy]quinazolin-2-yl}amino)cyclohexanol | 359.48 |
| 262 | 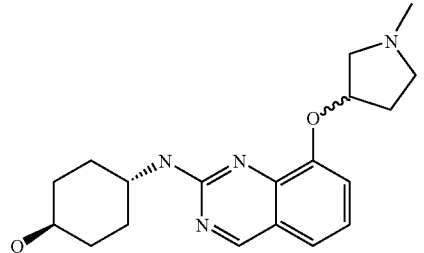 | trans-4-({8-[(1-methylpyrrolidin-3-yl)oxy]quinazolin-2-yl}amino)cyclohexanol | 343.44 |
| 263 | 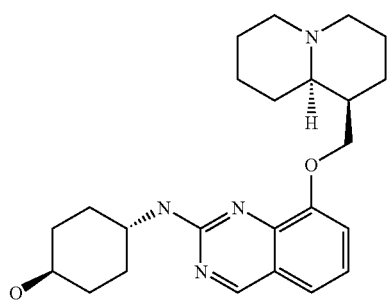 | trans-4-({8-[(1R, 9aR)-octahydro-2H-quinolizin-1-ylmethoxy]quinazolin-2-yl}amino)cyctohexanol | 411.56 |
| 264 | 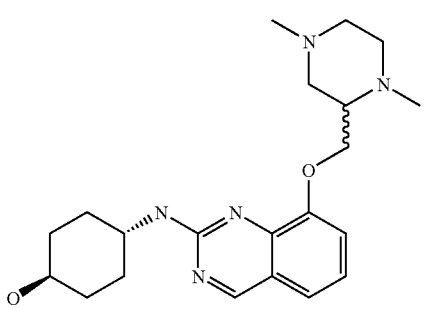 | trans-4-({8-[(1,4-dimethylpiperazin-2-yl)methoxy]quinazolin-2-yl}amino)cyclohexanol | 386.51 |
| 265 | 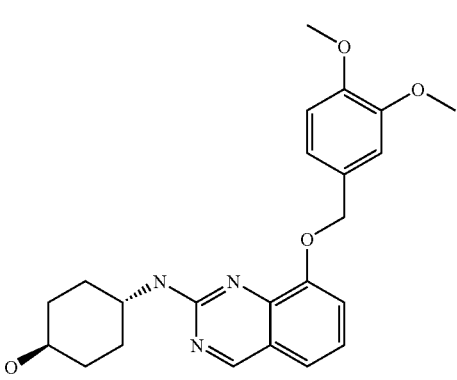 | trans-4-({8-[(3,4-dimethoxybenzyl)oxy]quinazolin-2-yl}amino)cyclohexanol | 410.48 |

-continued

| ID | Structure | Name | LC/MS m/z |
|---|---|---|---|
| 266 | 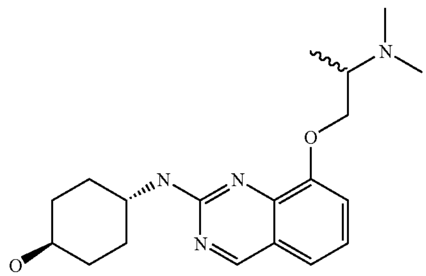 | trans-4-({8-[2-(dimethylamino)propoxy]quinazolin-2-yl}amino)cyclohexanol | 345.46 |
| 267 | 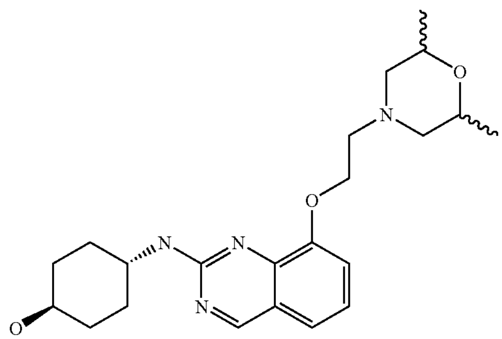 | trans-4-({8-[2-(2,6-dimethylmorpholin-4-yl)ethoxy]quinazolin-2-yl}amino)cyclohexanol | 401.52 |

The following examples nos. 268-298 were prepared with non-critical substitutions and/or method changes in an analogous way to example 144:

| ID | Structure | Name | LC/MS m/z |
|---|---|---|---|
| 268 | 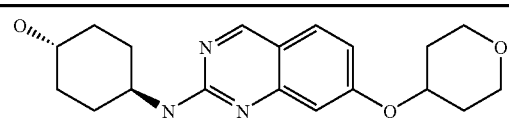 | trans-4-{[7-(tetrahydro-2H-pyran-4-yloxy)quinazolin-2-yl]amino}cyclohexanol | 344.4 |
| 269 | 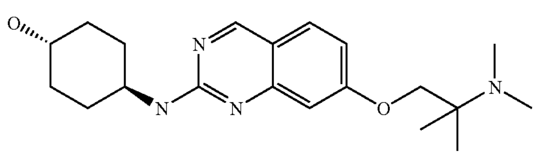 | trans-4-({7-[2-(dimethylamino)-2-methylpropoxy]quinazolin-2-yl}amino)cyclohexanol | 359.5 |
| 270 | 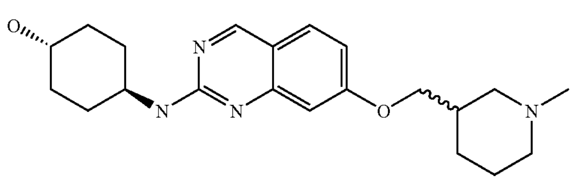 | trans-4-({7-[(1-methylpiperidin-3-yl)methoxy]quinazolin-2-yl}amino)cyclohexanol | 371.5 |
| 271 | 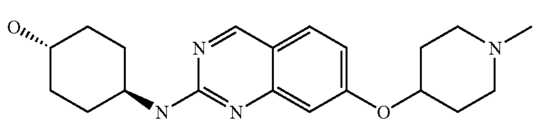 | trans-4-({7-[(1-methylpiperidin-4-yl)oxy]quinazolin-2-yl}amino)cyclohexanol | 357.5 |
| 272 | 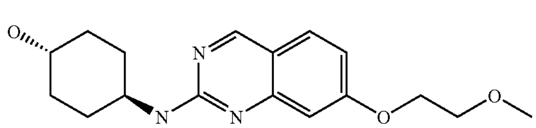 | trans-4-{[7-(2-methoxyethoxy)quinazolin-2-yl]amino}cyclohexanol | 318.4 |

-continued

| ID | Structure | Name | LC/MS m/z |
|---|---|---|---|
| 273 | 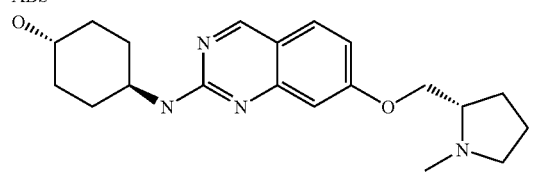 | trans-4-[(7-{[(2S)-1-methylpyrrolidin-2-yl]methoxy}quinazolin-2-yl)amino]cyclohexanol | 357.5 |
| 274 | 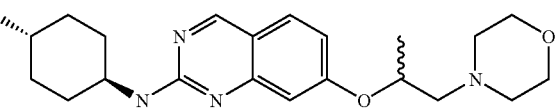 | trans-4-{[7-(1-methyl-2-morpholin-4-ylethoxy)quinazolin-2-yl]amino}cyclohexanol | 387.5 |
| 275 | 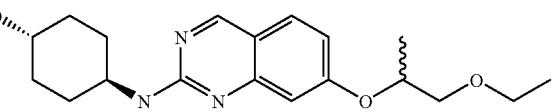 | trans-4-{[7-(2-ethoxy-1-methylethoxy)quinazolin-2-yl]amino}cyclohexanol | 346.4 |
| 276 | 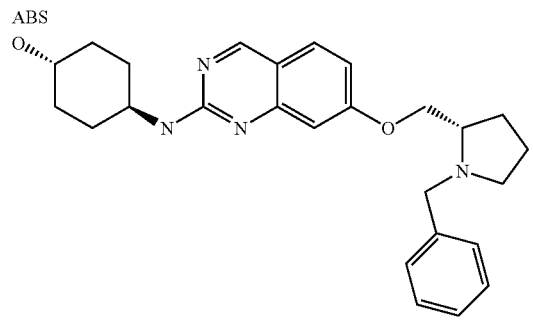 | trans-4-[(7-{[(2S)-1-benzylpyrrolidin-2-yl]methoxy}quinazolin-2-yl)amino]cyclohexanol | 433.6 |
| 277 | 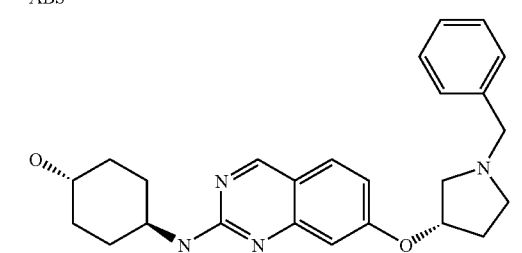 | trans-4-[(7-{[(3S)-1-benzylpyrrolidin-3-yl]oxy}quinazolin-2-yl)amino]cyclohexanol | 419.5 |
| 278 | 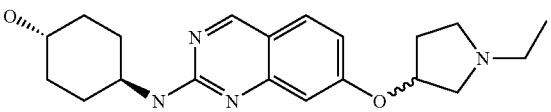 | trans-4-({7-[(1-ethylpyrrolidin-3-yl)oxy]quinazolin-2-yl}amino)cyclohexanol | 357.5 |
| 279 | 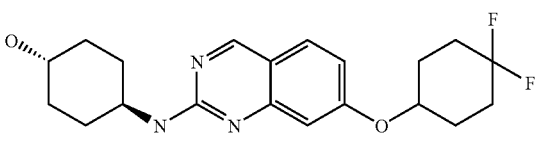 | trans-4-({7-[(4,4-difluorocyclohexyl)oxy]quinazolin-2-yl}amino)cyclohexanol | 378.4 |
| 280 | 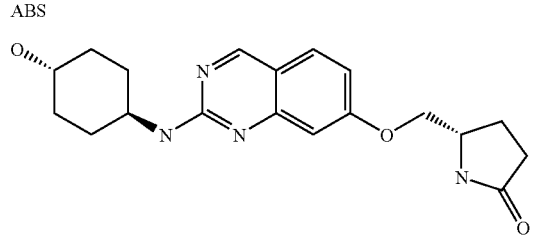 | (5S)-5-[({2-[(trans-4-hydroxycyclohexyl)amino]quinazolin-7-yl}oxy)methyl]pyrrolidin-2-one | 357.4 |

| ID | Structure | Name | LC/MS m/z |
|---|---|---|---|
| 281 | 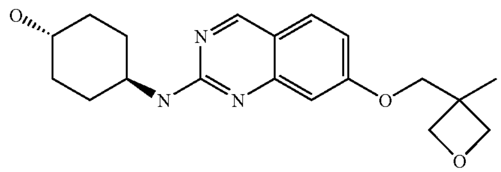 | trans-4-({7-[(3-methyloxetan-3-yl)methoxy]quinazolin-2-yl}amino)cyclohexanol | 344.4 |
| 282 | 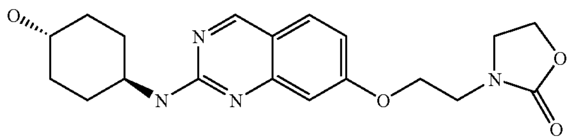 | 3-[2-({2-[(trans-4-hydroxycyclohexyl)amino]quinazolin-7-yl}oxy)ethyl]-1,3-oxazolidin-2-one | 373.4 |
| 283 | ABS | trans-4-({7-[(1R,9aR)-octahydro-2H-quinolizin-1-ylmethoxy]quinazolin-2-yl}amino)cyclohexanol | 411.6 |
| 284 | ABS | (5R)-5-[({2-[(trans-4-hydroxycyclohexyl)amino]quinazolin-7-yl}oxy)methyl]pyrrolidin-2-one | 357.4 |
| 285 | ABS | trans-4-[(7-{[(3R)-1-benzylpyrrolidin-3-yl]oxy}quinazolin-2-yl)amino]cyclohexanol | 419.5 |
| 286 | 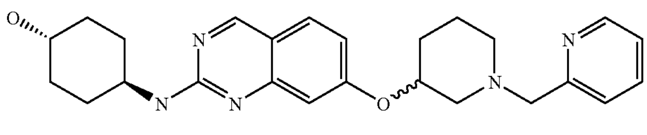 | trans-4-[(7-{[1-(pyridin-2-ylmethyl)piperidin-3-yl]oxy}quinazolin-2-yl)amino]cyclohexanol | 434.6 |
| 287 | 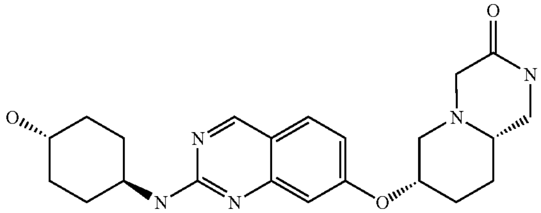 | (7S,9aS)-7-({2-[(trans-4-hydroxycyclohexyl)amino]quinazolin-7-yl}oxy)hexahydro-2H-pyrido[1,2-a]pyrazin-3(4H)-one | 412.5 |

| ID | Structure | Name | LC/MS m/z |
|---|---|---|---|
| 288 | 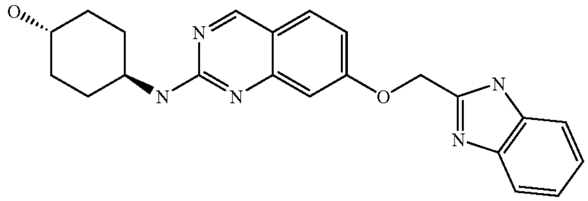 | trans-4-{[7-(1H-benzimidazol-2-ylmethoxy)quinazolin-2-yl]amino}cyclohexanol | 390.5 |
| 289 | 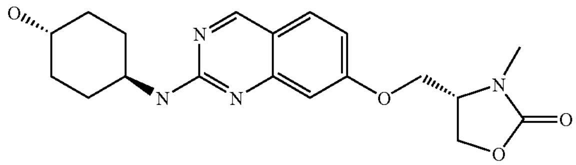 | 4-[({2-[(trans-4-hydroxycyclohexyl)amino]quinazolin-7-yl}oxy)methyl]-3-methyl-1,3-oxazolidin-2-one | 373.4 |
| 290 | 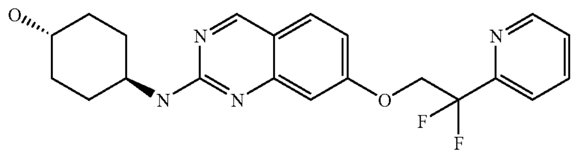 | trans-4-{[7-(2,2-difluoro-2-pyridin-2-ylethoxy)quinazolin-2-yl]amino}cyclohexanol | 401.4 |
| 291 | ABS | trans-4-[(7-{[(1S,2S)-2-methoxycyclohexyl]oxy}quinazolin-2-yl)amino]cyclohexanol | 372.5 |
| 292 | ABS | (1S)-1-[2-({2-[(trans-4-hydroxycyclohexyl)amino]quinazolin-7-yl}oxy)ethyl]-N-methyl-3,4-dihydro-1H-isochromene-6-carboxamide | 477.6 |
| 293 | 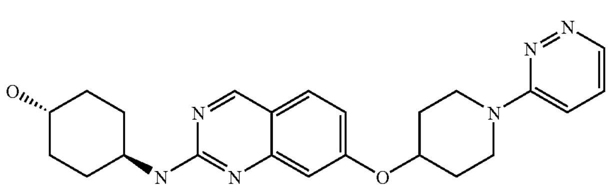 | trans-4-({7-[(1-pyridazin-3-ylpiperidin-4-yl)oxy]quinazolin-2-yl}amino)cyclohexanol | 421.5 |

| ID | Structure | Name | LC/MS m/z |
|---|---|---|---|
| 294 | ABS | trans-4-[(7-{[(2R)-1-benzylpyrrolidin-2-yl]methoxy}quinazolin-2-yl)amino]cyclohexanol | 433.6 |
| 295 | 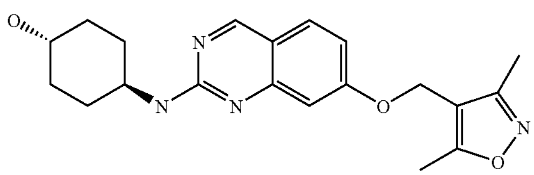 | trans-4-({7-[(3,5-dimethylisoxazol-4-yl)methoxy]quinazolin-2-yl}amino)cyclohexanol | 369.4 |
| 296 | ABS | trans-4-[(7-{[(1R,2S)-2-(dimethylamino)-1-phenylpropyl]oxy}quinazolin-2-yl)amino]cyclohexanol | 421.6 |
| 297 | 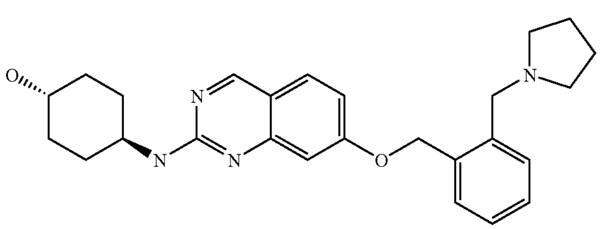 | trans-4-[(7-{[2-(pyrrolidin-1-ylmethyl)benzyl]oxy}quinazolin-2-yl)amino]cyclohexanol | 433.6 |
| 298 | 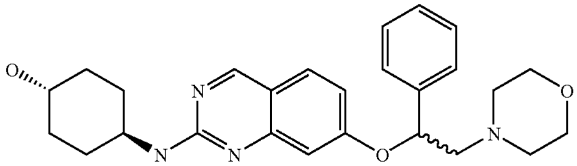 | trans-4-{[7-(2-morpholin-4-yl-1-phenylethoxy)quinazolin-2-yl]amino}cyclohexanol | 449.6 |

The following examples nos. 299-531 were prepared with non-critical substitutions and/or method changes in an analogous way to example 77:

| ID | Structure | Name | LCMS m/z |
|---|---|---|---|
| 299 | 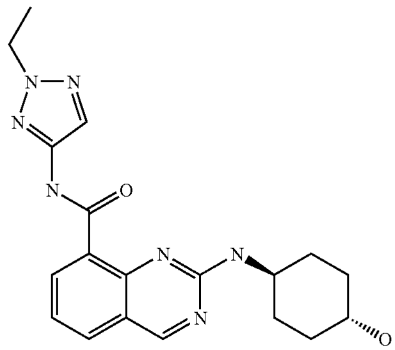 | N-(2-ethyl-2H-1,2,3-triazol-4-yl)-2-[(trans-4-hydroxycyclohexyl)amino]quinazoline-8-carboxamide | 382.4 |
| 300 | 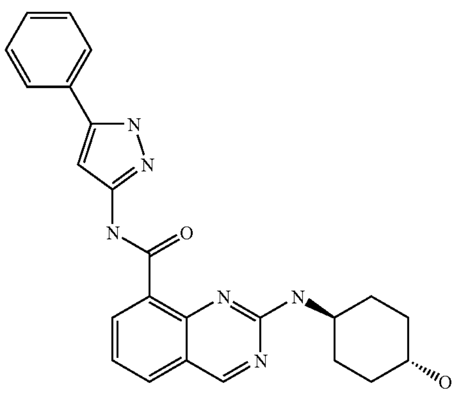 | 2-[(trans-4-hydroxycyclohexyl)amino]-N-(5-phenyl-1H-pyrazol-3-yl)quinazoline-8-carboxamide | 429.5 |
| 301 | 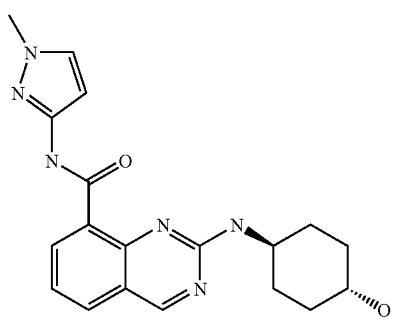 | 2-[(trans-4-hydroxycyclohexyl)amino]-N-(1-methyl-1H-pyrazol-3-yl)quinazoline-8-carboxamide | 367.4 |
| 302 | 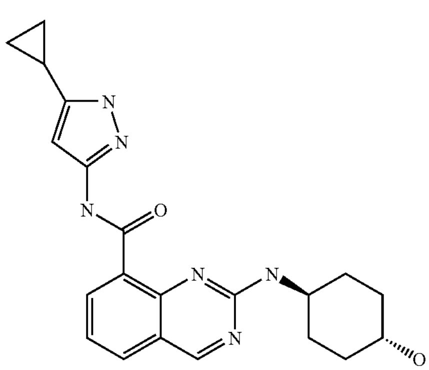 | N-(5-cyclopropyl-1H-pyrazol-3-yl)-2-[(trans-4-hydroxycyclohexyl)amino]quinazoline-8-carboxamide | 393.5 |

-continued

| ID | Structure | Name | LCMS m/z |
|---|---|---|---|
| 303 | 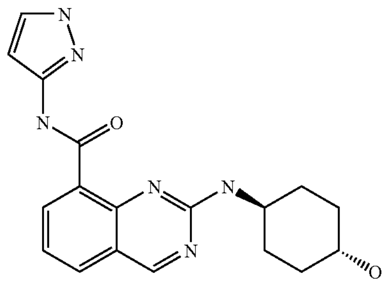 | 2-[(trans-4-hydroxycyclohexyl)amino]-N-1H-pyrazol-3-ylquinazoline-8-carboxamide | 353.4 |
| 304 | 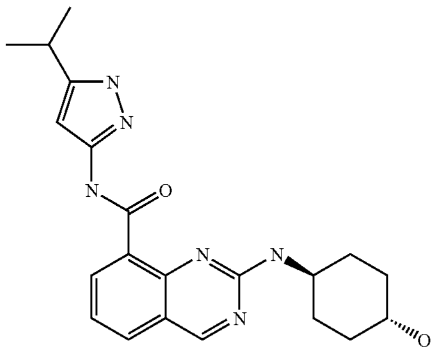 | 2-[(trans-4-hydroxycyclohexyl)amino]-N-1H-isopropyl-1H-pyrazol-3-yl)quinazoline-8-carboxamide | 395.5 |
| 305 | 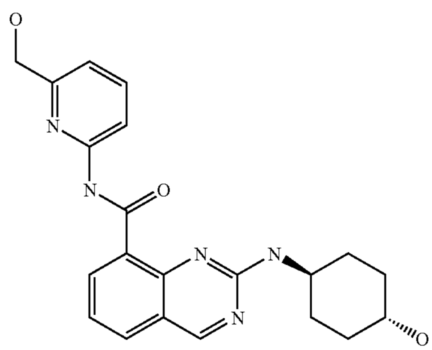 | 2-[(trans-4-hydroxycyclohexyl)amino]-N-[6-(hydroxymethyl)pyridin-2-yl]quinazoline-8-carboxamide | 394.5 |
| 306 | 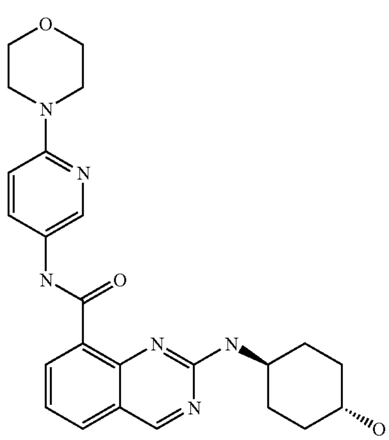 | 2-[(trans-4-hydroxycyclohexyl)amino]-N-(6-morpholin-4-ylpyridin-3-yl)quinazoline-8-carboxamide | 449.5 |

-continued

| ID | Structure | Name | LCMS m/z |
|---|---|---|---|
| 307 | 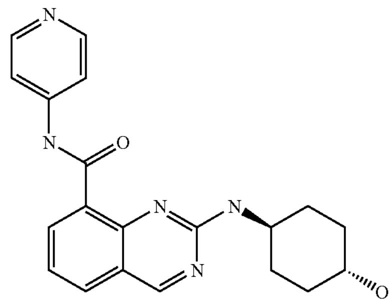 | 2-[(trans-4-hydroxycyclohexyl)amino]-N-pyridin-4-ylquinazoline-8-carboxamide | 364.4 |
| 308 | 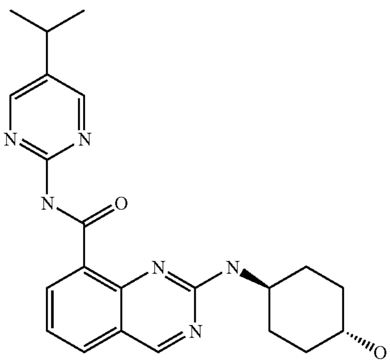 | 2-[(trans-4-hydroxycyclohexyl)amino]-N-(5-isopropylpyrimidin-2-yl)quinazoline-8-carboxamide | 407.5 |
| 309 | 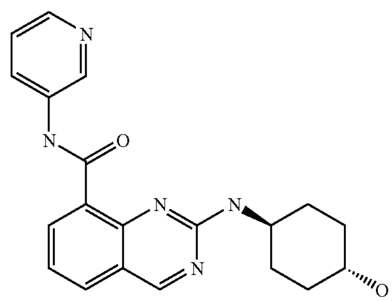 | 2-[(trans-4-hydroxycyclohexyl)amino]-N-pyridin-3-ylquinazoline-8-carboxamide | 364.4 |
| 310 | 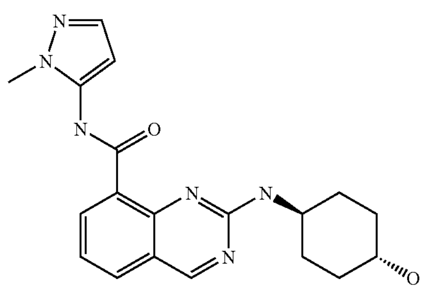 | 2-[(trans-4-hydroxycyclohexyl)amino]-N-(1-methyl-1H-pyrazol-5-yl)quinazoline-8-carboxamide | 367.4 |
| 311 | 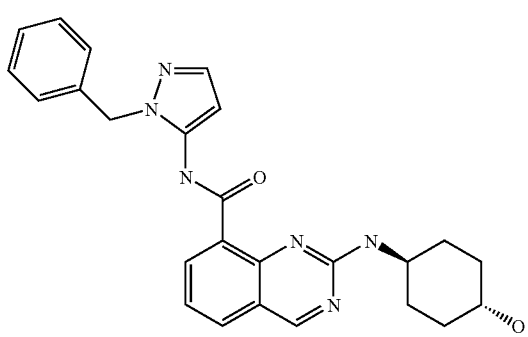 | N-(1-benzyl-1H-pyrazol-5-yl)-2-[(trans-4-hydroxycyclohexyl)amino]quinazoline-8-carboxamide | 443.5 |

-continued

| ID | Structure | Name | LCMS m/z |
|---|---|---|---|
| 312 | 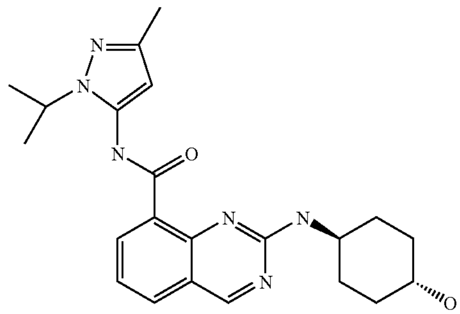 | 2-[(trans-4-hydroxycyclohexyl)amino]-N-(1-isopropyl-3-methyl-1H-pyrazol-5-yl)quinazoline-8-carboxamide | 409.5 |
| 313 | 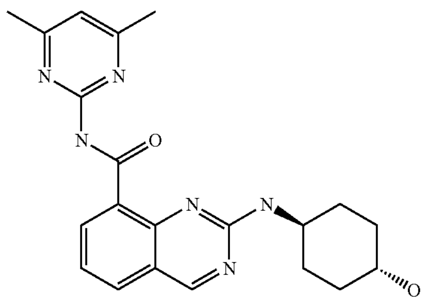 | N-(4,6-dimethylpyrimidin-2-yl)-2-[(trans-4-hydroxycyclohexyl)amino]quinazoline-8-carboxamide | 393.5 |
| 314 | 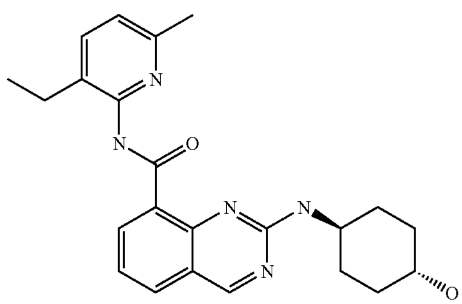 | N-(3-ethyl-6-methylpyridin-2-yl)-2-[(trans-4-hydroxycyclohexyl)amino]quinazoline-8-carboxamide | 406.5 |
| 315 | 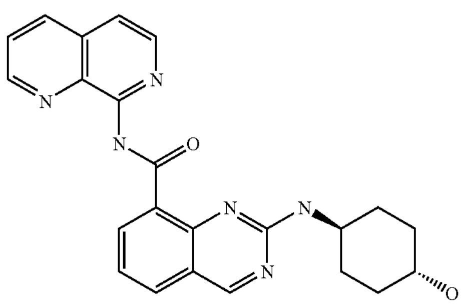 | 2-[(trans-4-hydroxycyclohexyl)amino]-N-1,7-naphthyridin-8-ylquinazoline-8-carboxamide | 415.5 |
| 316 | 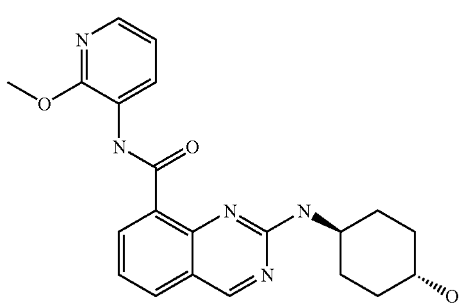 | 2-[(trans-4-hydroxycyclohexyl)amino]-N-(2-methoxypyridin-3-yl)quinazoline-8-carboxamide | 394.5 |

-continued

| ID | Structure | Name | LCMS m/z |
|---|---|---|---|
| 317 | 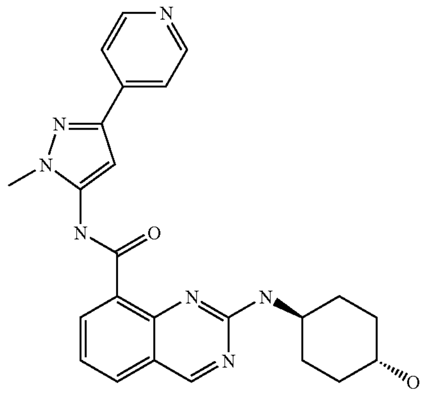 | 2-[(trans-4-hydroxycyclohexyl)amino]-N-(1-methyl-3-pyridin-4-yl-1H-pyrazol-5-yl)quinazoline-8-carboxamide | 444.5 |
| 318 | 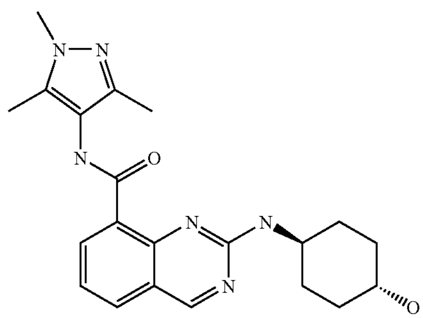 | 2-[(trans-4-hydroxycyclohexyl)amino]-N-(1,3,5-trimethyl-1H-pyrazol-4-yl)quinazoline-8-carboxamide | 395.5 |
| 319 | 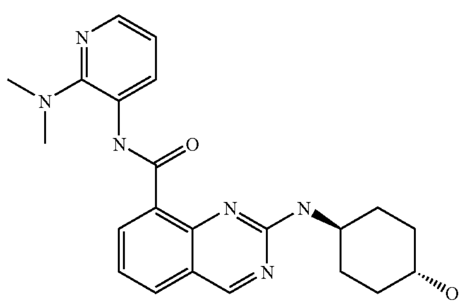 | N-[2-(dimethylamino)pyridin-3-yl]-2-[(trans-4-hydroxycyclohexyl)amino]quinazoline-8-carboxamide | 407.5 |
| 320 | 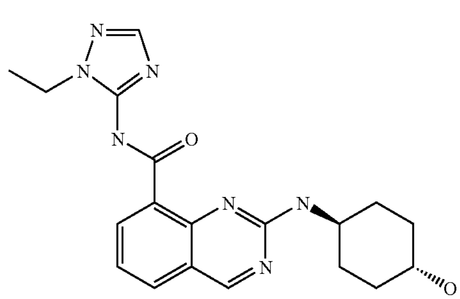 | N-(1-ethyl-1H-1,2,4-triazol-5-yl)-2-[(trans-4-hydroxycyclohexyl)amino]quinazoline-8-carboxamide | 382.4 |

| ID | Structure | Name | LCMS m/z |
|---|---|---|---|
| 321 | 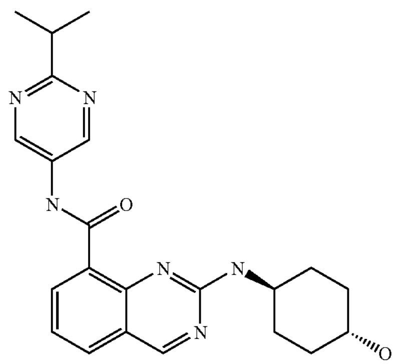 | 2-[(trans-4-hydroxycyclohexyl)amino]-N-(2-isopropylpyrimidin-5-yl)quinazoline-8-carboxamide | 407.5 |
| 322 | 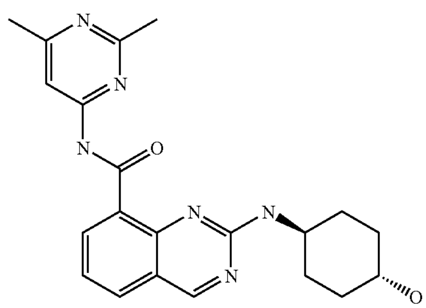 | N-(2,6-dimethylpyrimidin-4-yl)-2-[(trans-4-hydroxycyclohexyl)amino]quinazoline-8-carboxamide | 393.5 |
| 323 | 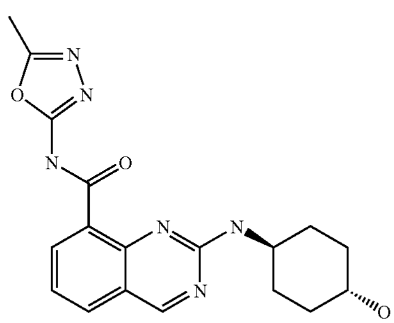 | 2-[(trans-4-hydroxycyclohexyl)amino]-N-(5-methyl-1,3,4-oxadiazol-2-yl)quinazoline-8-carboxamide | 369.4 |
| 324 | 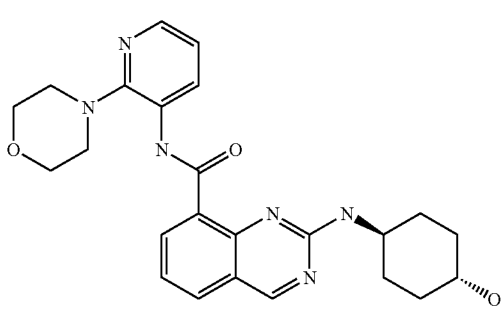 | 2-[(trans-4-hydroxycyclohexyl)amino]-N-(2-morpholin-4-ylpyridin-3-yl)quinazoline-8-carboxamide | 449.5 |

-continued

| ID | Structure | Name | LCMS m/z |
|---|---|---|---|
| 325 | 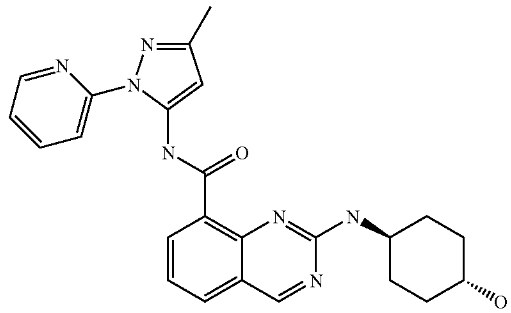 | 2-[(trans-4-hydroxycyclohexyl)amino]-N-(3-methyl-1-pyridin-2-yl-1H-pyrazol-5-yl)quinazoline-8-carboxamide | 444.5 |
| 326 | 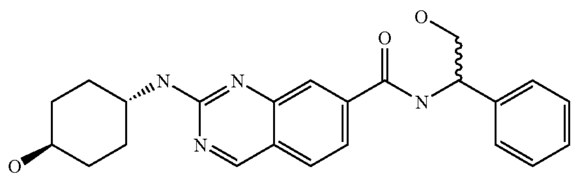 | 2-{(trans-4-hydroxycyclohexyl)amino]-N-(2-hydroxy-1-phenylethyl)quinazoline-7-carboxamide | 407.5 |
| 327 | 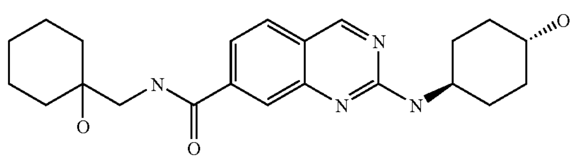 | 2-[(trans-4-hydroxycyclohexyl)amino]-N-[(1-hydroxycyclohexyl)methyl]quinazoline-7-carboxamide | 399.5 |
| 328 | 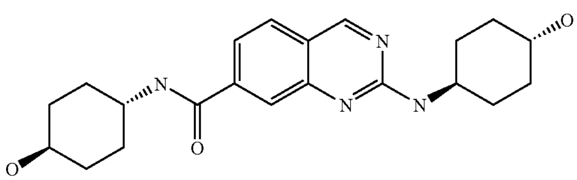 | N-(trans-4-hydroxycyclohexyl)2[(trans-4-hydroxycyclohexyl)amino]quinazoline-7-carboxamide | 385.5 |
| 329 | 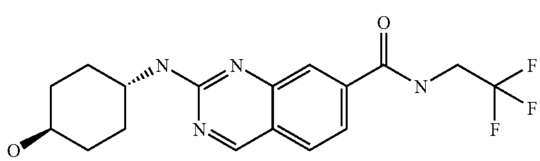 | 2-[(trans-4-hydroxycyclohexyl)amino]-N-(2,2,2-trifluoroethyl)quinazoline-8-carboxamide | 369.4 |
| 330 | 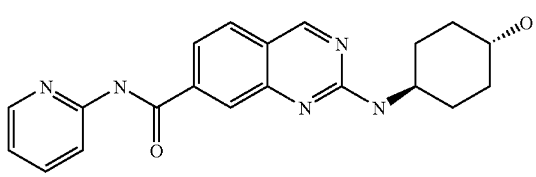 | 2-[(trans-4-hydroxycyclohexyl)amino]-N-pyridin-2-ylquinazoline-7-carboxamide | 364.4 |
| 331 | 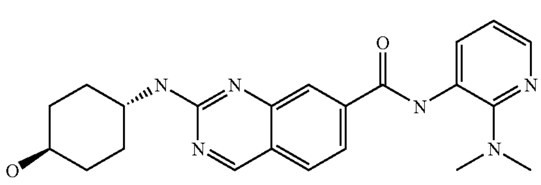 | N-[2-(dimethylamino)pyridin-3-yl]-2-[(trans-4-hydroxycyclohexyl)amino]quinazoline-7-carboxamide | 407.5 |
| 332 | 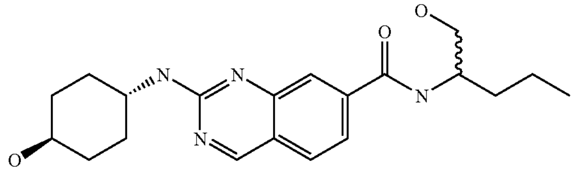 | 2-[(trans-4-hydroxycyclohexyl)amino]-N-[1-(hydroxymethyl)butyl]quinazoline-7-carboxamide | 373.5 |

-continued

| ID | Structure | Name | LCMS m/z |
|---|---|---|---|
| 333 | 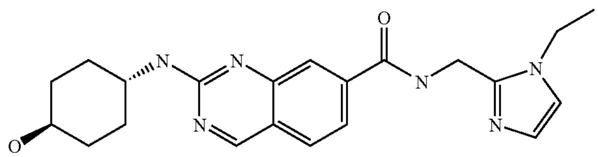 | N-[(1-ethyl-1H-imidazol-2-yl)methyl]-2-([trans-4-hydroxycyclohexyl)amino]quinazoline-7-carboxamide | 395.5 |
| 334 | ABS | 2-[(trans-4-hydroxycyclohexyl)amino]-N-[(1S)-1-(hydroxymethyl)propyl]quinazoline-7-carboxamide | 359.4 |
| 335 | 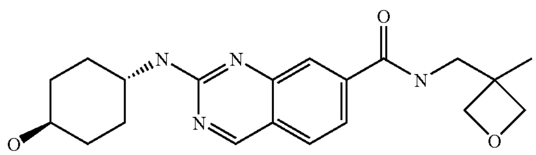 | 2-[(trans-4-hydroxycyclohexyl)amino]-N-[(3-methyloxetan-3-yl)methyl]quinazoline-7-carboxamide | 371.5 |
| 336 | 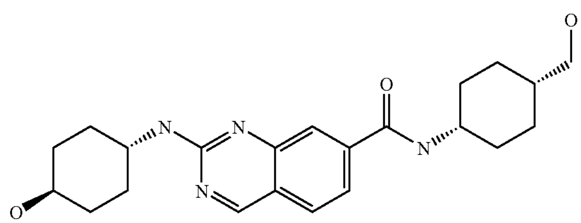 | 2-[(trans-4-hydroxycyclohexyl)amino]-N-[cis-4-(hydroxymethyl)cyclohexyl]quinazoline-7-carboxamide | 399.5 |
| 337 | ABS | 2-[(trans-4-hydroxycyclohexyl)amino]-N-[(1R)-2-hydroxy-1-phenylethyl]quinazoline-7-carboxamide | 407.5 |
| 338 | 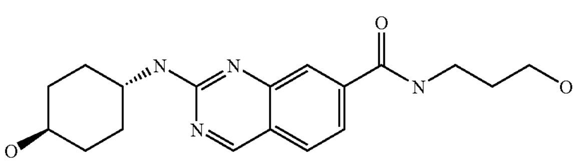 | 2-[(trans-4-hydroxycyclohexyl)amino]-N-(3-hydroxypropyl)quinazoline-7-carboxamide | 345.4 |
| 339 | 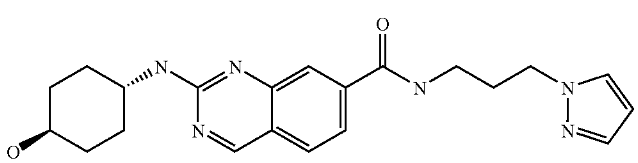 | 2-[(trans-4-hydroxycyclohexyl)amino]-N-[3-(1H-pyrazol-1-yl)propyl]quinazolin-7-carboxamide | 395.5 |
| 340 | 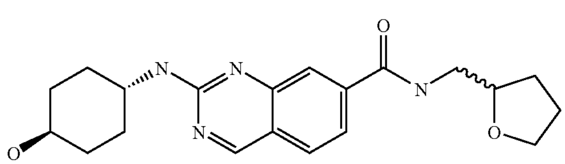 | 2-[(trans-4-hydroxycyclohexyl)amino]-N-(tetrahydrofuran-2-ylmethyl)quinazoline-7-carboxamide | 371.5 |

-continued

| ID | Structure | Name | LCMS m/z |
|---|---|---|---|
| 341 | 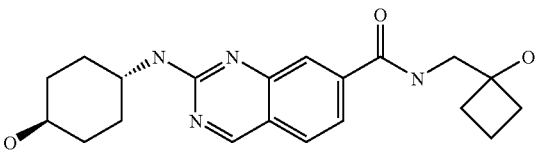 | N-[(1-hydroxycyclobutyl)methyl]-2-[(trans-4-hydroxycyclohexyl)amino]quinazoline-7-carboxamide | 371.5 |
| 342 | 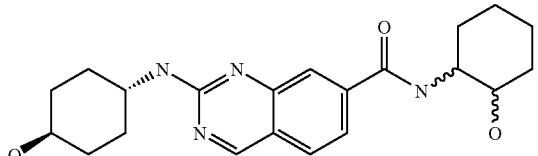 | N-(2-hydroxycyclohexyl)-2-[(trans-4-hydroxycyclohexyl)amino]quinazoline-7-carboxamide | 385.5 |
| 343 | 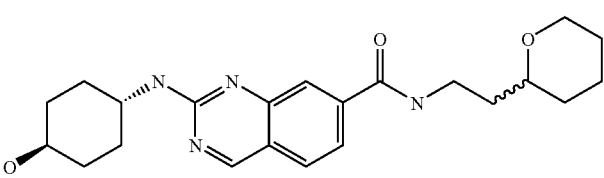 | 2-[(trans-4-hydroxycyclohexyl)amino]-N-[2-(tetrahydro-2H-pyran-2-yl)ethyl]quinazoline-7-carboxamide | 399.5 |
| 344 | 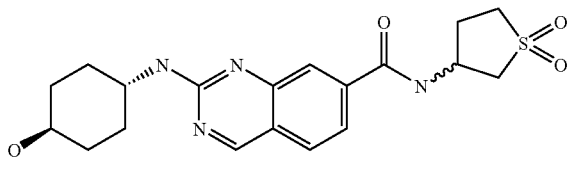 | N-(1,1-dioxidotetrahydro-3-thienyl)-2-[(trans-4-hydroxycyclohexyl)amino]quinazoline-7-carboxamide | 405.5 |
| 345 | 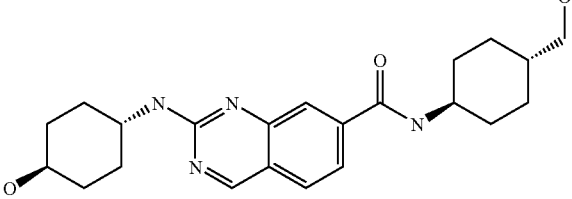 | 2-[(trans-4-hydroxycyclohexyl)amino]-N-[trans-4-(hydroxymethyl)cyclohexyl]quinazoline-7-carboxamide | 399.5 |
| 346 | 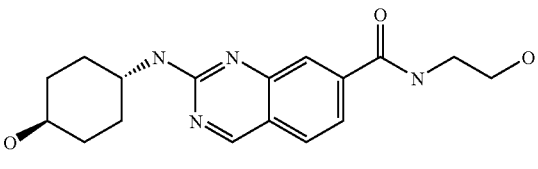 | 2-[(trans-4-hydroxycyclohexyl)amino]-N-(2-hydroxyethyl)quinazoline-7-carboxamide | 331.4 |
| 347 | 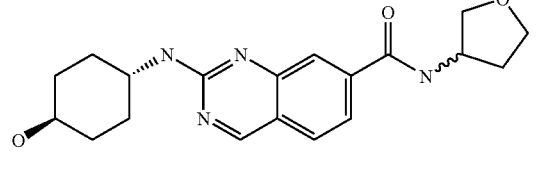 | 2-[(trans-4-hydroxycyclohexyl)amino]-N-(tetrahydrofuran-3-yl)quinazoline-7-carboxamide | 357.4 |
| 348 | 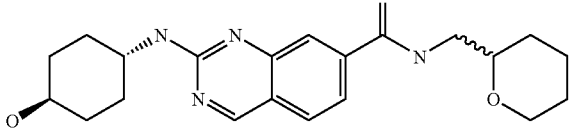 | 2-[(trans-4-hydroxycyclohexyl)amino]-N-(tetrahydro-2H-pyran-2-ylmethyl)quinazoline-7-carboxamide | 385.5 |

-continued

| ID | Structure | Name | LCMS m/z |
|---|---|---|---|
| 349 | 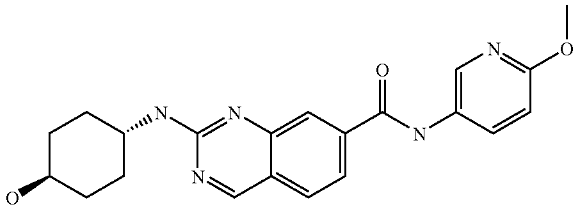 | 2-[(trans-4-hydroxycyclohexyl)amino]-N-(6-methoxypyridin-3-yl)quinazoline-7-carboxamide | 394.5 |
| 350 | ABS | 2-[(trans-4-hydroxycyclohexyl)amino]-N-{[(1S,2S)-2-(hydroxymethyl)cyclopropyl]methyl}quinazoline-7-carboxamide | 371.5 |
| 351 | 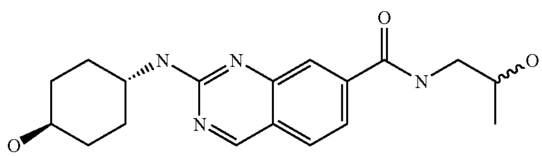 | 2-[(trans-4-hydroxycyclohexyl)amino]-N-(2-hydroxypropyl)quinazoline-7-carboxamide | 345.4 |
| 352 | 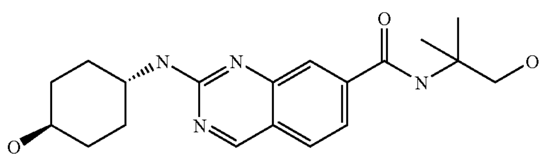 | 2-[(trans-4-hydroxycyclohexyl)amino]-N-(2-hydroxy-1,1-dimethylethyl)quinazoline-7-carboxamide | 359.4 |
| 353 | 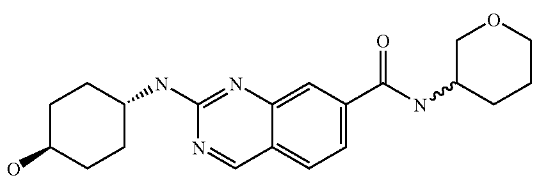 | 2-[(trans-4-hydroxycyclohexyl)amino]-N-(tetrahydro-2H-pyran-3-yl)quinazoline-7-carboxamide | 371.5 |
| 354 | 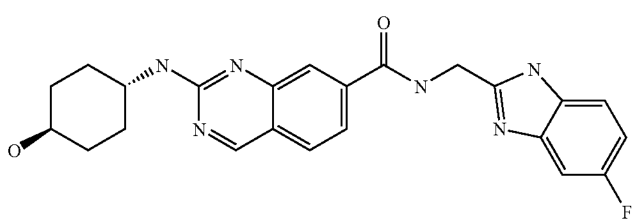 | N-[(5-fluoro-1H-benzimidazol-2-yl)methyl]-2-[(trans-4-hydroxycyclohexyl)amino]quinazoline-7-carboxamide | 435.5 |
| 355 | 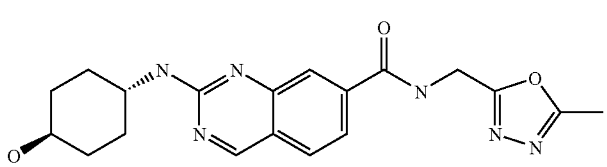 | 2-[(trans-4-hydroxycyclohexyl)amino]-N-[(5-methyl-1,3,4-oxadiazol-2-yl)methyl]quinazoline-7-carboxamide | 383.4 |
| 356 | 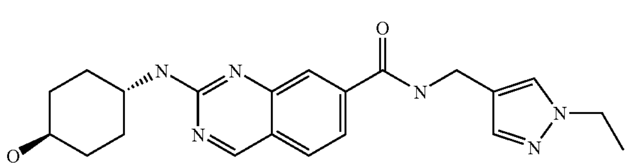 | N-[(1-ethyl-1H-pyrazol-4-yl)methyl]-2-[(trans-4-hydroxycyclohexyl)amino]quinazoline-7-carboxamide | 395.5 |

-continued

| ID | Structure | Name | LCMS m/z |
|---|---|---|---|
| 357 | 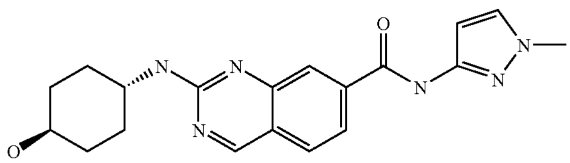 | 2-[(trans-4-hydroxycyclohexyl)amino]-N-(1-methyl-1H-pyrazol-3-yl)quinazoline-8-carboxamide | 367.4 |
| 358 | 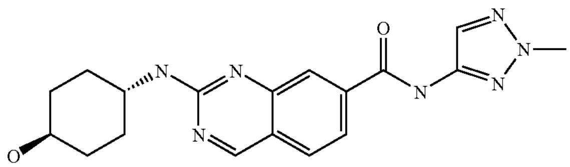 | 2-[(trans-4-hydroxycyclohexyl)amino]-N-(2-methyl-2H-1,2,3-triazol-4-yl)quinazoline-7-carboxamide | 368.4 |
| 359 | 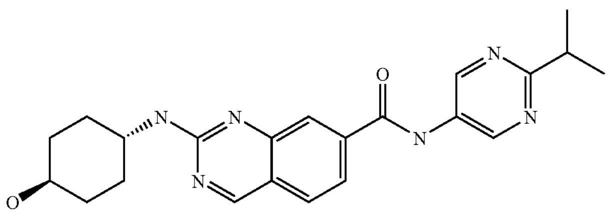 | 2-[(trans-4-hydroxycyclohexyl)amino]-N-(2-isopropylpyrimidin-5-yl)quinazoline-7-carboxamide | 407.5 |
| 360 | 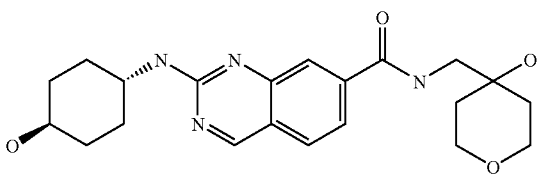 | 2-[(trans-4-hydroxycyclohexyl)amino]-N-[(4-hydroxytetrahydro-2H-pyran-4-yl)methyl]quinazoline-7-carboxamide | 401.5 |
| 361 | 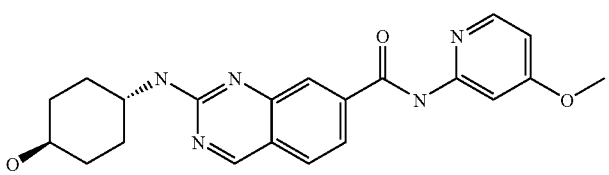 | 2-[(trans-4-hydroxycyclohexyl)amino]-N-(4-methoxypyridin-2-yl)quinazoline-7-carboxamide | 394.5 |
| 362 | 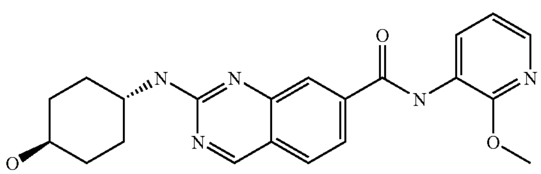 | 2-[(trans-4-hydroxycyclohexyl)amino]-N-(2-methoxypyridin-3-yl)quinoline carboxamide | 394.5 |
| 363 | ABS | 2-[(trans-4-hydroxycyclohexyl)amino]-N-[(1R)-2-hyrdroxy-1-methylethyl]quinoline-7-carboxamide | 345.4 |
| 364 | 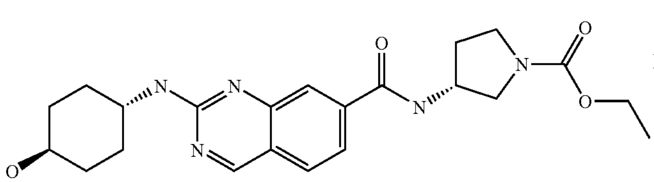 | ethyl 3-[({2-[(trans-4-hydroxycyclohexyl)amino]quinazolin-7-yl}carbonyl)amino]pyrrolidine-1-carboxylate | 428.5 |

-continued

| ID | Structure | Name | LCMS m/z |
|---|---|---|---|
| 365 | 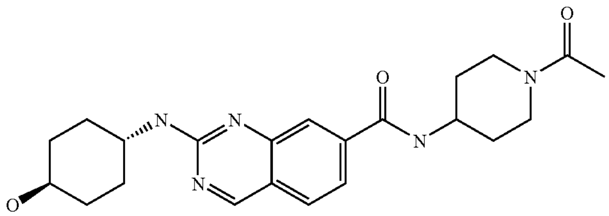 | N-(1-acetylpiperidin-4-yl)-2-[(trans-4-hydroxycyclohexyl)amino]quinazoline-7-carboxamide | 412.5 |
| 366 | 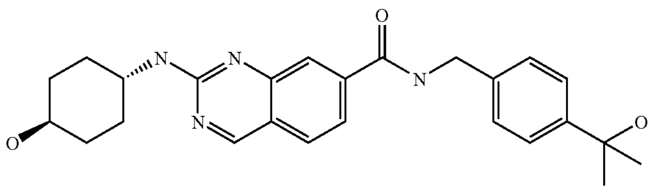 | 2-[(trans-4-hydroxycyclohexyl)amino]-N-[4-(1-hydroxy-1-methylethyl)benzyl]quinazoline-7-carboxamide | 435.5 |
| 367 | 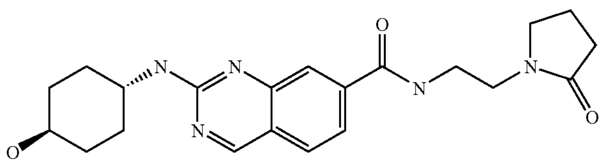 | 2-[(trans-4-hydroxycyclohexyl)amino]-N-[2-(2-oxopyrrolidin-1-yl)ethyl]quinazoline-7-carboxamide | 398.5 |
| 368 | 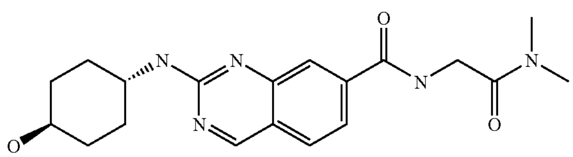 | N-[2-(dimethylamino)-2-oxoethyl]-2-[(trans-4-hydroxycyclohexyl)amino]quinazoline-7-carboxamide | 372.4 |
| 369 | 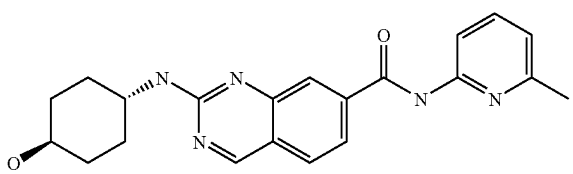 | 2-[(trans-4-hydroxycyclohexyl)amino]-N-(6-methylpyridin-2-yl)quinazoline-7-carboxamide | 378.5 |
| 370 | 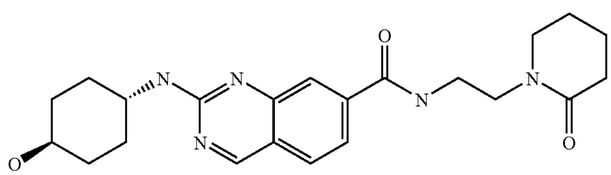 | 2-[(trans-4-hydroxycyclohexyl)amino]-N-(2-(2-oxopiperidin-1-yl)ethyl]quinazoline-7-carboxamide | 412.5 |
| 371 | ABS | N-[(3R)-1-acetylpyrrolidin-3-yl]-2-[(trans-4-hydroxycyclohexyl)amino]quinazoline-7-carboxamide | 398.5 |
| 372 | ABS | 2-[(trans-4-hydroxycyclohexyl)amino]-N-[(1S)-2-hydroxy-1-phenylethyl]quinazoline-7-carboxamide | 407.5 |

| ID | Structure | Name | LCMS m/z |
|---|---|---|---|
| 373 | ABS | 2-(cyclohexylamino)-N-[(1S)-2-hydroxy-1-phenylethyl]quinazoline-7-carboxamide | 391.5 |
| 374 | ABS | 2-(cyclohexylamino)-N-[(1S)-1-(hydroxymethyl)-3-methylbutyl]quinazoline-7-carboxamide | 371.5 |
| 375 | ABS | 2-[(trans-4-hydroxycyclohexyl)amino]-N-[(1S)-1-(hydroxymethyl)-3-methylbutyl]quinazoiine-7-carboxamide | 387.5 |
| 376 | ABS | 2-(cyclohexylamino)-N-[(1S)-1-(hydroxymethyl)butyl]quinazoline-7-carboxamide | 357.5 |
| 377 | ABS | 2-[(trans-4-hydroxycyclohexyl)amino]-N-[(1S)-1-(hydroxymethyl)butyl]quinazoline-7-carboxamide | 373.5 |
| 378 | 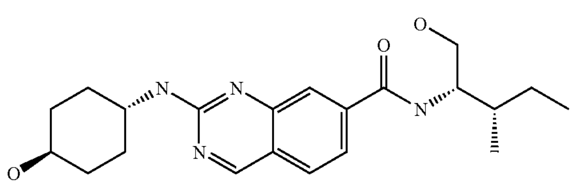 | 2-((trans-4-hydroxycyclohexyl)amino)-N-[(1S,2S)-1-(hydroxymethyl)-2-methylbutyl]quinazoline-7-carboxamide | 387.5 |
| 379 | 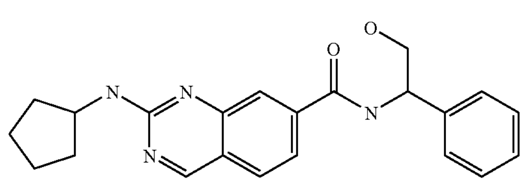 | 2-(cyclopentylamino)-N-(2-hydroxy-1-phenylethyl)quinazoline-7-carboxamide | 377.5 |

-continued

| ID | Structure | Name | LCMS m/z |
|---|---|---|---|
| 380 | ABS | 2-(cyclohexylamino)-N-[(1S,2S)-1-(hydroxymethyl)-2-methylbutyl]quinazoline-7-carboxamide | 371.5 |
| 381 | 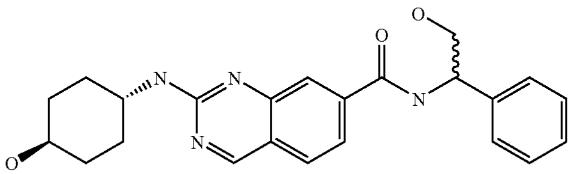 | 2-[(trans-4-hydroxycyclohexyl)amino]-N-(2-hydroxy-1-phenylethyl)quinazoline-7-carboxamide | 407.5 |
| 382 | ABS | 2-[(trans-4-hydroxycyclohexyl)amino]-N-[(1S)-1-(hydroxymethyl)-2-methylpropyl]quinazoline-7-carboxamide | 373.5 |
| 383 | 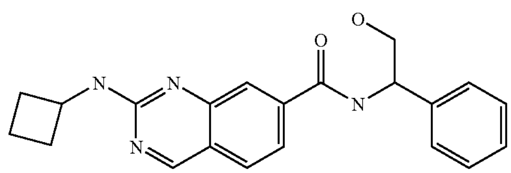 | 2-(cyclobutylamino)-N-(2-hydroxy-1-phenylethyl)quinazoline-7-carboxamide | 363.4 |
| 384 | ABS | 2-(cyclopentylamino)-N-[(1S)-2-hydroxy-1-phenylethyl]quinazoline-7-carboxamide | 377.5 |
| 385 | 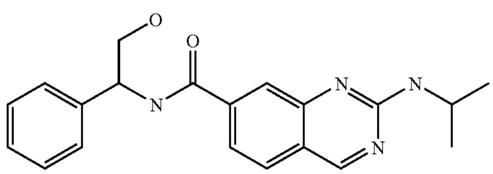 | N-(2-hydroxy-1-phenylethyl)-2-(isopropylamino)quinazoline-7-carboxamide | 351.4 |
| 386 | ABS | N-[(1S)-2-cyclohexyl-1-(hydroxymethyl)ethyl]-2-[(trans-4-hydroxycyclohexyl)amino]quinazoline-7-carboxamide | 427.6 |
| 387 | ABS | 2-(cyclopentylamino)-N-[(1S)-1-(hydroxymethyl)butyl]quinazoline-7-carboxamide | 343.4 |

-continued

| ID | Structure | Name | LCMS m/z |
|---|---|---|---|
| 388 | ABS | 2-(cyctohexylamino)-N-[(1S)-1-(hydroxymethyl)propyl]quinazoline-7-carboxamide | 343.4 |
| 389 | ABS | 2-(cyclohexylamino)-N-[(1S)-1-(hydroxymethyl)-2-methylpropyl]quinazoline-7-carboxamide | 357.5 |
| 390 | ABS | 2-(cyclopentylamino)-N-[(1S)-1-(hydroxymethyl)-3-methylbutyl]quinazoline-7-carboxamide | 357.5 |
| 391 | 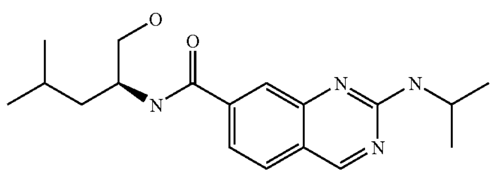 | N-[(1S)-1-(hydroxymethyl)-3-methylbutyl]-2-(isopropylamino)quinazoline-7-carboxamide | 331.4 |
| 392 | ABS | 2-(cyclobutylamino)-N-[(1S)-2-hydroxy-1-phenylethyl]quinazoline-7-carboxamide | 363.4 |
| 393 | ABS | 2-(cyclohexylamino)-N-[(1S)-2-cyclohexyl-1-(hydroxymethyl)ethyl]quinazoline-7-carboxamide | 411.6 |
| 394 | ABS | N-[(1S)-2-hydroxy-1-phenylethyl]-2-(isopropylamino)quinazoline-7-carboxamide | 351.4 |
| 395 | ABS | N-[(1S)-1-benzyl-2-hydroxyethyl]-2-(cyclohexylamino)quinazoline-7-carboxamide | 405.5 |

-continued

| ID | Structure | Name | LCMS m/z |
|---|---|---|---|
| 396 | ABS | 2-(cyclopentylamino)-N-[(1S,2S)-1-(hydroxymethyl)-3-methylbutyl]quinazoline-7-carboxamide | 357.5 |
| 397 | ABS | 2-(cyclobutylamino)-N-[(1S)-1-(hydroxymethyl)-3-methylbutyl]quinazoline-7-carboxamide | 343.4 |
| 398 | ABS | 2-(cyclobutylamino)-N-[(1S)-1-(hydroxymethyl)butyl]quinazoline-7-carboxamide | 329.4 |
| 399 | ABS | 2-(cyclohexylamino)-N-[(1S)-2-hydroxy-1-methylethyl]quinazoline-7-carboxamide | 329.4 |
| 400 | 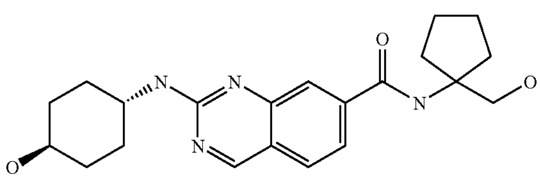 | 2-[(trans-4-hydroxycyclohexyl)amino]-N-[1-(hydroxymethyl)cyclopentyl]quinazoline-7-carboxamide | 385.5 |
| 401 | 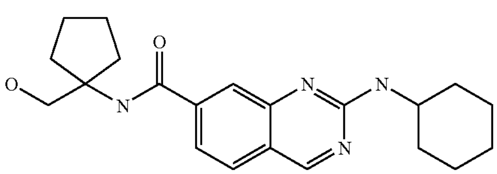 | 2-(cyclohexylamino)-N-[1-(hydroxymethyl)cyclopentyl]quinazoline-7-carboxamide | 369.5 |
| 402 | ABS | N-[(1S)-1-benzyl-2-hydroxyethyl]-2-[(trans-4-hydroxycyclohexyl)amino]quinazoline-7-carboxamide | 421.5 |
| 403 | ABS | 2-[(trans-4-hydroxycyclohexyl)amino]-N-[(1S)-2-hydroxy-1-methylethyl]quinazoline-7-carboxamide | 345.4 |

-continued

| ID | Structure | Name | LCMS m/z |
|---|---|---|---|
| 404 | 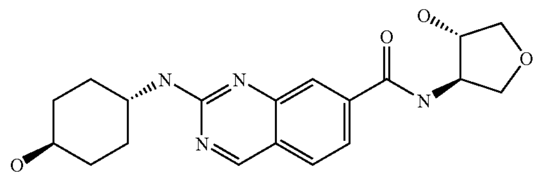 | 2-[(trans-4-hydroxycyclohexyl)amino]-N-[(3R,4S)-4-hydroxytetrahydrofuran-3-yl]quinazoline-7-carboxamide | 373.4 |
| 405 | 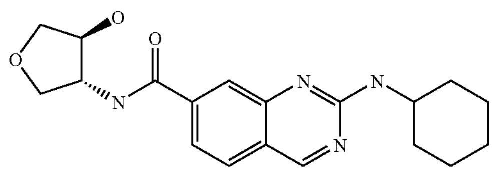 | 2-(cyclohexylamino)-N-[(3R,4S)-4-hydroxytetrahydrofuran-3-yl]quinazoline-7-carboxamide | 357.4 |
| 406 | ABS | N-[(1S)-1-(hydroxymethyl)butyl]-2-(isopropylamino)quinazoline-7-carboxamide | 317.4 |
| 407 | ABS | 2-(cyclopentylamino)-N-[(1S)-1-(hydroxymethyl)-2-methylpropyl]quinazoline-7-carboxamide | 343.4 |
| 408 | ABS | N-[(1S)-1-benzyl-2-hydroxyethyl]-2-(cyclopentylamino)quinazoline-7-carboxamide | 391.5 |
| 409 | ABS | N-[(1S,2S)-1-(hydroxymethyl)-2-methylbutyl]-2-(isopropylamino)quinazoline-7-carboxamide | 331.4 |
| 410 | 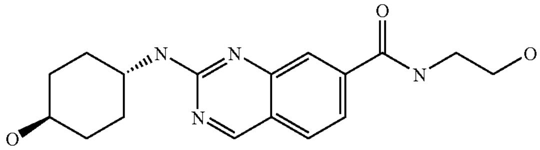 | 2-[(trans-4-hydroxycyclohexyl)amino]-N-(2-hydroxyethyl)quinazoline-7-carboxamide | 331.4 |
| 411 | ABS | N-[(1S)-1-(hydroxymethyl)propyl]-2-(isopropylamino)quinazoline-7-carboxamide | 303.4 |

| ID | Structure | Name | LCMS m/z |
|---|---|---|---|
| 412 | 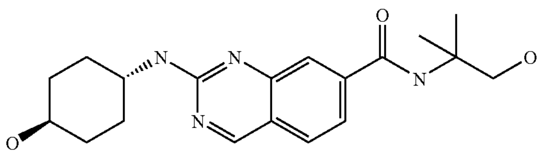 | 2-[(trans-4-hydroxycyclohexyl)amino]-N-(2-hydroxy-1,1-dimethylethyl)quinazoline-7-carboxamide | 359.4 |
| 413 | 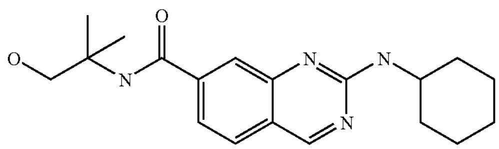 | 2-(cyclohexylamino)-N-(2-hydroxy-1,1-dimethylethyl)quinazoline-7-carboxamide | 343.4 |
| 414 | ABS | 2-(cyclobutylamino)-N-[(1S,2S)-1-(hydroxymethyl)-2-methylbutyl]quinazoline-7-carboxamide | 343.4 |
| 415 | ABS | N-((1S)-1-benzyl-2-hydroxyethyl]2-(isopropylamino)quinazoline-7-carboxamide | 365.5 |
| 416 | ABS | 2-(cyclobutylamino)-N-[(1S)-1-(hydroxymethyl)propyl]quinazoline-7-carboxamide | 315.4 |
| 417 | ABS | 2-[(trans-4-hydroxycyclohexyl)amino]-N-[(1S)-2-hydroxy-1-(1H-imidazol-4-ylmethyl)ethyl]quinazoline-7-carboxamide | 411.5 |
| 418 | ABS | 2-(cyclopentylamino)-N-[(1S)-2-hydroxy-1-methylethyl]quinazoline-7-carboxamide | 315.4 |
| 419 | ABS | N-[(1S)-2-cyclohexyl-1-(hydroxymethyl)ethyl]-2-(cyclopentylamino)quinazoline-7-carboxamide | 397.5 |

-continued

| ID | Structure | Name | LCMS m/z |
|---|---|---|---|
| 420 | ABS | N-[(1S)-1-benzyl-2-hydroxyethyl]-2-(cyclobutylamino)quinazoline-7-carboxamide | 377.5 |
| 421 | 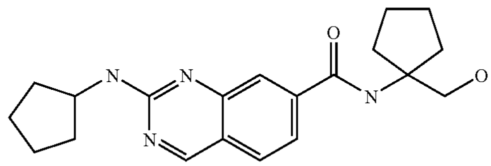 | 2-(cyclopentylamino)-N-[1-(hydroxymethyl)cyclopentyl]quinazoline-7-carboxamide | 355.5 |
| 422 | 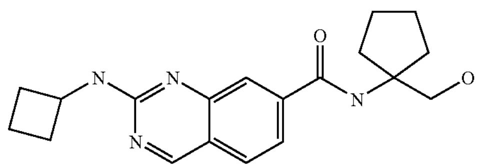 | 2-(cyctobutylamino)-N-[1-(hydroxymethyl)cyclopentyl]quinazoline-7-carboxamide | 341.4 |
| 423 | 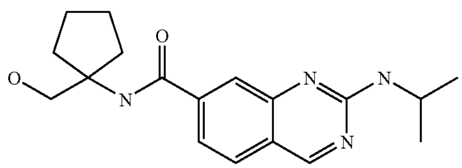 | N-[1-(hydroxymethyl)cyclopentyl]-2-(isopropylamino)quinazoline-7-carboxamide | 329.4 |
| 424 | ABS | 2-(cyclobutylamino)-N-[(1S)-1-(hydroxymethyl)-2-methylpropyl]quinazoline-7-carboxamide | 329.4 |
| 425 | 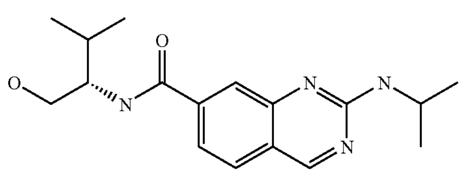 | N-[(1S)-1-(hydroxymethyl)-2-methylpropyl]-2-(isopropylamino)quinazoline-7-carboxamide | 317.4 |
| 426 | 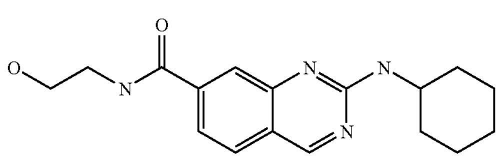 | 2-(cyclohexylamino)-N-(2-hydroxyethyl)quinazoline-7-carboxamide | 315.4 |
| 427 | 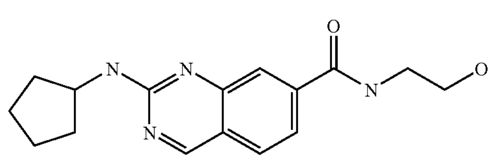 | 2-(cyclopentylamino)-N-(2-hydroxyethyl)quinazoline-7-carboxamide | 301.4 |

-continued

| ID | Structure | Name | LCMS m/z |
|---|---|---|---|
| 428 | ABS | 2-(cyclobutylamino)-N-[(1S)-2-cyclohexyl-1-(hydroxymethyl)ethyl]quinazoline-7-carboxamide | 383.5 |
| 429 | ABS | N-[(1S)-2-cyclohexyl-1-(hydroxymethyl)ethyl]-2-(isopropylamino)quinazoline-7-carboxamide | 371.5 |
| 430 | 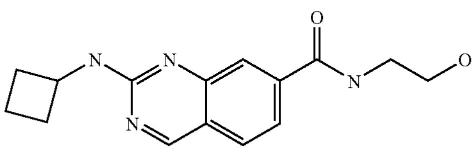 | 2-(cyclobutylamino)-N-(2-hydroxyethyl)quinazoline-7-carboxamide | 287.3 |
| 431 | 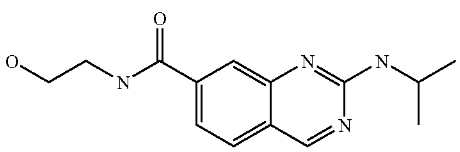 | N-(2-hydroxyethyl)-2-(isopropylamino)quinazoline-7-carboxamide | 275.3 |
| 432 | 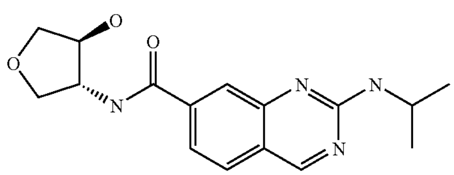 | N-((3R,4S)-4-hydroxytetrahydrofuran-3-yl]-2-(isopropylamino)quinazoline-7-carboxamide | 317.4 |
| 433 | 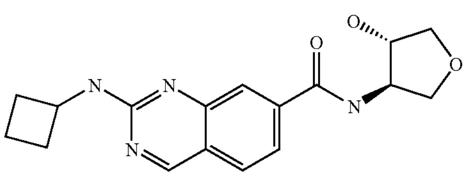 | 2-(cyclobutylamino)-N-[(3R,4S)-4-hydroxytetrahydrofuran-3-yl]quinazoline-7-carboxamide | 329.4 |
| 434 | ABS | N-[(1S)-2-hydroxy-1-methylethyl]-2-(isopropylamino)quinazoline-7-carboxamide | 289.4 |
| 435 | 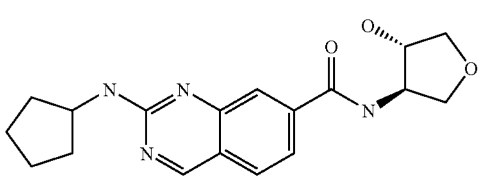 | 2-(cyclopentylamino)-N-[(3R,4S)-4-hydroxytetrahydrofuran-3-yl]quinazoline-7-carboxamide | 343.4 |

| ID | Structure | Name | LCMS m/z |
|---|---|---|---|
| 436 | ABS | 2-(cyctopentylamino)-N-[(1S)-1-(hydroxymethyl)propyl]quinazoline-7-carboxamide | 329.4 |
| 437 | ABS | 2-(cyclobutylamino)-N-[(1S)-2-hydroxy-1-methylethyl]quinazoline-7-carboxamide | 301.4 |
| 438 | 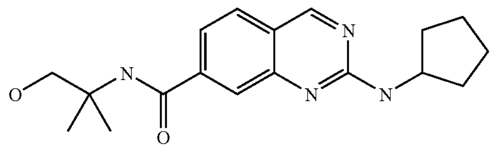 | 2-(cyclopentylamino)-N-(2-hydroxy-1,1-dimethylethyl)quinazoline-7-carboxamide | 329.4 |
| 439 | 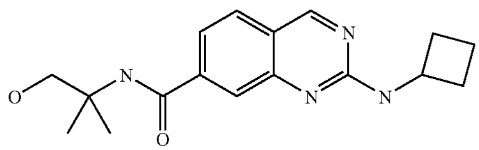 | 2-(cyclobutylamino)-N-(2-hydroxy-1,1-dimethylethyl)quinazoline-7-carboxamide | 315.4 |
| 440 | 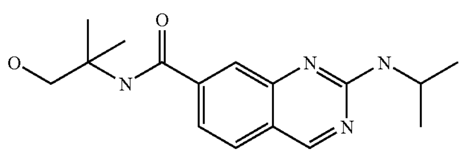 | N-(2-hydroxy-1,1-dimethylethyl)-2-(isopropylamino)quinazoline-7-carboxamide | 303.4 |
| 441 | ABS | 2-[(trans-4-hydroxycyclohexyl)amino]-N-[(1S)-1-(hydroxymethyl)propyl]quinazoline-8-carboxamide | 359.4 |
| 442 | 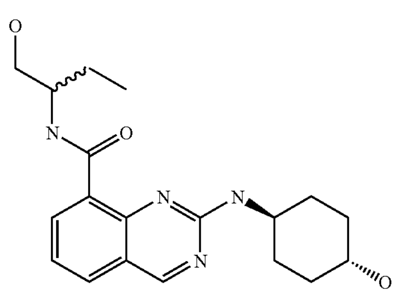 | 2-[(trans-4-hydroxycyclohexyl)amino]-N-[1-(hydroxymethyl)propyl]quinazoline-8-carboxamide | 359.4 |

-continued

| ID | Structure | Name | LCMS m/z |
|---|---|---|---|
| 443 | 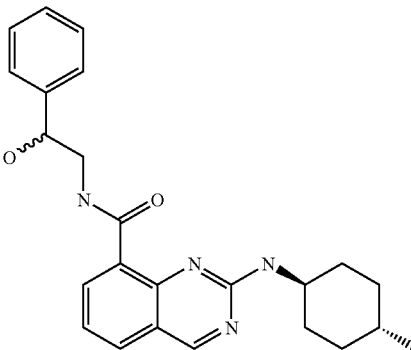 | 2-[(trans-4-hydroxycyclohexyl)amino]-N-(2-hydroxy-2-phenylethyl)quinazoline-8-carboxamide | 407.5 |
| 444 | 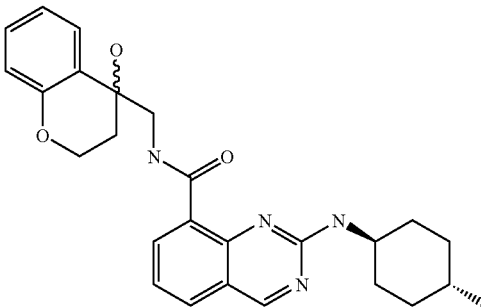 | 2-[(trans-4-hydroxycyclohexyl)amino]-N-[(4-hydroxy-3,4-dihydro-2H-chromen-4-yl)methyl]quinazoline-8-carboxamide | 449.5 |
| 445 | 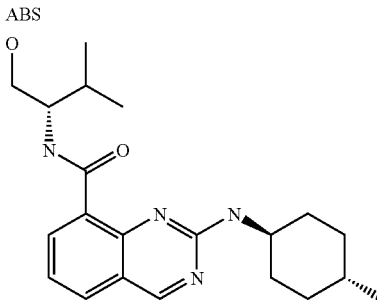 | 2-[(trans-4-hydroxycyclohexyl)amino]-N-[(1S)-1-(hydroxymethyl)-2-methylpropyl]quinazoline-8-carboxamide | 373.5 |
| 446 | 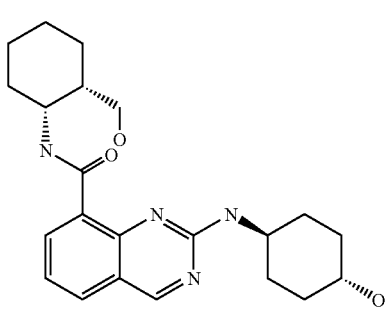 | 2-[(trans-4-hydroxycyclohexyl)amino]-N-[(1R,2S)-2-(hydroxymethyl)cyclohexyl]quinazoline-8-carboxamide | 399.5 |
| 447 | 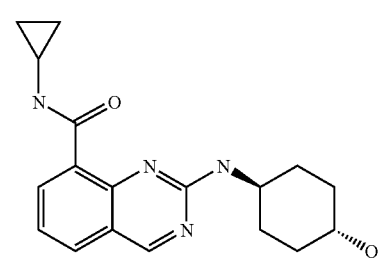 | N-cyclopropyl-2-[(trans-4-hydroxycyclohexyl)amino]quinazoline-8-carboxamide | 327.4 |

-continued

| ID | Structure | Name | LCMS m/z |
|---|---|---|---|
| 448 | 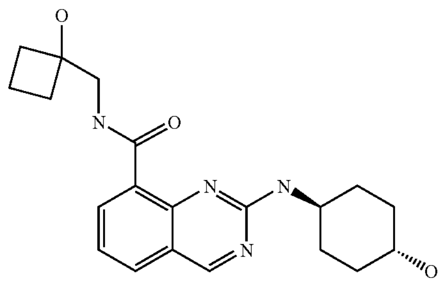 | N-[(1-hydroxycyclobutyl)methyl]-2-[(trans-4-hydroxycyclohexyl)amino]quinazoline-8-carboxamide | 371.5 |
| 449 | 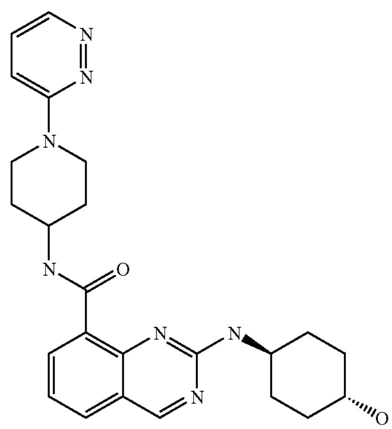 | 2-[(trans-4-hydroxycyclohexyl)amino]-N-(1-pyridazin-3-ylpiperidin-4-yl)quinazoline-8-carboxamide | 448.5 |
| 450 | 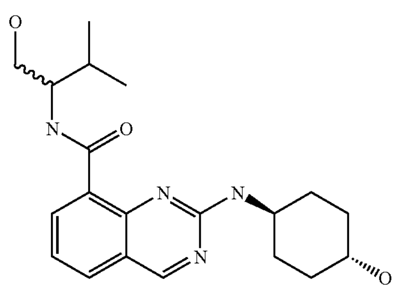 | 2-[(trans-4-hydroxycyclohexyl)amino]-N-[1-(hydroxymethyl)-2-methylpropyl]quinazoline-8-carboxamide | 373.5 |
| 451 | 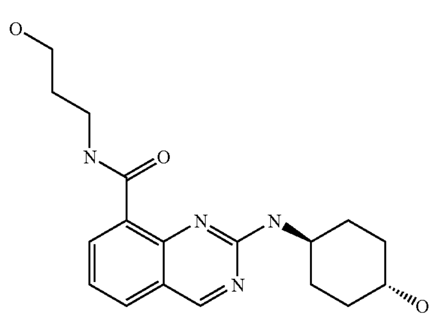 | 2-[(trans-4-hydroxycyclohexyl)amino]-N-(3-hydroxypropyl)quinazoline-8-carboxamide | 345.4 |

-continued

| ID | Structure | Name | LCMS m/z |
|---|---|---|---|
| 452 | 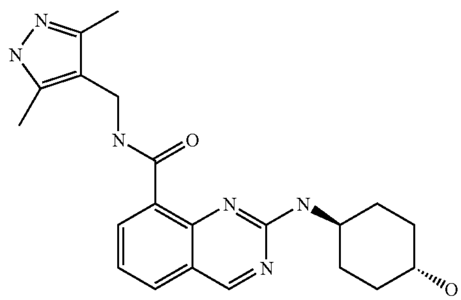 | N-[(3,5-dimethyl-1H-pyrazol-4-yl)methyl]-2-[(trans-4-hydroxycyclohexyl)amino]quinazoline-8-carboxamide | 395.5 |
| 453 | 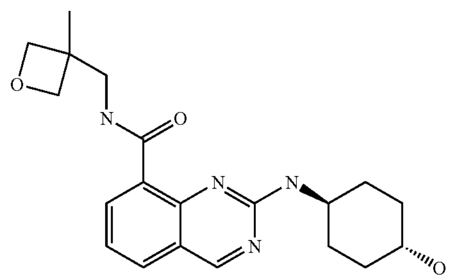 | 2-[(trans-4-hydroxycyclohexylamino]-N-[(3-methyloxetan-3-yl)methyl]quinazoline-8-carboxamide | 371.5 |
| 454 | 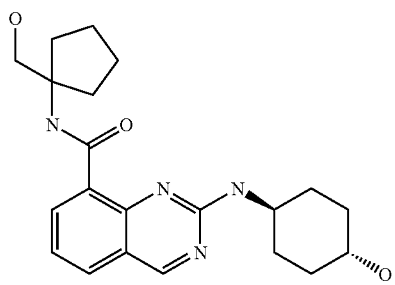 | 2-[(trans-4-hydroxycyclohexyl)amino]-N-[1-(hydroxymethyl)cyclopentyl]quinazoline-8-carboxamide | 385.5 |
| 455 | 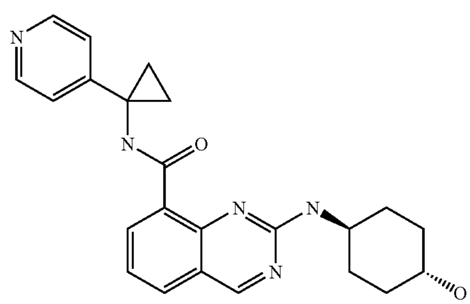 | 2-[(trans-4-hydroxycyclohexyl)amino]-N-(1-pyridin-4-ylcyclopropyl)quinazoline-8-carboxamide | 404.5 |
| 456 | 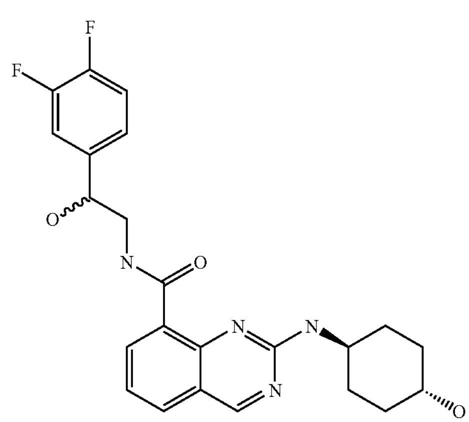 | N-[2-(3,4-difluorophenyl)-2-hydroxyethyl]-2-[(trans-4-hydroxycyclohexyl)amino]quinazoline-8-carboxamide | 443.5 |

-continued

| ID | Structure | Name | LCMS m/z |
|---|---|---|---|
| 457 | 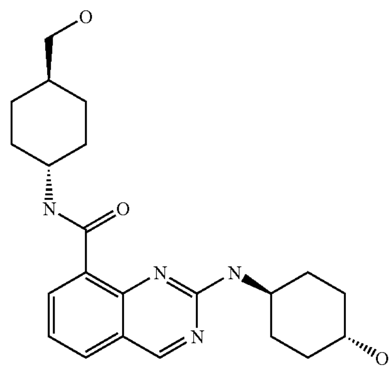 | 2-[(trans-4-hydroxycyclohexyl)amino]-N-[trans-4-(hydroxymethyl)cyclohexyl]quinazoline-8-carboxamide | 399.5 |
| 458 | ABS | 2-[(trans-4-hydroxycyclohexyl)amino]-N-[(1R)-1-(hydroxymethyl)propyl]quinazoline-8-carboxamide | 359.4 |
| 459 | 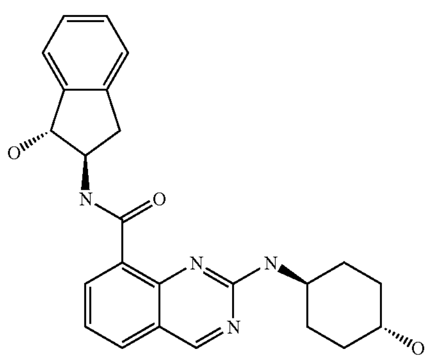 | 2-[(trans-4-hydroxycyclohexyl)amino]-N-[(1R,2R)-1-hydroxy-2,3-dihydro-1H-inden-2-yl]quinazoline-8-carboxamide | 419.5 |
| 460 | 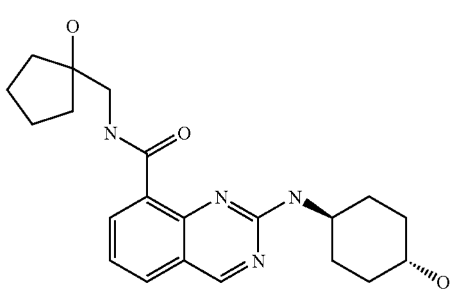 | 2-[(trans-4-hydroxycyclohexyl)amino]-N-[(1-hydroxycyclopentyl)methyl]quinazoline-8-carboxamide | 385.5 |

-continued

| ID | Structure | Name | LCMS m/z |
|---|---|---|---|
| 461 | 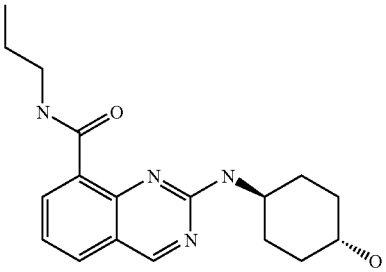 | 2-[(trans-4-hydroxycyclohexyl)amino]-N-propylquinazoline-8-carboxamide | 329.4 |
| 462 | 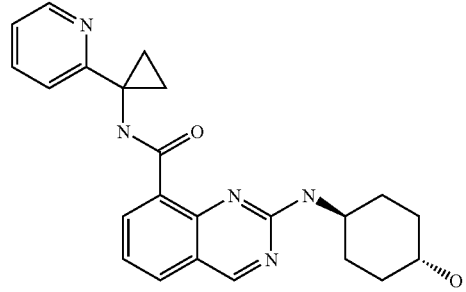 | 2-[(trans-4-hydroxycyclohexyl)amino]-N-(1-pyridin-2-ylcyclopropyl)quinazoline-8-carboxamide | 404.5 |
| 463 | 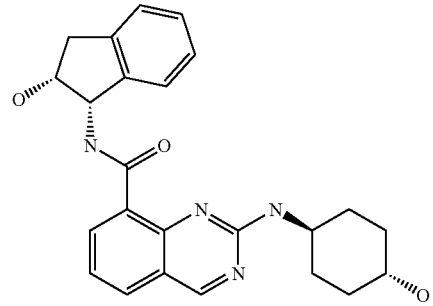 | 2-[(trans-4-hydroxycyclohexyl)amino]-N-[(1S,2R)-2-hydroxy-2,3-dihydro-1H-inden-1-yl]quinazoline-8-carboxamide | 419.5 |
| 464 | 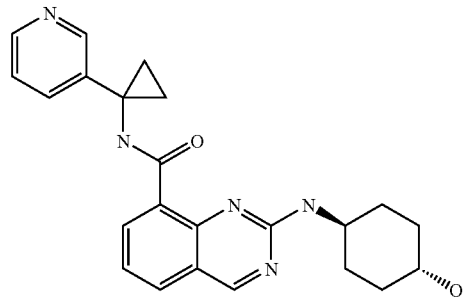 | 2-[(trans-4-hydroxycyclohexyl)amino]-N-(1-pyridin-3-ylcyclopropyl)quinazoline-8-carboxamide | 404.5 |
| 465 | 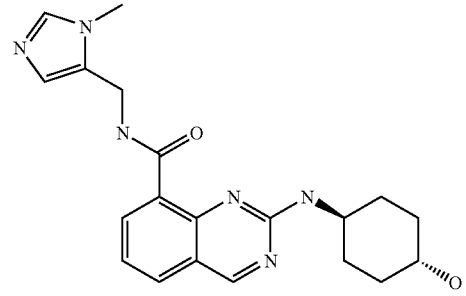 | 2-[(trans-4-hydroxycyclohexyl)amino]-N-[(1-methyl-1H-imidazol-5-yl)methyl]quinazoline-8-carboxamide | 381.5 |

-continued

| ID | Structure | Name | LCMS m/z |
|---|---|---|---|
| 466 | 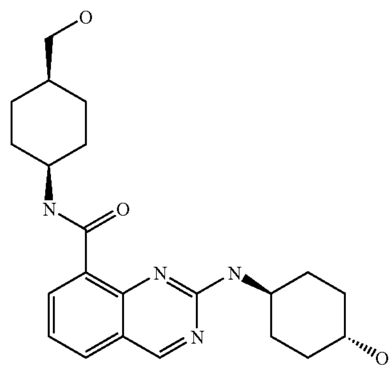 | 2-[(trans-4-hydroxycyclohexyl)amino]-N-[cis-4-(hydroxymethyl)cyclohexyl]quinazoline-8-carboxamide | 399.5 |
| 467 | 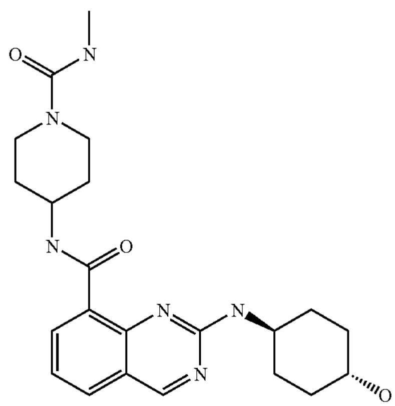 | 2-[(trans-4-hydroxycyclohexyl)amino]-N-{1-[(methylamino)carbonyl]piperidin-4-yl}quinazoline-8-carboxamide | 427.5 |
| 468 | 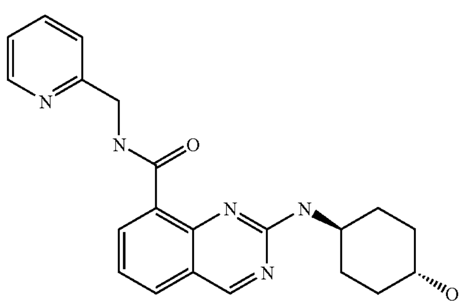 | 2-[(trans-4-hydroxycyclohexyl)amino]-N-(pyridin-2-ylmethyl)quinazoline-8-carboxamide | 378.5 |
| 469 | 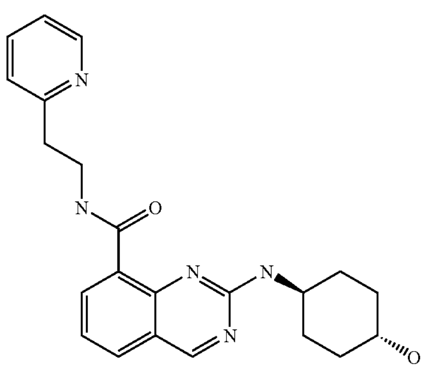 | 2-[(trans-4-hydroxycyclohexyl)amino]-N-(2-pyridin-2-ylethyl)quinazoline-8-carboxamide | 392.5 |

-continued

| ID | Structure | Name | LCMS m/z |
|---|---|---|---|
| 470 | ABS | 2-[(trans-4-hydroxycyclohexyl)amino]-N-[(1S)-2-hydroxy-1-phenylethyl]quinazoline-8-carboxamide | 407.5 |
| 471 | ABS | 2-[(trans-4-hydroxycyclohexyl)amino]-N-[(1R)-2-hydroxy-1-phenylethyl]quinazoline-8-carboxamide | 407.5 |
| 472 | ABS | 2-[(trans-4-hydroxycyclohexyl)amino]-N-[(1R,2S)-2-hydroxy-1-methyl-2-phenylethyl]quinazoline-8-carboxamide | 421.5 |
| 473 | 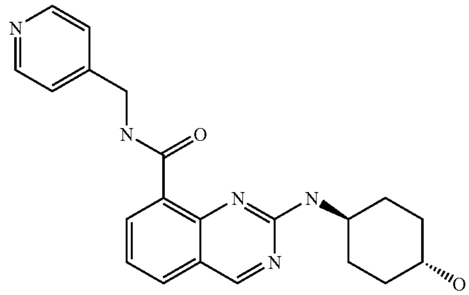 | 2-[(trans-4-hydroxycyclohexyl)amino]-N-(pyridin-4-ylmethyl)quinazoline-8-carboxamide | 378.5 |

-continued

| ID | Structure | Name | LCMS m/z |
|---|---|---|---|
| 474 | 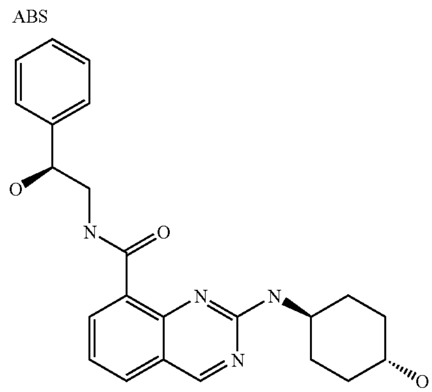 | 2-[(trans-4-hydroxycyclohexyl)amino]-N-[(2S)-2-hydroxy-2-phenylethyl]quinazoline-8-carboxamide | 407.5 |
| 475 | 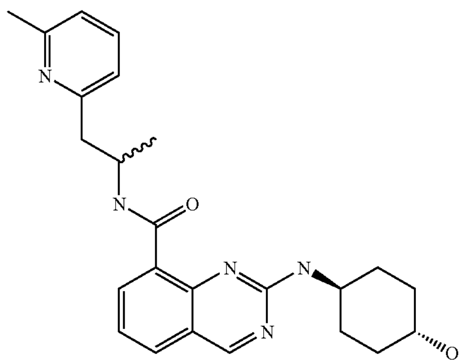 | 2-[(trans-4-hydroxycyclohexyl)amino]-N-[1-methyl-2-(6-methylpyridin-2-yl)ethyl]quinazoline-8-carboxamide | 420.5 |
| 476 | 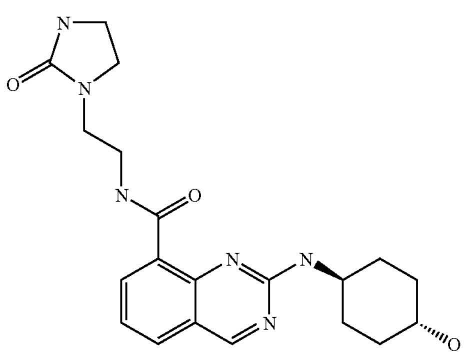 | 2-[(trans-4-hydroxycyclohexyl)amino]-N-[2-(2-oxoimidazolidin-1-yl)ethyl]quinazoline-8-carboxamide | 399.5 |
| 477 | 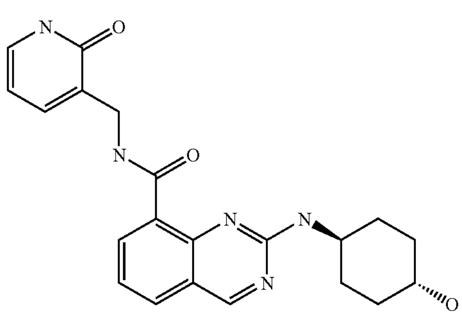 | 2-[(trans-4-hydroxycyclohexyl)amino]-N-[(2-oxo-1,2-dihydropyridin-3-yl)methyl]quinazoline-8-carboxamide | 394.5 |

-continued

| ID | Structure | Name | LCMS m/z |
|---|---|---|---|
| 478 | 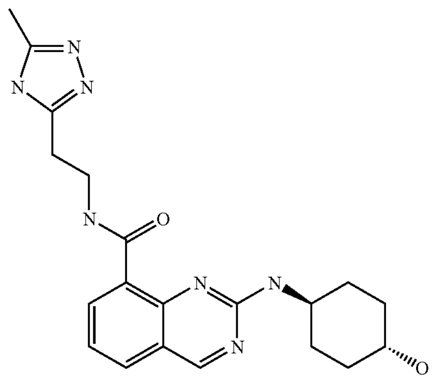 | 2-[(trans-4-hydroxycyclohexyl)amino]-N-[2-(5-methyl-4H-1,2,4-triazol-3-yl)ethyl]quinazoline-8-carboxamide | 396.5 |
| 479 | 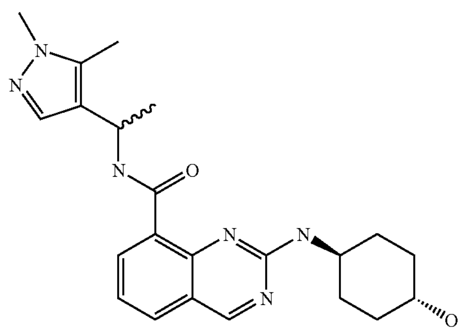 | N-[1-(1,5-dimethyl-1H-pyrazol-4-yl)ethyl]-2-[(trans-4-hydroxycyclohexyl)amino]quinazoline-8-carboxamide | 409.5 |
| 480 | 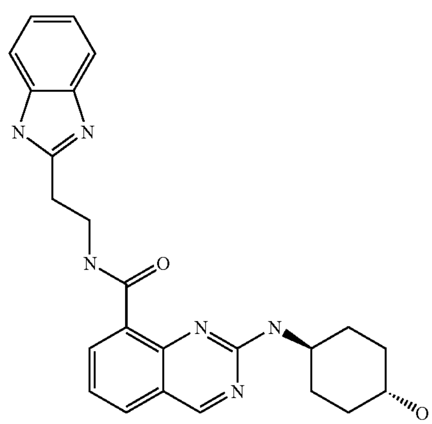 | N-[2-(1H-benzimidazol-2-yl)ethyl]-2-[(trans-4-hydroxycyclohexyl)amino]quinazoline-8-carboxamide | 431.5 |
| 481 | 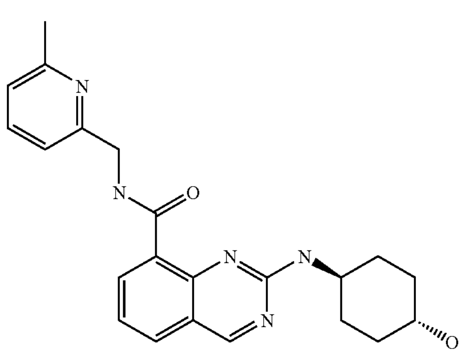 | 2-[(trans-4-hydroxycyclohexyl)amino]-N-[(6-methylpyridin-2-yl)methyl]quinazoline-carboxamide | 392.5 |

-continued

| ID | Structure | Name | LCMS m/z |
|---|---|---|---|
| 482 | 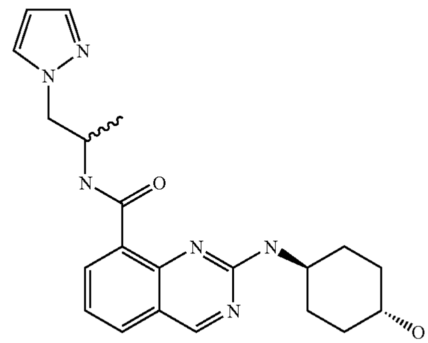 | 2-[(trans-4-hydroxycyclohexyl)amino]-N-[1-methyl-2-(1H-pyrazol-1-yl)ethyl]quinazoline-8-carboxamide | 395.5 |
| 483 | 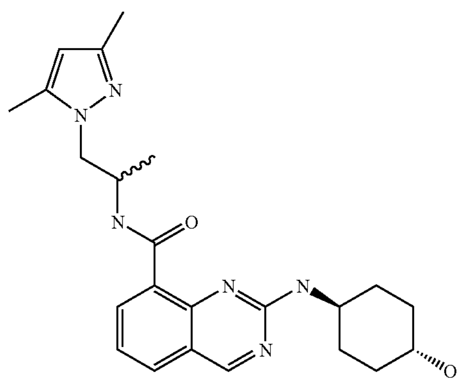 | N-[2-(3,5-dimethyl-1H-pyrazol-1-yl)-1-methylethyl]-2-[(trans-4-hydroxycyclohexyl)amino]quinazoline-8-carboxamide | 423.5 |
| 484 | 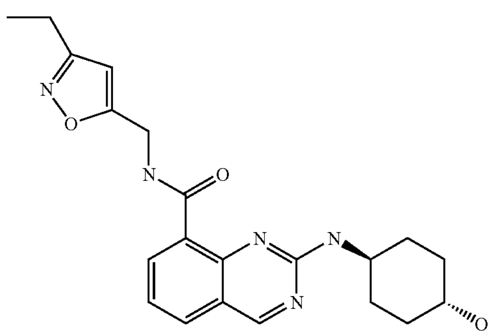 | N-[(3-ethylisoxazol-5-yl)methyl]-2-[(trans-4-hydroxycyclohexyl)amino]quinazoline-8-carboxamide | 396.5 |
| 485 | 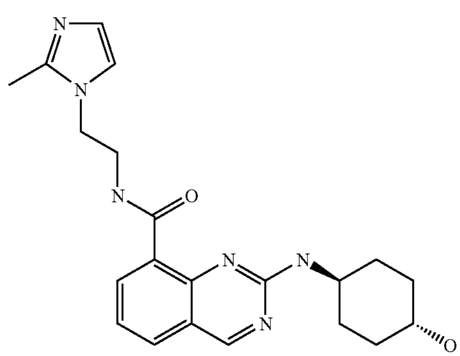 | 2-[(trans-4-hydroxycyclohexyl)amino]-N-[2-(2-methyl-1H-imidazol-1-yl)ethyl]quinazoline-8-carboxamide | 395.5 |

-continued

| ID | Structure | Name | LCMS m/z |
|---|---|---|---|
| 486 | 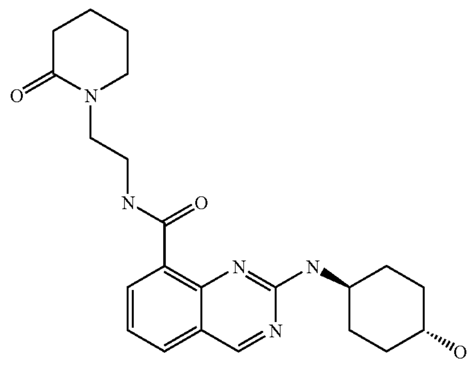 | 2-[(trans-4-hydroxycyclohexyl)amino]-N-[2-(2-oxopiperidin-1-yl)ethyl]quinazoline-8-carboxamide | 412.5 |
| 487 | 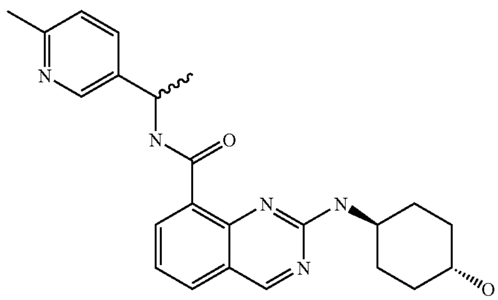 | 2-[(trans-4-hydroxycyclohexyl)amino]-N-[1-(6-methylpyridin-3-yl)ethyl]quinazoline-8-carboxamide | 406.5 |
| 488 | 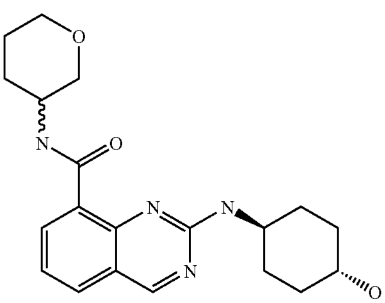 | 2-[(trans-4-hydroxycyclohexyl)amino]-N-(tetrahydro-2H-pyran-3-yl)quinazoline-8-carboxamide | 371.5 |
| 489 | 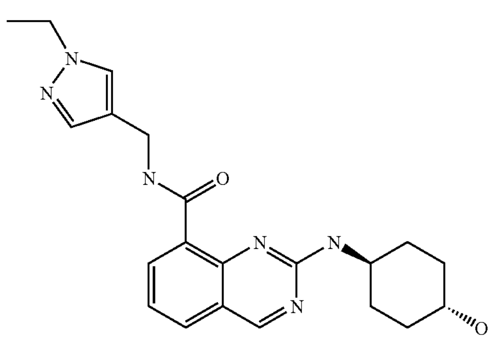 | N-[(1-ethyl-1H-pyrazol-4-yl)methyl]-2-[(trans-4-hydroxycyclohexyl)amino]quinazoline-8-carboxamide | 395.5 |

-continued

| ID | Structure | Name | LCMS m/z |
|---|---|---|---|
| 490 | 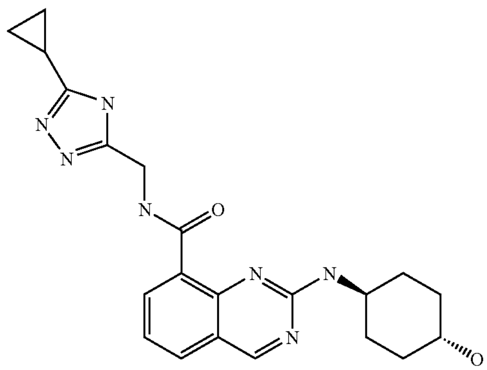 | N-[(5-cyclopropyl-4H-1,2,4-triazol-3-yl)methyl]-2-[(trans-4-hydroxycyclohexyl)amino]quinazoline-8-carboxamide | 408.5 |
| 491 | 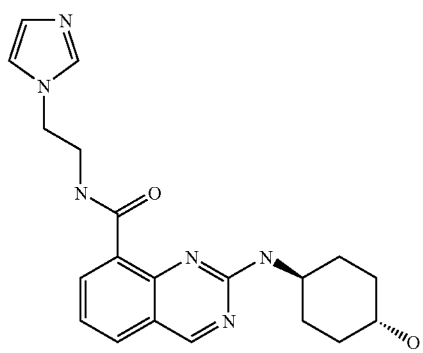 | 2-[(trans-4-hydroxycycbohexyl)amino]-N-[2-(1H-imidazol-1-yl)ethyl]quinazoline-8-carboxamide | 381.5 |
| 492 | 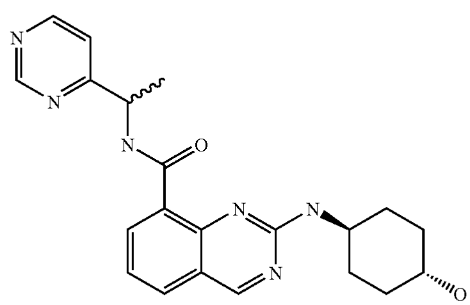 | 2-[(trans-4-hydroxycyclohexyl)amino]-N-(1-pyrimidin-4-ylethyl)quinazoline-8-carboxamide | 393.5 |
| 493 | 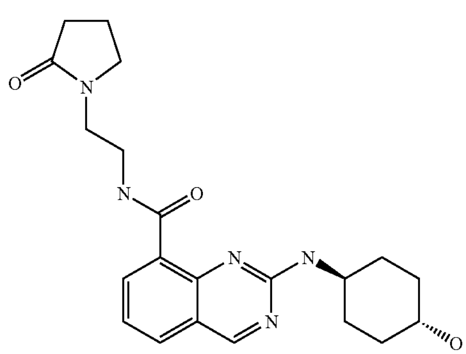 | 2-[(trans-4-hydroxycyclohexyl)amino]-N-(2-(2-oxopyrrolidin-1-yl)ethyl]quinazoline-8-carboxamide | 398.5 |

-continued

| ID | Name | LCMS m/z |
|---|---|---|
| 494 | 2-[(trans-4-hydroxycyclohexyl)amino]-N-(2-imidazol[1,2-a]pyridin-2-ylethyl)quinazoline-8-carboxamide | 431.5 |
| 495 | 2-[(trans-4-hydroxycyclohexyl)amino]-N-(1-methyl-2-(3-methylpyridin-2-yl)ethyl]quinazoline-8-carboxamide | 420.5 |
| 496 | N-[(1-ethyl-3,5-dimethyl-1H-pyrazol-4-yl)methyl]-2-[(trans-4-hydroxycyclohexyl)amino]quinazoline-8-carboxamide | 423.5 |
| 497 | N-[(4-cyclohexyl-4H-1,2,4-triazol-3-yl)methyl]-2-[(trans-4-hydroxycyclohexyl)amino]quinazoline-8-carboxamide | 450.6 |

| ID | Name | LCMS m/z |
|---|---|---|
| 498 | 2-[(trans-4-hydroxycyclohexyl)amino]-N-[2-(3-methyl-1H-pyrazol-1-yl)ethyl]quinazoline-8-carboxamide | 395.5 |
| 499 | 2-[(trans-4-hydroxycyclohexyl)amino]-N-(2-imidazo[1,2-a]pyrimidin-2-ylethyl)quinazoline-8-carboxamide | 432.5 |
| 500 | 2-[(trans-4-hydroxycyclohexyl)amino]-N-[(3-isopropyl-1,2,4-oxadiazol-5-yl)methyl]quinazoline-8-carboxamide | 411.5 |
| 501 | 2-[(trans-4-hydroxycyclohexyl)amino]-N-[(5-phenyl-1,2,4-oxadiazol-3-yl)methyl]quinazoline-8-carboxamide | 445.5 |

-continued

| ID | Structure | Name | LCMS m/z |
|---|---|---|---|
| 502 | 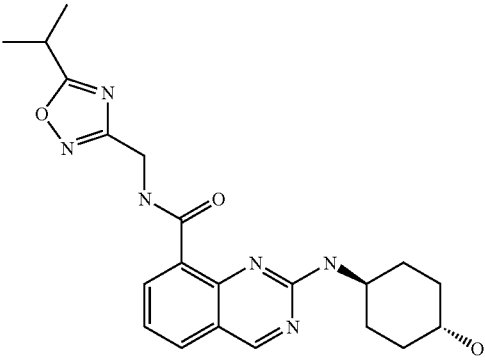 | 2-[(trans-4-hydroxycyclohexyl)amino]-N-[(5-isopropyl-1,2,4-oxadiazol-3-yl)methyl]quinazoline-8-carboxamide | 411.5 |
| 503 | 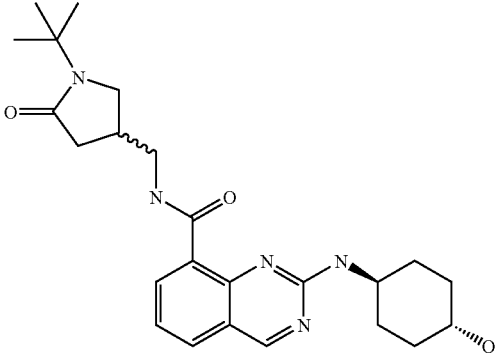 | N-[(1-tert-butyl-5-oxopyrrolidin-3-yl)methyl]-2-[(trans-4-hydroxycyclohexyl)amino]quinazoline-8-carboxamide | 440.6 |
| 504 | 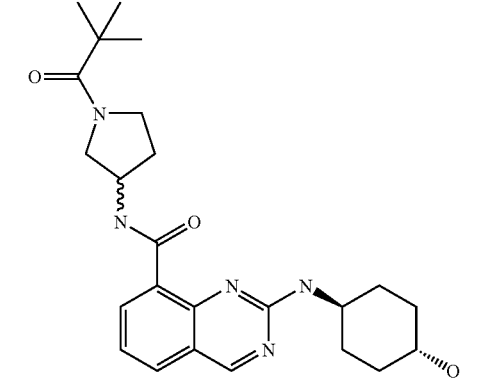 | N-[1-(2,2-dimethylpropanoyl)pyrrolidin-3-yl]-2-[(trans-4-hydroxycyclohexyl)amino]quinazoline-8-carboxamide | 440.6 |
| 505 | 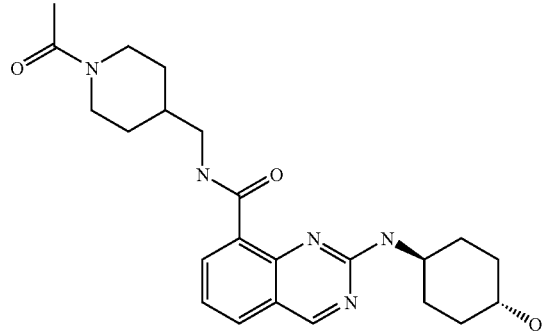 | N-[(1-acetylpiperidin-4-yl)methyl]-2-[(trans-4-hydroxycyclohexyl)amino]quinazoline-8-carboxamide | 426.5 |

| ID | Structure | Name | LCMS m/z |
|---|---|---|---|
| 506 | 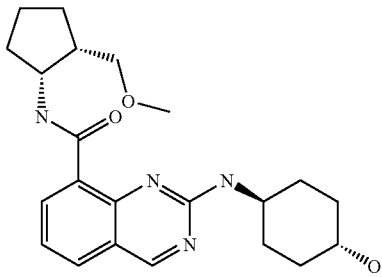 | 2-[(trans-4-hydroxycyclohexyl)amino]-N-[(1R,2S)-2-(methoxymethyl)cyclopentyl]quinazoline-8-carboxamide | 399.5 |
| 507 | 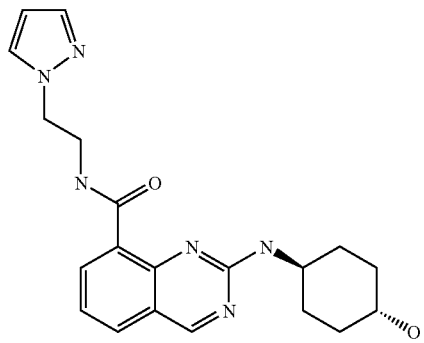 | 2-[(trans-4-hydroxycyclohexyl)amino]-N-[2-(1H-pyrazol-1-yl)ethyl]quinazoline-8-carboxamide | 381.5 |
| 508 | 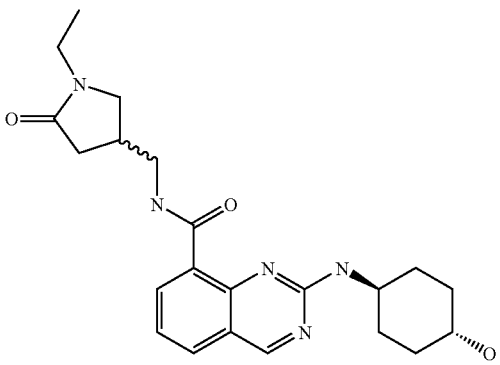 | N-[(1-ethyl-5-oxopyrrolidin-3-yl)methyl]-2-[(trans-4-hydroxycyclohexyl)amino]quinazoline-8-carboxamide | 412.5 |
| 509 | 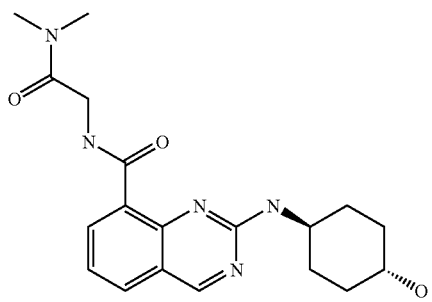 | N-[2-(dimethylamino)-2-oxoethyl]-2-[(trans-4-hydroxycyclohexyl)amino]quinazoline-8-carboxamide | 372.4 |

-continued

| ID | Structure | Name | LCMS m/z |
|---|---|---|---|
| 510 | 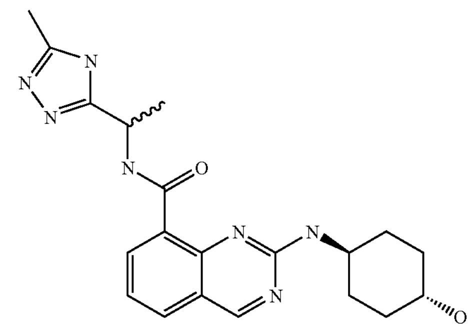 | 2-[(trans-4-hydroxycyclohexyl)amino]-N-[1-(5-methyl-4H-1,2,4-triazol-3-yl)ethyl]quinazoline-8-carboxamide | 396.5 |
| 511 | 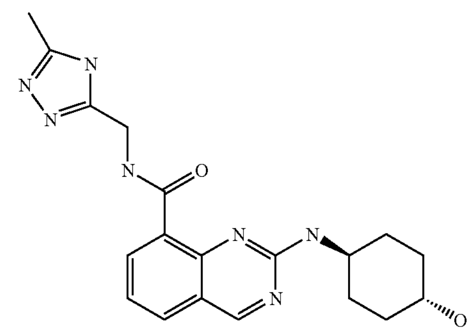 | 2-[(trans-4-hydroxycyclohexyl)amino]-N-[(5-methyl-4H-1,2,4-triazol-3-yl)methyl]quinazoline-8-carboxamide | 382.4 |
| 512 | 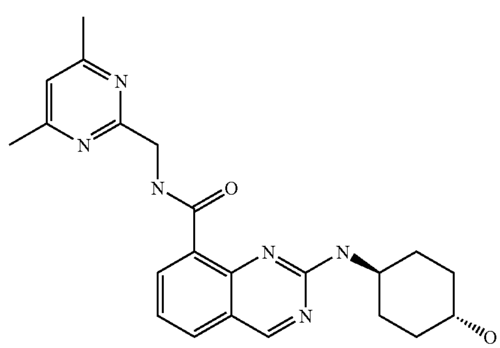 | N-[(4,6-dimethylpyrimidin-2-yl)methyl]-2-[(trans-4-hydroxycyclohexyl)amino]quinazoline-8-carboxamide | 407.5 |
| 513 | 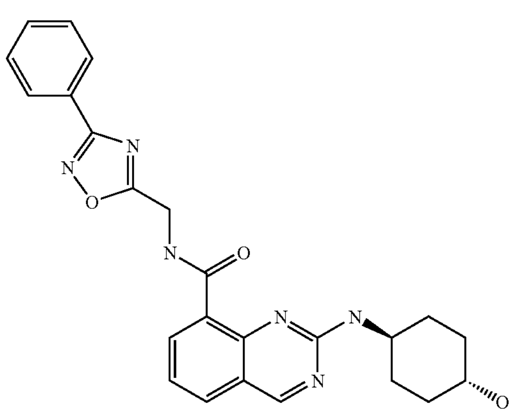 | 2-[(trans-4-hydroxycyclohexyl)amino]-N-[(3-phenyl-1,2,4-oxadiazol-5-yl)methyl]quinazoline-8-carboxamide | 445.5 |

| ID | Structure | Name | LCMS m/z |
|---|---|---|---|
| 514 | 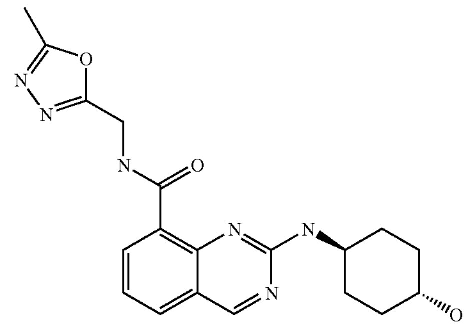 | 2-[(trans-4-hydroxycyclohexyl)amino]-N-[(5-methyl-1,3,4-oxadiazol-2-yl)methyl]quinazoline-8-carboxamide | 383.4 |
| 515 | 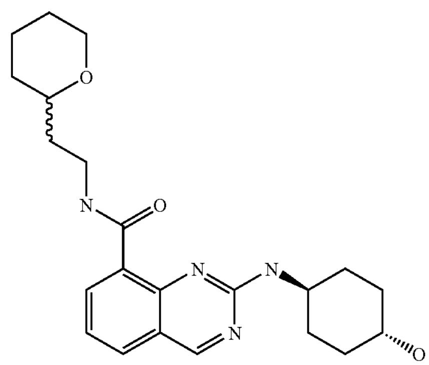 | 2-[(trans-4-hydroxycyclohexyl)amino]-N-[2-(tetrahydro-2H-pyran-2-yl)ethyl]quinazoline-8-carboxamide | 399.5 |
| 516 | 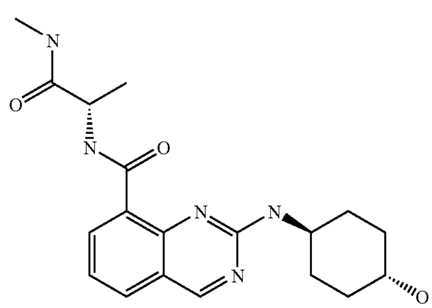 | 2-[(trans-4-hydroxycyclohexyl)amino]-N-[(1S)-1-methyl-2-(methylamino)-2-oxoethyl]quinazoline-8-carboxamide | 372.4 |
| 517 | 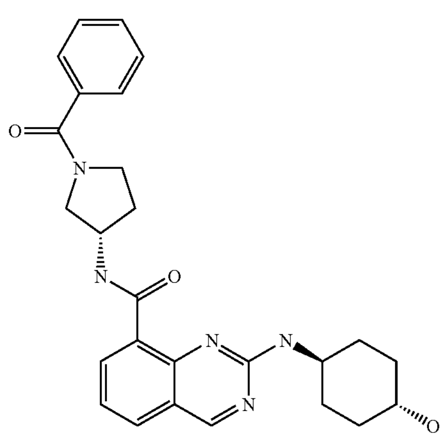 | N-(1-benzoylpyrrolidin-3-yl)-2-[(trans-4-hydroxycyclohexyl)amino]quinazoline-8-carboxamide | 460.6 |

-continued

| ID | Structure | Name | LCMS m/z |
|---|---|---|---|
| 518 | 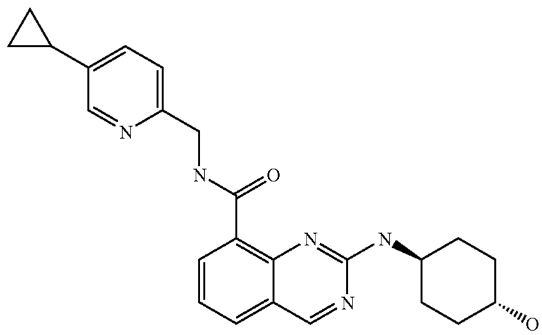 | N-[(5-cyclopropylpyridin-2-yl)methyl]-2-[(trans-4-hydroxycyclohexyl)amino]quinazoline-8-carboxamide | 418.5 |
| 519 | 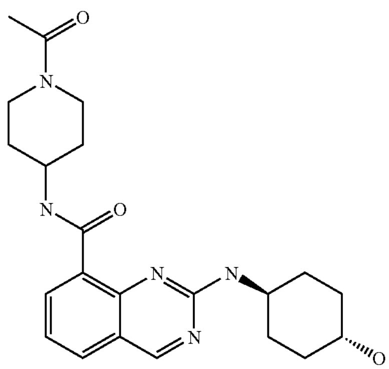 | N-(1-acetylpiperidin-4-yl)-2-[(trans-4-hydroxycyclohexyl)amino]quinazoline-8-carboxamide | 412.5 |
| 520 | 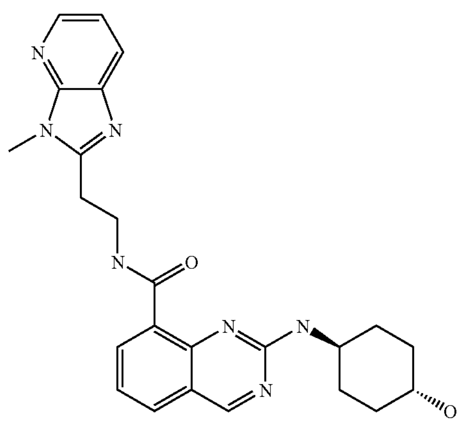 | 2-[(trans-4-hydroxycyclohexyl)amino]-N-[2-(3-methyl-3H-imidazo[4,5-b]pyridin-2-yl)ethyl]quinazoline-8-carboxamide | 446.5 |
| 521 | 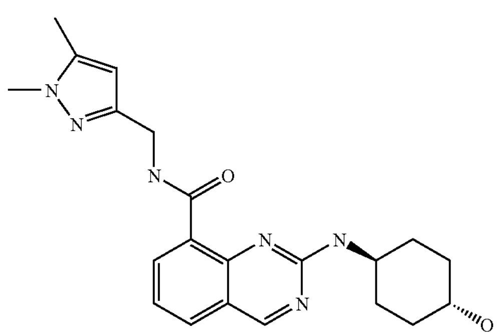 | N-[(1,5-dimethyl-1H-pyrazol-3-yl)methyl]-2-[(trans-4-hydroxycyclohexyl)amino]quinazoline-8-carboxamide | 395.5 |

| ID | Structure | Name | LCMS m/z |
|---|---|---|---|
| 522 | 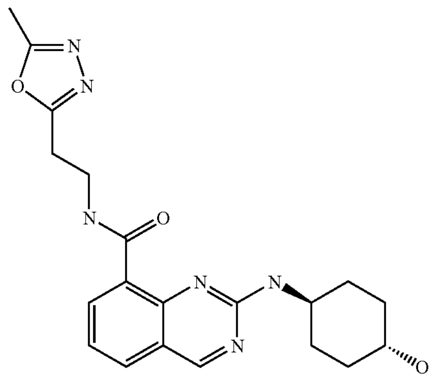 | 2-[(trans-4-hydroxycyclohexyl)amino]-N-[2-(5-methyl-1,3,4-oxadiazol-2-yl)ethyl]quinazoline-8-carboxamide | 397.5 |
| 523 | 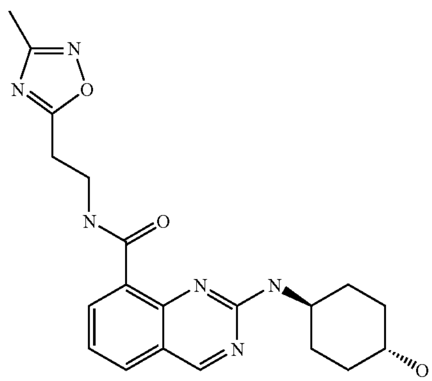 | 2-[(trans-4-hydroxycyclohexyl)amino]-N-[2-(3-methyl-1,2,4-oxadiazol-5-yl)ethyl]quinazoline-8-carboxamide | 397.5 |
| 524 | 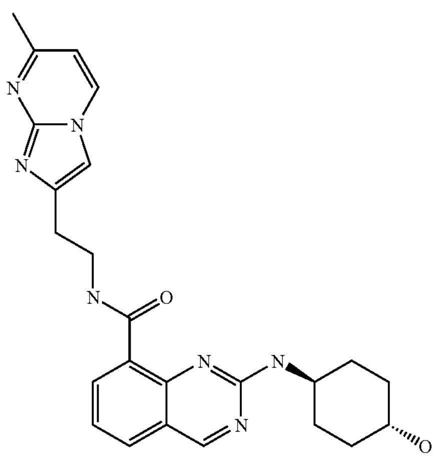 | 2-[(trans-4-hydroxycyclohexyl)amino]-N-[2-(7-methylimidazo[1,2-a]pyrimidin-2-yl)ethyl]quinazoline-8-carboxamide | 446.5 |
| 525 | 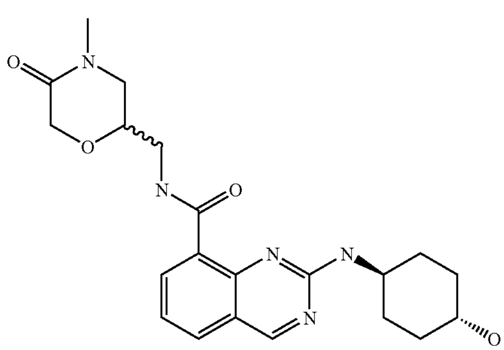 | 2-[(trans-4-hydroxycyclohexyl)amino]-N-[(4-methyl-5-oxomorpholin-2-yl)methyl]quinazoline-8-carboxamide | 414.5 |

| ID | Structure | Name | LCMS m/z |
|---|---|---|---|
| 526 | 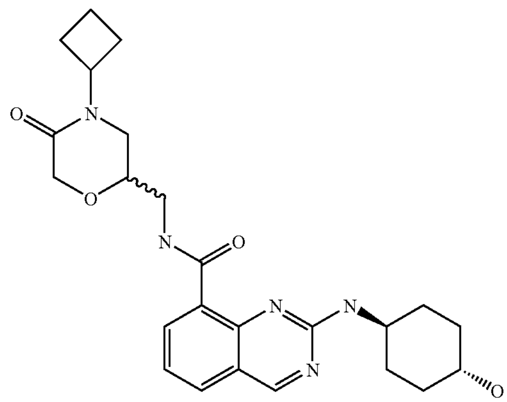 | N-[(4-cyclobutyl-5-oxomorpholin-2-yl)methyl]-2-[(trans-4-hydroxycyclohexyl)amino]quinazoline-8-carboxamide | 454.5 |
| 527 | 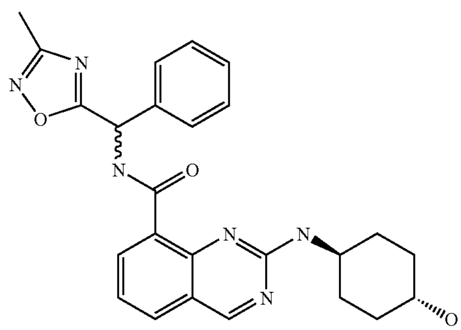 | 2-[(trans-4-hydroxycyclohexyl)amino]-N-[(3-methyl-1,2,4-oxadiazol-5-yl)(phenyl)methyl]quinazoline-8-carboxamide | 459.5 |
| 528 | 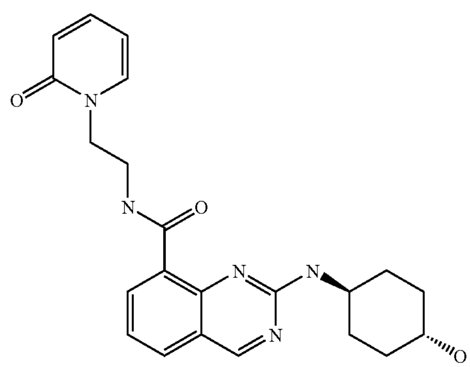 | 2-[(trans-4-hydroxycyclohexyl)amino]-N-[2-(2-oxopyridin-1(2H)-yl)ethyl]quinazoline-8-carboxamide | 408.5 |
| 529 | 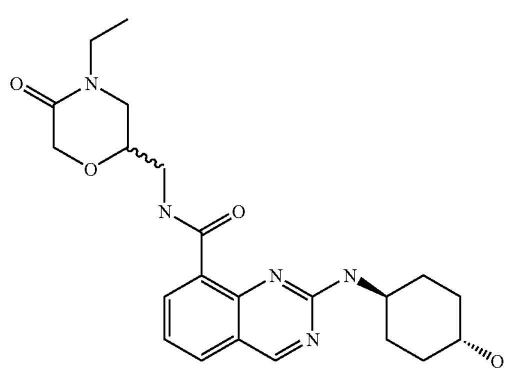 | N-[(4-ethyl-5-oxomorpholin-2-yl)methyl]-2-[(trans-4-hydroxycyclohexyl)amino]quinazoline-8-carboxamide | 428.5 |

-continued

| ID | Structure | Name | LCMS m/z |
|---|---|---|---|
| 530 | 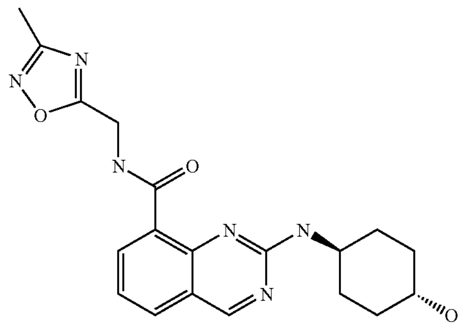 | 2-[(trans-4-hydroxycyclohexyl)amino]-N-[(3-methyl-1,2,4-oxadiazol-5-yl)methyl]quinazoline-8-carboxamide | 383.4 |
| 531 | 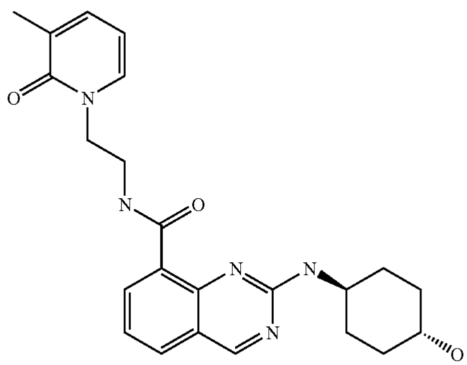 | 2-[(trans-4-hydroxycyclohexyl)amino]-N-[2-(3-methyl-2-oxopyridin-1(2H)-yl)ethyl]quinazoline-8-carboxamide | 422.5 |

Biological Activity

The percentage of inhibition (at 1 μM or 10 μM unless otherwise stated) and/or the Ki (in nM unless otherwise stated) for the compounds exemplified in the present application were obtained according to the protocol below:

% Inhibition and $K_i$ Determination

A coupled spectrophotometric assay, coupling JNK1α1 activity to the oxidation of β-NADH to NAD+ through the action of pyruvate kinase (PK) and lactic dehydrogenase (LDH), was used to determine the potency (percent inhibition at 1 or 10 μM or $K_i$) of compounds against JNK1α1 (Genbank Accession Number: L26318). The final reaction conditions were as follows: 20 mM HEPES pH 7.6, 10 mM $MgCl_2$, 1 mM DTT, 200 μM peptide substrate (KRELVEPLTPSGEAP-NQALLR), 300 μM NADH, 500 μM PEP (phophoenolpyruvate), 9-10 units/mL LDH, 8-12 units/mL PK, 40 nM JNK1α1_364nHis (catalytic domain containing amino acids 1-364 and N-terminal hexahistidine tag, previously activated by MKK4 and MKK7beta in vitro), 0-100 μM test compound, 2.5% DMSO, and 50 μM ATP (2.5×Km). The reaction was monitored by following the decrease in absorbance at 340 nm. The initial reaction rate was determined by the slope of the change in absorbance. To calculate percent inhibition the rate of the reaction in the presence of 1 or 10 μM compound was compared to the rate of the reaction with only DMSO multiplied by 100 percent. Note, the background rate of the above reaction in the presence of 10 μM PHA-00738186 was subtracted from all rates. To calculate the $K_i$, the reaction rates (with the background subtracted) were plotted vs. the compound concentration (0-100 μM) and fit to the tight binding for competitive inhibitors (Morrison) equation (see below).

$$Y=(-X+Eo-(Ki*(1+A/Km))+((X-Eo+(Ki*(1+A/Km)))^2+4*Eo*(Ki*(1+A/Km)))^0.5)*(Vm*A/(Km+A)/(2*Eo)))$$ Formula:

Parameters: Eo, Ki, A, Km, Vo

Y is initial reaction velocity;

X is inhibitor concentration;

A is [ATP];

Ki is inhibition constant;

Vm is Vmax;

Eo is total (initial) enzyme concentration;

Km is ATP Km;

The compounds were prepared in 100% DMSO at a 40× concentration. For percent inhibition experiments this would be 400 or 40 μM for 10 and 1 μM final concentration, respectively. For the Ki determination 3× serial dilutions were made starting at 4 mM (100 μM at 1×) in DMSO. A total of 11 concentrations were used for the analysis. The compounds were added to the reaction plate first. Next, a solution containing the HEPES, $MgCl_2$, DTT, peptide substrate, NADH, PEP, PK/LDH enzyme, and JNK1α1_364nHis enzyme was added to the assay plate. The plate was incubated at room temperature for 15 minutes. Then the plate was warmed to 30° C. for 5 minutes. The reaction was initiated with the addition of ATP. The reaction was run in a plate reader at 30° C. for 20 minutes with absorbance readings made about every 10 seconds.

JNK1α1 364nHis Purification Procedure

Growth and Induction Conditions

BL21 (DE3) cells containing JNK1α1_364nHis vector were grown at 37° C. until optical density ($OD_{600}$) was between 0.6 to 0.8. Expression was induced by addition of isopropylthiogalactoside (IPTG) to a final concentration of 0.1-0.2 mM and incubated at 23° C. overnight. The cells were harvested at 5000 rpm for 15 minutes at 4° C. The cell pellet can be stored at −80° C. for future purification.

Purification Procedure
1. Cell pellet (1 L culture) was resuspended with lysis buffer at 5-10 mL/wet cell pellet. The maximum and minimum volumes were 350 mL and 60 mL.

| Lysis Buffer | 1 L |
|---|---|
| 25 mM Tris-HCl, pH 8.0 | 25 mL of 1M |
| 300 mM NaCl | 60 mL of 5M |
| 14 mM β-ME (add fresh) | 1 mL of 14M stock |
| 20 mM Imidazole | 5 mL of 4M |
| dH$_2$O | 909 mL |

The lysis buffer was filtered before use.

2. The cell were lyzed with microfluidizer (three times) and ultracentrifuged at 40,000 rpm for 45 minutes at 4° C. The supernatant was transferred to a chilled flask. A 20 ul aliquot was saved for gel analysis.
3. Ni-NTA column (23 mL) lines were rinsed with lysis buffer. The column (23 mL) was washed with 160 mL of lysis buffer at 5 mL/min.
4. The supernatant was loaded onto Ni-NTA column at 4 mL/min.
5. The unbound was washed with 160 mL of lysis buffer at 5 mL/min.
6. The protein was eluted with imidazole gradient (from 20 mM to 0.5M). The elution buffer was prepared as follows:

| Elution Buffer | 250 mL |
|---|---|
| 25 mM Tris-HCl, pH 7.5 | 6.25 mL of 1M |
| 300 mM NaCl | 15 mL of 5M |
| 14 mM β-ME (add fresh) | 0.25 mL of 14M stock |
| 0.5M Imidazole | 31.25 mL of 4M |
| dH$_2$O | 197.25 mL |

The elution buffer was filtered before use

7. The elution settings were as follows. The record speed was set @1.0 mm/min.

| BP | % B | FR | FS |
|---|---|---|---|
| 0 | 0 | 3 | 8 |
| 200 | 100 | 3 | 8 |
| 250 | 100 | 3 | 8 |

At the end of the elution the record speed was returned to 0.1 mm/min. Referring to the template above, BP means break point, % B means % buffer grading, FR means flow rate, and FS means fraction size.

8. The peak fractions were pooled. A 40 ul aliquot was saved for gel analysis.
9. The sample was concentrated down to 4-6 mL with ultrafiltration cell under nitrogen.
10. While sample was being concentrated, the Superdex 200 column was washed with 450 mL Superdex buffer at 2 mL/min. The Superdex buffer was prepared as follows:

| Superdex buffer | 1 L |
|---|---|
| 25 mM Hepes pH 7.5, | 25 mL |
| 5% Glycerol | 100 mL |
| 10 mM DTT | 1.54 g |
| 50 mM NaCl | 10 mL |
| dH$_2$O | 865 mL |

To prepare the protein that was used for the assay, Dundee buffer was used for Superdex column. The Dundee buffer was prepared as follows:

| Dundee Buffer | 1 L |
|---|---|
| 50 mM Tris Cl pH 7.5, | 50 mL |
| 270 mM Sucrose | 92.4 g |
| 150 mM NaCl | 30 mL |
| 0.1 mM EGTA | 1 mL |
| 0.1% bMe | 1 mL |
| 0.03% Brij-35 | 1 mL |
| 1 mM Benzamidine | 1 mL |
| 0.2 mM PMSF | 1 mL |
| dH$_2$O | to 1 L |

11. The concentrated sample was transferred to pre-chilled 1.5 mL tubes and spinned at max for 10 minutes in cold room. The supernatant was transferred to 50 mL chilled tube.
12. The sample was injected (total volume equals total sample loop volume plus 0.3 mL) to pre-washed loop (4-6 mL). A 5 ul aliquat was saved of the remaining sample for SDS-PAGE (a detergent).
13. The protein was eluted overnight according to the following settings. The record speed was set at 0.2 mm/min.

| BP | FR | FS | Injection valve |
|---|---|---|---|
| 0 | 0.5 | 5 | I |
| 20 | 0.5 | 5 | I |
| 20.1 | 0.5 | 5 | L |
| 400 | 0.5 | 5 | L |

At the completion of the elution, the record speed was returned to 0.1 mm/min. Referring to the template above, BP means break point, FR means flow rate, FS means fraction size, I means inject, and L means load.

14. The peak fractions were pooled and the pool concentration was measured. The protein was concentrated down to 7-8 mg/mL in hepes buffer protein. Aliquots of the protein were placed into chilled 0.5 mL tubes at 100 ul/tube, which were then snapped frozen in liquid nitrogen and stored at −80° C.

The following procedure to regenerate the Ni-NTA and the Superdex 200 columns was used:

NI-NTA Column

The Ni-NTA column was washed with 80 mL of dH$_2$O at 5 mL/min. Next it was washed with 80 mL of 0.1M EDTA, pH8.0 at 5 mL/min. The flow was collected through in flask for proper disposal. The column was further washed with 150 mL of dH$_2$O at 5 mL/min. and charged with 60 mL of 100 mM NiCl$_2$ at 5 mL/min. The flow was collected through in the same waste flask. The column was then washed with 60 mL of dH$_2$O at 5 mL/min and the flow was again collected through in the same waste flask. The column was then washed with 160 mL of dH$_2$O at 5 mL/min.

Superdex 200 Column

The Superdex 200 column was washed with 700 mL of filtered dH$_2$O at 2 mL/min.

The data obtained from the compounds of the invention according to the above protocol are tabulated below. The column with "#" heading refers to compound number as exemplified in the Examples section. The column with "Ki" heading refers to Ki (in nM). The column with "% Inhibition" heading refers to percent inhibition of JNK-1 at 1 μM or 10 μM (in %) unless otherwise stated. ND refers to no data was taken.

| # | Ki (nM) | % Inhibition JNK-1 |
|---|---|---|
| 1 | 76 | ND |
| 2 | 77 | ND |
| 3 | 50 | ND |
| 4 | 0.8 | ND |
| 5 | 79 | ND |
| 6 | 39 | ND |
| 7 | 20 | ND |
| 8 | >50 | ND |
| 9 | 17 | ND |
| 10 | 42 | ND |
| 11 | 26 | ND |
| 12 | 29 | ND |
| 13 | 36 | ND |
| 14 | >50 | ND |
| 15 | 24 | ND |
| 16 | 31 | ND |
| 17 | >30 | ND |
| 18 | 32 | ND |
| 19 | 13 | ND |
| 20 | 44 | ND |
| 21 | >50 | ND |
| 22 | >50 | ND |
| 23 | 2 | ND |
| 24 | 25 | ND |
| 25 | 14 | ND |
| 26 | 7 | ND |
| 27 | 4 | ND |
| 28 | 32 | ND |
| 29 | 22 | ND |
| 30 | 18 | ND |
| 31 | 3 | ND |
| 32 | 8 | ND |
| 33 | 7 | ND |
| 34 | 17 | ND |
| 35 | 8 | ND |
| 36 | 8 | ND |
| 37 | 2 | ND |
| 38 | 14 | ND |
| 39 | 7 | ND |
| 40 | 8 | ND |
| 41 | 14 | ND |
| 42 | 5 | ND |
| 43 | 8 | ND |
| 44 | 11 | ND |
| 45 | 21 | ND |
| 46 | 5 | ND |
| 47 | >50 | ND |
| 48 | 15 | ND |
| 49 | 3 | ND |
| 50 | 3 | ND |
| 51 | 8 | ND |
| 52 | 15 | ND |
| 53 | 21 | ND |
| 54 | 8 | ND |
| 55 | 5 | ND |
| 56 | 17 | ND |
| 57 | 4 | ND |
| 58 | 261 | ND |
| 59 | 4340 | ND |
| 60 | 157 | ND |
| 61 | 525 | ND |
| 62 | 432 | ND |
| 63 | 460 | ND |
| 64 | 456 | ND |
| 65 | 485 | ND |
| 66 | ND | ND |
| 67 | ND | ND |
| 68 | ND | ND |
| 69 | ND | ND |
| 70 | ND | ND |
| 71 | ND | 359 |
| 72 | ND | 337 |
| 73 | ND | 420 |
| 74 | ND | 123 |
| 75 | ND | 160 |
| 76 | 127 | ND |
| 77 | 261 | ND |
| 78 | 4340 | ND |
| 79 | 292 | ND |
| 80 | 525 | ND |
| 81 | 63 | ND |
| 82 | 235 | ND |
| 83 | 247 | ND |
| 84 | 1960 | ND |
| 85 | 3010 | ND |
| 86 | 220 | ND |
| 87 | 60 | ND |
| 88 | 114 | ND |
| 89 | 269 | ND |
| 90 | 354 | ND |
| 91 | 643 | ND |
| 92 | 379 | ND |
| 93 | 31 | ND |
| 94 | 148 | ND |
| 95 | 74 | ND |
| 96 | 391 | ND |
| 97 | 55 | ND |
| 98 | 33 | ND |
| 99 | 18 | ND |
| 100 | 120 | ND |
| 101 | 94 | ND |
| 102 | 992 | ND |
| 103 | 176 | ND |
| 104 | 66 | ND |
| 105 | 703 | ND |
| 106 | 223 | ND |
| 107 | 250 | ND |
| 108 | 126 | ND |
| 109 | 678 | ND |
| 110 | 86 | ND |
| 111 | 142 | ND |
| 112 | >10000 | ND |
| 113 | 271 | ND |
| 114 | 1550 | ND |
| 115 | 230 | ND |
| 116 | 2450 | ND |
| 117 | 250 | ND |
| 118 | 222 | ND |
| 119 | 377 | ND |
| 120 | 147 | ND |
| 121 | 169 | ND |
| 122 | 82 | ND |
| 123 | 634 | ND |
| 124 | 410 | ND |
| 125 | 520 | ND |
| 126 | 382 | ND |
| 127 | 3490 | ND |
| 128 | 3500 | ND |
| 129 | 130 | ND |
| 130 | 141 | ND |
| 131 | 77 | ND |
| 132 | 78 | ND |
| 133 | 210 | ND |
| 134 | 127 | ND |
| 135 | 300 | ND |
| 136 | 257 | ND |
| 137 | 263 | ND |

| # | Ki (nM) | % Inhibition JNK-1 |
|---|---|---|
| 138 | 950 | ND |
| 139 | 16 | ND |
| 140 | 52 | ND |
| 141 | 29 | ND |
| 142 | 226 | ND |
| 143 | 337 | ND |
| 144 | 127 | ND |
| 145 | 123 | ND |
| 146 | 178 | ND |
| 147 | 460 | ND |
| 148 | 456 | ND |
| 149 | 485 | ND |
| 150 | 359 | ND |
| 151 | 432 | ND |
| 152 | 420 | ND |
| 153 | 185 | ND |
| 154 | 403 | ND |
| 155 | 156 | ND |
| 156 | 988 | ND |
| 157 | 1780 | ND |
| 158 | 201 | ND |
| 159 | 190 | ND |
| 160 | 70 | ND |
| 161 | 111 | ND |
| 162 | 260 | ND |
| 163 | 1740 | ND |
| 164 | 416 | ND |
| 165 | 153 | ND |
| 166 | 296 | ND |
| 167 | 644 | ND |
| 168 | 574 | ND |
| 169 | 231 | ND |
| 170 | 2150 | ND |
| 171 | 483 | ND |
| 172 | 3570 | ND |
| 173 | 1910 | ND |
| 174 | 999 | ND |
| 175 | 880 | ND |
| 176 | 422 | ND |
| 177 | 914 | ND |
| 178 | 744 | ND |
| 179 | 665 | ND |
| 180 | 570 | ND |
| 181 | 780 | ND |
| 182 | 146 | ND |
| 183 | 220 | ND |
| 184 | 674 | ND |
| 185 | 885 | ND |
| 186 | 607 | ND |
| 187 | 414 | ND |
| 188 | 374 | ND |
| 189 | 877 | ND |
| 190 | 342 | ND |
| 191 | 698 | ND |
| 192 | 1130 | ND |
| 193 | 1410 | ND |
| 194 | 1460 | ND |
| 195 | 81 | ND |
| 196 | 56 | ND |
| 197 | 143 | ND |
| 198 | 50 | ND |
| 199 | 98 | ND |
| 200 | 186 | ND |
| 201 | 70 | ND |
| 202 | 77 | ND |
| 203 | 815 | ND |
| 204 | 303 | ND |
| 205 | 29 | ND |
| 206 | 495 | ND |
| 207 | 1060 | ND |
| 208 | 1130 | ND |
| 209 | ND | ND |
| 210 | 1710 | ND |
| 211 | 1030 | ND |
| 212 | 1950 | ND |
| 213 | 780 | ND |
| 214 | 1300 | ND |
| 215 | 250 | ND |
| 216 | 480 | ND |
| 217 | 775 | ND |
| 218 | 843 | ND |
| 219 | 1160 | ND |
| 220 | 1930 | ND |
| 221 | 2220 | ND |
| 222 | 2950 | ND |
| 223 | 3280 | ND |
| 224 | 3370 | ND |
| 225 | 5160 | ND |
| 226 | 5270 | ND |
| 227 | 6620 | ND |
| 228 | 11500 | ND |
| 229 | ND | 17% @10 uM |
| 230 | ND | 43% @10 uM |
| 231 | ND | 43% @10 uM |
| 232 | ND | 46% @10 uM |
| 233 | ND | 46% @10 uM |
| 234 | ND | 19% @10 uM |
| 235 | ND | 15% @10 uM |
| 236 | ND | 49% @10 uM |
| 237 | ND | 41% @10 uM |
| 238 | ND | 46% @10 uM |
| 239 | 67 | ND |
| 240 | 79 | ND |
| 241 | 98 | ND |
| 242 | 112 | ND |
| 243 | 233 | ND |
| 244 | 234 | ND |
| 245 | 239 | ND |
| 246 | 257 | ND |
| 247 | 274 | ND |
| 248 | 303 | ND |
| 249 | 323 | ND |
| 250 | ND | 24% @1 uM |
| 251 | ND | 19% @1 uM |
| 252 | ND | 59% @10 uM |
| 253 | ND | 38% @10 uM |
| 254 | ND | 17% @1 uM |
| 255 | ND | 12% @1 uM |
| 256 | ND | 29% @1 uM |
| 257 | ND | 62% @10 uM |
| 258 | ND | 30% @1 uM |
| 259 | ND | 65% @10 uM |
| 260 | ND | 34% @1 uM |
| 261 | ND | 42% @10 uM |
| 262 | ND | 61% @10 uM |
| 263 | ND | 31% @10 uM |
| 264 | ND | 46% @10 uM |
| 265 | ND | 47% @1 uM |
| 266 | ND | 14% @1 uM |
| 267 | ND | 18% @1 uM |
| 268 | ND | 67% @1 uM |
| 269 | ND | 29% @1 uM |
| 270 | ND | 40% @1 uM |
| 271 | ND | 41% @1 uM |
| 272 | ND | 63% @1 uM |
| 273 | ND | 24% @1 uM |
| 274 | ND | 25% @1 uM |
| 275 | ND | 52% @1 uM |
| 276 | ND | 22% @1 uM |
| 277 | ND | 46% @1 uM |
| 278 | ND | 27% @1 uM |
| 279 | ND | 54% @1 uM |
| 280 | ND | 37% @1 uM |
| 281 | ND | 72% @1 uM |
| 282 | ND | 71% @1 uM |
| 283 | ND | 33% @1 uM |
| 284 | ND | 53% @1 uM |
| 285 | ND | 29% @1 uM |
| 286 | ND | 42% @1 uM |
| 287 | ND | 62% @1 uM |
| 288 | ND | 39% @1 uM |
| 289 | ND | 69% @1 uM |

| # | Ki (nM) | % Inhibition JNK-1 |
|---|---------|--------------------|
| 290 | ND | 53% @1 uM |
| 291 | ND | 37% @1 uM |
| 292 | ND | 54% @1 uM |
| 293 | ND | 52% @1 uM |
| 294 | ND | 24% @1 uM |
| 295 | ND | 71% @1 uM |
| 296 | ND | 14% @1 uM |
| 297 | ND | 28% @1 uM |
| 298 | ND | 18% @1 uM |
| 299 | ND | ND |
| 300 | ND | ND |
| 301 | ND | ND |
| 302 | ND | ND |
| 303 | ND | ND |
| 304 | ND | ND |
| 305 | ND | ND |
| 306 | ND | ND |
| 307 | ND | ND |
| 308 | ND | ND |
| 309 | ND | ND |
| 310 | ND | ND |
| 311 | ND | 36% @10 uM |
| 312 | ND | 76% @10 uM |
| 313 | ND | 71% @10 uM |
| 314 | ND | 11% @1 uM |
| 315 | ND | 52% @10 uM |
| 316 | ND | 18% @1 uM |
| 317 | ND | 31% @1 uM |
| 318 | ND | 37% @1 uM |
| 319 | ND | 27% @1 uM |
| 320 | ND | 19% @1 uM |
| 321 | ND | 39% @1 uM |
| 322 | ND | 18% @1 uM |
| 323 | ND | 42% @1 uM |
| 324 | ND | 26% @10 uM |
| 325 | ND | 9% @1 uM |
| 326 | 193 | ND |
| 327 | 254 | ND |
| 328 | 257 | ND |
| 329 | 345 | ND |
| 330 | 354 | ND |
| 331 | 410 | ND |
| 332 | 424 | ND |
| 333 | 455 | ND |
| 334 | 480 | ND |
| 335 | 483 | ND |
| 336 | 516 | ND |
| 337 | 568 | ND |
| 338 | 637 | ND |
| 339 | 801 | ND |
| 340 | 836 | ND |
| 341 | 836 | ND |
| 342 | 839 | ND |
| 343 | 855 | ND |
| 344 | 869 | ND |
| 345 | 885 | ND |
| 346 | 945 | ND |
| 347 | 963 | ND |
| 348 | 978 | ND |
| 349 | 1010 | ND |
| 350 | 1040 | ND |
| 351 | 1060 | ND |
| 352 | 1100 | ND |
| 353 | 1170 | ND |
| 354 | 1230 | ND |
| 355 | 1390 | ND |
| 356 | 1480 | ND |
| 357 | 1550 | ND |
| 358 | 1700 | ND |
| 359 | 1720 | ND |
| 360 | 1730 | ND |
| 361 | 1810 | ND |
| 362 | 1810 | ND |
| 363 | 1950 | ND |
| 364 | 1990 | ND |
| 365 | 2060 | ND |
| 366 | 2170 | ND |
| 367 | 2180 | ND |
| 368 | 2290 | ND |
| 369 | 2310 | ND |
| 370 | 2470 | ND |
| 371 | 2490 | ND |
| 372 | 73.5 | ND |
| 373 | 74 | ND |
| 374 | 102 | ND |
| 375 | 107 | ND |
| 376 | 139 | ND |
| 377 | 147 | ND |
| 378 | 160 | ND |
| 379 | 177 | ND |
| 380 | 187 | ND |
| 381 | 193 | ND |
| 382 | 195 | ND |
| 383 | 200 | ND |
| 384 | 257 | ND |
| 385 | 263 | ND |
| 386 | 271 | ND |
| 387 | 297 | ND |
| 388 | 303 | ND |
| 389 | 318 | ND |
| 390 | 333 | ND |
| 391 | 365 | ND |
| 392 | 385 | ND |
| 393 | 387 | ND |
| 394 | 391 | ND |
| 395 | 422 | ND |
| 396 | 424 | ND |
| 397 | 428 | ND |
| 398 | 447 | ND |
| 399 | 461 | ND |
| 400 | 478 | ND |
| 401 | 490 | ND |
| 402 | 605 | ND |
| 403 | 637 | ND |
| 404 | 667 | ND |
| 405 | 722 | ND |
| 406 | 730 | ND |
| 407 | 735 | ND |
| 408 | 743 | ND |
| 409 | 772 | ND |
| 410 | 945 | ND |
| 411 | 1100 | ND |
| 412 | 1100 | ND |
| 413 | 1270 | ND |
| 414 | 1310 | ND |
| 415 | 1490 | ND |
| 416 | 1550 | ND |
| 417 | 1680 | ND |
| 418 | 1720 | ND |
| 419 | 3030 | ND |
| 420 | ND | 21% @1 uM |
| 421 | ND | 15% @1 uM |
| 422 | ND | 13% @1 uM |
| 423 | ND | 15% @1 uM |
| 424 | ND | 22% @1 uM |
| 425 | ND | 11% @1 uM |
| 426 | ND | 23% @1 uM |
| 427 | ND | 21% @1 uM |
| 428 | ND | 17% @1 uM |
| 429 | ND | 25% @1 uM |
| 430 | ND | 11% @1 uM |
| 431 | ND | 15% @1 uM |
| 432 | ND | 15% @1 uM |
| 433 | ND | 24% @1 uM |
| 434 | ND | 15% @1 uM |
| 435 | ND | 22% @1 uM |
| 436 | ND | 85% @10 uM |
| 437 | ND | 57% @10 uM |
| 438 | ND | 63% @10 uM |
| 439 | ND | 44% @10 uM |
| 440 | ND | 48% @10 uM |
| 441 | 57 | ND |

| # | Ki (nM) | % Inhibition JNK-1 |
|---|---|---|
| 442 | 83 | ND |
| 443 | 104 | ND |
| 444 | 106 | ND |
| 445 | 110 | ND |
| 446 | 112 | ND |
| 447 | 119 | ND |
| 448 | 130 | ND |
| 449 | 138 | ND |
| 450 | 144 | ND |
| 451 | 166 | ND |
| 452 | 166 | ND |
| 453 | 170 | ND |
| 454 | 221 | ND |
| 455 | 235 | ND |
| 456 | 254 | ND |
| 457 | 275 | ND |
| 458 | 374 | ND |
| 459 | 399 | ND |
| 460 | 400 | ND |
| 461 | 451 | ND |
| 462 | 471 | ND |
| 463 | 486 | ND |
| 464 | 685 | ND |
| 465 | 782 | ND |
| 466 | 962 | ND |
| 467 | 2050 | ND |
| 468 | ND | 15% @1 uM |
| 469 | ND | 10% @1 uM |
| 470 | ND | 27% @1 uM |
| 471 | ND | 19% @1 uM |
| 472 | ND | 25% @1 uM |
| 473 | ND | 34% @1 uM |
| 474 | ND | 37% @1 uM |
| 475 | ND | 11% @1 uM |
| 476 | ND | 10% @1 uM |
| 477 | ND | 14% @1 uM |
| 478 | ND | 12% @1 uM |
| 479 | ND | 13% @1 uM |
| 480 | ND | 11% @1 uM |
| 481 | ND | 14% @1 uM |
| 482 | ND | 13% @1 uM |
| 483 | ND | 71% @10 uM |
| 484 | ND | 57% @10 uM |
| 485 | ND | 72% @10 uM |
| 486 | ND | 50% @10 uM |
| 487 | ND | 51% @10 uM |
| 488 | ND | 40% @1 uM |
| 489 | ND | 16% @1 uM |
| 490 | ND | 40% @10 uM |
| 491 | ND | 13% @1 uM |
| 492 | ND | 12% @1 uM |
| 493 | ND | 11% @1 uM |
| 494 | ND | 16% @1 uM |
| 495 | ND | 76% @10 uM |
| 496 | ND | 41% @1 uM |
| 497 | ND | 13% @1 uM |
| 498 | ND | 11% @1 uM |
| 499 | ND | 8% @1 uM |
| 500 | ND | 38% @10 uM |
| 501 | ND | 60% @10 uM |
| 502 | ND | 50% @10 uM |
| 503 | ND | 54% @10 uM |
| 504 | ND | 40% @10 uM |
| 505 | ND | 58% @10 uM |
| 506 | ND | 37% @1 uM |
| 507 | ND | 25% @1 uM |
| 508 | ND | 21% @1 uM |
| 509 | ND | 49% @10 uM |
| 510 | ND | 25% @10 uM |
| 511 | ND | 47% @10 uM |
| 512 | ND | 31% @10 uM |
| 513 | ND | 21% @1 uM |
| 514 | ND | 11% @1 uM |
| 515 | ND | 19% @1 uM |
| 516 | ND | 26% @1 uM |
| 517 | ND | 16% @1 uM |
| 518 | ND | 60% @10 uM |
| 519 | ND | 9% @1 uM |
| 520 | ND | 10% @1 uM |
| 521 | ND | 49% @1 uM |
| 522 | ND | 18% @1 uM |
| 523 | ND | 44% @10 uM |
| 524 | ND | 47% @10 uM |
| 525 | ND | 41% @10 uM |
| 526 | ND | 41% @10 uM |
| 527 | ND | 34% @1 uM |
| 528 | ND | 26% @1 uM |
| 529 | ND | 16% @1 uM |
| 530 | ND | 26% @1 uM |
| 531 | ND | 26% @1 uM |

Various embodiments of the present invention have been described above but a person skilled in the art realizes further minor alterations that would fall into the scope of the present invention. The breadth and scope of the present invention should not be limited by any of the above-described exemplary embodiments, but should be defined only in accordance with the following claims and their equivalents.

We claim:

1. A compound of formula (I):

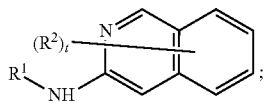

(Ia1)

or a pharmaceutically acceptable salt thereof, wherein:
$R^1$ is —$(CR^3R^4)_v$(3-10)-membered cycloalkyl;
$R^2$ is halo, cyano, nitro, —$CF_3$, —$CHF_2$, —$CH_2F$, trifluoromethoxy, azido, hydroxy, $(C_1-C_6)$alkoxy, $(C_1-C_6)$alkyl, $(C_2-C_6)$alkenyl, $(C_2-C_6)$alkynyl, —(C=O)—$R^5$, —(C=O)—O—$R^5$, —O—(C=O)—$R^5$, —$NR^5$(C=O)—$R^7$, —(C=O)—$NR^5R^6$, —$NR^5R^6$, —$NR^5OR^6$, —$S(O)_kNR^5R^6$, —$S(O)_j(C_1-C_6)$alkyl, —O—$SO_2$—$R^5$, —$NR^5$—S(O)$_k$—$R^6$, —$(CR^5R^6)_v$(3-10)-membered cycloalkyl, —$(CR^5R^6)_v(C_6-C_{10}$aryl), —$(CR^5R^6)_v$(4-10)-membered heterocyclyl, —$(CR^5R^6)_q$(C=O)$(CR^5R^6)_v$(3-10)-membered cycloalkyl, —$(CR^5R^6)_q$(C=O)$(CR^5R^6)_v(C_6-C_{10}$)aryl, —$(CR^5R^6)_q$(C=O)$(CR^5R^6)_v$(4-10)-membered heterocyclyl, —$(CR^5R^6)_q$(C=O)$(CR^5R^6)_v$(3-10)-membered cycloalkyl, —$(CR^5R^6)_q$O$(CR^5R^6)_v(C_6-C_{10}$)aryl, —$(CR^5R^6)_q$S(O)$_j(CR^5R^6)_v$(4-10)-membered heterocyclyl, —$(CR^5R^6)_q$S(O)$_j(CR^5R^6)_v(C_6-C_{10}$)aryl, or —$(CR^5R^6)_q$S(O)$_j(CR^5R^6)_v$(4-10)-membered heterocyclyl;
each of $R^3$, $R^4$, $R^5$, $R^6$ and $R^7$ are independently selected from H, $(C_1-C_6)$alkyl, —$(CR^8R^9)_p$(3-10)-membered cycloalkyl, —$(CR^8R^9)_p(C_6-C_{10}$)aryl, and —$(CR^8R^9)_p$ (4-10)-membered heterocyclyl;
any carbon atoms of the $(C_1-C_6)$alkyl, the (3-10)-membered cycloalkyl, the $(C_6-C_{10})$aryl and the (4-10)-membered heterocyclyl moieties of the foregoing $R^1$, $R^2$, $R^3$, $R^4$, $R^5$, $R^6$ and $R^7$ are optionally substituted with 1 to 3 $R^{11}$ substituents each independently selected from oxo, halo, cyano, nitro, —$CF_3$, —$CHF_2$, —$CH_2F$, trifluoromethoxy, azido, hydroxy, $(C_1-C_6)$alkoxy, $(C_1-C_6)$alkyl, $(C_2-C_6)$alkenyl, $(C_2-C_6)$alkynyl, —(C=O)—$R^8$, —(C=O)—O—$R^8$, —O—(C=O)—$R^8$, —$NR^8$(C=O)—$R^{10}$, —$NR^8$(C=O)—O—$R^{10}$, —(C=O)—$NR^8R^9$, —(C=O)—$NR^8R^{9a}$, —$NR^8R^9$, —$NR^8OR^9$, —$S(O)_kNR^8R^9$, —$S(O)_jR^8$, —O—$SO_2$—$R^8$, —$NR^8$—S(O)$_k$—$R^9$, —$NR^8$—S(O)$_k$—$R^{9a}$, —$(CR^8R^9)_p$(3-10)-membered cycloalkyl, —$(CR^8R^9)_p(C_6-C_{10}$aryl), —$(CR^8R^9)_p$(4-10)-membered heterocyclyl, —$(CR^8R^9)_q$(C=O)$(CR^8R^9)_p$(3-10)-membered cycloalkyl, —$(CR^8R^9)_q$(C=O)$(CR^8R^9)_p(C_6-C_{10}$)aryl, —$(CR^8R^9)_q$(C=O)$(CR^8R^9)_p$(4-10)-membered heterocyclyl, —$(CR^8R^9)_v$O$(CR^8R^9)_p$(3-10)-membered cycloalkyl, —$(CR^8R^9)_v$O$(CR^8R^9)_p(C_6-C_{10}$)aryl, —$(CR^8R^9)_v$O$(CR^8R^9)_p$(4-10)-membered heterocyclyl, —$(CR^8R^9)_q$S(O)$_j(CR^8R^9)_p(C_6-C_{10}$)aryl, or —$(CR^8R^9)_q$S(O)$_j(CR^8R^9)_p$(4-10)-membered heterocyclyl;
wherein any carbon atoms of each of the $(C_1-C_6)$alkyl, the (3-10)-membered cycloalkyl, the $(C_6-C_{10})$aryl and the (4-10)-membered heterocyclyl moieties of the foregoing $R^{11}$ are optionally substituted with 1 to 3 $R^{12}$ substituents each independently selected from halo, cyano, nitro, —$CF_3$, —$CHF_2$, —$CH_2F$, trifluoromethoxy, azido, hydroxy, $(C_1-C_6)$alkoxy, $(C_1-C_6)$alkyl, $(C_2-C_6)$alkenyl, $(C_2-C_6)$alkynyl, —(C=O)—$R^8$, —(C=O)—O—$R^8$, —O—(C=O)—$R^8$, —$NR^8$(C=O)—$R^{10}$, —(C=O)—$NR^8R^9$, —$NR^8R^9$, —$NR^8OR^9$, —$S(O)_kNR^8R^9$, —$S(O)_j(C_1-C_6)$alkyl, —O—$SO_2$—$R^8$, and —$NR^8$—$S(O)_k$—$R^9$;
any nitrogen atoms of the (4-10)-membered heterocyclyl of the foregoing $R^2$, $R^3$, $R^4$, $R^5$, $R^6$, $R^7$, $R^{11}$, are optionally substituted with 1 to 3 $R^{13}$ substituents each independently selected from $(C_1-C_6)$alkyl, $(C_2-C_6)$alkenyl, $(C_2-C_6)$alkynyl, —(C=O)—$R^8$, —(C=O)—$R^{9a}$, —(C=O)—O—$R^8$, —(C=O)—$NR^8R^9$, —$(CR^8R^9)_q$—$NR^8R^9$, —$(CR^8R^9)_p$(3-10)-membered cycloalkyl, —$(CR^8R^9)_p(C_6-C_{10}$aryl), —$(CR^8R^9)_p$(4-10)-membered heterocyclyl, —$(CR^8R^9)_q$(C=O)$(CR^8R^9)_p$(3-10)-membered cycloalkyl, —$(CR^8R^9)_q$(C=O)$(CR^8R^9)_p(C_6-C_{10}$)aryl, or —$(CR^8R^9)_p$(C=O)$(CR^8R^9)_p$(4-10)-membered heterocyclyl;
each $R^8$, $R^9$, and $k^{10}$ are independently H or $(C_1-C_6)$alkyl;
each $R^{9a}$ is independently —$(CR^8R^9)_p$(3-10)-membered cycloalkyl, —$(CR^8R^9)_p(C_6-C_{10}$ aryl), or —$(CR^8R^9)_p$(4-10)-membered heterocyclyl;
p and q are each independently 0, 1, 2, 3, 4, or 5;
v is each independently 1, 2, 3, 4, or 5;
j is independently 0, 1, or 2;
t is 1, 2, 3, or 4;
and
k is 1 or 2.

2. The compound according to claim 1, wherein $R^2$ is halo, hydroxy, $(C_1-C_6)$alkoxy, $(C_1-C_6)$alkyl, —(C=O)—$R^5$, —(C=O)—$NR^5R^6$, —$(CR^5R^6)_v$(3-10)-membered cycloalkyl, —$(CR^5R^6)_v(C_6-C_{10}$aryl), —$(CR^5R^6)_v$(4-10)-membered heterocyclyl, —$(CR^5R^6)_q$O$(CR^5R^6)_v$(3-10)-membered cycloalkyl, —$(CR^5R^6)_q(CR^5R^6)_v(C_6-C_{10}$)aryl, or —$(CR^5R^6)_q$O$(CR^5R^6)_v$(4-10)-membered heterocyclyl.

3. The compound according to claim 1, wherein any carbon atoms of the $(C_1-C_6)$alkyl, the (3-10)-membered cycloalkyl, the $(C_6-C_{10})$aryl and the (4-10)-membered heterocyclyl moieties of the foregoing $R^1$, $R^2$, $R^3$, $R^4$, $R^5$, $R^6$ and $R^7$ are optionally substituted with 1 to 3 $R^{11}$ substituents each independently selected from halo, cyano, hydroxy, $(C_1-C_6)$alkoxy, $(C_1-C_6)$alkyl, —(C=O)—$R^8$, —$NR^8$(C=O)—$R^{10}$, —(C=O)—$NR^8R^9$, —(C=O)—$NR^8R^{9a}$, —$NR^8R^9$, —$S(O)_jR^8$, —$NR^8$—S(O)$_k$—$R^9$, —$NR^8$—S(O)$_k$—$R^{9a}$, —$(CR^8R^9)_p$(3-10)-membered cycloalkyl, —$(CR^8R^9)_p(C_6-C_{10}$aryl), —$(CR^8R^9)_p$(4-10)-membered heterocyclyl, —$(CR^8R^9)_q$(C=O)$(CR^8R^9)_p$(3-10)-membered cycloalkyl, —$(CR^8R^9)_q$(C=O)$(CR^8R^9)_p(C_6-C_{10}$)aryl, and —$(CR^8R^9)_q$(C=O)$(CR^8R^9)_p$(4-10)-membered heterocyclyl.

4. The compound according to claim 1, wherein any carbon atoms of the $(C_1-C_6)$alkyl, the (3-10)-membered cycloalkyl, the $(C_6-C_{10})$aryl and the (4-10)-membered heterocyclyl moieties of the foregoing $R^{11}$ are optionally substituted with 1 to 3 $R^{12}$ substituents each independently selected from halo, hydroxy, $(C_1-C_6)$alkoxy, $(C_1-C_6)$alkyl, and —$NR^8R^9$.

5. The compound according to claim 1, wherein any nitrogen atoms of the (4-10)-membered heterocyclyl of the foregoing $R^2$, and $R^{11}$ are optionally substituted with 1 to 3 $R^{13}$ substituents each independently selected from $(C_1-C_6)$alkyl, —(C=O)—$R^8$, —(C=O)—$R^{9a}$, —(C=O)—O—$R^8$, —(C=O)—$NR^8R^9$, —$(CR^8R^9)_q$—$NR^8R^9$, —$(CR^8R^9)_p$(3-10)-membered cycloalkyl, and —$(CR^8R^9)_p$(C6-$C_{10}$aryl), —$(CR^8R^9)_p$(4-10)-membered heterocyclyl.

6. A pharmaceutical composition comprising an effective amount of a compound according to claim 1, or a pharmaceutically acceptable salt thereof, and a pharmaceutically acceptable carrier.

* * * * *

SEQUENCE LISTING

<160> NUMBER OF SEQ ID NOS: 1

<210> SEQ ID NO 1
<211> LENGTH: 21
<212> TYPE: PRT
<213> ORGANISM: Unknown
<220> FEATURE:
<223> OTHER INFORMATION: Synthetic

<400> SEQUENCE: 1

Lys Arg Glu Leu Val Glu Pro Leu Thr Pro Ser Gly Glu Ala Pro Asn
1               5                   10                  15

Gln Ala Leu Leu Arg
            20